(12) United States Patent
Zhang et al.

(10) Patent No.: US 9,951,010 B2
(45) Date of Patent: Apr. 24, 2018

(54) COMPOUNDS AS CRTH2 ANTAGONIST AND USES THEREOF

(71) Applicant: SUNSHINE LAKE PHARMA CO., LTD., Dongguan, Guangdong (CN)

(72) Inventors: Yingjun Zhang, Dongguan (CN); Tianzhu Yu, Dongguan (CN); Bing Liu, Dongguan (CN); Xiangyu Zhang, Dongguan (CN); Shiguo Zhang, Dongguan (CN); Changchung Cheng, Dongguan (CN); Jiancun Zhang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/504,018

(22) PCT Filed: Sep. 11, 2015

(86) PCT No.: PCT/CN2015/089455
§ 371 (c)(1),
(2) Date: Feb. 15, 2017

(87) PCT Pub. No.: WO2016/037591
PCT Pub. Date: Mar. 17, 2016

(65) Prior Publication Data
US 2017/0267634 A1 Sep. 21, 2017

(30) Foreign Application Priority Data

Sep. 13, 2014 (CN) .......................... 2014 1 0465498

(51) Int. Cl.
| | | |
|---|---|---|
| *C07D 209/14* | (2006.01) | |
| *C07D 401/04* | (2006.01) | |
| *A61K 31/454* | (2006.01) | |
| *C07D 401/14* | (2006.01) | |
| *A61K 31/4709* | (2006.01) | |
| *A61K 31/405* | (2006.01) | |
| *C07D 401/12* | (2006.01) | |
| *C07D 471/04* | (2006.01) | |
| *A61K 31/4375* | (2006.01) | |
| *C07D 403/12* | (2006.01) | |
| *A61K 31/498* | (2006.01) | |
| *A61K 45/06* | (2006.01) | |

(52) U.S. Cl.
CPC .......... *C07D 209/14* (2013.01); *A61K 31/405* (2013.01); *A61K 31/4375* (2013.01); *A61K 31/454* (2013.01); *A61K 31/4709* (2013.01); *A61K 31/498* (2013.01); *A61K 45/06* (2013.01); *C07D 401/04* (2013.01); *C07D 401/12* (2013.01); *C07D 401/14* (2013.01); *C07D 403/12* (2013.01); *C07D 471/04* (2013.01); *C07B 2200/13* (2013.01)

(58) Field of Classification Search
CPC .................................................. C07D 209/14
See application file for complete search history.

(56) References Cited

U.S. PATENT DOCUMENTS

| | | |
|---|---|---|
| 7,534,897 B2 | 5/2009 | Tanimoto et al. |
| 7,842,692 B2 | 11/2010 | Kugimiya et al. |
| 7,888,383 B2 | 2/2011 | Sandham |
| 7,956,082 B2 | 6/2011 | Kugimiya et al. |
| 8,097,644 B2 | 1/2012 | Beard et al. |
| 8,143,285 B2 | 3/2012 | Kugimiya et al. |
| 8,431,703 B2 | 4/2013 | Sandham et al. |
| 9,126,984 B2 | 9/2015 | Crosignani et al. |
| 9,233,098 B2 | 1/2016 | Zhang et al. |
| 2005/0256117 A1 | 11/2005 | Chen et al. |
| 2011/0105509 A1 | 5/2011 | Kaila et al. |
| 2014/0275074 A1 | 9/2014 | Hata et al. |
| 2015/0225367 A1 | 8/2015 | Crosignani et al. |
| 2016/0229849 A1 | 8/2016 | Verner et al. |

FOREIGN PATENT DOCUMENTS

| | | |
|---|---|---|
| WO | 2010142934 A | 12/2010 |
| WO | 2015079224 A | 4/2015 |
| WO | 2015067782 A | 5/2015 |
| WO | 2015074124 A | 5/2015 |
| WO | 2015138273 A | 9/2015 |
| WO | 2015159233 A | 10/2015 |

OTHER PUBLICATIONS

Vippagunta et al. (2001).*
Banker et al. (1997).*
Wolff (1996).*
International Search Report of PCT/CN2015/089455.
Written Opinion of PCT/CN2015/089455.

* cited by examiner

*Primary Examiner* — Paul V Ward
(74) *Attorney, Agent, or Firm* — Kam W. Law; Squire Patton Boggs (US) LLP

(57) ABSTRACT

The compounds of Formula (I) which can be used as CRTH2 receptor antagonists are provided. The compounds of Formula (I) can be used in the treatment and prevention of asthma, allergic rhinitis and atopic dermatitis, as well as other diseases mediated by prostaglandin D2 (PGD2) at the CRTH2 receptor.

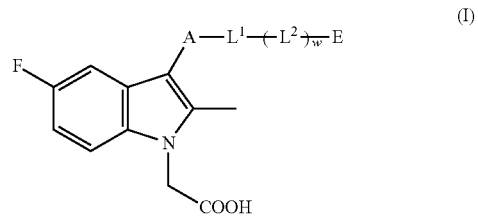

(I)

16 Claims, 19 Drawing Sheets

COMPOUNDS AS CRTH2 ANTAGONIST AND USES THEREOF

CROSS-REFERENCE TO RELATED APPLICATIONS

This is a U.S. national stage application of the International Patent Application No. PCT/CN2015/089455, filed Sep. 11, 2015, which claims priorities to Chinese Patent Application No. 201410465498.9, filed Sep. 13, 2014, both of which are incorporated herein by reference in their entirety.

FIELD OF THE INVENTION

The present invention specifically relates to the compounds or crystalline forms thereof as CRTH2 receptor antagonists, and to the use of the compounds in the treatment and prevention of asthma, allergic rhinitis and atopic dermatitis, as well as other inflammatory diseases mediated by $PGD_2$ at the CRTH2 receptor, in which the cell includes eosinophilic granulocyte, basophilic granulocyte and Th2 lymphocyte.

BACKGROUND OF THE INVENTION

CRTH2 is a G-protein-coupled chemoattractant receptor, expressed on Th2 cells and eosinophilic granulocytes. Th2-polarization has been observed in allergic diseases, such as asthma, allergic rhinitis, atopic dermatitis and allergic conjunctivitis. Th2 cells generate Th2 cells factors, such as IL-4, IL-5 and IL-3, to regulate allergic diseases. In allergic diseases, these Th2 cells factors directly or indirectly induce immigration, activation, priming and prolonged survival of effector cells, such as eosinophilic granulocytes and basophilic granulocytes.

$PGD_2$ (prostaglandin D2), a ligand for CRTH2, is produced from mast cells and other important effector cells in allergic diseases. In human cells, $PGD_2$ induces immigration and activation of Th2 cells, eosinophilic granulocytes and basophilic via CRTH2. Therefore, antagonists inhibiting the combination of CRTH2 and $PGD_2$ should be useful for the treatment of Th2-dependent allergic diseases, such as asthma, allergic rhinitis, atopic dermatitis, and allergic conjunctivitis. It is reported that antagonists of CRTH2 receptors are also useful for the treatment of other eosinophilic granulocytes-related diseases such as Churg-Strauss syndrome and nasal sinusitis.

Conventionally, as CRTH2 inhibitors, indolyl acetic acid derivatives (see WO2005/019171, incorporated herein by reference), phenoxy acetic acid derivatives (see WO2005/115382, incorporated herein by reference), pyrimidinyl acetic acid derivatives (see WO2004/096777, incorporated herein by reference), di-fused ring derivatives (see CN103373996, incorporated herein by reference), isoquinoline derivatives (WO2010/074244, incorporated herein by reference) and the like have been reported.

SUMMARY OF THE INVENTION

The present invention provides a series of indole derivatives of which N atom of indole is substituted with carboxylic acid, which are $PGD_2$ antagonists at CRTH2 receptor, and can be used in the treatment of diseases mediated by $PGD_2$ at the CRTH2 receptor. The compounds of the present invention have advantages such as better inhibitory activities, better efficacy in vivo and stability in liver microsome, and the like.

In one aspect, provided herein is a compound having Formula (I) or a stereoisomer, a geometric isomer, a tautomer, an N-oxide, a hydrate, a solvate, a metabolite, an ester, a pharmaceutically acceptable salt or a prodrug thereof,

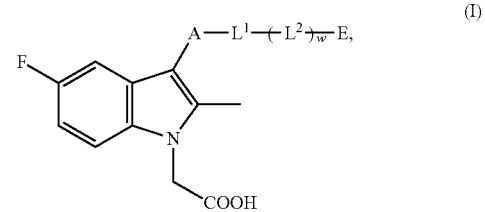

wherein

A is 6- to 9-membered heterocyclylene, 4-membered heterocyclylene, spiro heterobicyclylene, fused heterobicyclylene, bridged heterobicyclylene, spiro bicyclylene, fused bicyclylene, bridged bicyclylene, cycloalkylene, heteroarylene or arylene; A is optionally substituted with 1, 2, 3 or 4 independent $R^2$;

E is heterocyclyl, cycloalkyl, spiro heterobicyclyl, fused heterobicyclyl, bridged heterobicyclyl, aryl or heteroaryl; E is optionally substituted with 1, 2, 3 or 4 independent $R^{2c}$;

$L^1$ is —O—, —S($=$O)$_t$—, —S—, —N($R^1$)—, —CH$_2$—, —CH(OH)—, —C($=$O)O—, —N($R^1$)—C($=$O)—, —C($=$O)—(CH$_2$)$_n$—, —C($=$O)—, —OC($=$O)—, —C($=$S)—, —C($=$O)—N($R^1$)—, —C($=$S)—N($R^1$)— or —(CH$_2$)$_n$—C($=$O)—;

each $L^2$ is independently a bond, —O—, —S($=$O)$_t$—, —S—, —N($R^1$)—, —C($=$O)O—, —N($R^1$)—C($=$O)—, —C($=$O)—(CH$_2$)$_n$—, —CH$_2$—, —C($=$O)—, —OC($=$O)—, —C($=$S)—, —C($=$O)—N($R^1$)—, —C($=$S)—N($R^1$)— or —(CH$_2$)$_n$—C($=$O)—;

w is 0, 1, 2, 3 or 4;

each n is independently 0, 1, 2, 3 or 4;

each t is independently 0, 1 or 2;

each $R^{1a}$ and $R^1$ is independently H, $C_{1-4}$ alkyl, halo-$C_{1-4}$-alkyl, $C_{1-4}$alkylacyl or hydroxy;

each $R^{2c}$ and $R^2$ is independently H, $C_{1-4}$alkyl, $C_{1-4}$ haloalkyl, hydroxy, nitro, amino, cyano, halogen, carboxy, $C_{1-4}$ alkoxy, $C_{1-4}$ alkylamino, $C_{1-4}$ alkylthio, alkylacyl, $C_{3-12}$ cycloalkyl, $C_{3-9}$ heterocyclyl, $C_{6-12}$ aryl, $C_{1-9}$ heteroaryl, amino-$C_{1-4}$-alkyl, hydroxy-$C_{1-4}$-alkyl, sulfo, $R^{2b}$-L-, aminosulfonyl or aminoacyl;

each L is independently —O—, —S($=$O)$_t$—, —S—, —N($R^{1a}$)—, —CH$_2$—, —C($=$O)—, —OC($=$O)—, —C($=$S)—, —C($=$O)—N($R^{1a}$)—, —C($=$S)—N($R^{1a}$)— or —(CH$_2$)$_n$—C($=$O)—; and each $R^{2b}$ is independently H, $C_{1-4}$ alkyl, $C_{1-4}$ haloalkyl, $C_{3-9}$ cycloalkyl, $C_{3-6}$ heterocyclyl, $C_{6-12}$ aryl, $C_{1-9}$ heteroaryl, amino-$C_{1-4}$-alkyl, amino or hydroxy-$C_{1-4}$-alkyl.

In some embodiments,

A is 6- to 9-membered heterocyclylene, 4-membered heterocyclylene, $C_{5-12}$ spiro heterobicyclylene, $C_{5-12}$ fused heterobicyclylene, $C_{5-12}$ bridged heterobicyclylene, $C_{5-12}$ spiro bicyclylene, $C_{5-12}$ fused bicyclylene, $C_{5-12}$ bridged bicyclylene, $C_{3-12}$ cycloalkylene, $C_{1-9}$ heteroarylene or $C_{6-12}$ arylene;

each of 6- to 9-membered heterocyclylene, 4-membered heterocyclylene, $C_{5-12}$ spiro bicyclylene, $C_{5-12}$ fused bicyclylene, C$_{5-12}$ bridged bicyclylene, C$_{5-12}$ spiro heterobicyclylene, C$_{5-12}$ fused heterobicyclylene, C$_{5-12}$ bridged heterobicyclylene, C$_{3-12}$ cycloalkylene, C$_{1-9}$ heteroarylene and C$_{6-12}$ arylene is optionally and independently substituted with 1, 2, 3 or 4 independent R$^2$; and wherein each R$^2$ is as defined herein.

In some embodiments,

A is one of the following sub-structures:

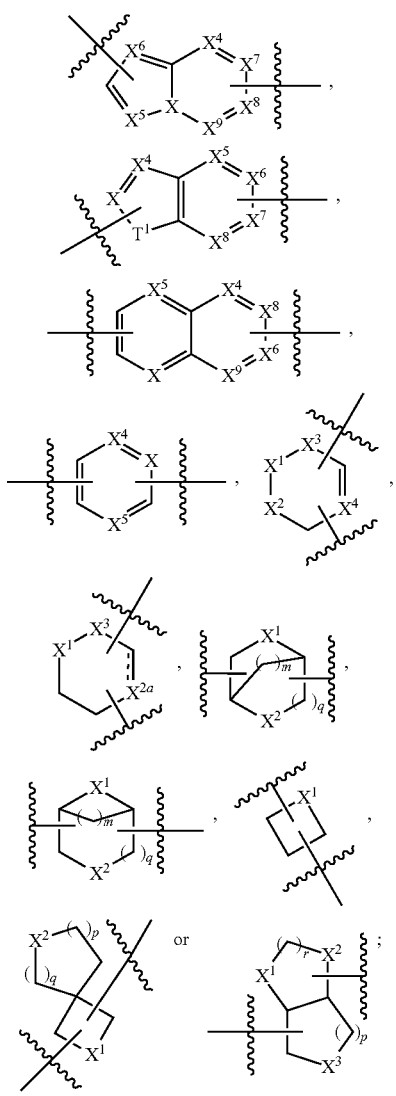

wherein when ═x═ is a single bond,

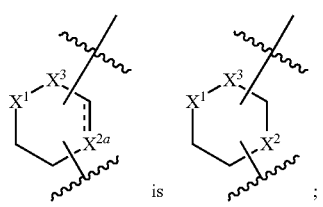

is

;

when ═x═ is a double bond,

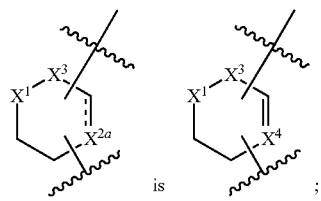

is

;

each X$^1$, X$^2$, T$^1$ and X$^3$ is independently —(CR$^3$R$^{3a}$)$_b$—, —O—, —N(R$^4$)— or —S—;

each X$^4$, X$^5$, X$^6$, X$^7$, X$^8$, X$^9$ and X is independently C(R$^3$) or N;

each b is independently 1, 2, 3 or 4;

each q, m, p and r is independently 0, 1, 2, 3, or 4;

each R$^3$ and R$^{3a}$ is independently H, C$_{1-4}$ alkyl, C$_{1-4}$ haloalkyl, hydroxy, nitro, cyano, halogen, amino, carboxy, C$_{1-4}$ alkoxy, C$_{1-4}$ alkylamino, C$_{1-4}$ alkylthio, C$_{1-4}$ alkylacyl, C$_{3-12}$ cycloalkyl, C$_{3-9}$ heterocyclyl, C$_{6-12}$ aryl, C$_{1-9}$ heteroaryl, amino-C$_{1-4}$-alkyl, hydroxy-C$_{1-4}$-alkyl, sulfo, aminosulfonyl or aminoacyl;

each R$^4$ is independently H, C$_{1-4}$ alkyl, C$_{1-4}$ haloalkyl, hydroxy, C$_{3-12}$ cycloalkyl, C$_{3-9}$ heterocyclyl, C$_{6-12}$ aryl, C$_{1-9}$ heteroaryl, amino-C$_{1-4}$-alkyl, or hydroxy-C$_{1-4}$-alkyl;

each moiety represented by A is optionally and independently substituted with 1, 2, 3 or 4 independent R$^2$; and wherein each R$^2$ is as defined herein.

In some embodiments,

A is

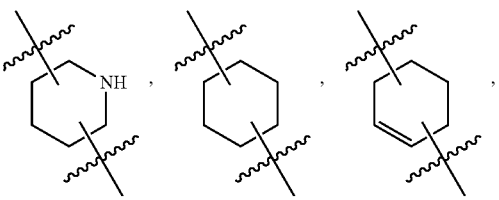

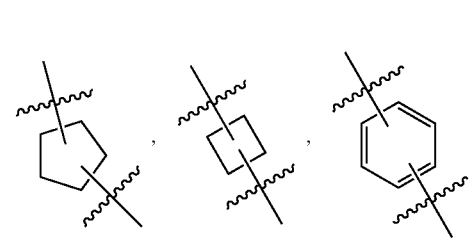

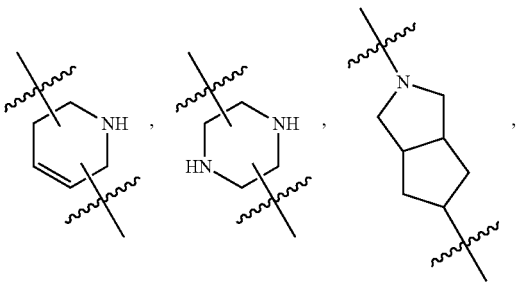

-continued

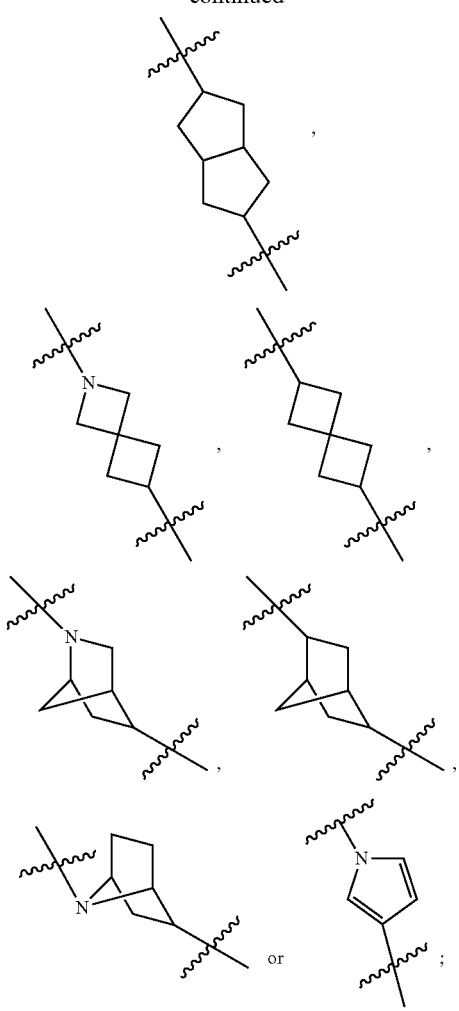

each moiety represented by A is optionally and independently substituted with 1, 2, 3 or 4 independent $R^2$; and wherein each $R^2$ is as defined herein.

In some embodiments, each $R^{3a}$ and $R^3$ is independently H, methyl, ethyl, propyl, butyl, hydroxy, nitro, cyano, F, Cl, Br, carboxy, methoxy, ethoxy, amino, trifluoromethyl, amino-$C_{1-4}$-alkyl, hydroxy-$C_{1-4}$-alkyl, sulfo, aminosulfonyl or aminoacyl; and each $R^4$ is independently H, methyl, ethyl, propyl, butyl, trifluoromethyl, hydroxy, amino-$C_{1-4}$-alkyl or hydroxy-$C_{1-4}$-alkyl.

In some embodiments,

E is $C_{1-9}$ heterocyclyl, $C_{5-12}$spiro heterobicyclyl, $C_{5-12}$fused heterobicyclyl, $C_{5-12}$bridged heterobicyclyl, $C_{3-12}$cycloalkyl, $C_{6-12}$ aryl or $C_{1-12}$ heteroaryl;

each of $C_{1-9}$ heterocyclyl, $C_{5-12}$ spiro heterobicyclyl, $C_{5-12}$ fused heterobicyclyl, $C_{5-12}$ bridged heterobicyclyl, $C_{3-12}$ cycloalkyl, $C_{6-12}$ aryl and $C_{1-12}$ heteroaryl is optionally independently substituted with 1, 2, 3 or 4 independent $R^{2c}$; and wherein each $R^{2c}$ is as defined herein.

In some embodiments,

E is one of the following monovalent groups:

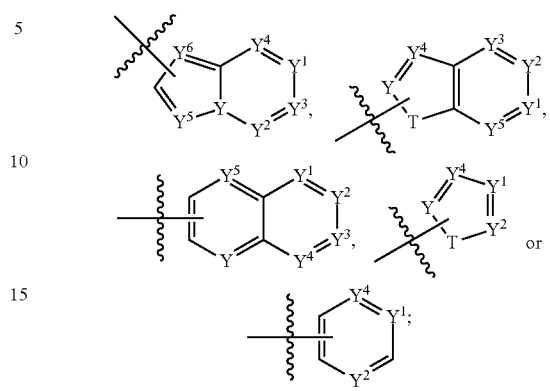

wherein each Y, $Y^1$, $Y^2$, $Y^3$, $Y^4$, $Y^5$ and $Y^6$ is independently N or CH;

each T is independently —O—, —S—, —NH— or —CH$_2$—;

each of the monovalent groups is optionally and independently substituted with 1, 2, 3 or 4 independent $R^{2c}$; and wherein each $R^{2c}$ is as defined herein.

In some embodiments, provided herein is a compound having Formula (II) or a stereoisomer, a geometric isomer, a tautomer, an N-oxide, a hydrate, a solvate, a metabolite, an ester, a pharmaceutically acceptable salt or a prodrug thereof,

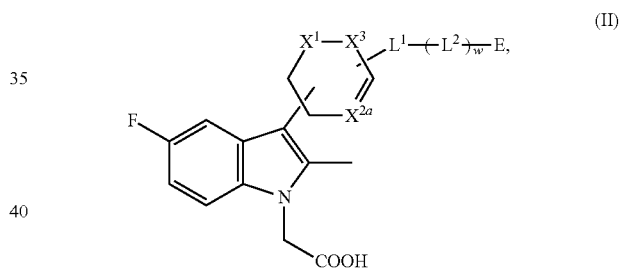

wherein when ═x═ is a single bond,

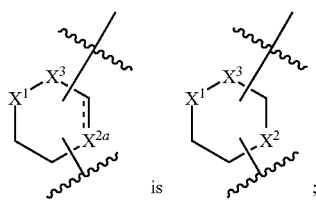

when ═x═ is a double bond,

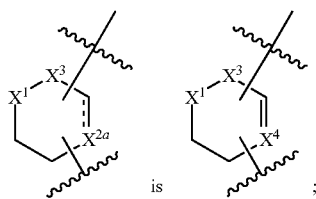

each $X^1$, $X^2$ and $X^3$ is independently —(CR$^3$R$^{3a}$)$_b$—, —O—, —N(R$^4$)— or —S—;

each $X^4$ is independently $C(R^3)$ or N;
each b is independently 1, 2, 3 or 4;
each $R^3$ and $R^{3a}$ is independently H, $C_{1-4}$ alkyl, $C_{1-4}$ haloalkyl, hydroxy, nitro, cyano, halogen, amino, carboxy, $C_{1-4}$ alkoxy, $C_{1-4}$ alkylamino, $C_{1-4}$ alkylthio, $C_{1-4}$ alkylacyl, $C_{3-12}$ cycloalkyl, $C_{3-9}$ heterocyclyl, $C_{6-12}$ aryl, $C_{1-9}$ heteroaryl, amino-$C_{1-4}$-alkyl, hydroxy-$C_{1-4}$-alkyl, sulfo, aminosulfonyl or aminoacyl;
each $R^4$ is independently H, $C_{1-4}$ alkyl, $C_{1-4}$ haloalkyl, hydroxy, $C_{3-12}$ cycloalkyl, $C_{3-9}$ heterocyclyl, $C_{6-12}$ aryl, $C_{1-9}$ heteroaryl, amino-$C_{1-4}$-alkyl or hydroxy-$C_{1-4}$-alkyl; and
wherein w, E, $L^1$, $L^2$ and t are as defined herein.

In some embodiments, provided herein is a compound having Formula (IIa) or a stereoisomer, a geometric isomer, a tautomer, an N-oxide, a hydrate, a solvate, a metabolite, an ester, a pharmaceutically acceptable salt or a prodrug thereof,

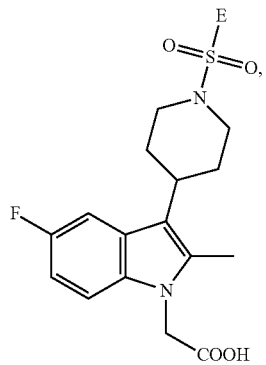
(IIa)

wherein E is as defined herein.
In some embodiments, E is one of the following aryl and heteroaryl groups:

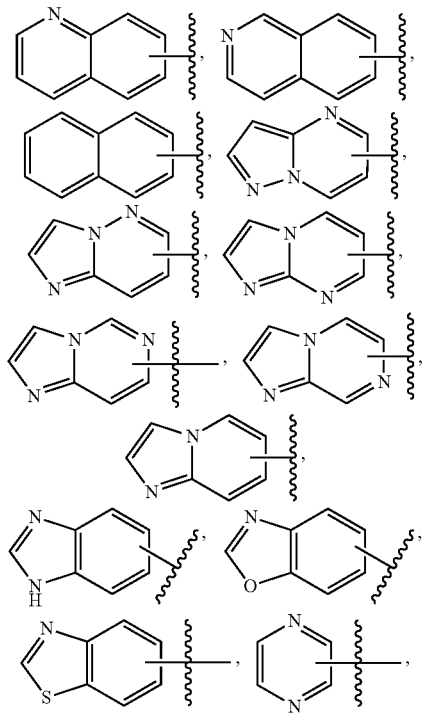

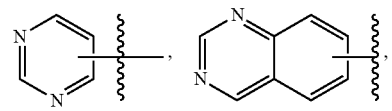

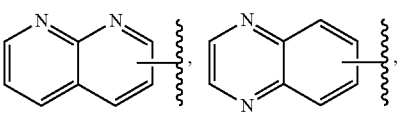

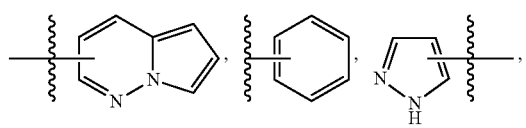

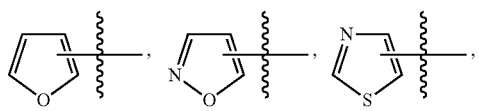

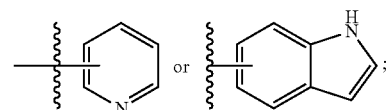

each moiety represented by E is optionally substituted with 1, 2, 3 or 4 independent $R^{2c}$; and
wherein $R^{2c}$ is as defined herein.

In some embodiments, each $R^{2c}$ and $R^2$ is independently H, methyl, ethyl, n-propyl, isopropyl, t-butyl, n-butyl, trifluoromethyl, hydroxy, nitro, amino, cyano, F, Cl, Br, carboxy, methoxy, ethoxy, isopropoxy, methylamino, ethylamino, dimethylamino, methylacyl, aminomethyl, hydroxymethyl, sulfo, $R^{2b}$-L-, aminosulfonyl or aminoacyl;

each $R^{2b}$ is independently H, methyl, ethyl, n-propyl, isopropyl, n-butyl, trifluoromethyl, cyclopentyl, cyclohexyl, cyclobutyl, morpholinyl, piperidyl, pyrrolyl, hydroxymethyl or amino; and
wherein L is as defined herein.

In some embodiments, wherein the pharmaceutically acceptable salt is an inorganic acid salt, organic acid salt, inorganic base salt, alkali metal salt or organic base salt.

In other embodiments, wherein the pharmaceutically acceptable salt is hydrochloride, hydrobromide, hydriodate, nitrate, sulfate, disulfate, phosphate, acetate, propionate, butyrate, lactate, mesylate, tosilate, maleate, benzoate, succinate, tartrate, citrate, oxalate, fumarate, taurinate, sodium salt, potassium salt or ammonium salt.

In one aspect, provided herein is a crystalline form of 2-(5-fluoro-3-(1-((4-fluorophenyl)sulfonyl)piperidin-4-yl)-2-methyl-1H-indol-1-yl)acetic acid (Formula VI), wherein the crystalline form is crystalline form I, crystalline form II, crystalline form III, crystalline form IV, crystalline form V or crystalline form VI,

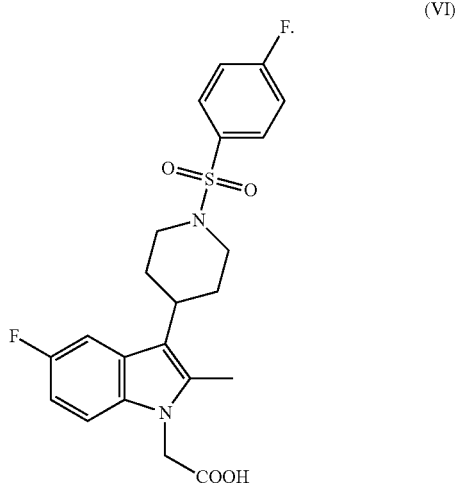 [SMILES: Cc1c(C2CCN(S(=O)(=O)c3ccc(F)cc3)CC2)c2cc(F)ccc2n1CC(=O)O]

(VI)

In some embodiments, the crystalline form I of 2-(5-fluoro-3-(1-((4-fluorophenyl)sulfonyl)piperidin-4-yl)-2-methyl-1H-indol-1-yl)acetic acid (Formula VI) has an X-ray powder diffraction (XRPD) pattern comprising peaks expressed in degrees 2θ at 3.80°, 13.20°, 15.46°, 17.24°, 18.90°, 19.27°, 19.57°, 23.84° and 28.39°, wherein the error margin is ±0.2°.

In some embodiments, the crystalline form I has an X-ray powder diffraction (XRPD) pattern comprising peaks expressed in degrees 2θ at 3.80°, 8.56°, 12.77°, 13.20°, 15.46°, 17.24°, 18.90°, 19.27°, 19.57°, 22.98°, 23.84°, 26.18°, 27.54°, 28.39°, 29.87°, 30.57° and 30.98°, wherein the error margin is ±0.2°.

In some embodiments, the crystalline form I has an X-ray powder diffraction (XRPD) pattern comprising peaks expressed in degrees 2θ at 3.80°, 7.69°, 8.56°, 9.72°, 10.57°, 12.77°, 13.20°, 13.66°, 14.05°, 15.46°, 15.80°, 16.09°, 16.87°, 17.24°, 17.79°, 18.16°, 18.53°, 18.90°, 19.27°, 19.57°, 20.19°, 20.69°, 20.91°, 21.84°, 22.62°, 22.98°, 23.31°, 23.84°, 24.47°, 25.51°, 25.75°, 26.18°, 26.65°, 27.54°, 28.11°, 28.39°, 28.68°, 28.99°, 29.27°, 29.56°, 29.87°, 30.57°, 30.98°, 31.25°, 32.14°, 32.69°, 32.90°, 33.72°, 34.23° and 34.76°, wherein the error margin is ±0.2°.

In some embodiments, the crystalline form I has an X-ray powder diffraction (XRPD) pattern substantially the same as shown in FIG. 1.

In some embodiments, the crystalline form I has a differential scanning calorimetry thermogram comprising endothermic peaks at 123.99° C.±3° C. and 217.23° C.±3° C.

In some embodiments, the crystalline form I has a differential scanning calorimetry thermogram substantially the same as shown in FIG. 2.

In some embodiments, the crystalline form I has a weight loss ratio of 3.991% in thermogravimetric analysis, showing the crystalline form I is 2-(5-fluoro-3-(1-((4-fluorophenyl)sulfonyl)piperidin-4-yl)-2-methyl-1H-indol-1-yl)acetic acid monohydrate.

In some embodiments, the crystalline form II of 2-(5-fluoro-3-(1-((4-fluorophenyl)sulfonyl)piperidin-4-yl)-2-methyl-1H-indol-1-yl)acetic acid (Formula VI) has an X-ray powder diffraction (XRPD) pattern comprising peaks expressed in degrees 2θ at 5.96°, 12.09°, 13.17°, 14.14°, 15.96°, 16.85°, 17.97°, 20.77°, 24.07°, 24.64° and 28.99°, wherein the error margin is ±0.2°.

In some embodiments, the crystalline form II has an X-ray powder diffraction (XRPD) pattern comprising peaks expressed in degrees 2θ at 5.96°, 12.09°, 13.17°, 14.14°, 15.96°, 16.85°, 17.97°, 18.41°, 20.77°, 22.84°, 24.07°, 24.64°, 25.81°, 28.99° and 29.77°, wherein the error margin is ±0.2°.

In some embodiments, the crystalline form II has an X-ray powder diffraction (XRPD) pattern comprising peaks expressed in degrees 2θ at 5.96°, 7.94°, 10.52°, 10.95°, 12.09°, 13.17°, 14.14°, 14.79°, 15.96°, 16.85°, 17.68°, 17.97°, 18.41°, 19.28°, 19.96°, 20.63°, 20.77°, 21.20°, 22.02°, 22.84°, 23.28°, 24.07°, 24.64°, 24.99°, 25.81°, 26.43°, 26.69°, 26.98°, 27.41°, 27.93°, 28.48°, 28.99°, 29.77°, 30.95°, 31.74°, 32.21°, 33.17°, 34.14°, 34.53°, 35.24°, 36.30°, 37.19°, 38.61° and 39.57°, wherein the error margin is ±0.2°.

In some embodiments, the crystalline form II has an X-ray powder diffraction (XRPD) pattern substantially the same as shown in FIG. 4.

In some embodiments, the crystalline form II has a differential scanning calorimetry thermogram comprising endothermic peaks at 142.11° C.±3° C. and 215.90° C.±3° C.

In some embodiments, the crystalline form II has a differential scanning calorimetry thermogram substantially the same as shown in FIG. 5.

In some embodiments, the crystalline form III of 2-(5-fluoro-3-(1-((4-fluorophenyl)sulfonyl)piperidin-4-yl)-2-methyl-1H-indol-1-yl)acetic acid (Formula VI) has an X-ray powder diffraction (XRPD) pattern comprising peaks expressed in degrees 2θ at 15.67°, 16.20°, 18.28°, 20.02°, 20.89°, 23.28° and 24.62°, wherein the error margin is ±0.2°.

In some embodiments, the crystalline form III has an X-ray powder diffraction (XRPD) pattern comprising peaks expressed in degrees 2θ at 13.33°, 15.67°, 16.20°, 17.44°, 18.28°, 20.02°, 20.89°, 23.28°, 24.62° and 26.95°, wherein the error margin is ±0.2°.

In some embodiments, the crystalline form III has an X-ray powder diffraction (XRPD) pattern comprising peaks expressed in degrees 2θ at 5.77°, 7.79°, 10.51°, 12.00°, 12.76°, 13.33°, 13.94°, 15.67°, 16.20°, 16.85°, 17.44°, 18.28°, 19.06°, 19.65°, 20.02°, 20.89°, 21.16°, 22.79°, 23.07°, 23.28°, 23.92°, 24.62°, 25.31°, 26.39°, 26.95°, 27.26°, 27.55°, 28.14°, 29.23°, 29.82°, 30.85°, 31.66°, 32.04°, 33.45°, 34.10°, 35.13°, 35.64°, 36.51°, 37.19° and 37.97°, wherein the error margin is ±0.2°.

In some embodiments, the crystalline form III has an X-ray powder diffraction (XRPD) pattern substantially the same as shown in FIG. 7.

In some embodiments, the crystalline form III has a differential scanning calorimetry thermogram comprising an endothermic peak at 152.50° C.±3° C.

In some embodiments, the crystalline form III has a differential scanning calorimetry thermogram substantially the same as shown in FIG. 8.

In some embodiments, the crystalline form IV of 2-(5-fluoro-3-(1-((4-fluorophenyl)sulfonyl)piperidin-4-yl)-2-methyl-1H-indol-1-yl)acetic acid (Formula VI) has an X-ray powder diffraction (XRPD) pattern comprising peaks expressed in degrees 2θ at 16.09°, 18.19°, 20.57°, 20.98°, 24.11°, 24.82° and 25.93°, wherein the error margin is ±0.2°.

In some embodiments, the crystalline form IV has an X-ray powder diffraction (XRPD) pattern comprising peaks expressed in degrees 2θ at 13.24°, 16.09°, 16.83°, 18.19°, 20.57°, 20.98°, 24.11°, 24.82°, 25.93°, 26.30° and 28.46°, wherein the error margin is ±0.2°.

In some embodiments, the crystalline form IV has an X-ray powder diffraction (XRPD) pattern comprising peaks expressed in degrees 2θ at 6.11°, 8.05°, 10.54°, 10.87°, 12.16°, 13.24°, 14.13°, 15.12°, 16.09°, 16.83°, 17.42°, 18.19°, 18.93°, 19.72°, 19.98°, 20.57°, 20.98°, 21.76°, 23.10°, 23.68°, 24.11°, 24.43°, 24.82°, 25.93°, 26.30°, 26.60°, 26.85°, 27.27°, 27.52°, 27.96°, 28.46°, 29.01°, 29.29°, 30.04°, 30.94°, 31.69°, 32.43°, 33.12°, 34.18°, 34.72°, 35.49°, 35.89°, 36.37°, 36.99°, 37.41°, 37.97° and 38.70°, wherein the error margin is ±0.2°.

In some embodiments, the crystalline form IV has an X-ray powder diffraction (XRPD) pattern substantially the same as shown in FIG. 10.

In some embodiments, the crystalline form IV has a differential scanning calorimetry thermogram comprising an endothermic peak at 185.0° C.±3° C.

In some embodiments, the crystalline form IV has a differential scanning calorimetry thermogram substantially the same as shown in FIG. 11.

In some embodiments, the crystalline form V of 2-(5-fluoro-3-(1-((4-fluorophenyl)sulfonyl)piperidin-4-yl)-2-methyl-1H-indol-1-yl)acetic acid (Formula VI) has an X-ray powder diffraction (XRPD) pattern comprising peaks expressed in degrees 2θ at 5.88°, 12.86°, 15.68°, 17.69°, 20.50°, 23.60° and 24.17°, wherein the error margin is ±0.2°.

In some embodiments, the crystalline form V has an X-ray powder diffraction (XRPD) pattern comprising peaks expressed in degrees 2θ at 5.88°, 11.91°, 12.86°, 15.68°, 17.69°, 20.17°, 20.50°, 23.60°, 24.17° and 25.31°, wherein the error margin is ±0.2°.

In some embodiments, the crystalline form V has an X-ray powder diffraction (XRPD) pattern comprising peaks expressed in degrees 2θ at 5.88°, 7.83°, 10.51°, 11.91°, 12.86°, 13.81°, 15.68°, 16.49°, 17.26°, 17.69°, 18.15°, 19.52°, 20.17°, 20.50°, 20.79°, 22.39°, 22.81°, 23.60°, 24.17°, 24.49°, 25.31°, 25.88°, 26.82°, 27.40°, 27.83°, 28.28°, 28.70°, 29.19°, 30.18°, 30.60°, 30.97°, 31.58°, 32.36°, 33.69°, 34.42°, 35.03°, 36.52° and 37.29°, wherein the error margin is ±0.2°.

In some embodiments, the crystalline form V has an X-ray powder diffraction (XRPD) pattern substantially the same as shown in FIG. 13.

In some embodiments, the crystalline form V has a differential scanning calorimetry thermogram comprising endothermic peaks at 159.91° C.±3° C. and 216.52° C.±3° C.

In some embodiments, the crystalline form V has a differential scanning calorimetry thermogram substantially the same as shown in FIG. 14.

In some embodiments, the crystalline form VI of 2-(5-fluoro-3-(1-((4-fluorophenyl)sulfonyl)piperidin-4-yl)-2-methyl-1H-indol-1-yl)acetic acid (Formula VI) has an X-ray powder diffraction (XRPD) pattern comprising peaks expressed in degrees 2θ at 5.84°, 12.83°, 13.20°, 15.72°, 17.63°, 23.62° and 28.94°, wherein the error margin is ±0.2°.

In some embodiments, the crystalline form VI has an X-ray powder diffraction (XRPD) pattern comprising peaks expressed in degrees 2θ at 5.84°, 11.96°, 12.83°, 13.20°, 15.72°, 17.63°, 23.62°, 24.20°, 24.46° and 28.94°, wherein the error margin is ±0.2°.

In some embodiments, the crystalline form VI has an X-ray powder diffraction (XRPD) pattern comprising peaks expressed in degrees 2θ at 5.84°, 7.83°, 11.96°, 12.83°, 13.20°, 13.76°, 15.72°, 16.49°, 17.63°, 18.30°, 18.87°, 19.55°, 20.43°, 20.74°, 20.98°, 22.67°, 23.03°, 23.62°, 24.20°, 24.46°, 25.18°, 25.88°, 26.62°, 27.17°, 27.47°, 27.84°, 28.36°, 28.94°, 30.12°, 30.41°, 30.79°, 31.52°, 31.80°, 32.70°, 34.33°, 36.11° and 36.62°, wherein the error margin is ±0.2°.

In some embodiments, the crystalline form VI has an X-ray powder diffraction (XRPD) pattern substantially the same as shown in FIG. 16.

In some embodiments, the crystalline form VI has a differential scanning calorimetry thermogram comprising endothermic peaks at 153.83° C.±3° C. and 216.70° C.±3° C.

In some embodiments, the crystalline form VI has a differential scanning calorimetry thermogram substantially the same as shown in FIG. 17.

In other aspect, provided herein is a pharmaceutical composition comprising the compound or a crystalline form thereof disclosed herein.

In some embodiments, the pharmaceutical composition disclosed herein further comprises at least one of pharmaceutically acceptable carriers, excipients, diluents, adjuvants and vehicles.

In some embodiments, the pharmaceutical composition further comprises one or more other active agents used in the treatment of a disease or condition mediated by PGD$_2$ at the CRTH2 receptor.

In some embodiments of the pharmaceutical composition, wherein the other active agent is a TNF-α inhibitor, a COX-1/COX-2 inhibitor, a COX-2 inhibitor, a glucocorticoid, an inactivated antibody for interleukin, a regulator for chemotactic factor receptors, an antagonist for histamine H1 receptor/antihistamine, a leukotriene D4 receptor antagonists, an LTD4 antagonist, a VLA-4 antagonist, a corticosteroids analogue, theophylline, a leukotriene biosynthetic inhibitor, an epoxidase-2 inhibitor, an opioids analgesic, an anticoagulant, a β-blocking agent, a β-adrenergic agonist, an angiotensin converting enzyme inhibitor, an HMG-CoA reductase inhibitor, a β2-agonist, a corticosteroid, an antihistamine, a leukotriene antagonist, an anti-IgE antibody therapy, an anti-infectious agent, an antifungal agent, immunosuppressor, an antagonist of PGD2 acting at other receptors, an inhibitor of phosphodiesterase type 4, a drug that modulates cytokine production, a drug that modulates the activity of Th2 cytokines IL-4 and IL-5 or a 5-lipoxygenase inhibitor.

In some embodiments of the pharmaceutical composition, wherein the other active agent is salmeterol, fluticasone, loratadine, montelukast, omalizumab, fusidic acid, clotrimazole, tacrolimus, pimecrolimus, DP antagonist, cilomilast, TNF-α converting enzyme (TACE)inhibitor, blocking monoclonal antibody or soluble receptor of IL-4 and IL-5 orzileuton.

In other aspect, provided herein is a use of the compound or a crystalline form thereof, or the pharmaceutical composition disclosed herein in the manufacture of a medicament for preventing, managing, treating or lessening diseases mediated by PGD$_2$ at the CRTH2 receptor.

In some embodiments of the use, wherein the disease mediated by PGD2 at the CRTH2 receptor is asthma, COPD, allergic asthma, perennial allergic rhinitis, seasonal allergic rhinitis, atopic dermatitis, contact hypersensitivity, conjunctivitis, eosinophilic bronchitis, food allergies, eosinophilic gastroenteritis, inflammatory bowel disease, ulcerative colitis and Crohn's disease, mastocytosis, autoimmune disease, acne, reperfusion injury or chronic obstructive pulmonary disease.

In some embodiments of the use, wherein the autoimmune disease is psoriasis, multiple sclerosis, allograft rejection, rheumatoid arthritis, psoriatic arthritis, systemic lupus erythematosus or osteoarthritis.

In other aspect, provided herein is a drug combination comprising the compound or a crystalline form thereof, and one or more pharmaceutical compositions disclosed herein for use in preventing, managing, treating or lessening diseases mediated by $PGD_2$ at the CRTH2 receptor simultaneously, respectively or successively.

In one aspect, the invention provides a method of preventing, managing, treating or lessening a disease or condition mediated by $PGD_2$ at the CRTH2 receptor in a patient comprising administrating to the patient a therapeutically effective amount of the compound or a crystalline form thereof, or the pharmaceutical composition disclosed herein.

In other aspect, provided herein is the compound or a crystalline form thereof, or the pharmaceutical composition disclosed herein used for preventing, managing, treating or lessening diseases mediated by $PGD_2$ at the CRTH2 receptor.

Also provided herein is the use of a compound of Formula (I) in the preparation of an agent for the treatment of a disease and condition mediated by $PGD_2$ at the CRTH2 receptor, wherein the agent also comprises an additional active agent useful for the treatment of the same diseases and conditions.

In a further aspect of the invention, there is provided a product comprising a novel compound of Formula (I) and one or more of the agents listed above as a combined preparation for simultaneous, separate or sequential use in the treatment of a disease or condition mediated by the action of $PGD_2$ at the CRTH2 receptor.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito:1999, and Smith et al., "March's Advanced Organic Chemistry", John Wiley & Sons, New York:2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

The term "comprise" is an open expression, it means comprising the contents disclosed herein, but don't exclude other contents.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization. Cis- and trans-isomers are diastereoisomers of each other.

The forming conditions of "cis-trans-isomer" comprise some factors (such as double bond (oximes, azos, alkenes) and cycle (alicyclic cycle)) limiting free rotation of a carbon atom existing in a molecule; and every atom which cannot rotate freely connecting with two different atoms or atom groups. Cis-trans isomerism forms two different isomers from each other, which are cis-isomer and trans-isomer respectively. The carbon ring atom on alicyclic cycle cannot rotate freely, when at least two carbon ring on the cycle respectively connect with two different atoms or atom groups, cis-trans isomerism can occur. On a cyclic compound, if two smaller substituents locate on the ipsolateral side of the cycle, the cyclic compound is cis form; if two smaller substituents locate on the different sides of the cycle respectively, the cyclic compound is trans form. Although cis-trans isomers have same functional groups, they have different physical properties (such as melting point, boiling point and dipole moment), chemical properties and biological activities. Unless otherwise stated, all cis-trans isomers forms of the compounds disclosed herein are within the scope of the invention.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); Principles of Asymmetric Synthesis (2nd Ed. Robert E. Gawley, Jeffrey Aubé, Elsevier, Oxford, UK, 2012); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972); Chiral Separation Techniques: A Practical Approach (Subramanian, G. Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Substitutions contemplated herein include only those substitutions that form stable compounds. In some embodiments, a suitable optional substituent 1 can be substituted with a corresponding and suitable optional substituent 2. In other embodiments, the corresponding and suitable optional substituent 2 is unsubstituted in general. Wherein the substituent may be but not limited to H, alkyl, haloalkyl, hydroxy, nitro, cyano, halogen, carboxy, alkoxy, alkylamino, alkylthio, alkylacyl, cycloalkyl, heterocyclyl, aryl, heteroaryl, aminoalkyl, amino, hydroxyalkyl, sulfo, aminosulfonyl or aminoacyl.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon group of 1-20 carbon atoms, wherein the alkyl group is optionally substituted with one or more substituents described herein. Unless otherwise stated, the alkyl group contains 1-20 carbon atoms. In some embodiments, the alkyl group contains 1-12 carbon atoms. In other embodiments, the alkyl group contains 1-6 carbon atoms. In other embodiments, the alkyl group contains 1-4 carbon atoms. In still other embodiments, the alkyl group contains 1-3 carbon atoms. In yet other embodiments, the alkyl group contains 2-4 carbon atoms. Further embodiments of the alkyl group include, but are not limited to, methyl, ethyl, n-propyl, isopropyl, n-butyl, isobutyl, sec-butyl, tert-butyl, n-pentyl, 2-pentyl, 3-pentyl, 2-methyl-2-butyl, 3-methyl-2-butyl, 3-methyl-1-butyl, 2-methyl-1-butyl, n-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-heptyl, n-octyl, and the like.

The term "halogen", "halogen atom" or "halo" used herein comprises fluorine (F), chlorine (Cl), bromine (Br), iodine (I).

The term "alkoxy" refers to an alkyl group, as defined herein, attached to the principal carbon chain through an oxygen atom. In some embodiments, the alkoxy group is lower $C_{1-3}$ alkoxy. Some non-limiting examples of the alkoxy group include methoxy, ethoxy, propoxy, and the like.

The term "haloalkyl" or "haloalkoxy" refers to an alkyl group or alkoxy group substituted with one or more identical or different halogen atoms, wherein the alkyl group and alkoxy group are as defined herein. Some non-limiting examples of the haloalkyl group and haloalkoxy group include trifluoromethyl, trifluoromethoxy, and the like.

The term "alkylthio" refers to a linear or branched $C_{1-10}$ alkyl chain binding to a bivalent sulphur atom, wherein the alkyl group is as defined herein. In some embodiments, the alkylthio group is lower $C_{1-3}$ alkylthio. Some non-limiting examples of such groups include methylthio ($CH_3S$—), ethylthio, and the like.

The term "alkylacyl" refers to a linear or branched chain alkyl containing 1 to 10 carbon atoms attached to —C(=O)—, wherein the alkyl group is as defined herein. In some embodiments, the alkylacyl group is lower $C_{1-3}$ alkylacyl. Some non-limiting examples of the alkylacyl group include acetyl, propionyl, and the like.

The term "aminoacyl" refers to —C(=O)$NH_2$.

The term "aminosulfonyl" refers to —S(=O)$_2NH_2$.

The term "amino" refers to —$NH_2$.

The term "aminoalkyl" refers to a group having Formula R'R"N—, wherein each of R' and R" is independently H, alkyl or haloalkyl. The alkyl is as defined herein. In some embodiments, the aminoalkyl group is lower $C_{1-4}$ aminoalkyl. Some non-limiting examples of the aminoalkyl include aminoethyl, aminomethyl, aminopropyl, and the like.

The term "alkylamino" refers to "N-alkylamino" and "N,N-dialkylamino", wherein the amino groups are independently substituted with one or two alkyl groups, respectively, and wherein the alkyl group is as defined herein. In some embodiments, the alkylamino group is lower alkylamino group having one or two $C_{1-6}$alkyl groups attached to nitrogen atom. In other embodiments, the alkylamino group is $C_{1-3}$lower alkylamino group. Some non-limiting examples of the alkylamino group include monoalkylamino or dialkylamino, such as N-methylamino, N-ethylamino, N,N-dimethylamino, N,N-diethylamino, and the like.

The term "hydroxyalkyl" or "hydroxyalkoxy" refers to an alkyl group or alkoxy group substituted with one or more hydroxy groups respectively, wherein the alkyl group and alkoxy group are as defined herein. Some non-limiting examples of such groups include hydroxymethyl, 1-hydroxyethyl, 1-hydroxypropyl, 1,2-dihydroxypropyl, hydroxymethoxy, 1-hydroxyethoxy, and the like.

The term "aryl" used alone or as part of a larger moiety as in "arylalkyl", "arylalkoxy" or "aryloxyalkyl" refers to monocyclic, bicyclic and tricyclic carbocyclic ring systems, in some embodiments of the invention, which can be replaced by or used as a arylene group. Wherein at least one ring in the system is aromatic, and wherein each ring in the system contains 3 to 7 ring members. The term "aryl" may be used interchangeably with the term "aryl ring" or "aromatic ring". Some non-limiting examples of the aryl group include phenyl, naphthyl and anthracene. Depending on the structure, the aryl group can be a monoradical or a diradical such as an arylene group. "Arylene" refers to a bivalent group in which at least one ring is aromatic, and wherein each ring in the system contains 3 to 7 ring members, some examples are phenylene, naphthylene, and the like. One or more hydrogen atoms on the cycle are each optionally independently substituted with one or more substituents described herein.

The term "heteroaryl" or "heteroaryl ring" as used interchangeably herein, used alone or as part of a larger moiety as in "heteroarylalkyl" or "heteroarylalkoxy," in some embodiments, replaced by or used as a heteroarylene group, refers to a monocyclic, bicyclic, tricyclic or tetracyclic ring system, wherein the bicyclic heteroaryl, tricyclic heteroaryl or tetracyclic heteroaryl ring system is formed by fusing, and at least one cycle in the ring system is aromaticity. Wherein, one or more ring atoms can be replaced independently and optionally by heteroatom selected from N, O, P, S. The heteroaryl system may be attached to the main structure at any heteroatom or carbon atom which results in the creation of a stable compound. The heteroaryl system group may be 3-7 membered monocyclic ring, 7-10 membered bicyclic ring or 10-15 membered tricyclic ring. Bicyclic heteroaryl ring having 7-10 ring atoms can be arranged as a bicyclo[4,5], [5,5], [5,6] or [6,6] system, and tricyclic heteroaryl ring having 10 or 15 ring atoms can be arranged as a tricyclo[5,5,6], [5,6,6] or [6,5,6] system. "Heteroarylene" is a divalent heteroaryl group. One or more hydrogen atoms on the cycle are each optionally independently substituted with one or more substituents described herein.

Some non-limiting examples of the heteroaryl system (including heteroaryl, heteroaryl ring) include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 4-methylisoxazol-5-yl, N-pyrrolyl, 2-pyrrolyl, 3-pyrrolyl, 2-pyridyl, 3-pyridyl, 4-pyridyl, 2-pyrimidinyl, 4-pyrimidinyl, pyrimidin-5-yl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, 1,3,4-thiadiazol-2-yl, pyrazinyl, pyrazin-2-yl, 1,3,5-triazinyl, benzo[d]thiazol-2-yl, imidazo[1,5-a]pyridin-6-yl, benzimidazolyl, benzoxazolyl, quinoxalinyl, 1,8-naphthyridinyl, benzofuryl, benzothienyl, benzothiazolyl, indolyl (e.g., 2-indolyl), purinyl, quinolinyl (e.g., 2-quinolinyl, 3-quinolinyl and 4-quinolinyl), isoquinolinyl (e.g., 1-isoquinolinyl, 3-isoquinolinyl or 4-isoquinolinyl), tetrahydronaphthyl, benzopyrazolyl, acridinyl, benzimidazolyl, benzindolyl, benzisoxazinyl, benzo[4,6]imidazo[1,2-a]pyridinyl, benzo[d]imidazo[2,1-b]thiazolyl, benzofuryl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, cinnolinyl, dibenzofuryl, imidazopyridyl, imidazothiazolyl, indazolyl, indolizinyl, indolyl, isobenzothianthrenyl, isoindolinyl, isoquinolinyl, isothiazolidinyl, isothiazolyl, naphthyridinyl, oxazolopyridinyl, oxazolyl, perimidinyl, phenanthridinyl, phenanthrolinyl, phenarsazinyl, phenazinyl, phenothiazinyl, phenoxazinyl, phthalazinyl, pteridinyl, pyridopyridyl, quinazolinyl, quinoxalinyl, thiophenyl, triazinyl, 2H-pyrrolo[3,4-c]pyridinyl, pyrazolo[2',1': 2,3]oxazolo[4,5-c]pyridinyl, imidazo[2',1':2,3]thiazolo[4,5-c]pyridinyl, imidazo[2',1':2,3]thiazolo[4,5-b]pyridinyl, imidazo[2',1':2,3]thiazolo[5,4-b]pyridinyl, pyrazolo[2',1':2,3]thiazolo[4,5-b]pyrazinyl, 1H-benzo[4,5]thieno[2,3-d]imidazolyl, imidazo[2',1': 2,3]thiazolo[4,5-b]pyrazinyl, imidazo[2',1':2,3]thiazolo[5,4-b]pyridyl, imidazo[2',1':2,3]thiazolo[4,5-c]pyridyl, and the like.

The term "carbocyclyl", "cycloaliphatic", "carbocycle" or "cycloalkyl" as used interchangeably herein refers to a monovalent or multivalent, non-aromatic, saturated or partially unsaturated ring consisting solely of carbon and hydrogen atoms and including 3-12 carbon atoms as a monocyclic ring or 7-12 carbon atoms as a bicyclic ring or tricyclic ring, and the ring system do not contain one aromatic ring (but an aromatic ring can be a substituent of it). Bicyclic carbocycles having 7-12 ring atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system. Depending on the structure, the carbocyclyl, cycloaliphatic, carbocycle or cycloalkyl group can be a monoradical or a diradical, i.e., in some embodiments, the carbocyclyl, cycloaliphatic, carbocycle or cycloalkyl group can be replaced by or used as carbocyclylene or cycloalkylene. Some non-limiting examples of the cycloaliphatic group include cycloalkyl, cycloalkenyl and cycloalkynyl. Further examples of the cycloaliphatic group include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantyl, and the like. One or more hydrogen atoms on the cycle are each optionally independently substituted with one or more substituents described herein.

The term "cycloalkylene" refers to a divalent, non-aromatic, saturated or partially unsaturated ring consisting solely of carbon and hydrogen atoms and including 3-12 carbon atoms as a monocyclic ring or 7-12 carbon atoms as a bicyclic ring or tricyclic ring, and the ring system do not contain one aromatic ring (but an aromatic ring can be a substituent of it). Bicyclic carbocycles can be arranged as a bicyclo[4,5], [5,5], [5,6] or [6,6] system. In some embodiments, the cycloalkylene group is a saturated or partially unsaturated monocyclic ring having 4 to 6 carbon atoms; in other embodiments, the cycloalkylene group is a saturated monocyclic ring having 6 carbon atoms or a monocyclic ring having one degree of unsaturation. Some non-limiting examples include cyclopropylene, cyclobutylene, cyclopentylene, 1-cyclopent-1-enylene, 1-cyclopent-2-enylene, 1-cyclopent-3-enylene, cyclohexylene, 1-cyclohex-1-enylene, 1-cyclohex-2-enylene, 1-cyclohex-3-enylene, cyclohexadienylene, cycloheptylene, cyclooctylene, cyclononylene, cyclodecylene, cycloundecylene, cyclododecylene, adamantylene, and the like. One or more hydrogen atoms on the cycle are each optionally independently substituted with one or more substituents described herein.

The term "heterocyclyl", "heterocycle", "heterocycloaliphatic" or "heterocyclic" as used interchangeably herein refers to a monocyclic ring system in which one or more ring members are independently selected from heteroatoms and that is completely saturated or that contains one or more units of unsaturation, but which is not aromatic, and the ring system do not contain one aromatic ring (but an aromatic ring can be a substituent of it). Depending on the structure, the heterocyclyl, heterocycle, heterocycloaliphatic or heterocyclic group can be a monoradical or a diradical, i.e., in some embodiments, the heterocyclyl, heterocycle, heterocycloaliphatic or heterocyclic group can be replaced by or used as heterocyclylene. The heterocyclyl system may be attached to the main structure at any heteroatom or carbon atom which results in the creation of a stable compound. One or more hydrogen atoms on the cycle are each optionally independently substituted with one or more substituents described herein. In some embodiments, the "heterocyclyl", "heterocycle", "heterocyclylene", "heterocycloaliphatic" or "heterocyclic" group is a monocyclic ring having 3-7 ring members (e.g., 1 to 6 carbon atoms and 1 to 3 heteroatoms selected from N, O, P and S; when the ring is a 3-membered ring, wherein only one ring atom is herteroatom).

The heterocyclyl may be a carbon radical or heteroatom radical. The heterocyclyl group also includes a group in which the heterocyclyl group is fused with a saturated or partially unsaturated ring or a heterocyclic ring. Some non-limiting examples of the heterocyclyl group include 1,2,3,6-tetrahydropyridinyl, piperidyl, piperazinyl, pyrrolidinyl, tetrahydrofuranyl, dihydrofuranyl, tetrahydrothienyl, tetrahydropyranyl, dihydropyranyl, tetrahydrothiopyranyl, azetidinyl, oxetanyl, thietanyl, homopiperidinyl, epoxypropyl, azepanyl, oxepanyl, thiepanyl, N-morpholinyl, 2-morpholinyl, 3-morpholinyl, thiomorpholinyl, homopiperazinyl, oxazepinyl, diazepinyl, thiazepinyl, pyrrolin-1-yl, 2-pyrrolinyl, 3-pyrrolinyl, 2H-pyranyl, 4H-pyranyl, dioxanyl, 1,3-dioxolanyl, dithianyl, dithiolanyl, dihydrothienyl, dioxolanyl, dihydropyrazinyl, dihydropyridyl, dihydropyrazolyl, dihydropyrimidinyl, dihydropyrrolyl, 1,4-dithianyl, morpholinyl, piperazinyl and piperidyl.

The term "heterocyclylene" refers to a monocyclic ring system in which one or more ring members are independently selected from heteroatoms and that is completely saturated or that contains one or more units of unsaturation, but which is not aromatic, and the ring system do not contain one aromatic ring (but an aromatic ring can be a substituent of it). The heterocyclylene group is a divalent group, the heterocyclylene system may be attached to the main structure at any heteroatom or carbon atom which results in the creation of a stable compound. One or more hydrogen atoms on the cycle are each optionally independently substituted with one or more substituents described herein. In some embodiments, the "heterocyclylene" group is a monocyclic ring having 3-7 ring members (e.g., 1 to 6 carbon atoms and 1 to 3 heteroatoms selected from N, O, P and S; when the ring is a 3-membered ring, wherein only one ring atom is heteroatom). In some embodiments, the heterocyclylene group is a saturated or partially unsaturated monocyclic ring having 5 to 6 atoms; in other embodiments, the cycloalkylene group is a saturated monocyclic ring having 6 atoms or a monocyclic ring having one degree of unsaturation.

The heterocyclylene may be a carbon radical or heteroatom radical. The heterocyclylene group also includes a group in which the heterocyclylene group is fused with a saturated or partially unsaturated ring or a heterocyclic ring. Some non-limiting examples of the heterocyclylene group include 1,2,3,6-tetrahydropyridinylene, piperidylene, piperazinylene, pyrrolidinylene, tetrahydrofuranylene, dihydrofuranylene, tetrahydrothienylene, tetrahydropyranylene, dihydropyranylene, tetrahydrothiopyranylene, azetidinylene, oxetanylene, thietanylene, homopiperidinylene, epoxypropylene, azepanylene, oxepanylene, thiepanylene, N-morpholinylene, 2-morpholinylene, 3-morpholinylene, thiomorpholinylene, homopiperazinylene, oxazepinylene, diazepinylene, thiazepinylene, pyrrolin-1-ylene, 2-pyrrolinylene, 3-pyrrolinylene, 2H-pyranylene, 4H-pyranylene, dioxanylene, 1,3-dioxanylene, dithianylene, dithiolanylene, dihydrothienylene, dioxolanylene, dihydropyrazinylene, dihydropyridylene, dihydropyrazolylene, dihydropyrimidinylene, dihydropyrrolylene, 1,4-dithianylene, morpholinylene, piperazinylene and piperidylene. In other embodiments, some non-limiting examples of the heterocyclylene group include pyrrolidinylene, piperidylene, azepanylene, N-morpholinylene, 2-morpholinylene, 3-morpholinylene, thiomorpholinylene, N-piperazinylene, 2-piperazinylene, 3-piperazinylene, homopiperazinylene, and the like.

The term "6- to 9-membered heterocyclylene" refers to a 6- to 9-membered mono heterocyclic system, which is divalent group. The heterocyclyl system may be attached to the main structure at any heteroatom or carbon atom which results in the creation of a stable compound. In some embodiments, the 6- to 9-membered heterocyclylene group is a saturated or partially unsaturated monocyclic ring having 6 to 7 atoms; In other embodiments, the 6- to 9-membered cycloalkylene group is a saturated monocyclic ring having 6 atoms or a monocyclic ring having one degree of unsaturation. Some non-limiting examples of the 6- to 9-membered heterocyclylene group include piperidylene, 1,2,3,6-tetrahydropyridin-1-ylene, piperazinylene, homopiperidinylene, N-morpholinylene, 2-morpholinylene, 3-morpholinylene, thiomorpholinylene, homopiperazinylene, dioxanylene, dihydropyridylene, dihydropyrimidinylene, morpholinylene, and the like. One or more hydrogen atoms on the cycle are each optionally independently substituted with one or more substituents described herein.

The term "4-membered heterocyclylene" refers to a 4-membered mono heterocyclic system, which is divalent group. The heterocyclyl system may be attached to the main structure at any heteroatom or carbon atom which results in the creation of a stable compound. Some non-limiting examples of the 4-membered heterocyclylene group include azetidinylene, oxetanylene, thietanylene, and the like.

The term "fused bicycle", "fused cycle", "fused bicyclyl" or "fused cyclyl" refers to a saturated or unsaturated fused ring system, which refers to a non-aromatic bicyclic ring system. Depending on the structure, the "fused bicycle", "fused cycle", "fused bicyclyl" or "fused cyclyl" group can be a monoradical or a diradical, i.e., in some embodiments, the "fused bicycle", "fused cycle", "fused bicyclyl" or "fused cyclyl" group can be replaced by or used as fused bicyclylene. Such system can comprises independent or conjugated unsaturated units, but the core structure does not comprise aromatic ring or heteroaromatic ring (but aromatic group can be used as substituents of the above group). Each ring in the fused bicycle group is either carbon cycle or heterocycloaliphatic, some non-limiting examples of such group include hexahydro-furo[3,2-b]furan, 2,3,3a,4,7,7a-hexahydro-1H-indene, 7-azabicyclo[2.2.1]heptane, fused bicyclo[3.3.0]octane, fused bicyclo[3.1.0]hexane and 1,2,3,4,4a,5,8,8a-octahydro-naphthalene. The fused bicyclyl group defined herein may be substituted or unsubstituted. Fused bicyclylene group is a divalent group.

The term "fused heterobicyclyl" refers to a saturated or unsaturated fused cyclic system, which is a non-aromatic bicyclic system, containing at most one degree of unsaturation, and at least one ring in the fused ring system contains one or more heteroatoms. Each ring in the fused ring system contains 3 to 7 ring members and that contains 1 to 6 carbon atoms and 1 to 3 heteroatoms selected from N, O, P and S. Some non-limiting examples of the fused heterobicyclyl group include hexahydro-2H-[1,4]dioxin[2,3-c]pyrrolyl, 3-azabicyclo[3.3.0]octyl, 3,7-diazabicyclo[3.3.0]octyl, 8-azabicyclo[4.3.0]nonyl, 8-azabicyclo[4.3.0]non-3-yl, 3-azabicyclo[4.3.0]non-3-yl, 5-dioxa-8-azabicyclo[4.3.0]nonyl, (1R,6S)-2,5-dioxa-8-azabicyclo[4.3.0]nonyl, (1R, 6R)-2,5-dioxa-8-azabicyclo[4.3.0]nonyl, isoindolinyl, 1,2,3,4-tetrahydroquinolyl, 3-aza-7-oxabicyclo[3.3.0]octyl, 3,7-diazabicyclo[3.3.0]octyl, 2,6-diazabicyclo[3.3.0]octyl, 2,7-diazabicyclo[3.3.0]octyl, 2,8-diazabicyclo[4.3.0]nonyl, 3-oxa-8-azabicyclo[4.3.0]nonyl, 2-oxa-8-azabicyclo[4.3.0]nonyl, 2,8-diaza-5-oxabicyclo[4.3.0]nonyl, 4,9-diazabicyclo[4.3.0]nonyl, 2,9-diazabicyclo[4.3.0]nonyl, 3,8-diazabicyclo[4.3.0]nonyl, 3,7-diazabicyclo[4.3.0]nonyl, 3,9-diazabicyclo[4.3.0]nonyl, 3-oxa-8-azabicyclo[4.3.0]nonyl, 3-thia-8-azabicyclo[4.3.0]nonyl, 5,6-dihydro-4H-pyrrolo[3,4-c]isoxazolyl, [1,2,4]triazolo[4,3-a]piperidyl, isoxazolo[4,3-c]piperidinyl, 4,5,6,7-tetrahydroisoxazolo[3,4-c]pyridinyl, [1,2,4]triazolo[4,3-a]piperazinyl, 2-oxa-7-azabicyclo[4.4.0]decyl, 1,5-dioxa-9-azabicyclo[4.4.0]decyl, 3-azabicyclo[4.4.0]decyl, 2,7-diaza-decahydronaphthyl, 2-oxa-8-azabicyclo[4.4.0]decyl, and the like.

The term "fused heterobicyclylene" refers to a saturated or unsaturated divalent fused cyclic system, which is a non-aromatic bicyclic system, containing at most one degree of unsaturation, and at least one ring in the fused ring system contains one or more heteroatoms. Each ring in the fused ring system contains 3 to 7 ring members and that contains 1 to 6 carbon atoms and 1 to 3 heteroatoms selected from N, O, P and S. Some non-limiting examples of the fused heterobicyclylene group include hexahydro-2H-[1,4]dioxin[2,3-c]pyrrolylene, 3-azabicyclo[3.3.0]octylene, 8-azabicyclo[4.3.0]nonylene, 8-azabicyclo[4.3.0]non-3-ylene, 3-azabicyclo[4.3.0]non-3-ylene, 1,5-dioxa-8-azabicyclo[4.3.0]nonylene, (1R,6S)-2,5-dioxa-8-azabicyclo[4.3.0]nonylene, (1R,6R)-2, 5-dioxa-8-azabicyclo[4.3.0]nonylene, isoindolinylene, 1,2,3,4-tetrahydroquinolylene, 3-aza-7-oxabicyclo[3.3.0]octylene, 3,7-diazabicyclo[3.3.0]octylene, 2,6-diazabicyclo[3.3.0]octylene, 2,7-diazabicyclo[3.3.0]octylene, 2,8-diazabicyclo[4.3.0]nonylene, 3-oxa-8-azabicyclo[4.3.0]nonylene, 2-oxa-8-azabicyclo[4.3.0]nonylene, 2,8-diaza-5-oxabicyclo[4.3.0]nonylene, 4,9-diazabicyclo[4.3.0]nonylene, 2,9-diazabicyclo[4.3.0]nonylene, 3,8-diazabicyclo[4.3.0]nonylene, 3,7-diazabicyclo[4.3.0]nonylene, 3,9-diazabicyclo[4.3.0]nonylene, 3-oxa-8-azabicyclo[4.3.0]nonylene, 3-thia-8-azabicyclo[4.3.0]nonylene, 5,6-dihydro-4H-pyrrolo[3,4-c]isoxazolylene, [1,2,4]triazolo[4,3-a]piperidylene, isoxazolo[4,3-c]piperidinylene, 4,5,6,7-tetrahydroisoxazolo[3,4-c]pyridinylene, [1,2,4]triazolo[4,3-a]piperazinylene, 2-oxa-7-azabicyclo[4.4.0]decylene, 1,5-dioxa-9-azabicyclo[4.4.0]decylene, 3-azabicyclo[4.4.0]decylene, 2,7-diaza-decahydronaphthylene, 2-oxa-8-azabicyclo[4.4.0]decylene, and the like.

The term "bridged bicyclyl" refers to a saturated or unsaturated bridged ring system, which refers to a bicyclic ring system that is not aromatic. Such a system may contain isolated or conjugated unsaturation, but not aromatic or heteroaromatic rings in its core structure (but may have aromatic substitution thereon), in which each ring contains 3 to 7 ring members. Some non-limiting examples of the bridged bicyclyl group include bicyclo[2.2.1]heptyl, and the like. The bridged bicyclyl group defined herein may be substituted or unsubstituted. "Bridged bicyclylene" refers to a divalent bridged bicyclyl group.

The term "bridged heterobicyclyl" refers to a saturated or unsaturated bridged ring system, which refers to a bicyclic ring system that is not aromatic, and contains at most one degree of unsaturated. And at least one ring in the system is inclusive of one or more heteroatoms, wherein each ring in the system contains 3 to 7 ring members, e.g., 1 to 6 carbon atoms and 1 to 3 heteroatoms selected from N, O, P or S. Some non-limiting examples include 2-oxa-5-azabicyclo[2.2.1]heptyl, 2-thio-5-azabicyclo[2.2.1]heptyl, 2,5-diazabicyclo[2.2.1]heptyl, and the like.

The term "bridged heterobicyclylene" refers to a saturated or unsaturated divalent bridged ring system, which refers to a bicyclic ring system that is not aromatic, and contains at most one degree of unsaturated. And at least one ring in the system is inclusive of one or more heteroatoms, wherein each ring in the system contains 3 to 7 ring members, e.g., 1 to 6 carbon atoms and 1 to 3 heteroatoms selected from N, O, P or S. Some non-limiting examples include 2-oxa-5-azabicyclo[2.2.1]heptylene, 2-thio-5-azabicyclo[2.2.1]heptylene, 2,5-diazabicyclo[2.2.1]heptylene, and the like.

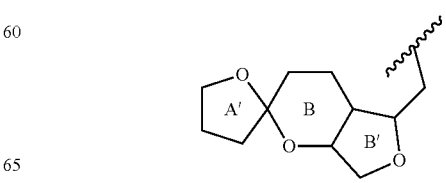

The term "spirocyclyl", "spirocycle", "spiro bicyclyl" or "spiro bicycle" refers to a ring originating from a particular annular carbon of another ring. For example, as depicted below, a saturated bridged ring system (ring B and B') is termed as "fused bicyclic", whereas ring A' and ring B share a carbon atom between the two saturated ring system, which terms as a "spirocyclyl". Each cyclic ring in a spirocyclyl can be either a carbocyclic ring or a heteroalicyclic ring. "Spiro bicyclylene" refers to a divalent spiro bicyclyl group.

The term "spiro heterobicyclyl" refers to a ring originating from a particular annular carbon of another ring. For example, as depicted above, a saturated bridged ring system (ring B and B') is termed as "fused bicyclic", whereas ring A' and ring B share a carbon atom between the two saturated ring system, which terms as a "spirocyclyl". And at least one ring in the system contains one or more heteroatoms, wherein each ring in the system contains 3 to 7 ring members and that contains 1 to 6 carbon atoms and 1 to 3 heteroatoms selected from N, O, P and S. Some non-limiting examples of the spiro heterobicyclyl group include 4-azaspiro[2,4]heptyl, 4-oxaspiro[2,4]heptyl, 5-azaspiro[2,4]heptyl, 2-azaspiro[4,5]decyl, 2-azaspiro[3,3]heptyl, 2-azaspiro[4.4]nonyl, 3-azaspiro[5.4]decyl, 2-oxa-6-azaspiro[3.3]heptyl, 2,6-diazaspiro[3.3]heptyl, 2-thia-6-azaspiro[3.3]heptyl, 2-thia-6-azaspiro[3.3]heptyl, and the like.

The term "spiro heterobicyclyl" refers to a ring originating from a particular annular carbon of another ring which is a divalent group. And at least one ring in the system contains one or more heteroatoms, wherein each ring in the system contains 3 to 7 ring members and that contains 1 to 6 carbon atoms and 1 to 3 heteroatoms selected from N, O, P and S. Some non-limiting examples of the spiro heterobicyclyl group include 4-azaspiro[2,4]heptylene, 4-oxaspiro[2,4]heptylene, 5-azaspiro[2,4]heptylene, 2-azaspiro[4,5]decylene, 2-azaspiro[3,3]heptylene, 2-azaspiro[4.4]nonylene, 3-azaspiro[5.4]decylene, 2-oxa-6-azaspiro[3.3]heptylene, 2,6-diazaspiro[3.3]heptyl, 2-thia-6-azaspiro[3.3]heptylene, and the like.

As described herein, a bond drawn from a substituent R to the center of one ring within a ring system represents substitution of the substituent R at any substitutable position on the ring. For example, Formula (a) represents any position on the ring A' or B' can be substituted with R, such as Formula (b), Formula (c), Formula (d), Formula (e), Formula (f), Formula (g) and Formula (h) shown.

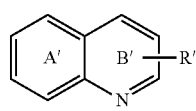

(a)

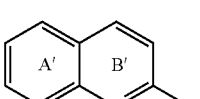

(b)

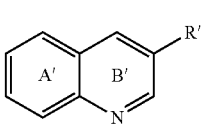

(c)

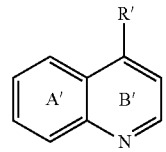

(d)

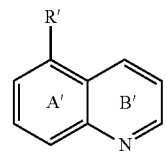

(e)

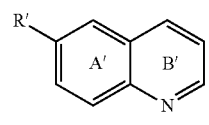

(f)

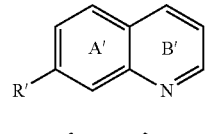

(g)

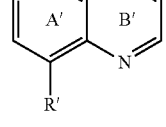

(h)

As described herein, a bond drawn from a substituent $(R)_n$ to the center of one ring within a ring system represents that any substitutable position on the rings can be substituted with substituent R and the total number of substituents R is n. For example, Formula (n') represents possible substitution of n substituents R in any of the position on ring A' or ring B'.

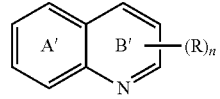

(n')

As described herein, two attachment points within a ring system, for example, either E" or E' on ring C as shown in Formula (j), can attach to the rest of the molecule and the groups of the rest of the molecule they attached can be interchanged with each other.

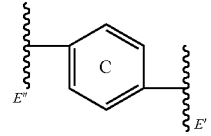

(j)

As described herein, the attachment point can attach to the rest of the molecule at any attachable position on the rings. For example, Formula (k) represents attaching at any attachable position on ring A' or ring B'.

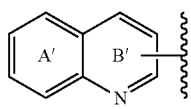

As described herein, the attachment points can attach to the rest of the molecule at any attachable position on the rings, meanwhile, the attachment points can be used interchangeably with each other. For example, Formula (m) represents attaching at any attachable position on the rings, and the two attachment points can be used interchangeably with each other. The dash line represents a bond that is absence or present.

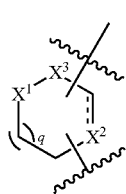

As described herein, "-(L$^2$)$_w$-" of the Formula (I) means, when w has different values, there are various numbers of L$^2$, and each L$^2$ is independent, they can be identical and different. For example, when w is 3, there are three identical or different L$^2$ groups, such as, each L$^2$ can be optionally —NH—, —C(=O)— and —CH$_2$—. "-(L$^2$)$_w$-" of examples in such case is —C(=O)—NH—CH$_2$—, —CH$_2$—C(=O)—NH— or other combination of the three groups.

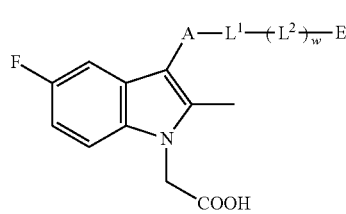

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups. For example, Formula (n') represents possible substitution of n substituents R in any of the position on ring A' or ring B', wherein each R is independently selected from identical or different groups. Also in Formula (I), each L$^2$ can be identical or different group.

A "hydrate" refers to a compound disclosed herein or a salt thereof, which further includes a stoichiometric or non-stoichiometeric amount of water bound by non-covalent intermolecular forces, and also refers to the complex where the solvent molecule is water.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine.

An "ester" refers to an in vivo hydrolysable ester of a compound of the Formula (I)-(IIc) containing hydroxy group, for example, a pharmaceutically acceptable ester which is hydrolysed in the human or animal body to produce the parent alcohol. Some non-limiting examples of in vivo hydrolysable ester forming groups for the compound of Formula (I)-(IIc) containing hydroxy include alkyl, phosphate, acetoxymethoxy, 2,2-dimethylpropionyloxymethoxy, alkylacyl, benzoyl, phenylacetyl, alkoxycarbonyl, dialkylcarbamoyl, N-(dialkylaminoethyl)-N-alkylcarbamoyl, and the like.

An "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g. a peroxycarboxylic acid) (See, Advanced Organic Chemistry, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

Compounds may exist in a number of different geometric isomeric and tautomeric forms, and references to compounds of the Formula (I) to (IIc) include all such forms. For the avoidance of doubt, where a compound can exist in one of several geometric isomeric or tautomeric forms and only one is specifically described or shown, all others are nevertheless embraced by Formula (I)-(IIc).

The term "prodrug" refers to a compound that is transformed in vivo into a compound of Formula (I)-(IIc). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic (C$_1$-C$_{24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, Journal of Medicinal Chemistry, 2008, 51, 2328-2345, all of which are incorporated herein by reference in their entireties.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

The various pharmaceutically acceptable salt forms of the compounds disclosed herein are useful. The term "pharmaceutically acceptable salt" refers to those salt forms which would be apparent to the pharmaceutical chemist, i.e., those which are substantially nontoxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flow ability of the resulting bulk drug. Conveniently, pharmaceutical compositions may be prepared from the active ingredients in combination with pharmaceutically acceptable carriers.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66:1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, 2-hydroxy propionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium salt, lithium salt, potassium salt, calcium salt, magnesium salt, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate. Amine salts include, but are not limited to, N,N'-dibenzylethylenediamine salt, chloroprocaine salt, choline salt, ammonia salt, isopropylamine salt, benzathine salt, cholinate, lysine salt, meglumine salt, piperazine salt, tromethaminesalt, diethanolamine salt and other hydroxyalkylamine salt, ethylenediamine salt, N-methylglucamine salt, procaine salt, N-benzylphenethylamine salt, 1-para-chlorobenzyl-2-pyrrolidin-1'-ylmethylbenzimidazole salt and other alkylamine salt, piperazine salt and tris(hydroxymethyl)amino methane salt. Alkali earth metal salts include, but are not limited to, barium salt, calcium salt and magnesium salt. Transition metal salts include, but are not limited to, zinc salt.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

"Inflammatory disorder/disease" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with the compounds disclosed herein encompass disorders associated with reactions of the specific defense system as well as with reactions of the nonspecific defense system.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas give a herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^2$H (deuterium, D), $^3$H $^{11}$C, $^{13}$C, $^{14}$C, $^{15}$N, $^{17}$O, $^{18}$O, $^{18}$F, $^{31}$P, $^{32}$P, $^{35}$S, $^{36}$Cl, $^{125}$I, respectively.

In another aspect, the compounds of the invention include isotopically enriched compounds as defined herein, for example those into which radioactive isotopes, such as $^3$H, $^{14}$C and $^{18}$F, or those into which non-radioactive isotopes, such as $^2$H and $^{13}$C are present. Such isotopically enriched compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F-enriched compound may be particularly desirable for PET or SPECT studies. Isotopically-enriched compounds of Formula (I)-(IIc) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. For example increased in vivo half-life or reduced dosage requirements or an improvement in therapeutic index. It is understood that deuterium in this context is regarded as a substituent of a compound of Formula (I)-(IIc). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. D$_2$O, d$_6$-acetone, DMSO-d$_6$.

By "combination" according to the invention, there is meant either a fixed combination in one dosage unit form, or a kit of parts for the combined administration where a compound of the invention and a combination partner may be administered independently at the same time or separately within time intervals that especially allow that the combination partners show a cooperative, e.g. synergistic effect. The terms "co-administration" or "combined administration" or the like as used herein are meant to encompass administration of the selected therapeutic agents to a single patient, and are intended to include treatment regimens in which the agents are not necessarily administered by the same route of administration or at the same time. The term "pharmaceutical combination" as used herein refers to a product obtained from mixing or combining active ingredients, and includes both fixed and non-fixed combinations of the active ingredients. The term "fixed combination" means that the active ingredients, e.g. a compound of the invention and a co-agent, are both administered to a patient simultaneously in the form of a single entity or dosage. The term "non-fixed combination" means that the active ingredients, e.g. a compound of the invention and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

A solvate involved to a crystalline form means having on a surface, in a lattice or on a surface and in a lattice, a solvent such as water, acetic acid, acetone, acetonitrile, benzene, chloroform, tetrachloromethane, dichloromethane, dimethyl sulfoxide, 1,4-dioxane, ethanol, ethyl acetate, butanol, tert-butanol, N,N-dimethylacetamide, N,N-dimethylformamide, formamide, formic acid, heptane, hexane, isopropanol, methanol, methylethylketone, methylpyrrolidone, mesitylene, nitromethane, polyethylene glycol, n-propanol, 2-acetone, pyridine, tetrahydrofuran, toluene, xylene, mixtures thereof etc. A specific example of a solvate is a hydrate, wherein the solvent on the surface, in the lattice or on the surface and in the lattice, is water. Hydrates may or may not have solvents other than water on the surface, in the lattice or on the surface and in the lattice of a substance. Solvate may contain a stoichiometric or nonstoichiometric amount of solvent molecules. For example, a solvate with a nonstoichiometric amount of solvent molecules may result from partial loss of solvent from the solvate. When the solvent is tightly bound to the drug (or the compound), the resulting complex will have a well-defined stoichiometry that is independent of humidity. However, when the solvent is weakly bound, as in channel solvates and hygroscopic compounds, the solvent content will be dependent on humidity and drying conditions. In such cases, the complex will often be non-stoichiometric.

"Hydrate" describes a solvate comprising the drug substance and a stoichiometric or non-stoichiometric amount of water.

The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding of a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

The crystalline form can be identified by multiple technological methods, such as X-Ray Powder Diffraction (XRPD), infrared spectroscopy (IR), melting point method, differential scanning calorimetry (DSC), thermogravimetric analysis (TGA), nuclear magnetic resonance method, Raman spectrum, X-Ray single crystal diffraction, solution reaction calorimetry, scanning electron microscope (SEM), quantitative analysis, solubility and solution rate, and so on.

X-Ray Powder Diffraction (XRPD) can be used in detecting the variation of crystaline form, degree of crystallinity, the crystal structure state, and the like message, which is a common method for identifying crystalline form. The peak position in XRPD pattern depends on the crystalline form structure, which is relatively insensitivity for experimental details; and the relative peak height depends on a number of factors having to do with sample preparation and instrument geometry. Thus, in some embodiments, the crystalline form is characterized by an X-ray powder diffraction pattern in which the peak positions are substantially in accordance with those shown in figures disclosed herein. Meanwhile, the measurement of 2θ in XRPD pattern may have some experimental error, for example the measurements of 2θ in XRPD pattern could be different because of different instruments and different samples. Therefore, the value of 2θ is not absolute. According to the state of the instrument for the experiment disclosed herein, the error margin in 2θ of the characteristic peaks is ±0.2°.

Differential scanning calorimetry (DSC) is a technology used for measuring the energy difference between sample and inert reference compound (usually α-$Al_2O_3$) as a function of temperature, which is performed through constant heating or cooling under program control. The relative peak height of DSC thermogram depends on many factors related to sample preparation and geometry of the instrument, while the peak position is relatively insensitive to experiment details. Thus, in some embodiments, the crystalline form disclosed herein is characterized by a DSC thermogram having some peaks in certain positions, which is substantially the same as DSC thermogram provided in appended figures of the present invention. Meanwhile, the DSC thermogram could have some experimental error, for example the peak position and the peak value in DSC thermogram could exist a little difference because of different instruments and different samples. Therefore, the peak position and the peak value in DSC thermogram is not absolute. According to the state of the instrument for the experiment disclosed herein, the error margin of the melting peaks is ±3° C.

Differential scanning calorimetry (DSC) also is used for analysis of determining whether there is a phenomenon of crystal transformation or mixed crystal which exists in crystalline form.

The solid having same chemical composition usually form different crystal structural polymorph (or called modification) under different thermodynamic conditions, this phenomenon is called polymorphism. The transformations among the modifications will occur when the temperature and pressure change, this phenomenon is called crystal transition. The properties of crystalline form are largely changed such as mechanics, electronics, magnetic because of crystal transition. The crystal transition process could be described in differential scanning calorimetry (DSC) thermogram when the transition temperature is in the measurable range.

The crystalline forms of the compound of the invention can induce crystal transformation under a suitable condition. In some embodiments, the crystalline form I, II, V and IV lose crystal water or crystal solvent under a high temperature and then transfer to crystalline VII, which has a DSC thermogram comprising characteristic endothermic peaks at 210° C. to 220° C.

According to the state of the instrument for the experiment disclosed herein. The error margin in the melting peaks is ±3° C.

Thermogravimetric analysis (TGA) is a technology used for measuring the quality change of a substance which varies with temperature under program control, which can apply to detecting the process of the solvent loss in the crystal, or sublimation and dissociation of the sample, and the crystal water and the crystal solvent contained in crystal may be speculated through analysis of the detection results. The measurement of quality change described in TGA curve depends on many factors related to sample preparation and instrument, which could be different because of different instruments and different samples.

As used herein, the value of 2θ described in an X-ray powder diffraction pattern is recorded in degree (°).

As used herein, term "substantially the same as shown in a figure" refers to an X-ray powder diffraction (XRPD) pattern, or a differential scanning calorimetry (DSC) thermogram, or a DVS profile having at least 50%, at least 60%, at least 70%, at least 80%, at least 90%, at least 95%, or at least 99% of the peaks shown in the figure.

As used herein, when referring to a spectrum and/or to data presented in a graph, the term "peak" refers to a feature that one skilled in the art would recognize as not attributable to background noise.

The crystalline form of 2-(5-fluoro-3-(1-((4-fluorophenyl)sulfonyl)piperidin-4-yl)-2-methyl-1H-indol-1-yl)acetic acid disclosed herein is substantially pure, wherein the crystalline form is form I, form II, form III, form IV, form V or form VI.

As used herein, a crystalline form that is "substantially pure" refers to a crystalline form that is substantially free of one or more other crystalline forms, i.e., the crystalline form has a purity of at least about 80%, at least about 85%, at least about 90%, at least about 93%, at least about 95%, at least about 98%, at least about 99%, at least about 99.5%, at least about 99.6%, at least about 99.7%, at least about 99.8%, or at least about 99.9%; or the crystalline form contains less than 20%, less than 10%, less than 5%, less than 3%, less than 1%, less than 0.5%, less than 0.1%, or less than 0.01% of the one or more other crystalline forms, based on the total volume or weight of the crystalline form and the one or more other crystalline forms.

As used herein, a crystalline form that is "substantially free" of one or more other crystalline forms refers to a crystalline form containing less than 20%, less than 10%, less than 5%, less than 4%, less than 3%, less than 2%, less than 1%, less than 0.5%, less than 0.1%, or less than 0.01% of the one or more other crystalline forms, based on the total volume or weight of the crystalline form and the one or more other crystalline forms.

As used herein, the term "relative intensity" refers to the intensity of a peak with respect to the intensity of the strongest peak in the X-ray powder diffraction (XRPD) pattern which is regarded as 100%.

As used herein, all numbers disclosed herein are approximate values, regardless whether the word "about" is used in connection therewith, which means within 10%, suitably within 5% and particularly within 1% of a given value or range. Alternatively, the term "about" means within an acceptable standard error of the mean, when considered by one of the ordinary skill in the art. Therefore, whenever a number having a value N is disclosed, any number having the value N+/−1%, N+/−2%, N+/−3%, N+/−5%, N+/−7%, N+/−8% or N+/−10% is specifically disclosed, wherein "+/−" refers to plus or minus.

The term "comprise" is an open expression, it means comprising the contents disclosed herein, but don't exclude other contents.

Description of Compounds of the Invention

The present invention provides a series of indole derivatives of which N atom of indole is substituted with carboxylic acid, which are PGD$_2$ antagonists at CRTH2 receptor, and can be used in the treatment of diseases mediated by PGD$_2$ at the CRTH2 receptor.

In one aspect, provided herein is a compound having Formula (I) or a stereoisomer, a geometric isomer, a tautomer, an N-oxide, a hydrate, a solvate, a metabolite, an ester, a pharmaceutically acceptable salt or a prodrug thereof,

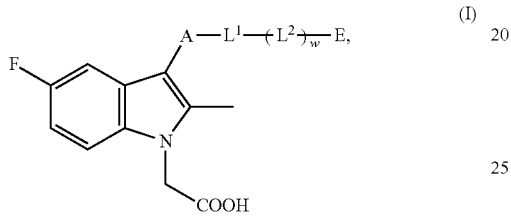

(I)

wherein A, E, L$^1$, L$^2$ and w are as defined herein.

In some embodiments, A is 6- to 9-membered heterocyclylene, 4-membered heterocyclylene, spiro heterobicyclylene, fused heterobicyclylene, bridged heterobicyclylene, spiro bicyclylene, fused bicyclylene, bridged bicyclylene, cycloalkylene, heteroarylene or arylene;

A is optionally substituted with 1, 2, 3 or 4 independent R$^2$; and wherein R$^2$ is as defined herein.

In some embodiments,

A is 6- to 9-membered heterocyclylene, 4-membered heterocyclylene, C$_{5-12}$ spiro heterobicyclylene, C$_{5-12}$ fused heterobicyclylene, C$_{5-12}$ bridged heterobicyclylene, C$_{5-12}$ spiro bicyclylene, C$_{5-12}$ fused bicyclylene, C$_{5-12}$ bridged bicyclylene, C$_{3-12}$ cycloalkylene, C$_{1-9}$ heteroarylene or C$_{6-12}$ arylene;

A is optionally substituted with 1, 2, 3 or 4 independent R$^2$; and wherein R$^2$ is as defined herein.

In some embodiments,

A is one of the following sub-structures:

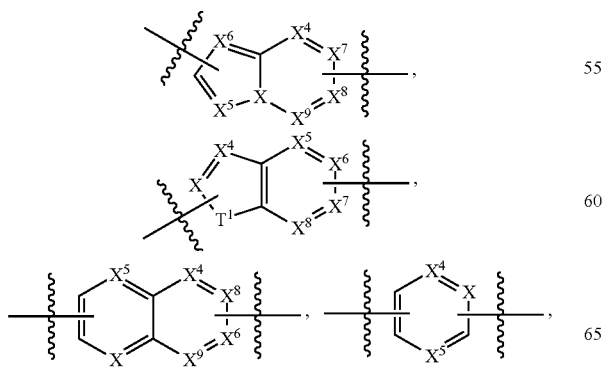

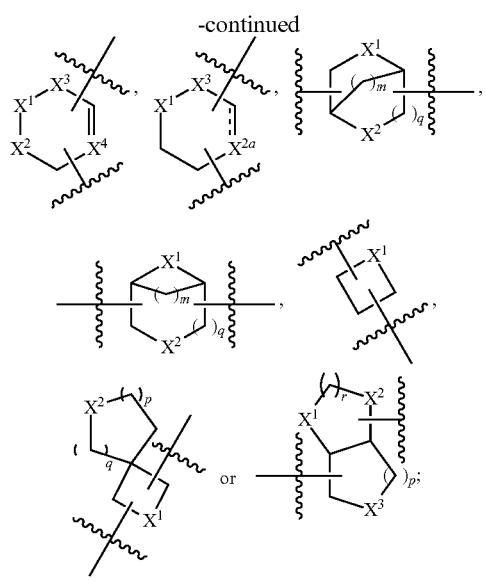

wherein when ═x═ is a single bond,

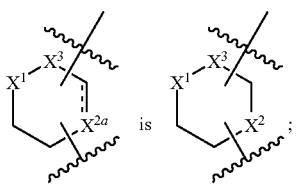

when ═x═ is a double bond,

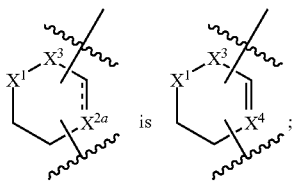

each X$^1$, X$^2$, T$^1$ and X$^3$ is independently —(CR$^3$R$^{3a}$)$_b$—, —O—, —N(R$^4$)— or —S—;

each X$^4$, X$^5$, X$^6$, X$^7$, X$^8$, X$^9$ and X is independently C(R$^3$) or N;

each b is independently 1, 2, 3 or 4;

each q, m, p and r is independently 0, 1, 2, 3 or 4;

each moiety represented by A is optionally and independently substituted with 1, 2, 3 or 4 independent R$^2$; and wherein R$^2$, R$^4$, R$^3$ and R$^{3a}$ are as defined herein.

In some embodiments,

A is

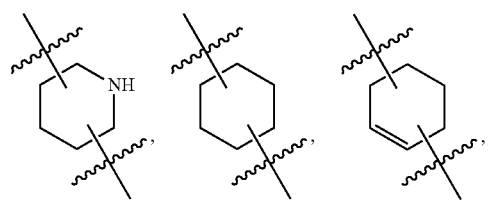

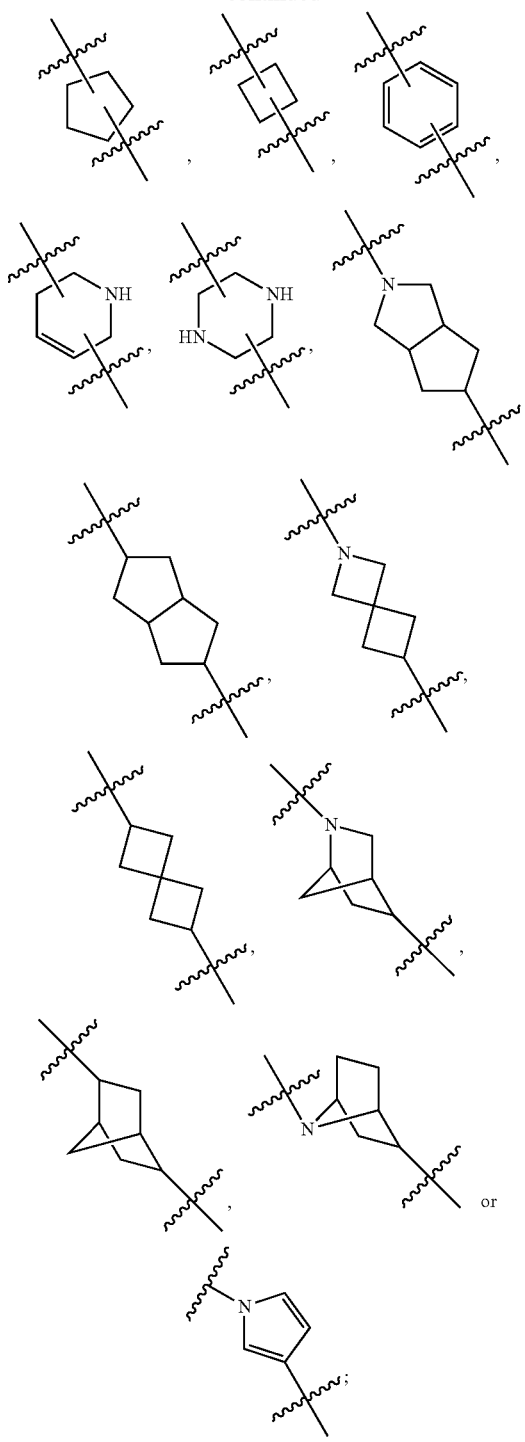

each moiety represented by A is optionally and independently substituted with 1, 2, 3 or 4 independent $R^2$; and wherein $R^2$ is as defined herein.

In some embodiments, each $R^3$ and $R^{3a}$ is independently H, $C_{1-4}$alkyl, $C_{1-4}$ haloalkyl, hydroxy, nitro, cyano, halogen, amino, carboxy, $C_{1-4}$ alkoxy, $C_{1-4}$ alkylamino, $C_{1-4}$ alkylthio, $C_{1-4}$ alkylacyl, $C_{3-12}$ cycloalkyl, $C_{3-9}$ heterocyclyl, $C_{6-12}$ aryl, $C_{1-9}$ heteroaryl, amino-$C_{1-4}$-alkyl, hydroxy-$C_{1-4}$-alkyl, sulfo, aminosulfonyl or aminoacyl.

In some embodiments, each $R^4$ is independently H, $C_{1-4}$ alkyl, $C_{1-4}$ haloalkyl, hydroxy, $C_{3-12}$ cycloalkyl, $C_{3-9}$ heterocyclyl, $C_{6-12}$ aryl, $C_{1-9}$ heteroaryl, amino-$C_{1-4}$-alkyl, or hydroxy-$C_{1-4}$alkyl.

In some embodiments, each $R^{3a}$ and $R^3$ is independently H, methyl, ethyl, propyl, butyl, hydroxy, nitro, cyano, F, Cl, Br, carboxy, methoxy, ethoxy, amino, trifluoromethyl, amino-$C_{1-4}$-alkyl, hydroxy-$C_{1-4}$-alkyl, sulfo, aminosulfonyl or aminoacyl.

In some embodiments, each $R^4$ is independently H, methyl, ethyl, propyl, butyl, trifluoromethyl, hydroxy, amino-$C_{1-4}$-alkyl or hydroxy-$C_{1-4}$-alkyl.

In some embodiments, each $R^2$ is independently H, $C_{1-4}$alkyl, $C_{1-4}$ haloalkyl, hydroxy, nitro, amino, cyano, halogen, carboxy, $C_{1-4}$ alkoxy, $C_{1-4}$ alkylamino, $C_{1-4}$ alkylthio, $C_{1-4}$ alkylacyl, $C_{3-12}$ cycloalkyl, $C_{3-9}$ heterocyclyl, $C_{6-12}$ aryl, $C_{1-9}$ heteroaryl, amino-$C_{1-4}$-alkyl, hydroxy-$C_{1-4}$-alkyl, sulfo, $R^{2b}$-L-, aminosulfonyl or aminoacyl; and wherein each L and $R^{2b}$ is as defined herein.

In some embodiments, each $R^2$ is independently H, methyl, ethyl, n-propyl, isopropyl, t-butyl, n-butyl, trifluoromethyl, hydroxy, nitro, amino, cyano, F, Cl, Br, carboxy, methoxy, ethoxy, isopropoxy, methylamino, ethylamino, dimethylamino, methylacyl, aminomethyl, hydroxymethyl, sulfo, $R^{2b}$-L-, aminosulfonyl or aminoacyl; and wherein each L and $R^{2b}$ is as defined herein.

In some embodiments,

E is heterocyclyl, cycloalkyl, spiro heterobicyclyl, fused heterobicyclyl, bridged heterobicyclyl, aryl or heteroaryl; E is optionally substituted with 1, 2, 3 or 4 independent $R^{2c}$; and wherein each $R^{2c}$ is as defined herein.

In some embodiments, E is $C_{1-9}$ heterocyclyl, $C_{5-12}$spiro heterobicyclyl, $C_{5-12}$fused heterobicyclyl, $C_{5-12}$bridged heterobicyclyl, $C_{3-12}$cycloalkyl, $C_{6-12}$ aryl or $C_{1-12}$ heteroaryl; and each $C_{1-9}$ heterocyclyl, $C_{5-12}$spiro heterobicyclyl, $C_{5-12}$fused heterobicyclyl, $C_{5-12}$bridged heterobicyclyl, $C_{3-12}$cycloalkyl, $C_{6-12}$ aryl and $C_{1-12}$ heteroaryl is optionally and independently substituted with 1, 2, 3 or 4 independent $R^{2c}$; and wherein each $R^{2c}$ is as defined herein.

In some embodiments,

E is one of the following sub-structures:

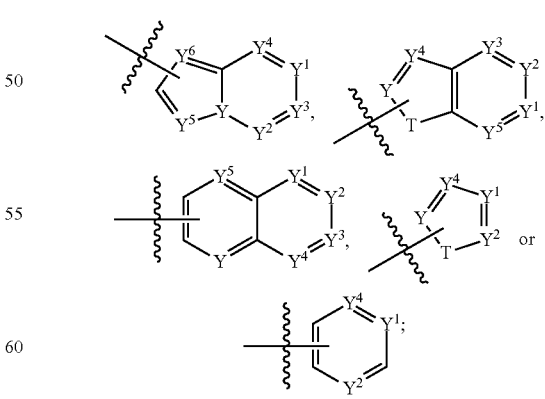

wherein each Y, $Y^1$, $Y^2$, $Y^3$, $Y^4$, $Y^5$ and $Y^6$ is independently N or CH;

each T is independently —O—, —S—, —NH— or —$CH_2$—; and each moiety represented by E is optionally and independently substituted with 1, 2, 3 or 4 independent $R^{2c}$; and wherein each $R^{2c}$ is as defined herein.

In some embodiments, E is one of the following substructures:

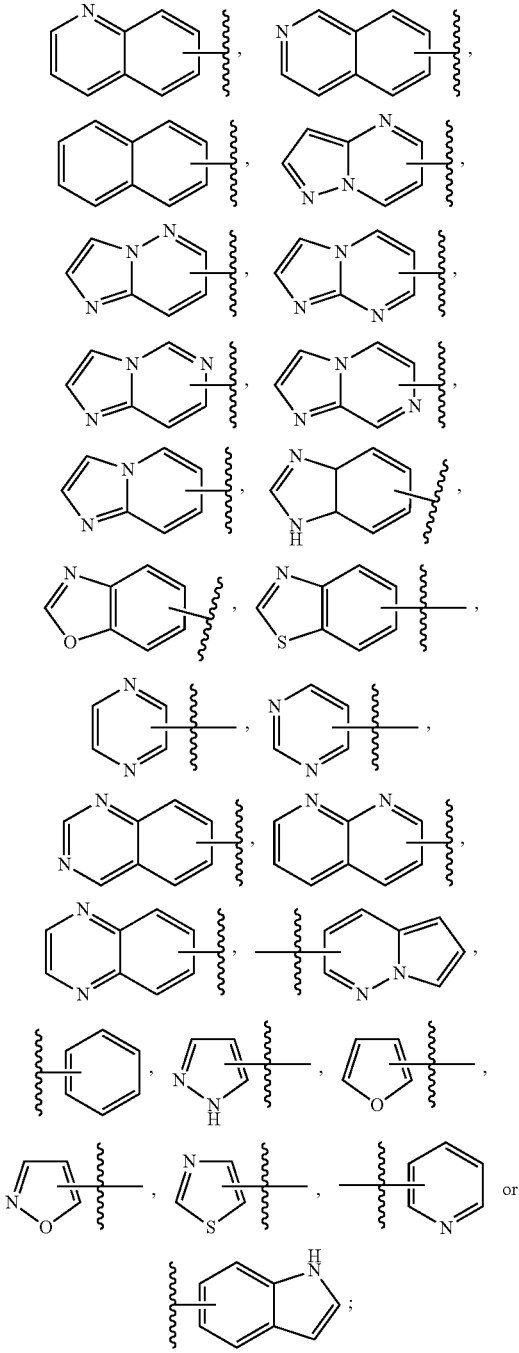

each moiety represented by E is optionally and independently substituted with 1, 2, 3 or 4 independent $R^{2c}$; and wherein each $R^{2c}$ is as defined herein.

In some embodiments, $L^1$ is —O—, —S—, —N($R^1$)—, —CH$_2$—, —CH(OH)—, —C(=O)O—, —N($R^1$)—C(=O)—, —C(=O)—(CH$_2$)$_n$—, —C(=O)—, —OC(=O)—, —C(=S)—, —C(=O)—N($R^1$)—, —C(=S)—N($R^1$)— or —(CH$_2$)$_n$—C(=O)—;

each $L^2$ is independently a bond, —O—, —S(=O)$_t$—, —S—, —N($R^1$)—, —C(=O)O—, —N($R^1$)—C(=O)—, —C(=O)—(CH$_2$)$_n$—, —CH$_2$—, —C(=O)—, —OC(=O)—, —C(=S)—, —C(=O)—N($R^1$)—, —C(=S)—N($R^1$)— or —(CH$_2$)$_n$—C(=O)—;

each $R^1$ is independently H, $C_{1-4}$ alkyl, halo-$C_{1-4}$-alkyl, $C_{1-4}$alkylacyl or hydroxy; and wherein each t and n is as defined herein.

In some embodiments, -$L^1$-($L^2$)$_w$- is —C(=O)—, —O—, —S—, —NH—, —NH—C(=O)—, —CH$_2$—, —S(=O)$_2$—, —C(=O)—NH—CH$_2$—, —N(CH$_3$)—C(=O)—, —C(=O)—NH—, —NH—CH$_2$—, —N(C(=O)—CH$_3$)—CH$_2$—, —NH—S(=O)$_2$—, —N(CH$_3$)—S(=O)$_2$—, —NH—C(=O)—NH—CH$_2$—, —C(=O)O— or —CH(OH)—.

In some embodiments, w is 0, 1, 2, 3 or 4.

In some embodiments, each n is independently 0, 1, 2, 3 or 4.

In some embodiments, each t is independently 0, 1 or 2.

In some embodiments, each $R^{2c}$ is independently H, $C_{1-4}$alkyl, $C_{1-4}$ haloalkyl, hydroxy, nitro, amino, cyano, halogen, carboxy, $C_{1-4}$ alkoxy, $C_{1-4}$ alkylamino, $C_{1-4}$ alkylthio, $C_{1-4}$ alkylacyl, $C_{3-12}$ cycloalkyl, $C_{3-9}$ heterocyclyl, $C_{6-12}$ aryl, $C_{1-9}$ heteroaryl, amino-$C_{1-4}$-alkyl, hydroxy-$C_{1-4}$-alkyl, sulfonyl, $R^{2b}$-L-, aminosulfonyl or aminoacyl; and wherein each L and $R^{2b}$ is as defined herein.

In some embodiments, each $R^{2c}$ is independently H, methyl, ethyl, n-propyl, isopropyl, t-butyl, n-butyl, trifluoromethyl, hydroxy, nitro, amino, cyano, F, Cl, Br, carboxy, methoxy, ethoxy, isopropoxy, methylamino, ethylamino, dimethylamino, methylacyl, aminomethyl, hydroxymethyl, sulfo, $R^{2b}$-L-, aminosulfonyl or aminoacyl; and wherein each L and $R^{2b}$ is as defined herein.

In some embodiments, each L is independently —O—, —S(=O)$_t$—, —S—, —N($R^{1a}$)—, —CH$_2$—, —C(=O)—, —OC(=O)—, —C(=S)—, —C(=O)—N($R^{1a}$)—, —C(=S)—N($R^{1a}$)— or —(CH$_2$)$_n$—C(=O)—;

each $R^{1a}$ is independently H, $C_{1-4}$ alkyl, halo-$C_{1-4}$-alkyl, $C_{1-4}$alkylacyl or hydroxy; and wherein each n and t is as defined herein.

In some embodiments, each $R^{2b}$ is independently H, $C_{1-4}$ alkyl, $C_{1-4}$ haloalkyl, $C_{3-9}$ cycloalkyl, $C_{3-6}$ heterocyclyl, $C_{6-12}$ aryl, $C_{1-9}$ heteroaryl, amino-$C_{1-4}$-alkyl, amino or hydroxy-$C_{1-4}$-alkyl.

In some embodiments, each $R^{2b}$ is independently H, methyl, ethyl, n-propyl, isopropyl, n-butyl, trifluoromethyl, cyclopentyl, cyclohexyl, cyclobutyl, morpholinyl, piperidyl, pyrrolyl, hydroxymethyl or amino.

In some embodiments, provided herein is a compound having Formula (II) or a stereoisomer, a geometric isomer, a tautomer, an N-oxide, a hydrate, a solvate, a metabolite, an ester, a pharmaceutically acceptable salt or a prodrug thereof,

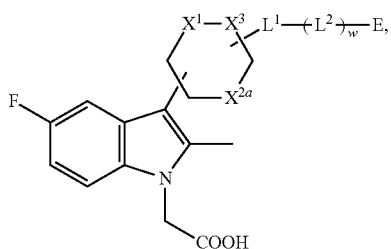
(II)

wherein when ═X²ᵃ is a single bond,

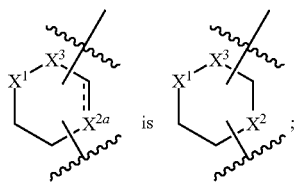

when ═X²ᵃ is a double bond,

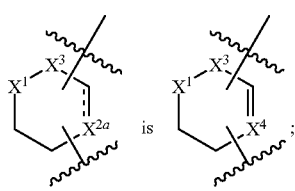

each $X^1$, $X^2$ and $X^3$ is independently —$(CR^3R^{3a})_b$—, —O—, —N($R^4$)— or —S—;
each $X^4$ is independently $C(R^3)$ or N;
each b is independently 1, 2, 3 or 4; and
wherein $R^3$, $R^{3a}$, $R^4$, E, $L^1$, $L^2$ and w are as defined herein.

In some embodiments, provided herein is a compound having Formula (IIa) or a stereoisomer, a geometric isomer, a tautomer, an N-oxide, a hydrate, a solvate, a metabolite, an ester, a pharmaceutically acceptable salt or a prodrug thereof,

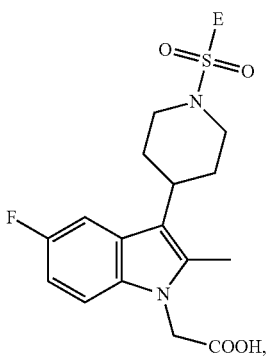
(IIa)

wherein E is as defined herein.

In some embodiments, provided herein is a compound having Formula (IIb) or a stereoisomer, a geometric isomer, a tautomer, an N-oxide, a hydrate, a solvate, a metabolite, an ester, a pharmaceutically acceptable salt or a prodrug thereof,

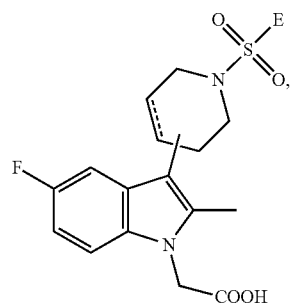
(IIb)

wherein ═ is a single bond or a double bond; and E is as defined herein.

In some embodiments, provided herein is a compound having Formula (IIc) or a stereoisomer, a geometric isomer, a tautomer, an N-oxide, a hydrate, a solvate, a metabolite, an ester, a pharmaceutically acceptable salt or a prodrug thereof, (IIc)

wherein ═ is a single bond or a double bond;
$X^4$ is $C(R^3)$ or N;
and wherein each of $R^3$, -$L^1$-$(L^2)_w$- and E is as defined herein.

In some embodiments, provided herein is a compound, wherein the pharmaceutically acceptable salt is an inorganic acid salt, organic acid salt, inorganic base salt, alkali metal salt or organic base salt.

In some embodiments, provided herein is a compound, wherein the pharmaceutically acceptable salt is hydrochloride, hydrobromide, hydriodate, nitrate, sulfate, disulfate, phosphate, acetate, propionate, butyrate, lactate, mesylate, tosilate, maleate, benzoate, succinate, tartrate, citrate, oxalate, fumarate, taurinate, sodium salt, potassium salt or ammonium salt.

In some embodiments, provided herein is one of the following structures or a stereoisomer, a geometric isomer, a tautomer, an N-oxide, a hydrate, a solvate, a metabolite, an ester, a pharmaceutically acceptable salt or a prodrug thereof,

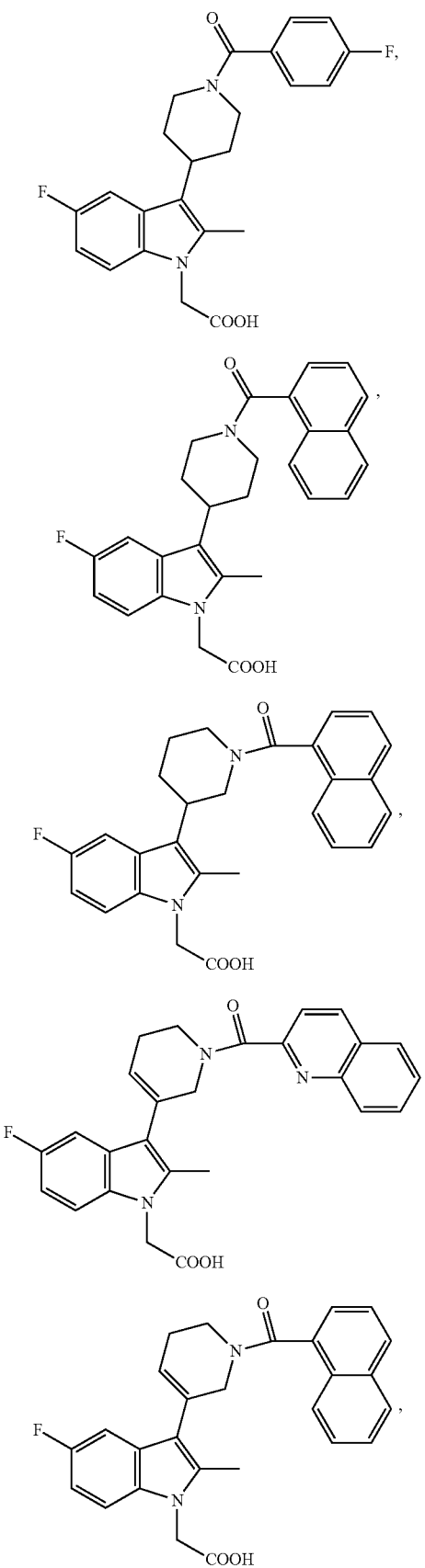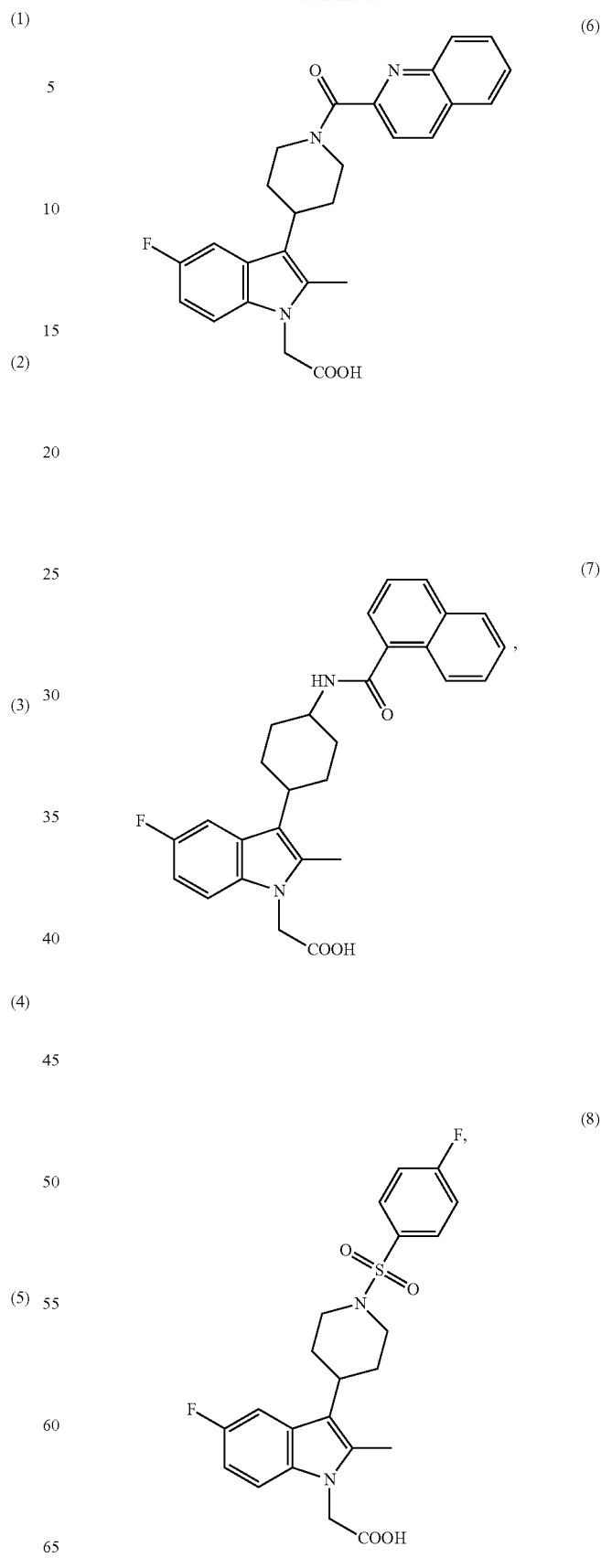

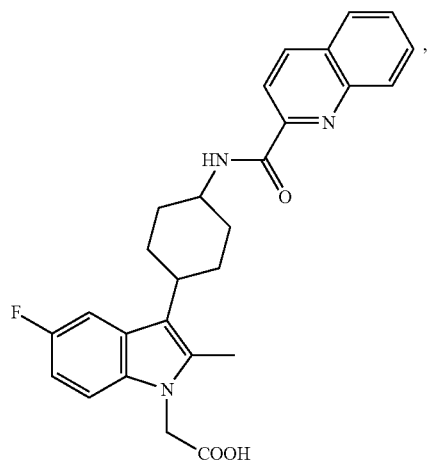
(9)
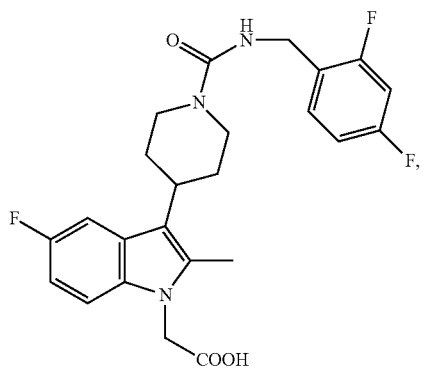
(12)
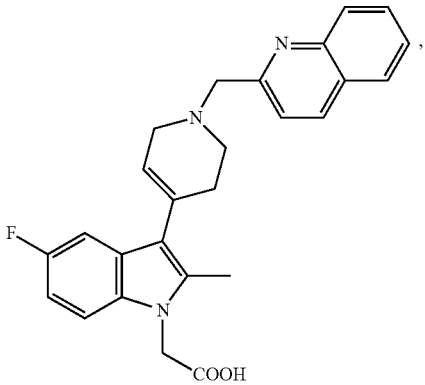
(13)
(10) HCl
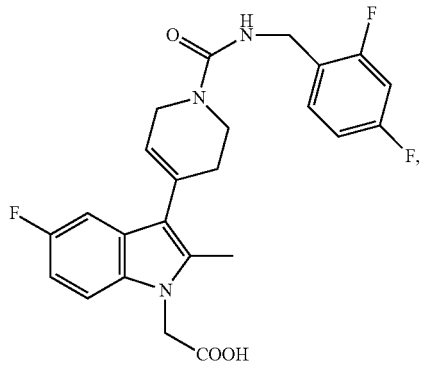
(14)
(11)
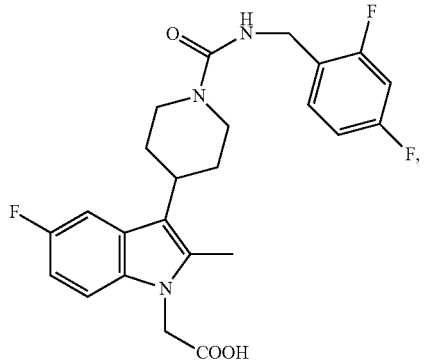
(15)

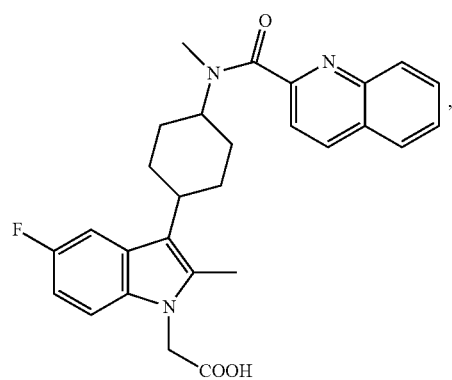
(16)
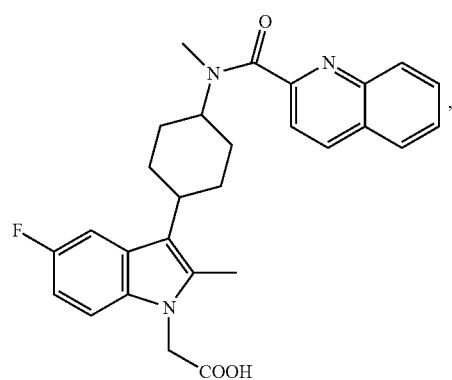
(17)
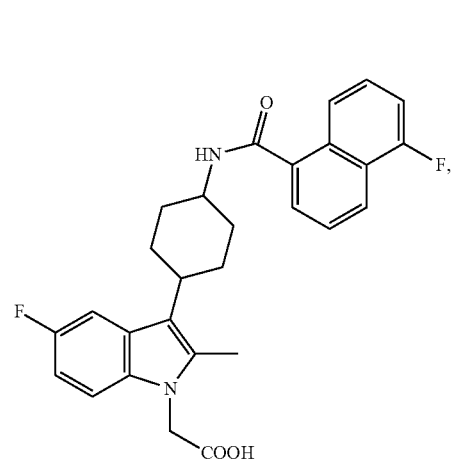
(18)
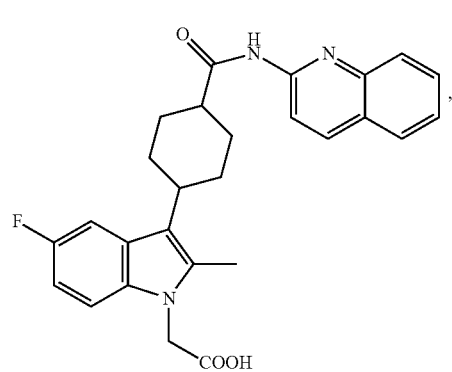
(19)
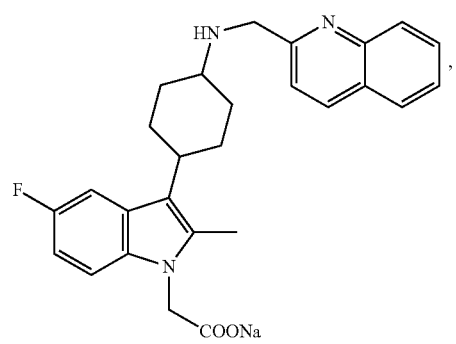
(20)
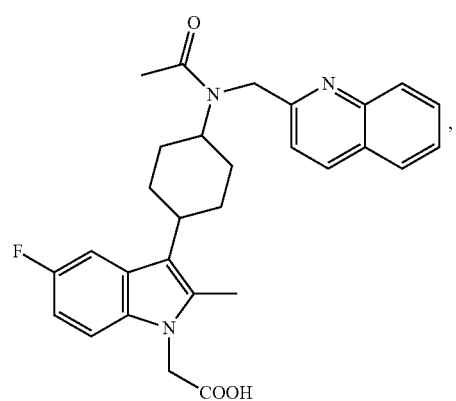
(21)
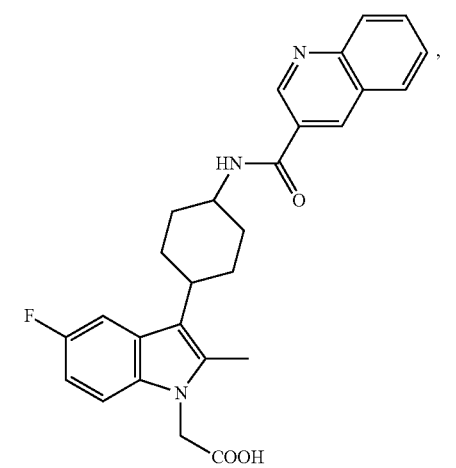
(22)
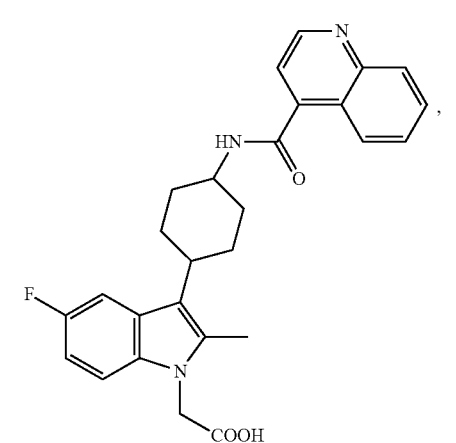
(23)

-continued
(24)
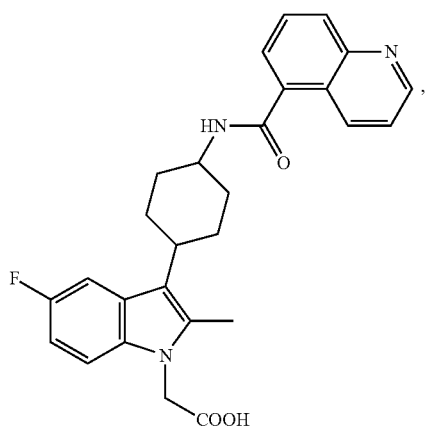
(25)
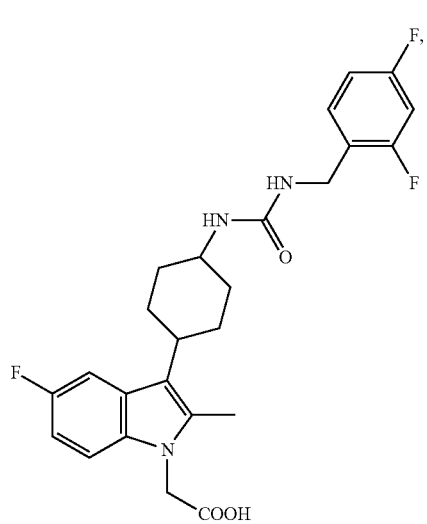
(26)
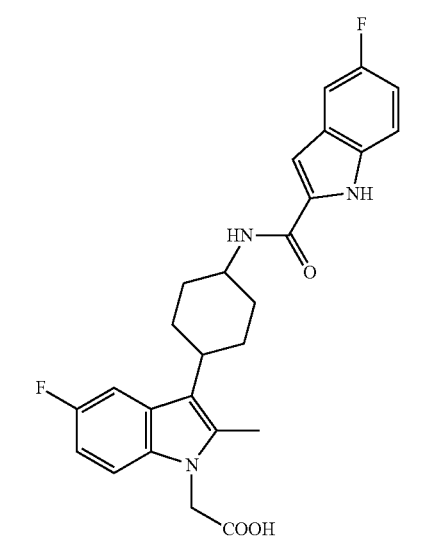
-continued
(27)
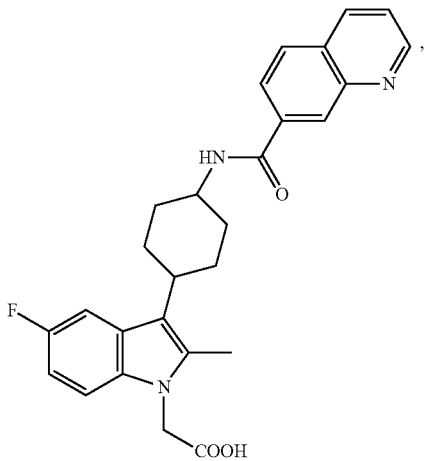
(28)
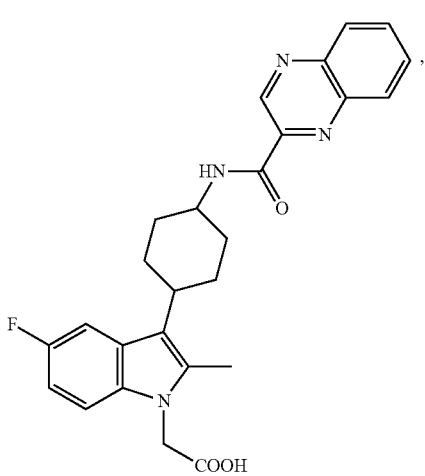
(29)
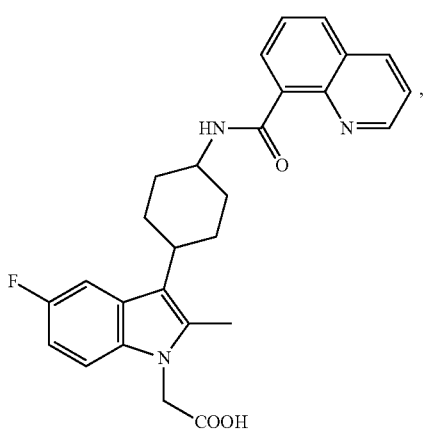

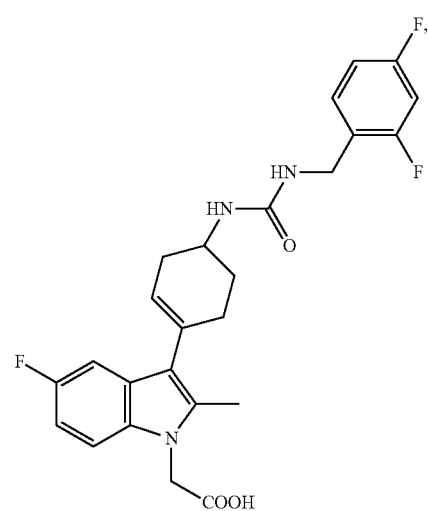
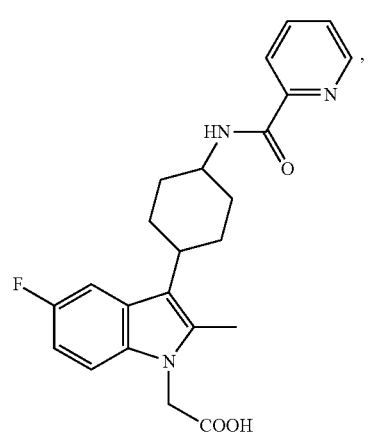
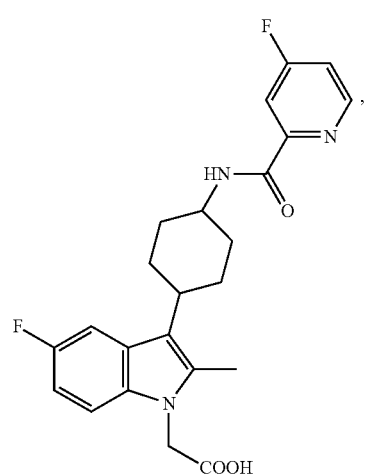
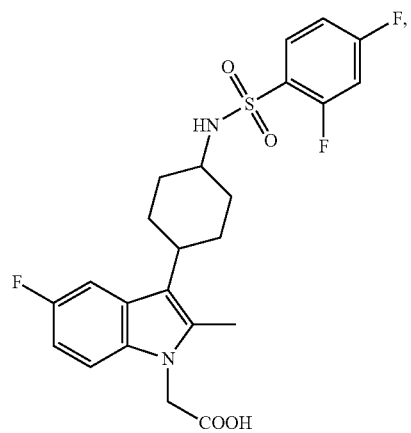

(37)
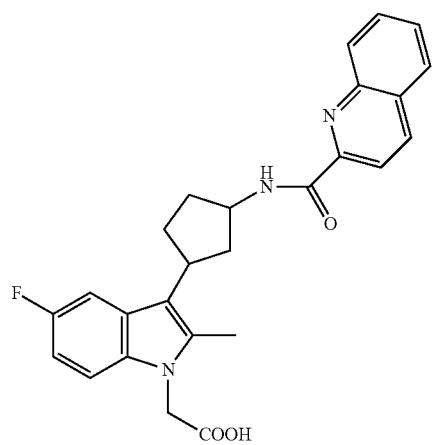
(38)
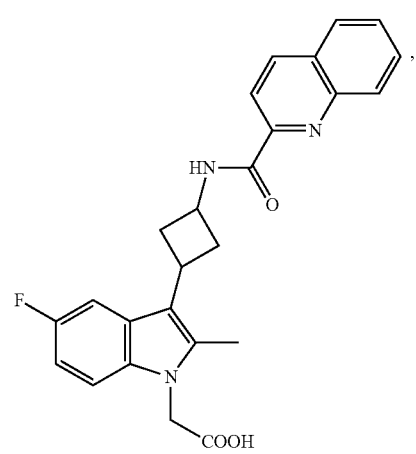
(39)
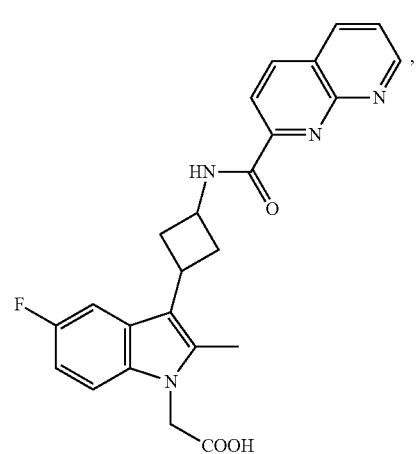
(40)
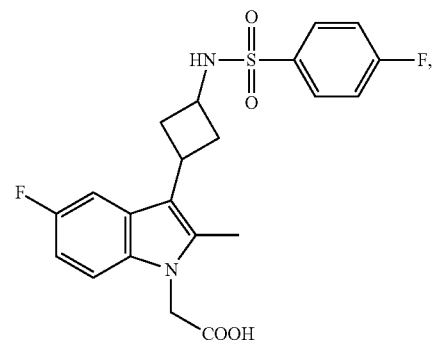
(41)
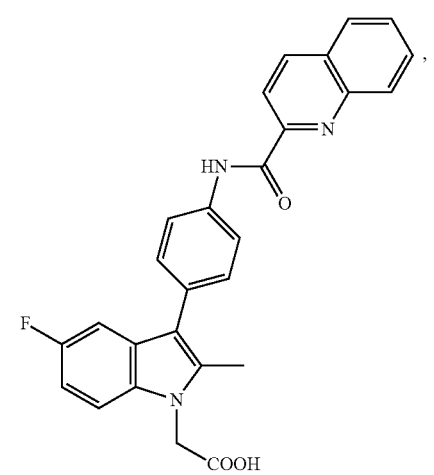
(42)
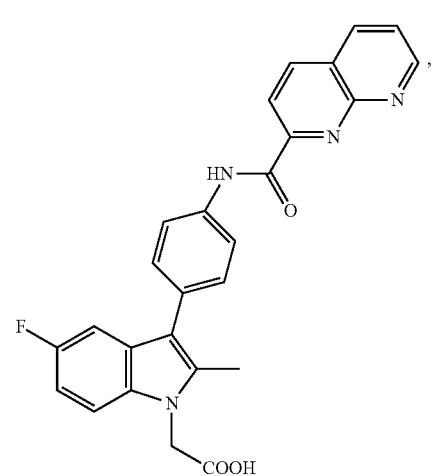
(43)
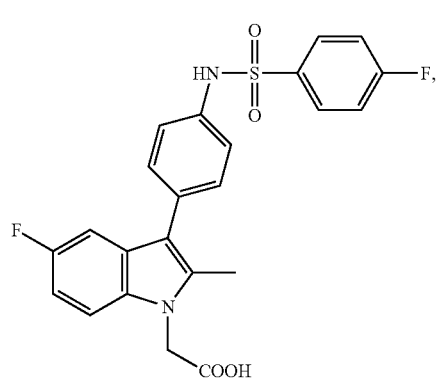

(44)
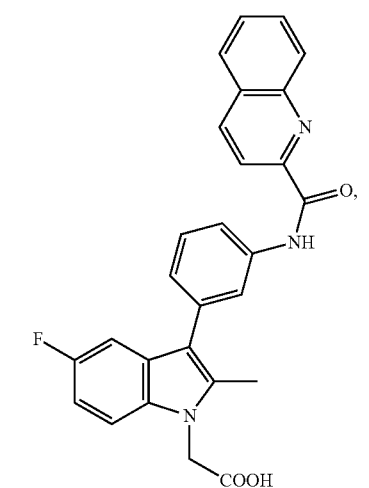
(45)
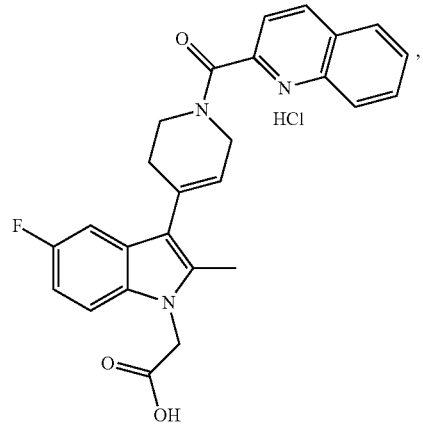
(46)
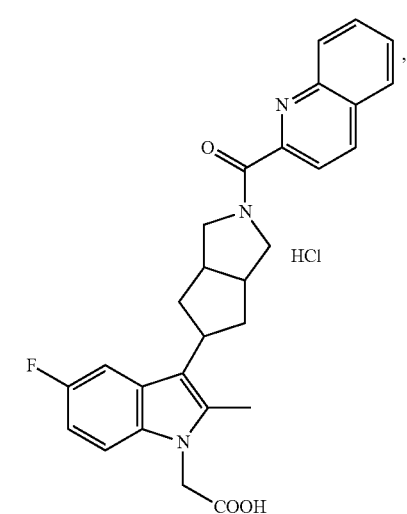
(47)
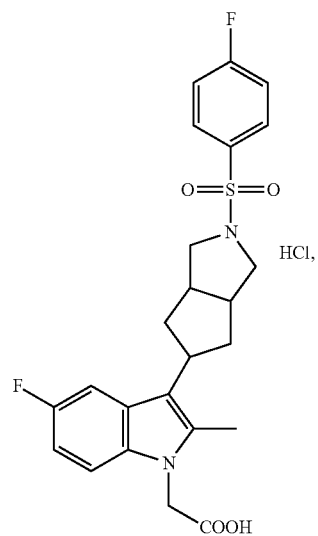
(48)
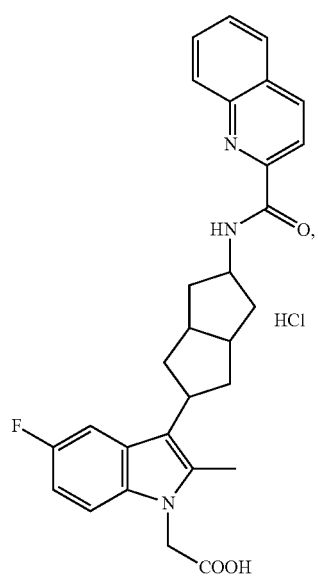
(49)
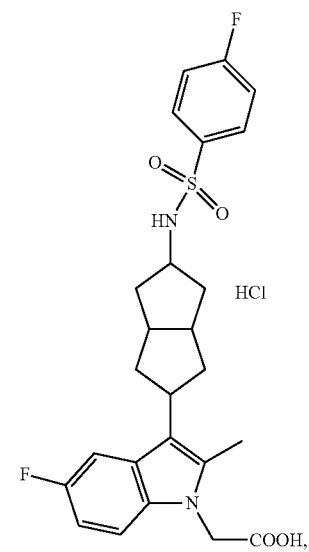

-continued
(50)
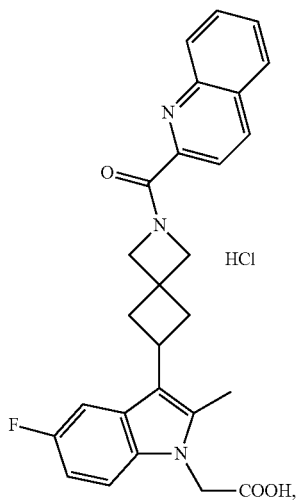
(51)
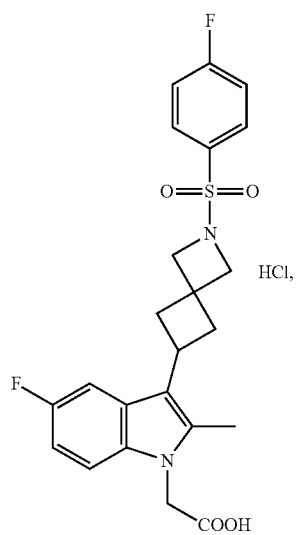
(52)
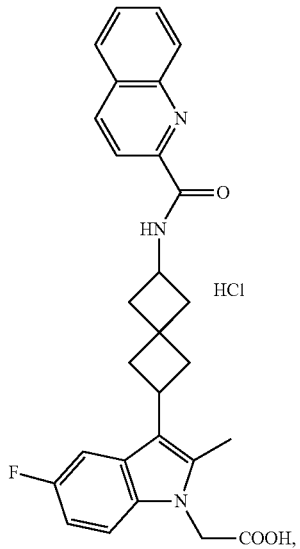
-continued
(53)
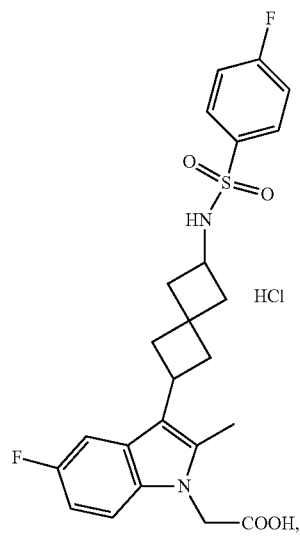
(54)
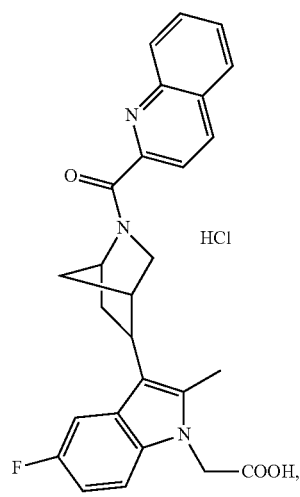
(55)
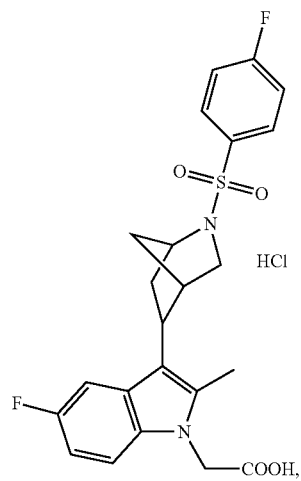

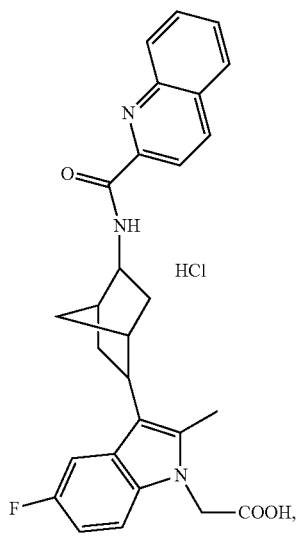
(56)
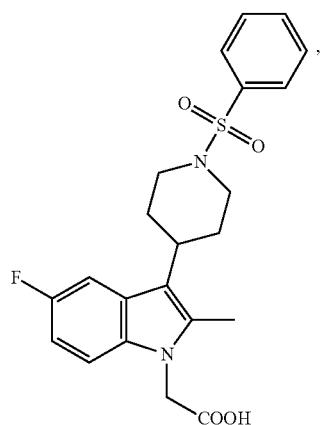
(59)
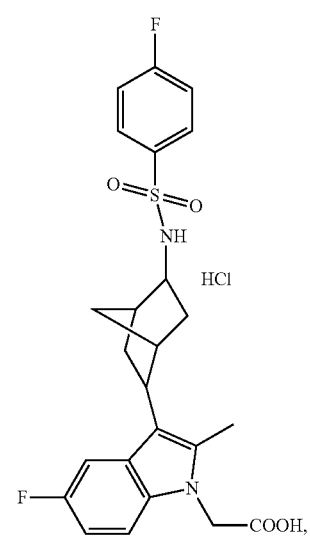
(57)
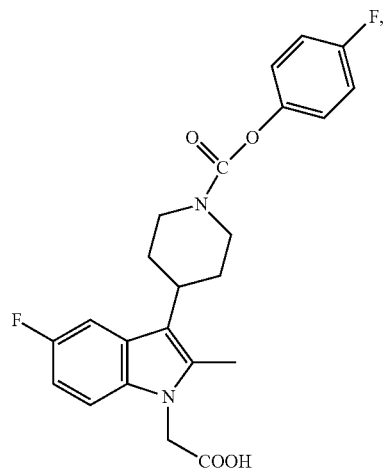
(60)
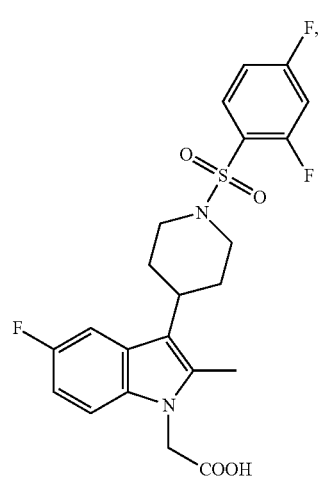
(58)
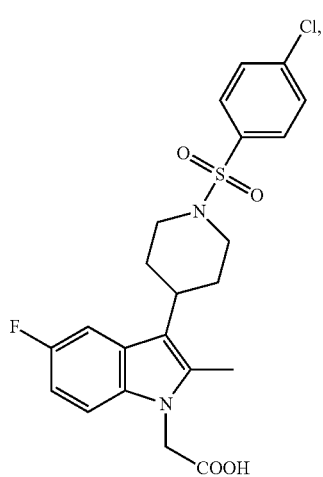
(61)

-continued
(62)
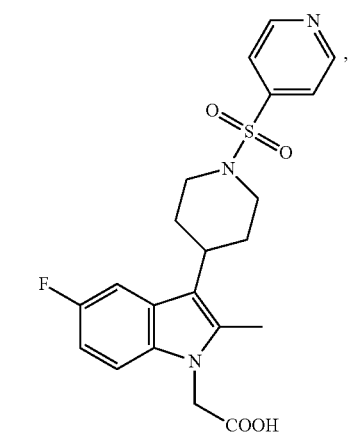
(63)
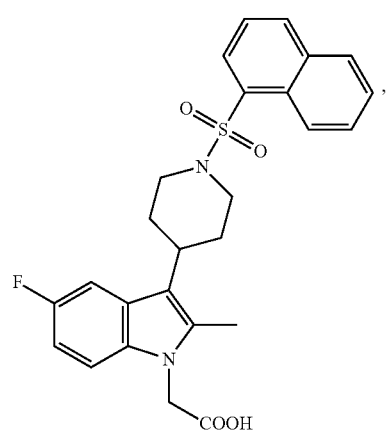
(64)
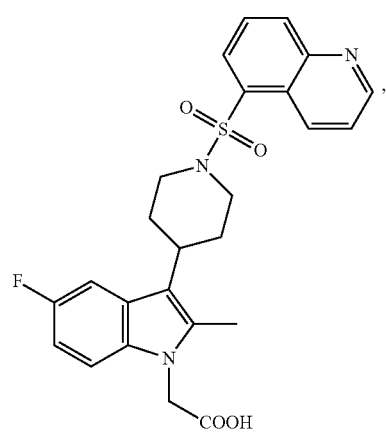
-continued
(65)
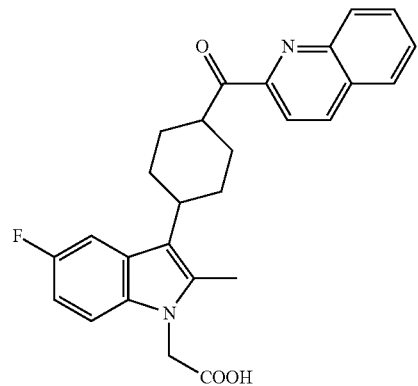
(66)
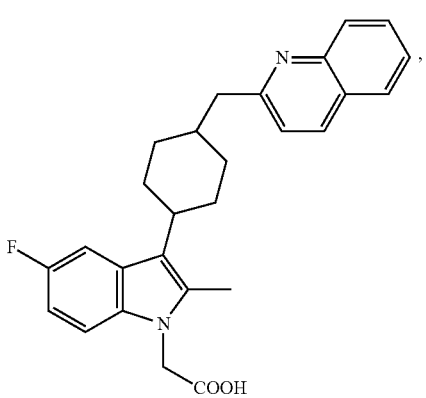
(67)
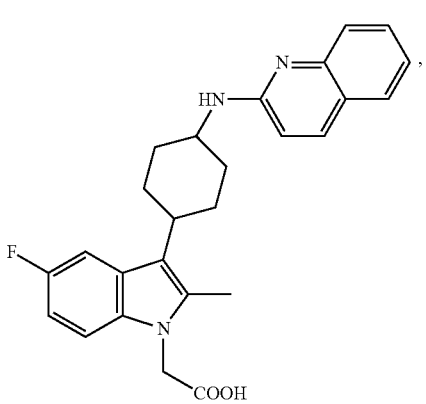
(68)
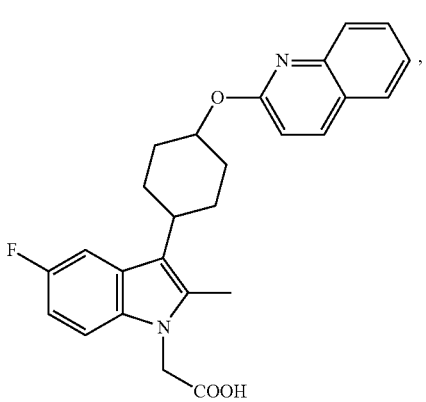

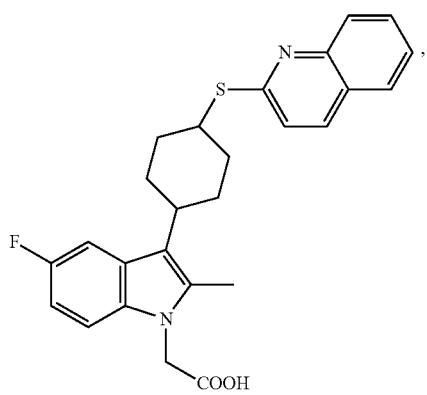
(69)
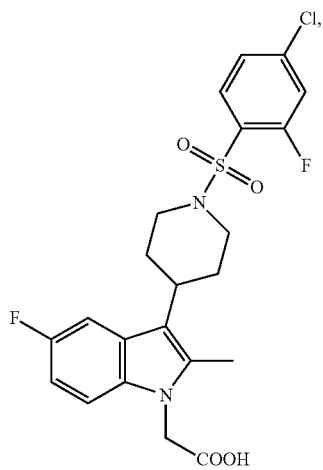
(73)
(70)
(74)
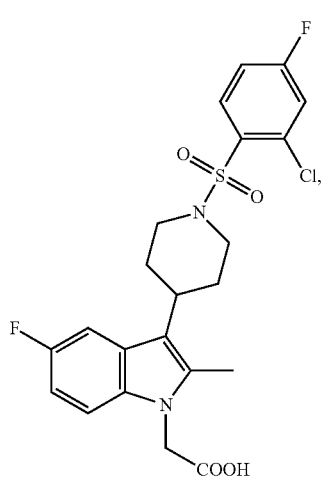
(71)
(72)
(75)
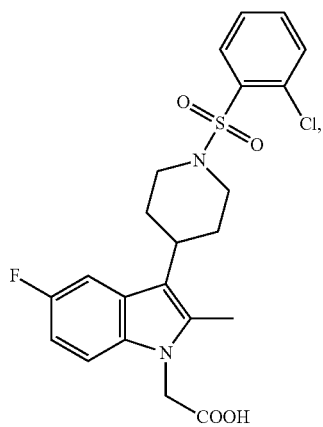

63
-continued
(76)
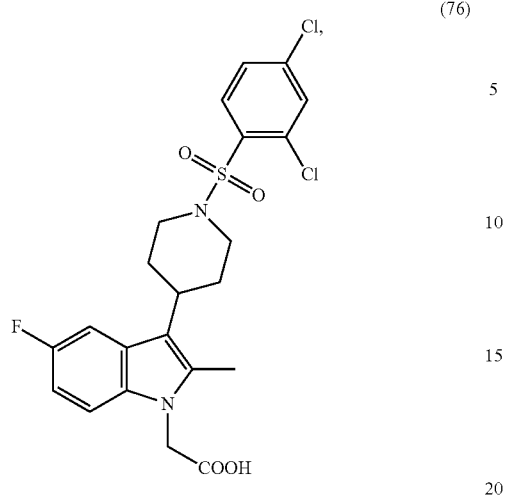
(77)
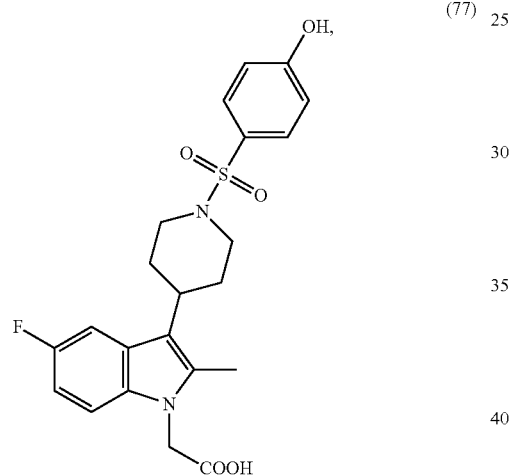
(78)
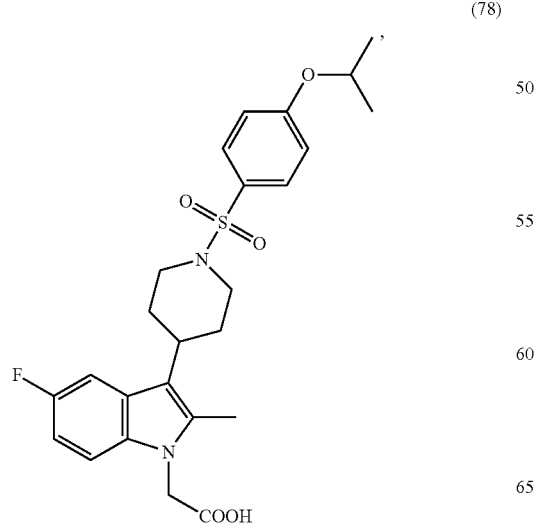
64
-continued
(79)
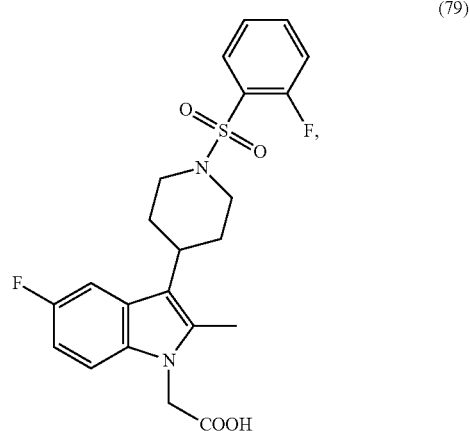
(80)
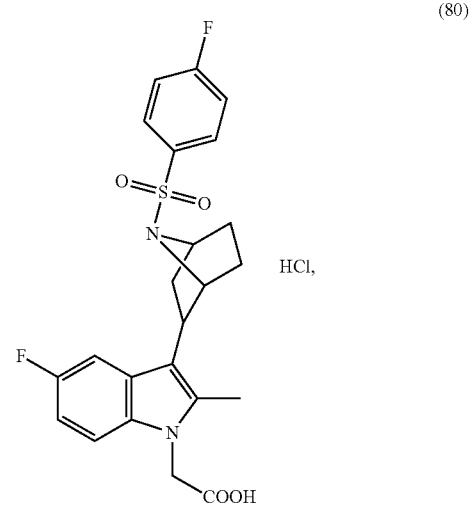
(81)
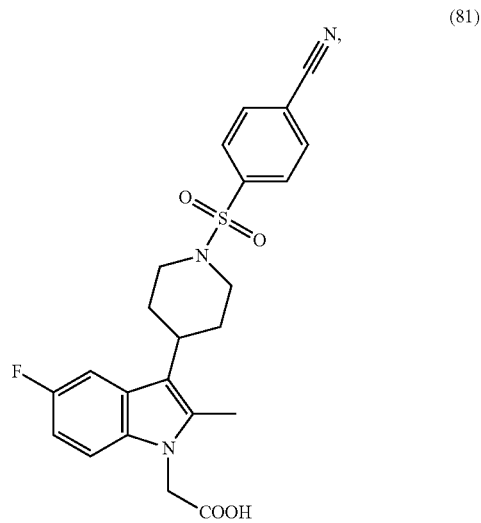

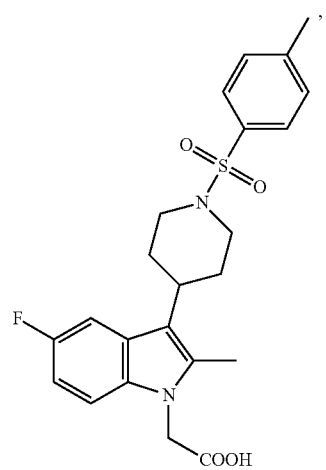
(82)
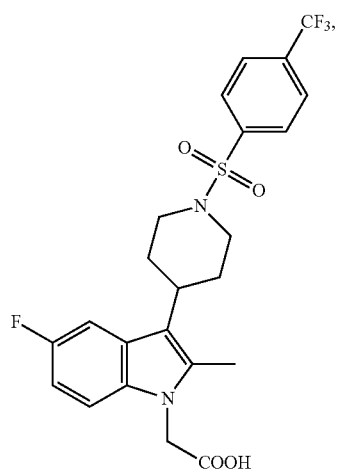
(83)
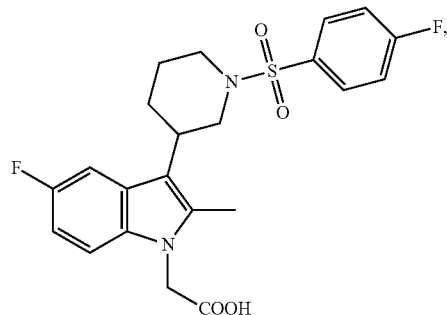
(84)
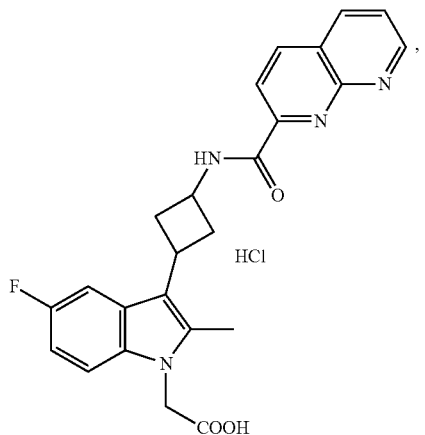
(85)
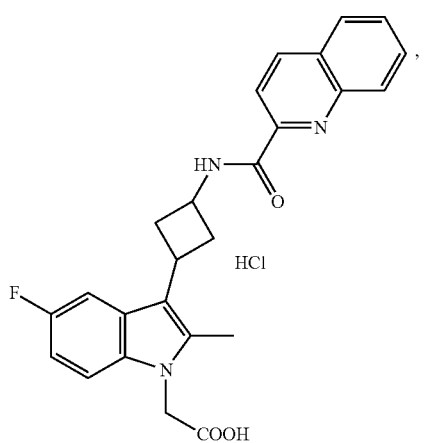
(86)
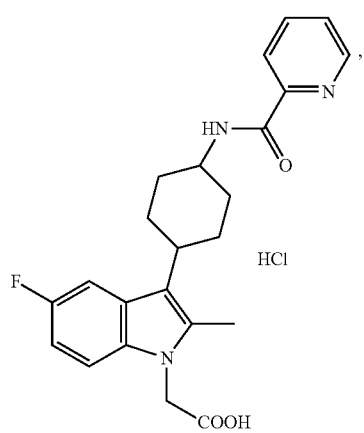
(87)

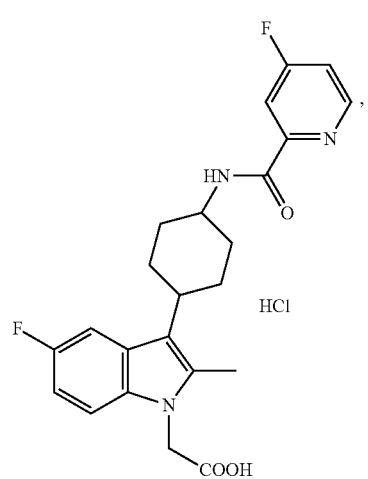
(88)
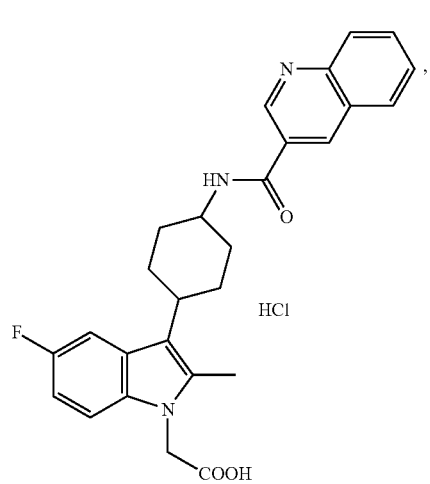
(91)
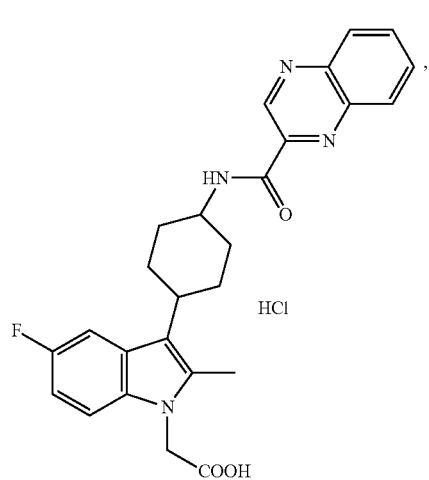
(89)
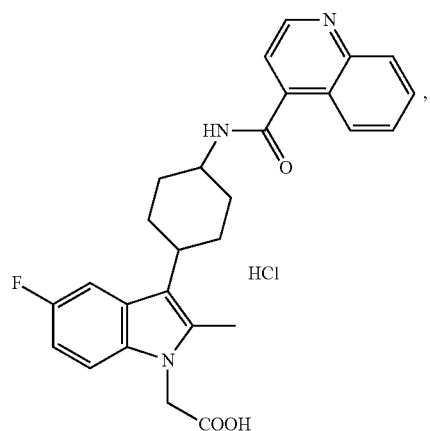
(92)
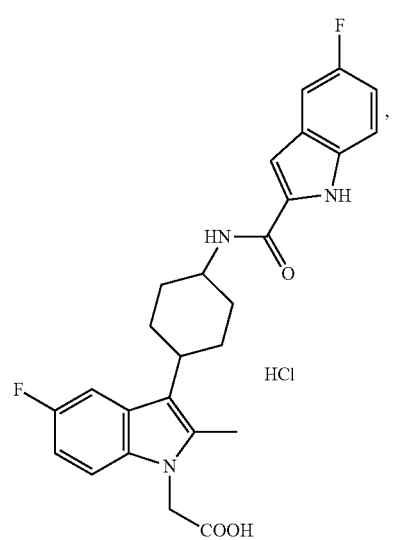
(90)
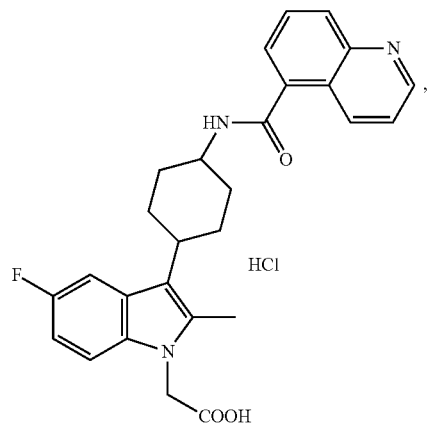
(93)

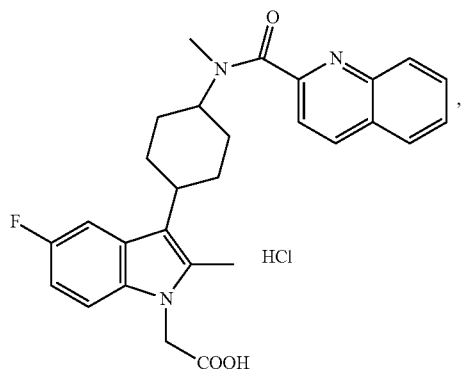
(94)
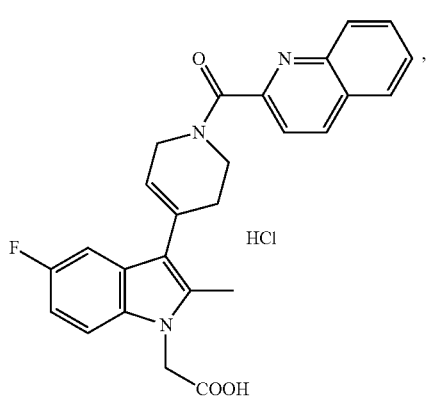
(98)
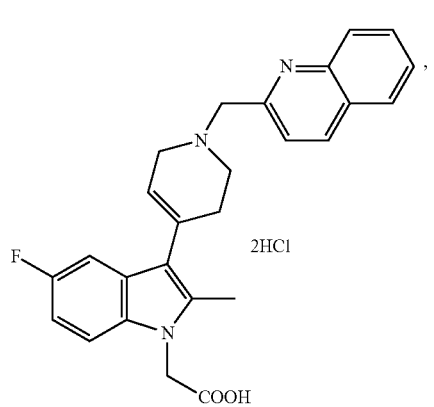
(95)
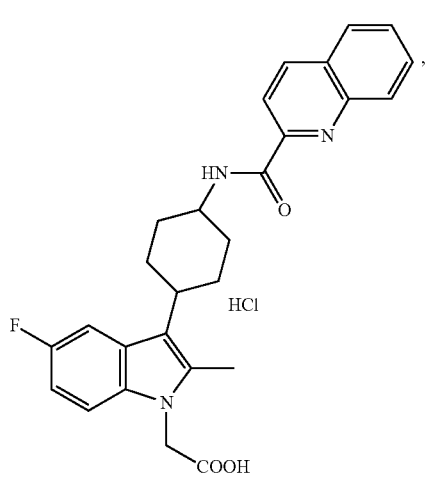
(99)
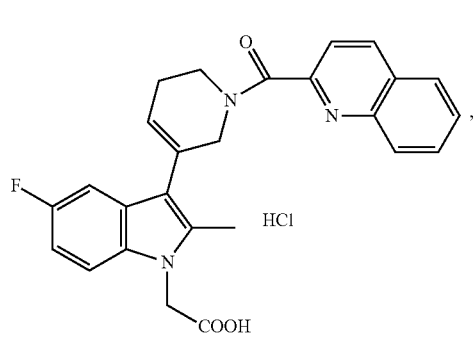
(96)
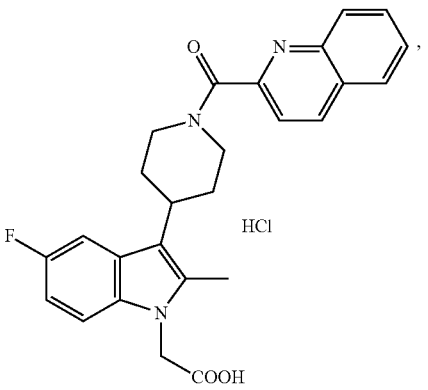
(100)
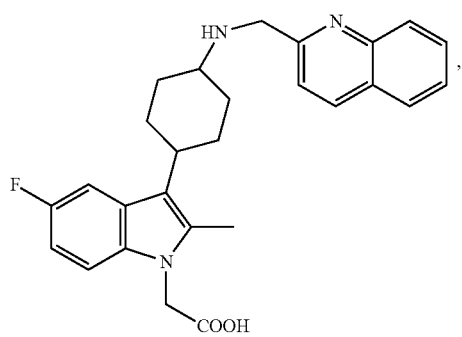
(97)

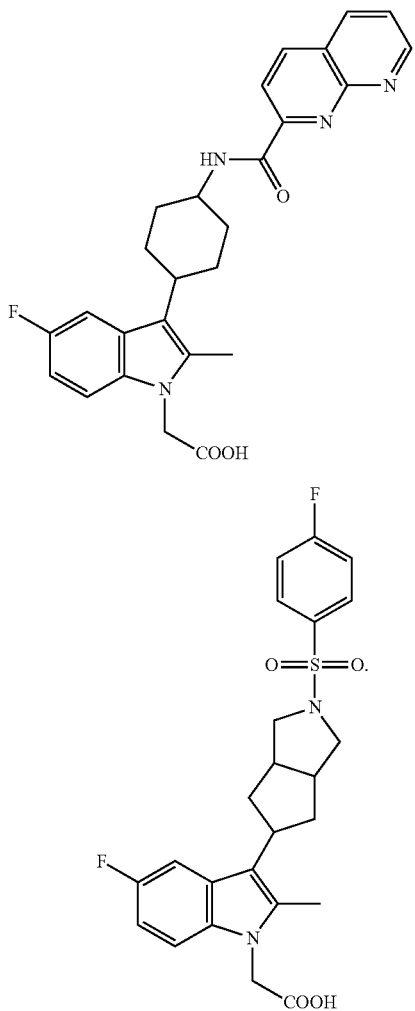

(101) or (102)

In one aspect, provided herein is a crystalline form of 2-(5-fluoro-3-(1-((4-fluorophenyl)sulfonyl)piperidin-4-yl)-2-methyl-1H-indol-1-yl)acetic acid (Formula VI), wherein the crystalline form is crystalline form I, crystalline form II, crystalline form III, crystalline form IV, crystalline form V or crystalline form VI,

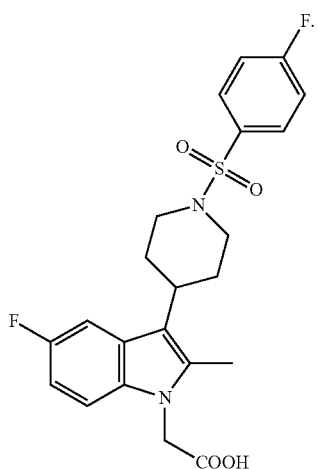

(VI)

In some embodiments, the crystalline form I of 2-(5-fluoro-3-(1-((4-fluorophenyl)sulfonyl)piperidin-4-yl)-2-methyl-1H-indol-1-yl)acetic acid (Formula VI) has an X-ray powder diffraction (XRPD) pattern comprising peaks expressed in degrees 2θ at 3.80°, 13.20°, 15.46°, 17.24°, 18.90°, 19.27°, 19.57°, 23.84° and 28.39°, wherein the error margin is ±0.2°.

In some embodiments, the crystalline form I has an X-ray powder diffraction (XRPD) pattern comprising peaks expressed in degrees 2θ at 3.80°, 8.56°, 12.77°, 13.20°, 15.46°, 17.24°, 18.90°, 19.27°, 19.57°, 22.98°, 23.84°, 26.18°, 27.54°, 28.39°, 29.87°, 30.57° and 30.98°, wherein the error margin is ±0.2°.

In some embodiments, the crystalline form I has an X-ray powder diffraction (XRPD) pattern comprising peaks expressed in degrees 2θ at 3.80°, 7.69°, 8.56°, 9.72°, 10.57°, 12.77°, 13.20°, 13.66°, 14.05°, 15.46°, 15.80°, 16.09°, 16.87°, 17.24°, 17.79°, 18.16°, 18.53°, 18.90°, 19.27°, 19.57°, 20.19°, 20.69°, 20.91°, 21.84°, 22.62°, 22.98°, 23.31°, 23.84°, 24.47°, 25.51°, 25.75°, 26.18°, 26.65°, 27.54°, 28.11°, 28.39°, 28.68°, 28.99°, 29.27°, 29.56°, 29.87°, 30.57°, 30.98°, 31.25°, 32.14°, 32.69°, 32.90°, 33.72°, 34.23° and 34.76°, wherein the error margin is ±0.2°.

In some embodiments, the crystalline form I has an X-ray powder diffraction (XRPD) pattern substantially the same as shown in FIG. 1.

In some embodiments, the crystalline form I has a differential scanning calorimetry thermogram comprising endothermic peaks at 123.99° C.±3° C. and 217.23° C.±3° C.

In some embodiments, the crystalline form I has a differential scanning calorimetry thermogram substantially the same as shown in FIG. 2.

In some embodiments, the crystalline form I has a weight loss ratio of 3.991%, in thermogravimetric analysis, showing the crystalline form I is 2-(5-fluoro-3-(1-((4-fluorophenyl)sulfonyl)piperidin-4-yl)-2-methyl-1H-indol-1-yl)acetic acid monohydrate.

In some embodiments, the crystalline form I has a TGA diagram substantially the same as shown in FIG. 3.

In some embodiments, the crystalline form I has a DVS profile substantially the same as shown in FIG. 19.

In some embodiments, the crystalline form II of 2-(5-fluoro-3-(1-((4-fluorophenyl)sulfonyl)piperidin-4-yl)-2-methyl-1H-indol-1-yl)acetic acid (Formula VI) has an X-ray powder diffraction (XRPD) pattern comprising peaks expressed in degrees 2θ at 5.96°, 12.09°, 13.17°, 14.14°, 15.96°, 16.85°, 17.97°, 20.77°, 24.07°, 24.64° and 28.99°, wherein the error margin is ±0.2°.

In some embodiments, the crystalline form II has an X-ray powder diffraction (XRPD) pattern comprising peaks expressed in degrees 2θ at 5.96°, 12.09°, 13.17°, 14.14°, 15.96°, 16.85°, 17.97°, 18.41°, 20.77°, 22.84°, 24.07°, 24.64°, 25.81°, 28.99° and 29.77°, wherein the error margin is ±0.2°.

In some embodiments, the crystalline form II has an X-ray powder diffraction (XRPD) pattern comprising peaks expressed in degrees 2θ at 5.96°, 7.94°, 10.52°, 10.95°, 12.09°, 13.17°, 14.14°, 14.79°, 15.96°, 16.85°, 17.68°, 17.97°, 18.41°, 19.28°, 19.96°, 20.63°, 20.77°, 21.20°, 22.02°, 22.84°, 23.28°, 24.07°, 24.64°, 24.99°, 25.81°, 26.43°, 26.69°, 26.98°, 27.41°, 27.93°, 28.48°, 28.99°, 29.77°, 30.95°, 31.74°, 32.21°, 33.17°, 34.14°, 34.53°, 35.24°, 36.30°, 37.19°, 38.61° and 39.57°, wherein the error margin is ±0.2°.

In some embodiments, the crystalline form II has an X-ray powder diffraction (XRPD) pattern substantially the same as shown in FIG. 4.

In some embodiments, the crystalline form II has a differential scanning calorimetry thermogram comprising endothermic peaks at 142.11° C.±3° C. and 215.90° C.±3° C.

In some embodiments, the crystalline form II has a differential scanning calorimetry thermogram substantially the same as shown in FIG. 5.

In some embodiments, the crystalline form II has a weight loss ratio of 9.054% in desolvation process measured by thermogravimetric analysis in a temperature range from about 30° C. to about 180° C., losing ethanol (theoretical value of a weight loss ratio in desolvation process of the 1:1 solvate is 9.36%). The results of DSC indicated that the crystalline form II can transfer to crystalline form VII in a temperature range from about 155° C. to about 170° C., and crystalline form VII can melt at a temperature between 210° C. and 220° C. This means that the crystalline form II is 2-(5-fluoro-3-(1-((4-fluorophenyl)sulfonyl)piperidin-4-yl)-2-methyl-1H-indol-1-yl)acetic acid monoethanolate.

In some embodiments, the crystalline form II has a TGA diagram substantially the same as shown in FIG. 6.

In some embodiments, the crystalline form III of 2-(5-fluoro-3-(1-((4-fluorophenyl)sulfonyl)piperidin-4-yl)-2-methyl-1H-indol-1-yl)acetic acid (Formula VI) has an X-ray powder diffraction (XRPD) pattern comprising peaks expressed in degrees 2θ at 15.67°, 16.20°, 18.28°, 20.02°, 20.89°, 23.28° and 24.62°, wherein the error margin is ±0.2°.

In some embodiments, the crystalline form III has an X-ray powder diffraction (XRPD) pattern comprising peaks expressed in degrees 2θ at 13.33°, 15.67°, 16.20°, 17.44°, 18.28°, 20.02°, 20.89°, 23.28°, 24.62° and 26.95°, wherein the error margin is ±0.2°.

In some embodiments, the crystalline form III has an X-ray powder diffraction (XRPD) pattern comprising peaks expressed in degrees 2θ at 5.77°, 7.79°, 10.51°, 12.00°, 12.76°, 13.33°, 13.94°, 15.67°, 16.20°, 16.85°, 17.44°, 18.28°, 19.06°, 19.65°, 20.02°, 20.89°, 21.16°, 22.79°, 23.07°, 23.28°, 23.92°, 24.62°, 25.31°, 26.39°, 26.95°, 27.26°, 27.55°, 28.14°, 29.23°, 29.82°, 30.85°, 31.66°, 32.04°, 33.45°, 34.10°, 35.13°, 35.64°, 36.51°, 37.19° and 37.97°, wherein the error margin is ±0.2°.

In some embodiments, the crystalline form III has an X-ray powder diffraction (XRPD) pattern substantially the same as shown in FIG. 7.

In some embodiments, the crystalline form III has a differential scanning calorimetry thermogram comprising an endothermic peak at 152.50° C.±3° C.

In some embodiments, the crystalline form III has a differential scanning calorimetry thermogram substantially the same as shown in FIG. 8.

In some embodiments, the crystalline form III has a weight loss ratio of 13.56% in desolvation and decomposition process measured by thermogravimetric analysis in a temperature range from about 30° C. to about 165° C., losing N,N-dimethylformamide (theoretical value of a weight loss ratio in desolvation and decomposition process of the 1:1 solvate is 14.01%). This means that the crystalline form 2-(5-fluoro-3-(1-((4-fluorophenyl)sulfonyl)piperidin-4-yl)-2-methyl-1H-indol-1-yl)acetic acid mono-N,N-dimethylformamide.

In some embodiments, the crystalline form III has a TGA diagram substantially the same as shown in FIG. 9.

In some embodiments, the crystalline form IV of 2-(5-fluoro-3-(1-((4-fluorophenyl)sulfonyl)piperidin-4-yl)-2-methyl-1H-indol-1-yl)acetic acid (Formula VI) has an X-ray powder diffraction (XRPD) pattern comprising peaks expressed in degrees 2θ at 16.09°, 18.19°, 20.57°, 20.98°, 24.11°, 24.82° and 25.93°, wherein the error margin is ±0.2°.

In some embodiments, the crystalline form IV has an X-ray powder diffraction (XRPD) pattern comprising peaks expressed in degrees 2θ at 13.24°, 16.09°, 16.83°, 18.19°, 20.57°, 20.98°, 24.11°, 24.82°, 25.93°, 26.30° and 28.46°, wherein the error margin is ±0.2°.

In some embodiments, the crystalline form IV has an X-ray powder diffraction (XRPD) pattern comprising peaks expressed in degrees 2θ at 6.11°, 8.05°, 10.54°, 10.87°, 12.16°, 13.24°, 14.13°, 15.12°, 16.09°, 16.83°, 17.42°, 18.19°, 18.93°, 19.72°, 19.98°, 20.57°, 20.98°, 21.76°, 23.10°, 23.68°, 24.11°, 24.43°, 24.82°, 25.93°, 26.30°, 26.60°, 26.85°, 27.27°, 27.52°, 27.96°, 28.46°, 29.01°, 29.29°, 30.04°, 30.94°, 31.69°, 32.43°, 33.12°, 34.18°, 34.72°, 35.49°, 35.89°, 36.37°, 36.99°, 37.41°, 37.97° and 38.70°, wherein the error margin is ±0.2°.

In some embodiments, the crystalline form IV has an X-ray powder diffraction (XRPD) pattern substantially the same as shown in FIG. 10.

In some embodiments, the crystalline form IV has a differential scanning calorimetry thermogram comprising an endothermic peak at 185.0° C.±3° C.

In some embodiments, the crystalline form IV has a differential scanning calorimetry thermogram substantially the same as shown in FIG. 11.

In some embodiments, the crystalline form IV has a weight loss ratio of 16.09% in desolvation and decomposition process measured by thermogravimetric analysis in a temperature range from about 50° C. to about 215° C., losing dimethyl sulfoxide (theoretical value of a weight loss ratio in desolvation and decomposition process of the 1:1 solvate is 14.84%). This means that the crystalline form IV is 2-(5-fluoro-3-(1-((4-fluorophenyl)sulfonyl)piperidin-4-yl)-2-methyl-1H-indol-1-yl)acetic acid mono-dimethyl sulfoxide.

In some embodiments, the crystalline form IV has a TGA diagram substantially the same as shown in FIG. 12.

In some embodiments, the crystalline form V of 2-(5-fluoro-3-(1-((4-fluorophenyl)sulfonyl)piperidin-4-yl)-2-methyl-1H-indol-1-yl)acetic acid (Formula VI) has an X-ray powder diffraction (XRPD) pattern comprising peaks expressed in degrees 2θ at 5.88°, 12.86°, 15.68°, 17.69°, 20.50°, 23.60° and 24.17°, wherein the error margin is ±0.2°.

In some embodiments, the crystalline form V has an X-ray powder diffraction (XRPD) pattern comprising peaks expressed in degrees 2θ at 5.88°, 11.91°, 12.86°, 15.68°, 17.69°, 20.17°, 20.50°, 23.60°, 24.17° and 25.31°, wherein the error margin is ±0.2°.

In some embodiments, the crystalline form V has an X-ray powder diffraction (XRPD) pattern comprising peaks expressed in degrees 2θ at 5.88°, 7.83°, 10.51°, 11.91°, 12.86°, 13.81°, 15.68°, 16.49°, 17.26°, 17.69°, 18.15°, 19.52°, 20.17°, 20.50°, 20.79°, 22.39°, 22.81°, 23.60°, 24.17°, 24.49°, 25.31°, 25.88°, 26.82°, 27.40°, 27.83°, 28.28°, 28.70°, 29.19°, 30.18°, 30.60°, 30.97°, 31.58°, 32.36°, 33.69°, 34.42°, 35.03°, 36.52° and 37.29°, wherein the error margin is ±0.2°.

In some embodiments, the crystalline form V has an X-ray powder diffraction (XRPD) pattern substantially the same as shown in FIG. 13.

In some embodiments, the crystalline form V has a differential scanning calorimetry thermogram comprising endothermic peaks at 159.91° C.±3° C. and 216.52° C.±3° C.

In some embodiments, the crystalline form V has a differential scanning calorimetry thermogram substantially the same as shown in FIG. 14.

In some embodiments, the crystalline form V has a weight loss ratio of 14.31% in desolvation and decomposition process measured by thermogravimetric analysis in a temperature range from about 110° C. to about 215° C., losing t-butanol (theoretical value of a weight loss ratio in desolvation and decomposition process of the 1:1 solvate is 14.18%). This means that the crystalline form V is 2-(5-fluoro-3-(1-((4-fluorophenyl)sulfonyl)piperidin-4-yl)-2-methyl-1H-indol-1-yl)acetic acid mono-t-butanolate.

In some embodiments, the crystalline form V has a TGA diagram substantially the same as shown in FIG. 15.

In some embodiments, the crystalline form VI of 2-(5-fluoro-3-(1-((4-fluorophenyl)sulfonyl)piperidin-4-yl)-2-methyl-1H-indol-1-yl)acetic acid (Formula VI) has an X-ray powder diffraction (XRPD) pattern comprising peaks expressed in degrees 2θ at 5.84°, 12.83°, 13.20°, 15.72°, 17.63°, 23.62° and 28.94°, wherein the error margin is ±0.2°.

In some embodiments, the crystalline form VI has an X-ray powder diffraction (XRPD) pattern comprising peaks expressed in degrees 2θ at 5.84°, 11.96°, 12.83°, 13.20°, 15.72°, 17.63°, 23.62°, 24.20°, 24.46° and 28.94°, wherein the error margin is ±0.2°.

In some embodiments, the crystalline form VI has an X-ray powder diffraction (XRPD) pattern comprising peaks expressed in degrees 2θ at 5.84°, 7.83°, 11.96°, 12.83°, 13.20°, 13.76°, 15.72°, 16.49°, 17.63°, 18.30°, 18.87°, 19.55°, 20.43°, 20.74°, 20.98°, 22.67°, 23.03°, 23.62°, 24.20°, 24.46°, 25.18°, 25.88°, 26.62°, 27.17°, 27.47°, 27.84°, 28.36°, 28.94°, 30.12°, 30.41°, 30.79°, 31.52°, 31.80°, 32.70°, 34.33°, 36.11° and 36.62°, wherein the error margin is ±0.2°.

In some embodiments, the crystalline form VI has an X-ray powder diffraction (XRPD) pattern substantially the same as shown in FIG. 16.

In some embodiments, the crystalline form VI has a differential scanning calorimetry thermogram comprising endothermic peaks at 153.83° C.±3° C. and 216.70° C.±3° C.

In some embodiments, the crystalline form VI has a differential scanning calorimetry thermogram substantially the same as shown in FIG. 17.

In some embodiments, the crystalline form VI has a weight loss ratio of 13.07% in desolvation and decomposition process measured by thermogravimetric analysis in a temperature range from about 100° C. to about 220° C., losing isopropanol (theoretical value of a weight loss ratio in desolvation and decomposition process of the 1:1 solvate is 11.82%). This means that the crystalline form III is 2-(5-fluoro-3-(1-((4-fluorophenyl)sulfonyl)piperidin-4-yl)-2-methyl-1H-indol-1-yl)acetic acid mono-isopropanolate.

In some embodiments, the crystalline form VI has a TGA diagram substantially the same as shown in FIG. 18.

Provided herein is a pharmaceutical composition comprising the compound disclosed herein.

In some embodiments, the pharmaceutical composition disclosed herein further comprises at least one of pharmaceutically acceptable carriers, excipients, diluents, adjuvants and vehicles.

In some embodiments, the pharmaceutical composition further comprises one or more other active agents used in the treatment of a disease or condition mediated by PGD$_2$ at the CRTH2 receptor.

In some embodiments of the pharmaceutical composition, the other active agent is a TNF-α inhibitor, a COX-1/COX-2 inhibitor, a COX-2 inhibitor, glucocorticoid, inactivated antibody for interleukin, a regulator for chemotactic factor receptors, an antagonist for histamine H1 receptor/antihistamine, a leukotriene D4 receptor antagonist, an LTD4 antagonist, a VLA-4 antagonist, a corticosteroids analogue, theophylline, a leukotriene biosynthetic inhibitor, an epoxidase-2 inhibitor, an opioids analgesic, an anticoagulant, a β-blocking agent, a β-adrenergic agonist, an angiotensin converting enzyme inhibitor, an HMG-CoA reductase inhibitor, a β2-agonist, corticosteroid, antihistamine, a leukotriene antagonist, an anti-IgE antibody therapy, an anti-infectious agent, an antifungal agent, immunosuppressor, other antagonist of PGD$_2$ acting at other receptors, an inhibitor of phosphodiesterase type 4, a drug that modulates cytokine production, a drug that modulates the activity of Th2 cytokines IL-4 and IL-5, a 5-lipoxygenase inhibitor.

In some embodiments of the pharmaceutical composition, wherein the active agent is salmeterol, fluticasone, loratadine, montelukast, omalizumab, fusidic acid, clotrimazole, tacrolimus, pimecrolimus, DP antagonist, cilomilast, TNF-α converting enzyme (TACE) inhibitor, blocking monoclonal antibody or soluble receptor of IL-4 and IL-5 orzileuton.

In other aspect, provided herein is use of the compound or the pharmaceutical composition disclosed herein in the manufacture of a medicament for preventing, managing, treating or lessening diseases mediated by PGD$_2$ at the CRTH2 receptor.

In some embodiments of the use, wherein the disease mediated by PGD2 at the CRTH2 receptor is asthma, COPD, allergic asthma, perennial allergic rhinitis, seasonal allergic rhinitis, atopic dermatitis, contact hypersensitivity, conjunctivitis, eosinophilic bronchitis, food allergies, eosinophilic gastroenteritis, inflammatory bowel disease, ulcerative colitis and Crohn's disease, mastocytosis, autoimmune disease, psoriasis, acne, multiple sclerosis, allograft rejection, reperfusion injury, chronic obstructive pulmonary disease, rheumatoid arthritis, psoriatic arthritis or osteoarthritis.

In other embodiments of the use, wherein the autoimmune disease is psoriasis, multiple sclerosis, allograft rejection, rheumatoid arthritis, psoriatic arthritis, systemic lupus erythematosus or osteoarthritis.

In other aspect, provided herein is a combination drug comprising the compound and one or more other active agents disclosed herein for use in preventing, managing, treating or lessening diseases mediated by PGD$_2$ at the CRTH2 receptor simultaneously, respectively or successively.

In other aspect, the invention provides a method of preventing, managing, treating or lessening a disease or condition mediated by PGD$_2$ at the CRTH2 receptor in a patient comprising administrating to the patient a therapeutically effective amount of the compound or the pharmaceutical composition disclosed herein.

In other aspect, provided herein is the compound or the pharmaceutical composition disclosed herein used for preventing, managing, treating or lessening diseases mediated by PGD$_2$ at the CRTH2 receptor.

There is also provided the use of a compound of Formula (I)-(IIc) and crystalline forms thereof in the preparation of an agent for the treatment of a disease and condition mediated by PGD$_2$ at the CRTH2 receptor, wherein the agent also comprises the other active agent useful for the treatment of the same diseases and conditions.

In a further aspect of the invention, there is provided a product comprising a novel compound of Formula (I)-(IIc)

and crystalline forms thereof and one or more of the agents listed above as a combined preparation for simultaneous, separate or sequential use in the treatment of a disease or condition mediated by the action of $PGD_2$ at the CRTH2 receptor.

Unless otherwise stated, all stereoisomers, geometric isomers, tautomers, N-oxides, hydrates, solvates, metabolites, salts and pharmaceutically acceptable prodrugs of the compounds disclosed herein are within the scope of the invention. In certain embodiments, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith. The compounds disclosed herein also include salts of the compounds which are not necessarily pharmaceutically acceptable salts, and which may be useful as intermediates for preparing and/or purifying compounds of Formula (I)-(IIc) and crystalline forms thereof, and/or for separating enantiomers of compounds of Formula (I)-(IIc) and crystalline forms thereof.

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, malic acid, 2-hydroxypropionic acid, citric acid, oxalic acid, glycolic acid and salicylic acid; a pyranosidyl acid, such as glucuronic acid and galacturonic acid; an alpha-hydroxy acid, such as citric acid and tartaric acid; an amino acid, such as aspartic acid and glutamic acid; an aromatic acid, such as benzoic acid and cinnamic acid; a sulfonic acid, such as p-toluenesulfonic acid, benzenesulfonic acid, methanesulfonic acid, ethanesulfonic acid, trifluoromethanesulfonic acid, and the like; or the combination thereof.

If the compound disclosed here in is an acid, the desired salt may be prepared by any suitable method, for example, treatment of the free acid with an inorganic or organic base, such as an amine (primary, secondary or tertiary), an alkali metal hydroxide, ammonium, $N^+(R^{14})_4$ salt or alkaline earth metal hydroxide, and the like. Some non-limiting examples of suitable salts include organic salts derived from amino acids, such as glycine and arginine; ammonia, such as primary, secondary and tertiary amine, $N^+(R^{14})_4$ salt, wherein $R^{14}$ is H, $C_{1-4}$ alkyl, $C_{6-10}$ aryl, $C_{6-10}$ aryl-$C_{1-4}$-alkyl, and the like; and cyclic amines, such as piperidine, morpholine and piperazine, and inorganic salts derived from sodium, calcium, potassium, magnesium, manganese, iron, copper, zinc, aluminum, lithium, and the like, and further include, when appropriate, nontoxic ammonium, quaternary ammonium and amine cations formed using counterions such as halide, hydroxide, carboxylate, sulfate, phosphate, nitrate, $C_{1-8}$ sulfonate or aryl sulfonate.

Uses of the Compounds and Compositions of the Invention

The compounds disclosed herein all can be used in the method of treating diseases and conditions mediated by $PGD_2$ at the CRTH2 receptor, which comprises administrating to a patient a suitable amount of the compound of Formula (I)-(IIc) and crystalline forms thereof.

In another aspect of the invention, novel compounds of Formula (I)-(IIc) and crystalline forms thereof provided herein are used in medicine, especially in treating diseases and conditions mediated by $PGD_2$ at the CRTH2 receptor.

As described above, these diseases and conditions comprise allergic asthma, perennial allergic rhinitis, seasonal allergic rhinitis, atopic dermatitis, contact hypersensitivity (including contact dermatitis), conjunctivitis, especially allergic conjunctivitis, eosinophilic bronchitis, food allergies, eosinophilic gastroenteritis, inflammatory bowel disease, ulcerative colitis and Crohn's disease, COPD, mastocytosis and also other $PGD_2$-mediated diseases, for example autoimmune diseases such as hyper IgE syndrome and systemic lupus erythematosus, psoriasis, acne, multiple sclerosis, allograft rejection, reperfusion injury, chronic obstructive pulmonary disease, as well as rheumatoid arthritis, psoriatic arthritis and osteoarthritis.

The compounds of general Formula (I) must be formulated in an appropriate manner depending upon the diseases or conditions they are required to treat Therefore, in a further aspect of the invention there is provided a pharmaceutical composition comprising a novel compound of general Formula (I)-(IIc) and crystalline forms thereof together with a pharmaceutical excipient or carrier. Other active materials may also be present, as may be considered appropriate or advisable for the disease or condition being treated or prevented. The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial or topical administration.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a novel compound of general Formula (I)-(IIb) and crystalline forms thereof in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water-in-oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general Formula (I)-(IIc) and crystalline forms thereof may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Compounds of general Formula (I)-(IIc) and crystalline forms thereof may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Typically, the dose of the compound will be about 0.01 to 100 mg/kg, so as to maintain the concentration of drug in the plasma at a concentration effective to inhibit $PGD_2$ at the CRTH2 receptor. The precise amount of a compound of general Formula (I)-(IIc) and crystalline forms thereof which is therapeutically effective, and the route by which such compound is best administered, are readily determined by one of ordinary skill in the art by comparing the blood level of the agent to the concentration required to have a therapeutic effect.

Typically a therapeutically effective dosage should produce a serum concentration of active ingredient of from about 0.1 ng/mL to about 50-100 µg/mL. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 mg to about 500 mg, from about 20 mg to about 250 mg or from about 25 mg to about 100 mg of the essential active ingredient or a combination of essential ingredients per dosage unit form. In certain embodiments, the pharmaceutical dosage unit forms are prepared to provide about 1 mg, 20 mg, 25 mg, 50 mg, 100 mg, 250 mg, 500 mg, 1000 mg or 2000 mg of the essential active ingredient. In certain embodiments, the pharmaceutical dosage unit forms are prepared to provide about 50 mg of the essential active ingredient.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

As described herein, an "effective amount" or "effective dose" is that amount effective for treating or lessening the severity of one or more of the aforementioned disorders. The compounds and compositions disclosed herein may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

Compounds of Formula (I)-(IIc) and crystalline forms thereof may be used in combination with one or more active agents which are useful in the treatment of the diseases and conditions listed above, although these active agents are not necessarily inhibitors of $PGD_2$ at the CRTH2 receptor. Therefore, the pharmaceutical composition described above may additionally contain one or more of these active agents.

There is also provided the use of a compound of Formula (I)-(IIc) and crystalline forms thereof in the preparation of an agent for the treatment of a disease and condition mediated by $PGD_2$ at the CRTH2 receptor, wherein the agent also comprises an additional active agent useful for the treatment of the same diseases and conditions. These additional active agents which may have a completely different mode of action include existing therapies for allergic and other inflammatory diseases including: β2 agonists such as salmeterol; corticosteroids such as fluticasone; antihistamines such as loratadine; leukotriene antagonists such as montelukast; anti-IgE antibody therapies such as omalizumab; anti-infectives such as fusidic acid (particularly for the treatment of atopic dermatitis); anti-fungals such as clotrimazole (particularly for the treatment of atopic dermatitis); immunosuppressants such as tacrolimus and particularly pimecrolimus in the case of inflammatory skin disease.

CRTH2 antagonists may also be combined with therapies that are in development for inflammatory indications including: other antagonists of $PGD_2$ acting at other receptors, such as DP antagonists; inhibitors of phosphodiesterase type 4 such as cilonilast; drugs that modulate cytokine production such as inhibitors of TNFα converting enzyme (TACE); drugs that modulate the activity of Th2 cytokines IL-4 and IL-5 such as blocking monoclonal antibodies and soluble receptors; PPAR-γ agonists such as rosiglitazone; 5-lipoxygenase inhibitors such as zileuton.

In a further aspect of the invention, there is provided a product comprising a novel compound of Formula (I)-(IIc) and a crystalline form and one or more of the agents listed above as a combined preparation for simultaneous, separate or sequential use in the treatment of a disease or condition mediated by the action of $PGD_2$ at the CRTH2 receptor.

The present application further provides a pharmaceutical composition comprising the compound represented by Formula (I)-(IIc) and crystalline forms thereof, a pharmaceutically acceptable salt thereof and a stereoisomer thereof and one or more therapeutically active substances selected from TNF-α inhibitors, COX-1/COX-2 inhibitors, COX-2 inhibitors, glucocorticoids, inactivated antibodies for interleukin, regulators for chemotactic factor receptor, antagonists for histamine H1 receptors/antihistamines, leukotriene antagonists, LTD4 antagonists, VLA-4 antagonists, corticosteroids, corticosteroids analogues, β2-agonists, theophylline, leukotriene biosynthetic inhibitors, epoxidase-2 inhibitor, phosphodiesterase type IV inhibitors, opioids analgesics, anticoagulants, β-blocking agents, β-adrenergic agonists, angiotensin converting enzyme inhibitors or HMG-CoA reductase inhibitors.

The "composition" described herein refers to any product produced by inert conjugation or polymerization of the active components and constituting carriers, or from decomposition of one or more components, or from other types of reactions or interactions of one or more components in the pharmaceutical composition. Therefore, the pharmaceutical composition of the present application includes any composition prepared by mixing the compound of Formula (I)-(IIc) and a crystalline form with one or more pharmaceutically acceptable excipients.

The pharmaceutical carrier employed may be, for example, a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen. Similarly, the carrier or diluent may include time delay material well known in the art, such as glyceryl monostearate or glycerol distearate, alone or with a wax.

In another aspect, some non-limiting examples of materials which can serve as pharmaceutically acceptable carriers include ion exchanger; aluminum; alumina; aluminum stearate; lecithin; serum protein such as human serum albumin; buffer substance such as phosphate; glycine; sorbic acid; potassium sorbate; partial glyceride mixture of saturated vegetable fatty acid; water; electrolyte such as protamine sulfate, disodium hydrogen phosphate and potassium hydrogen phosphate; salt such as sodium chloride and zinc salt; colloidal silica; magnesium trisilicate; polyvinyl pyrrolidone; polyacrylate; waxe; polyethylene-polyoxypropylene-block polymer; wool fat; sugar such as lactose, glucose and sucrose; starch such as corn starch and potato starch; cellulose and its derivative such as sodium carboxymethyl cellulose, ethyl cellulose and cellulose acetate; powdered tragacanth; malt; gelatin; talc; excipients such as cocoa butter and suppository waxes; oil such as peanut oil, cottonseed oil, safflower oil, sesame oil, olive oil, corn oil and soybean oil; glycol such as propylene glycol and polyethylene glycol; ester such as ethyl oleate and ethyl laurate; agar; buffering agent such as magnesium hydroxide and aluminum hydroxide; alginic acid; pyrogen-free water; isotonic saline; Ringer's solution; ethyl alcohol and phosphate buffer solution, as well as other non-toxic compatible lubricant such as sodium lauryl sulfate and magnesium stearate, coloring agent, releasing agent, coating agent, sweetening, flavoring and perfuming agent, preservative and antioxidant.

GENERAL SYNTHETIC PROCEDURES

Figure 1:
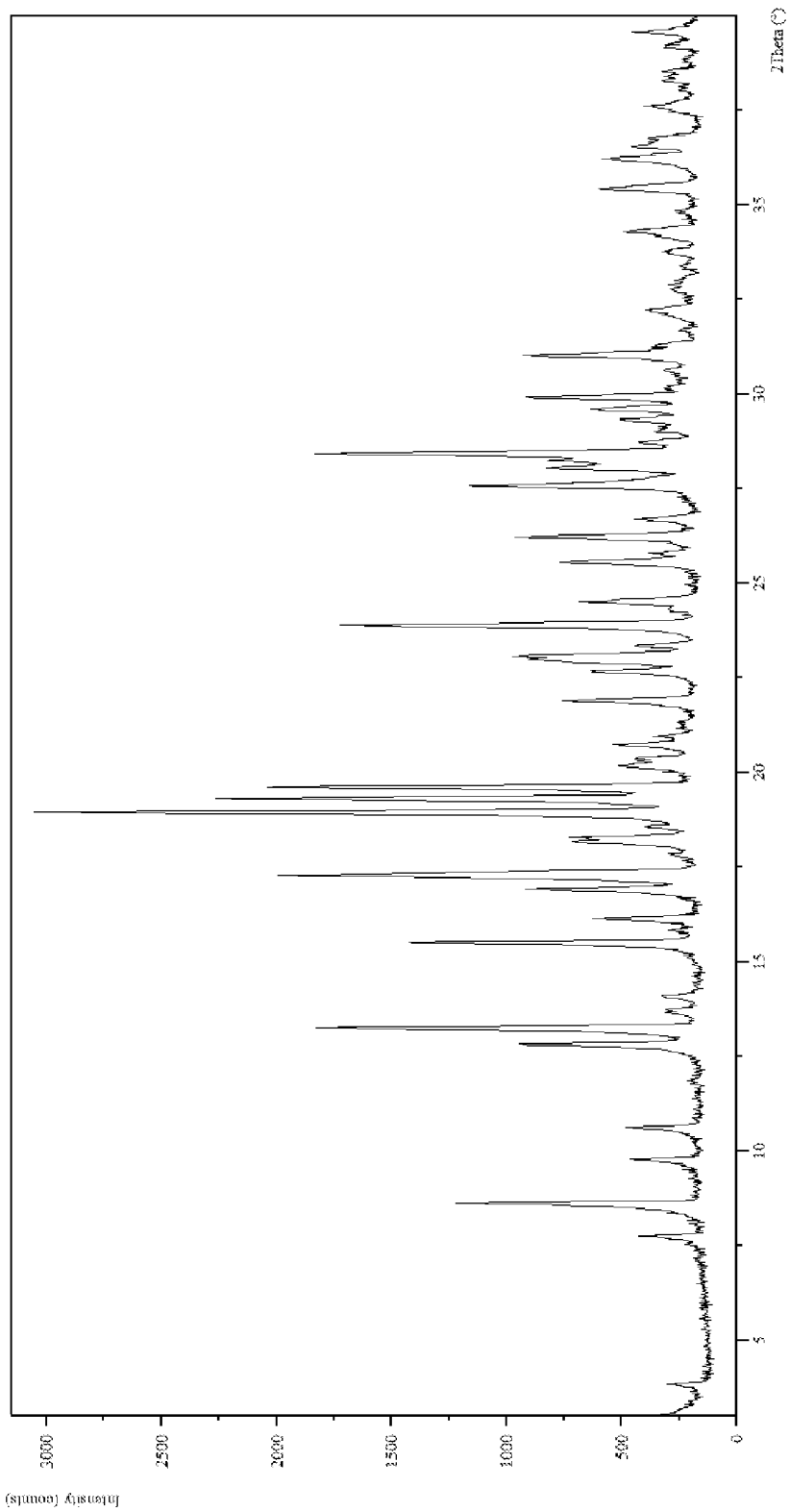
FIG. 1 provides an X-ray powder diffraction (XRPD) pattern of crystalline form I of the compound of Formula VI.
Figure 2:
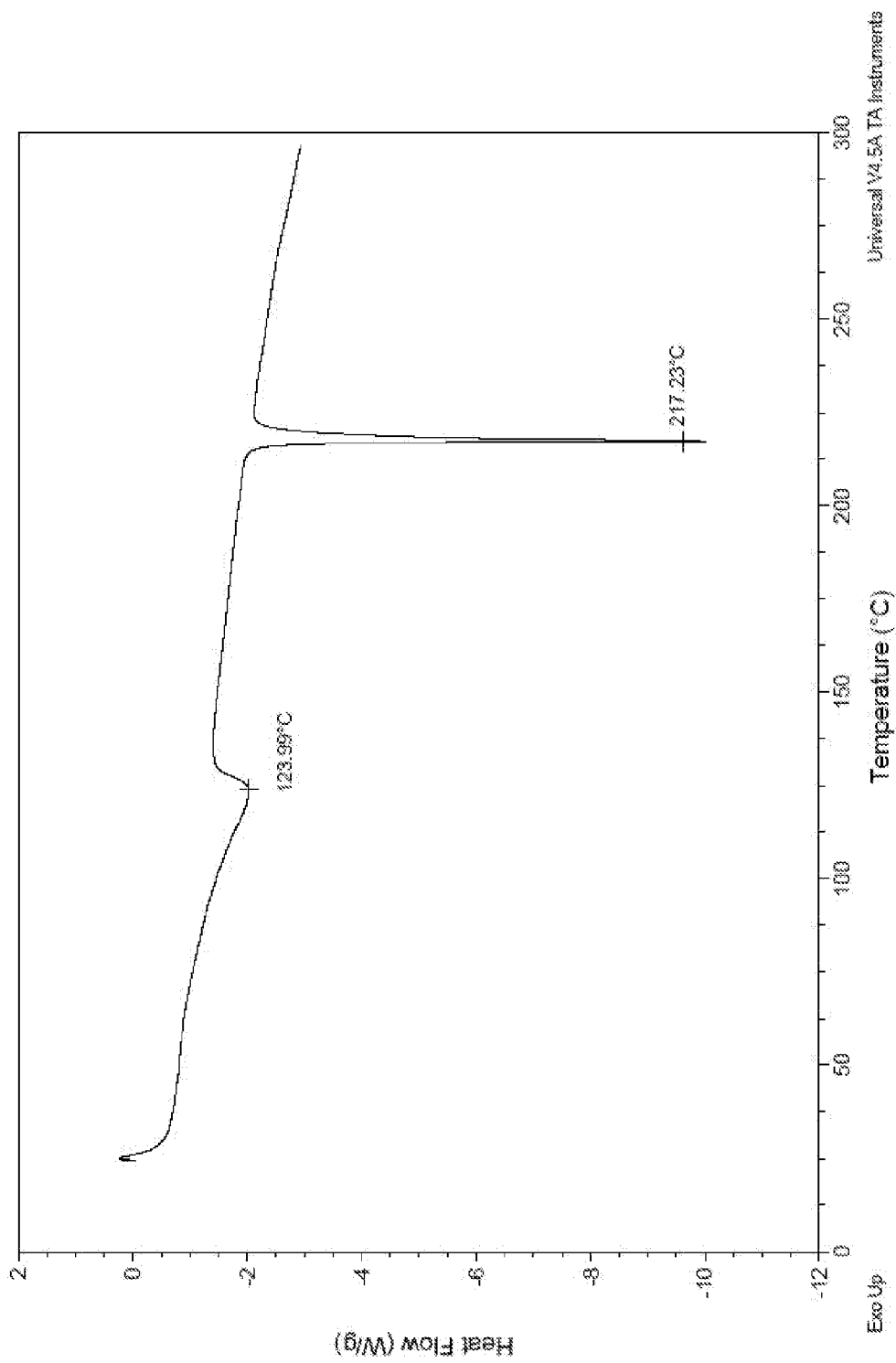
FIG. 2 provides a differential scanning calorimetry (DSC) curve of crystalline form I of the compound of Formula VI.
Figure 3:
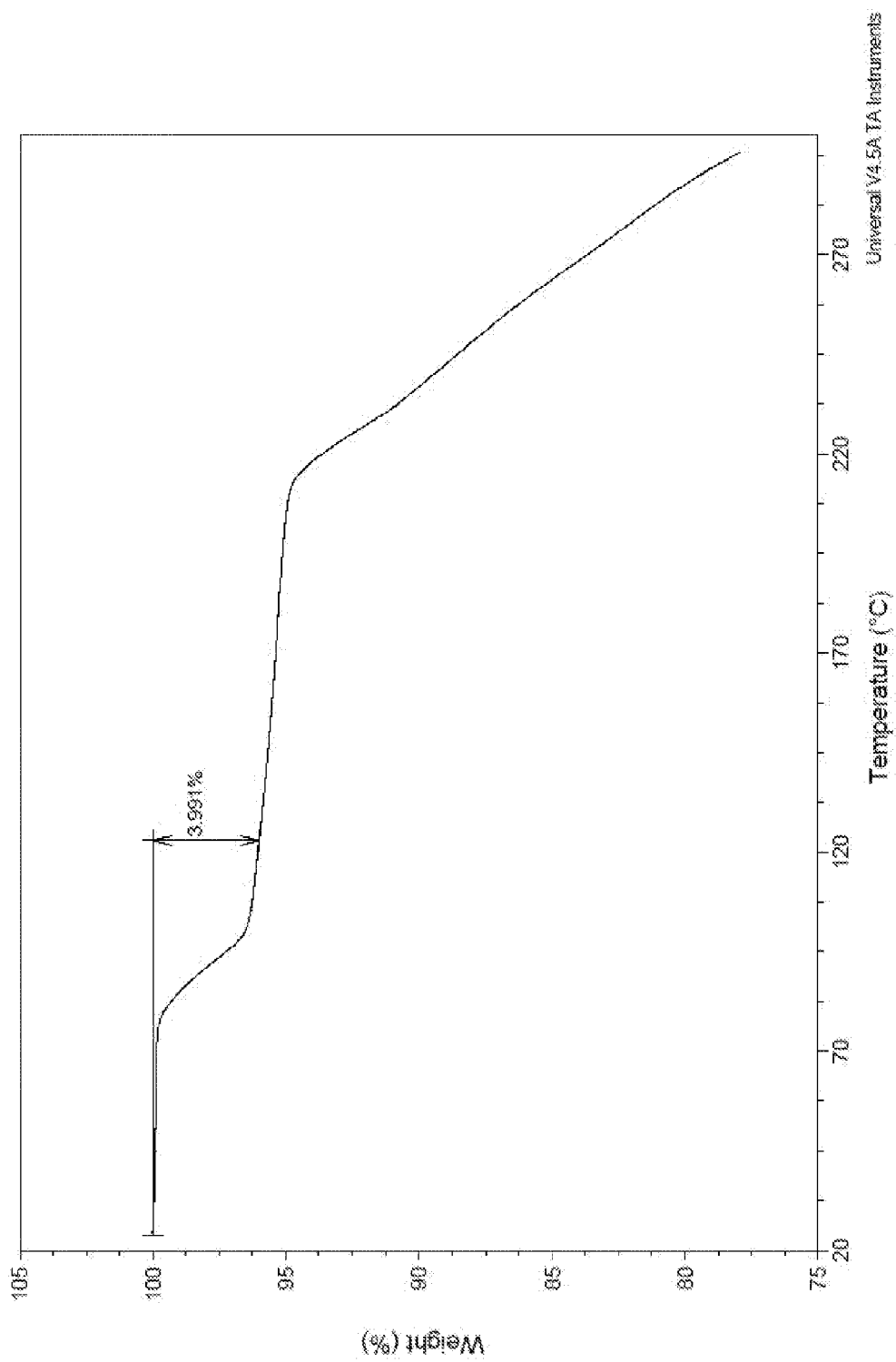
FIG. 3 provides a thermogravimetric analysis (TGA) diagram of crystalline form I of the compound of Formula VI.
Figure 4:
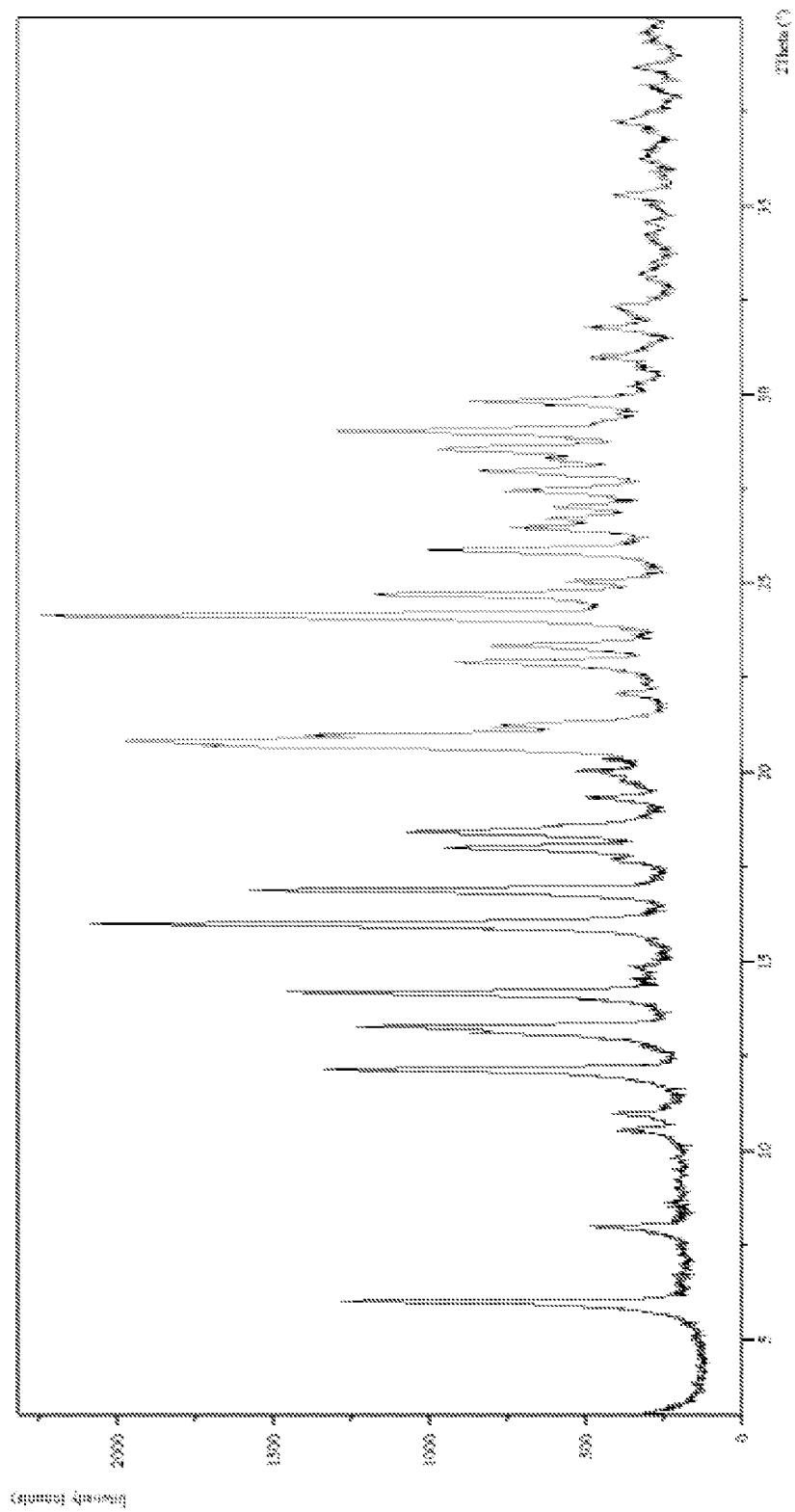
FIG. 4 provides an X-ray powder diffraction (XRPD) pattern of crystalline form II of the compound of Formula VI.
Figure 5:
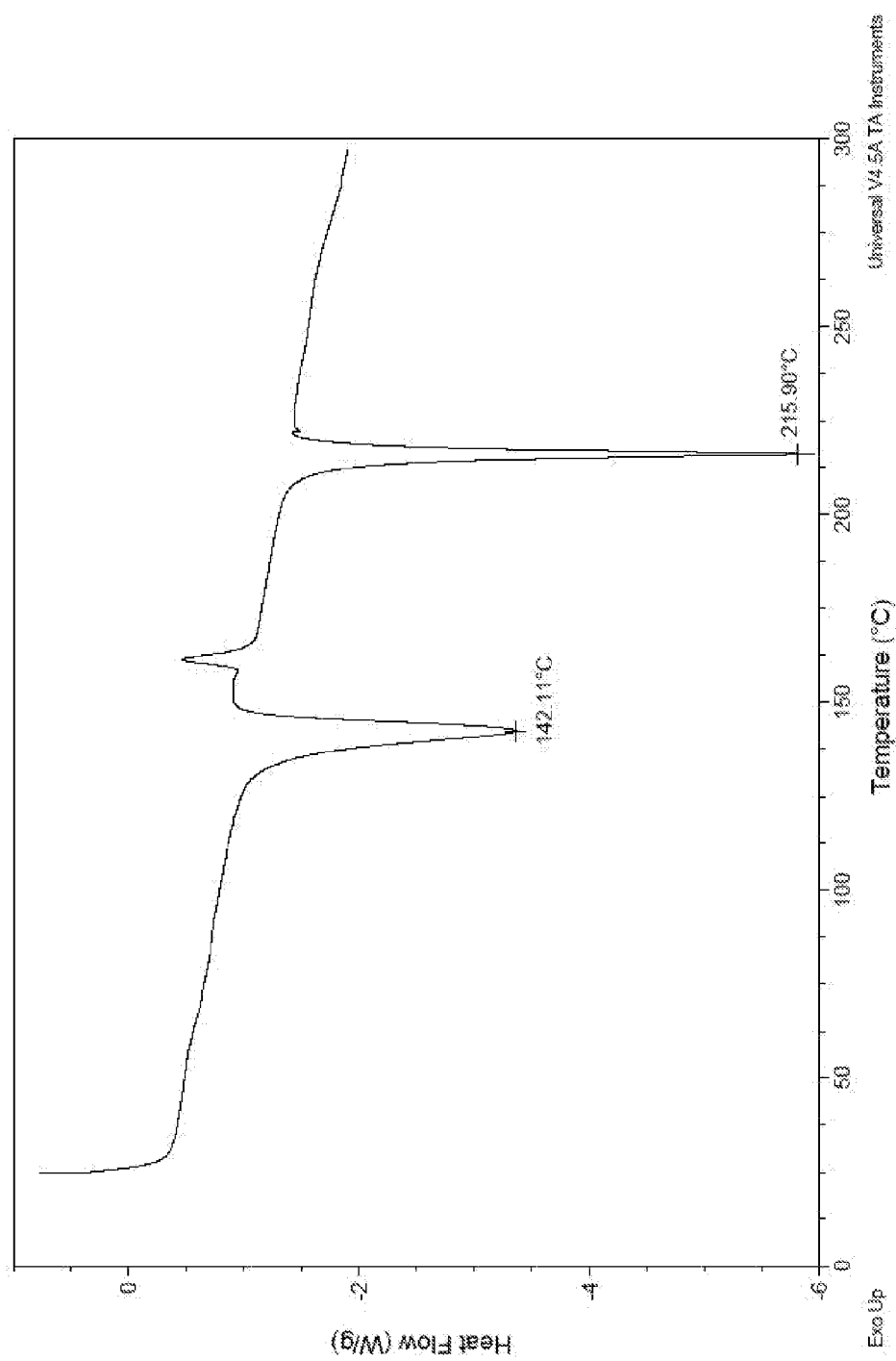
FIG. 5 provides a differential scanning calorimetry (DSC) curve of crystalline form II of the compound of Formula VI.
Figure 6:
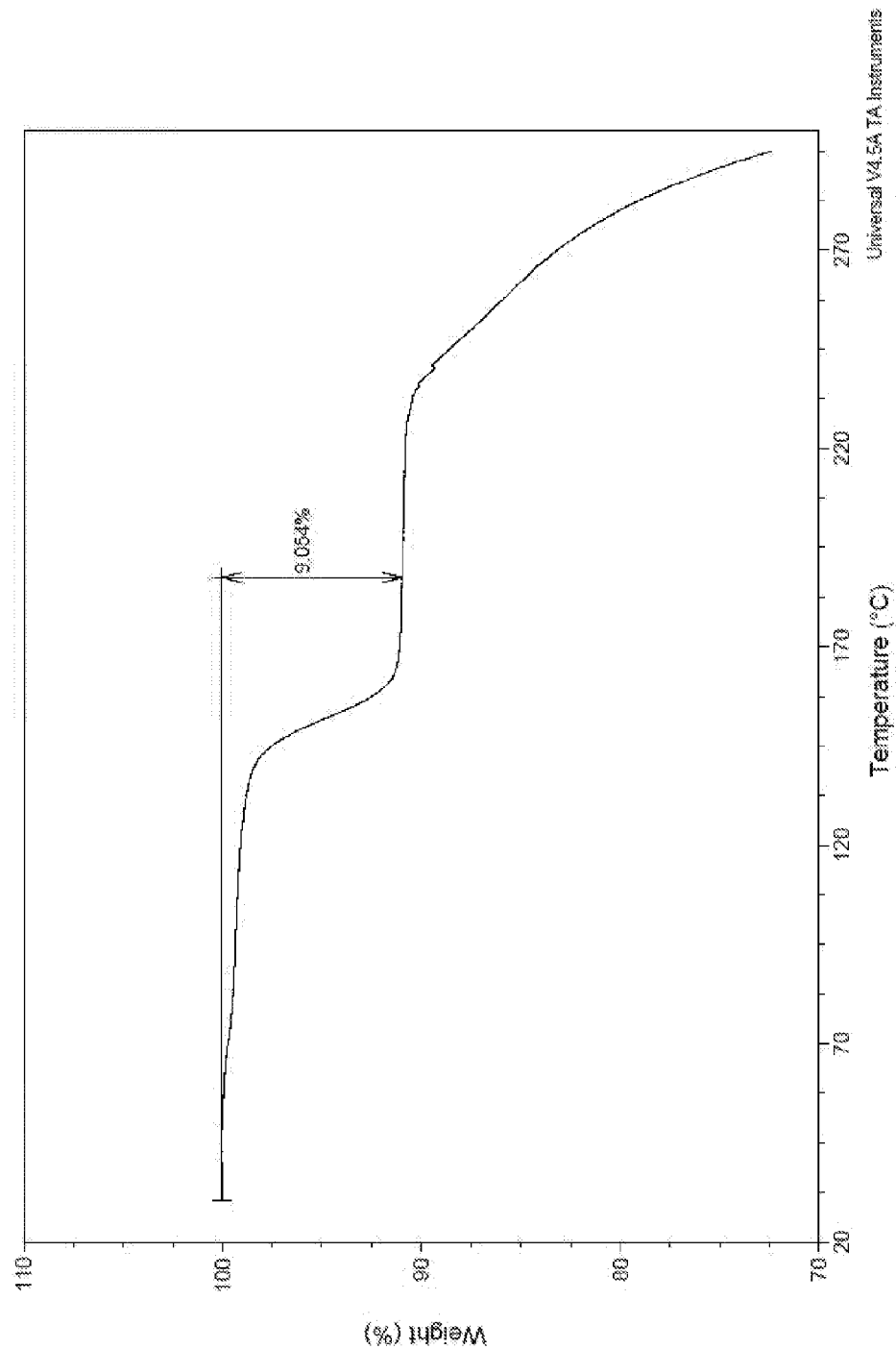
FIG. 6 provides a thermogravimetric analysis (TGA) diagram of crystalline form II of the compound of Formula VI.
Figure 7:
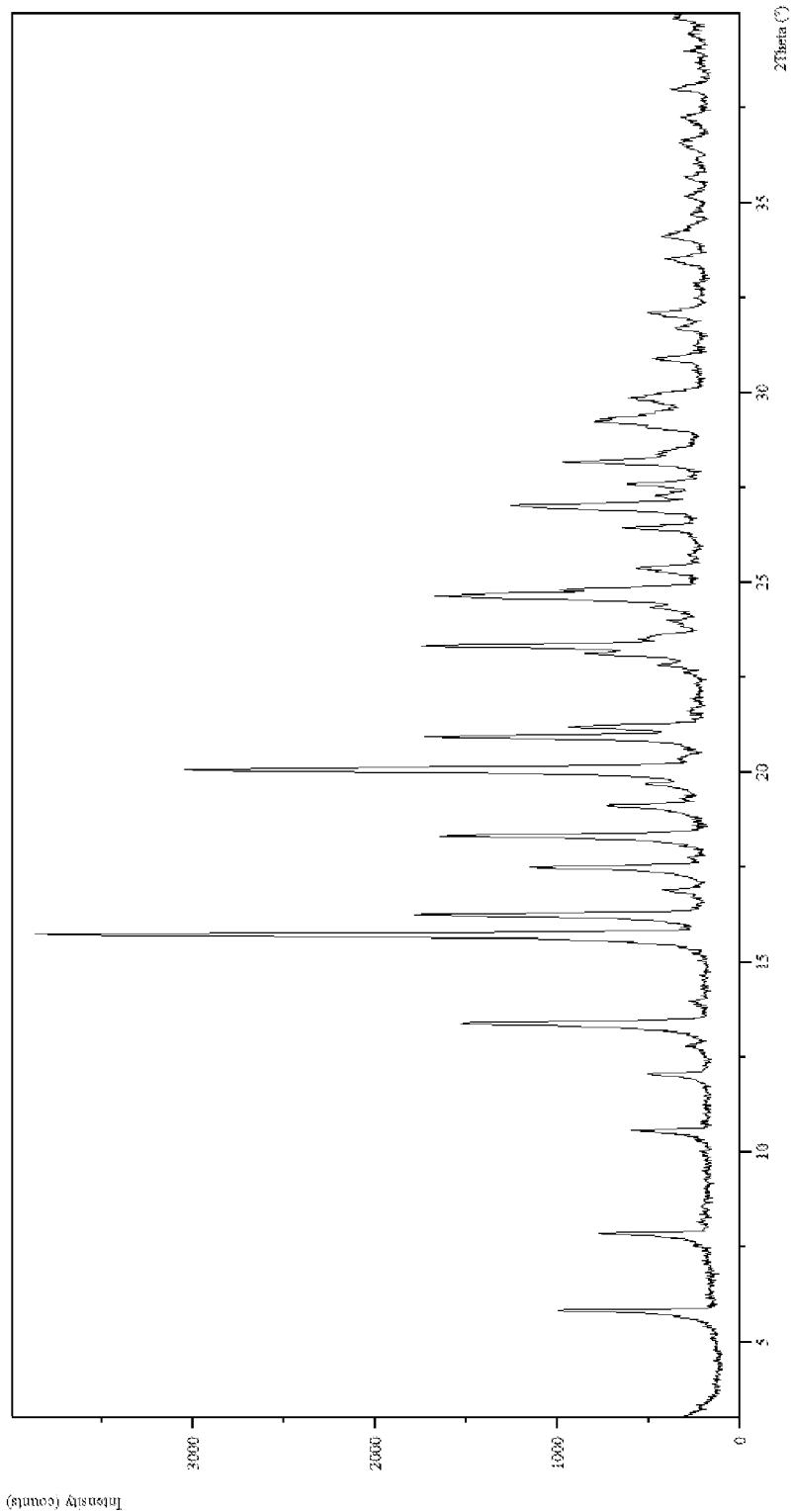
FIG. 7 provides an X-ray powder diffraction (XRPD) pattern of crystalline form III of the compound of Formula VI.
Figure 8:
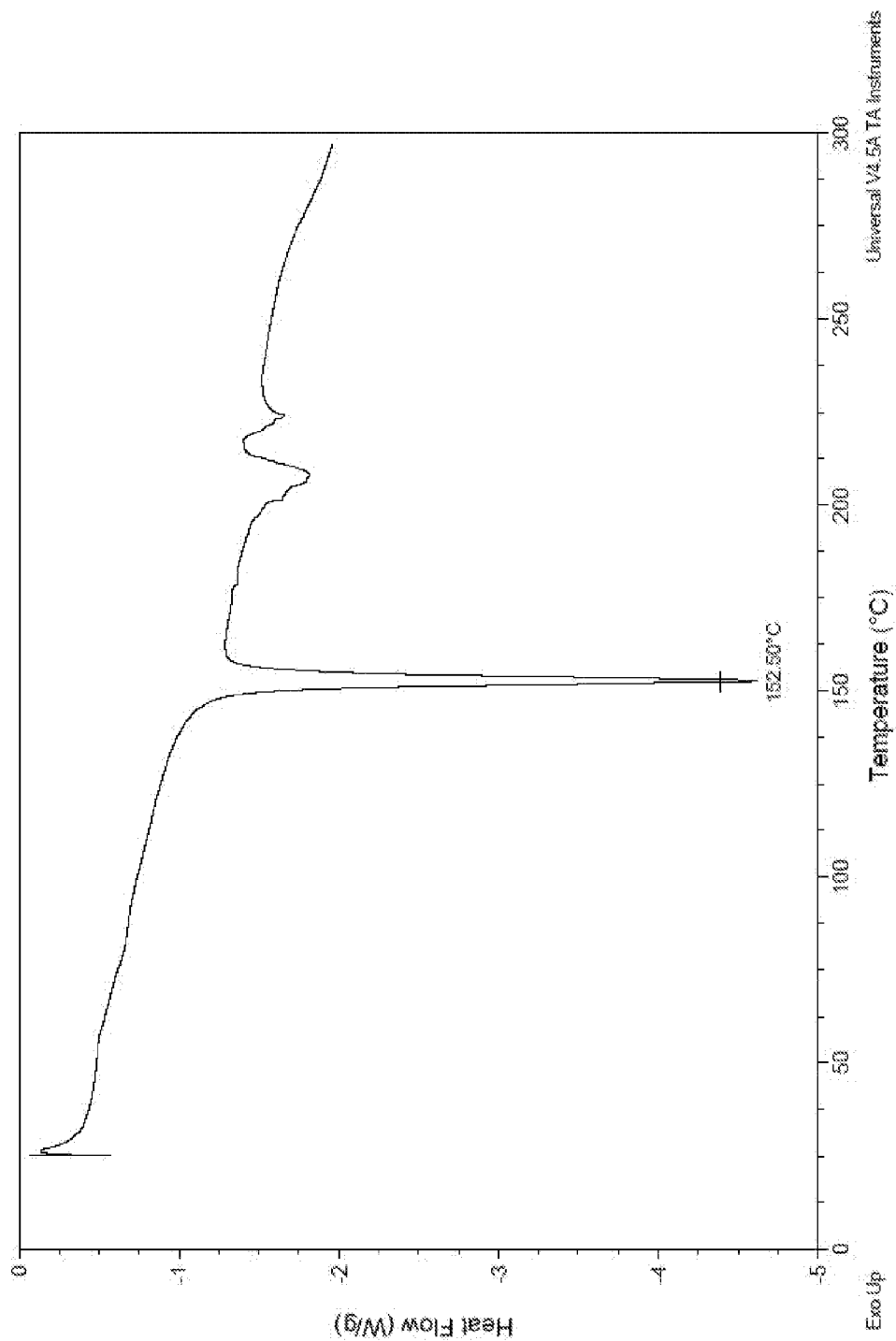
FIG. 8 provides a differential scanning calorimetry (DSC) curve of crystalline form III of the compound of Formula VI.
Figure 9:
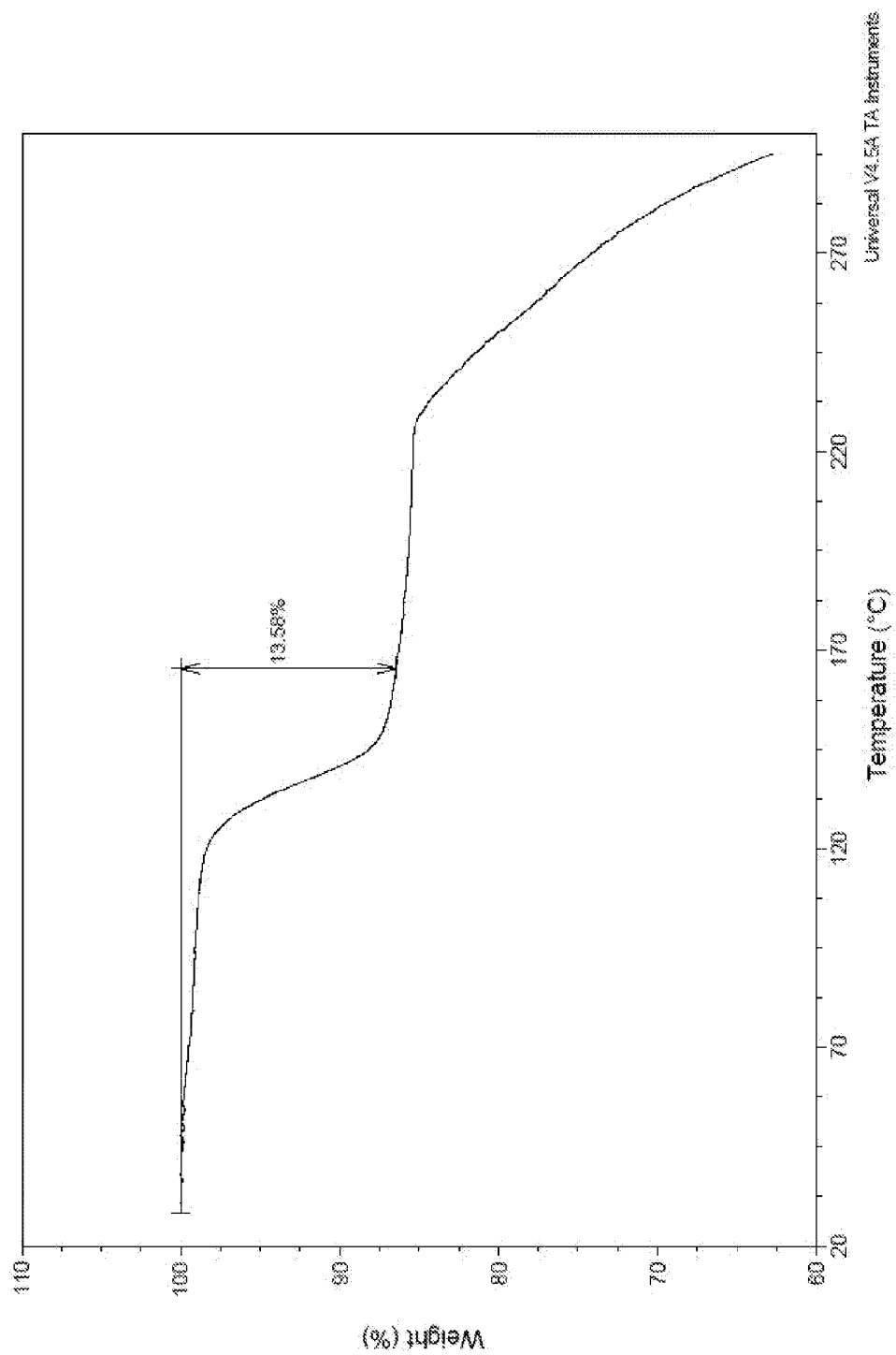
FIG. 9 provides a thermogravimetric analysis (TGA) diagram of crystalline form III of the compound of Formula VI.
Figure 10:
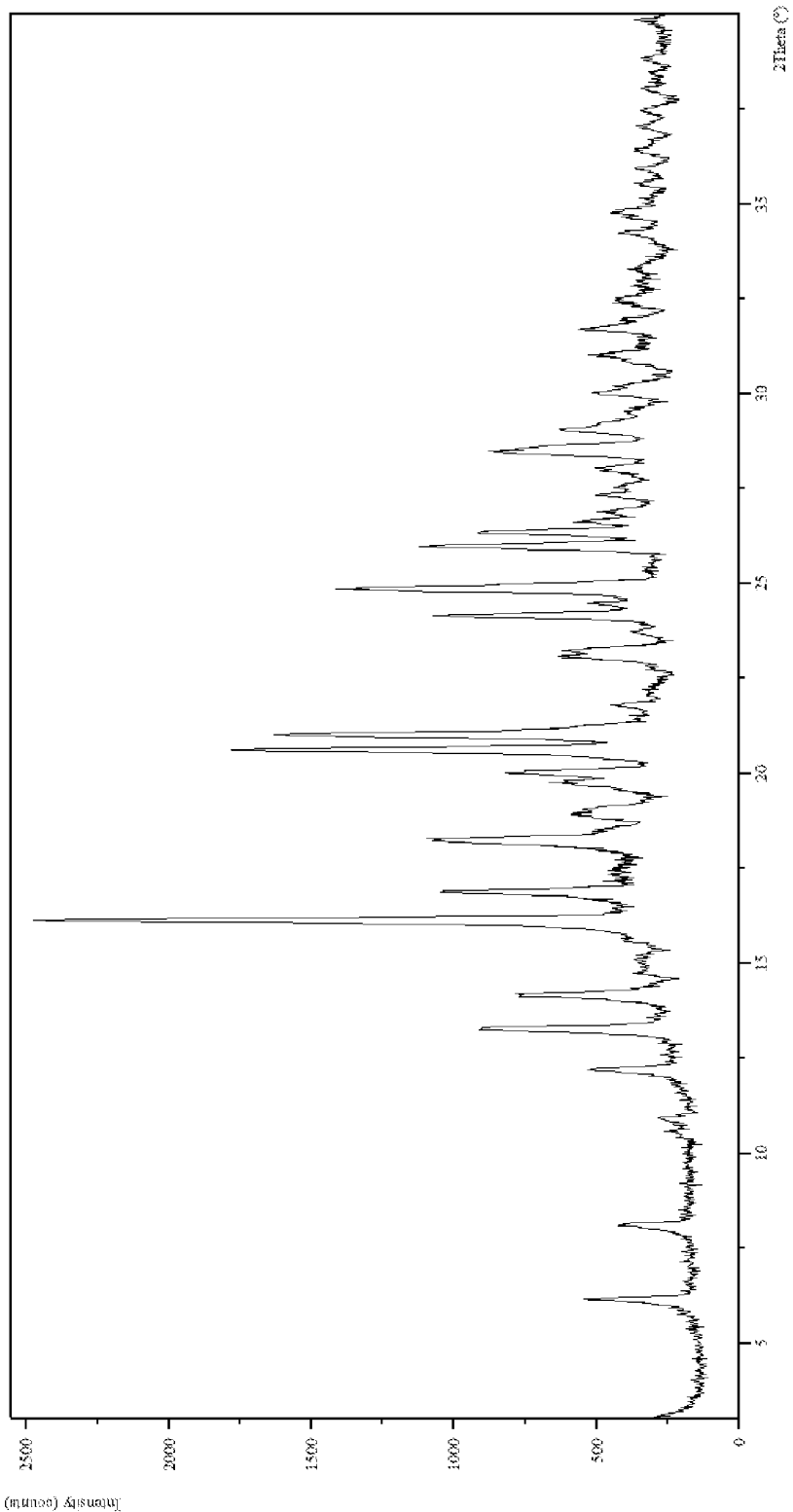
FIG. 10 provides an X-ray powder diffraction (XRPD) pattern of crystalline form IV of the compound of Formula VI.
Figure 11:
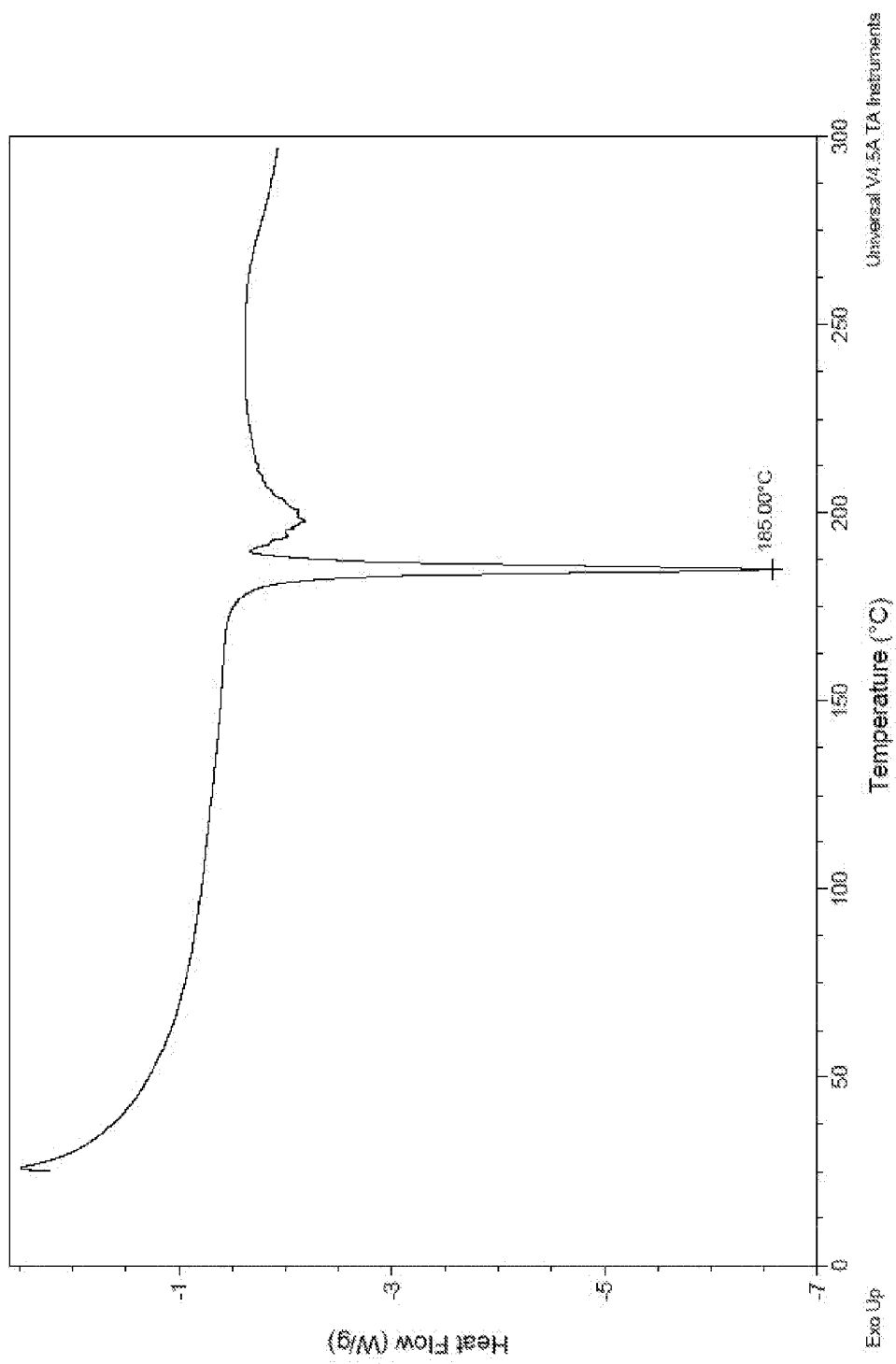
FIG. 11 provides a differential scanning calorimetry (DSC) curve of crystalline form IV of the compound of Formula VI.
Figure 12:
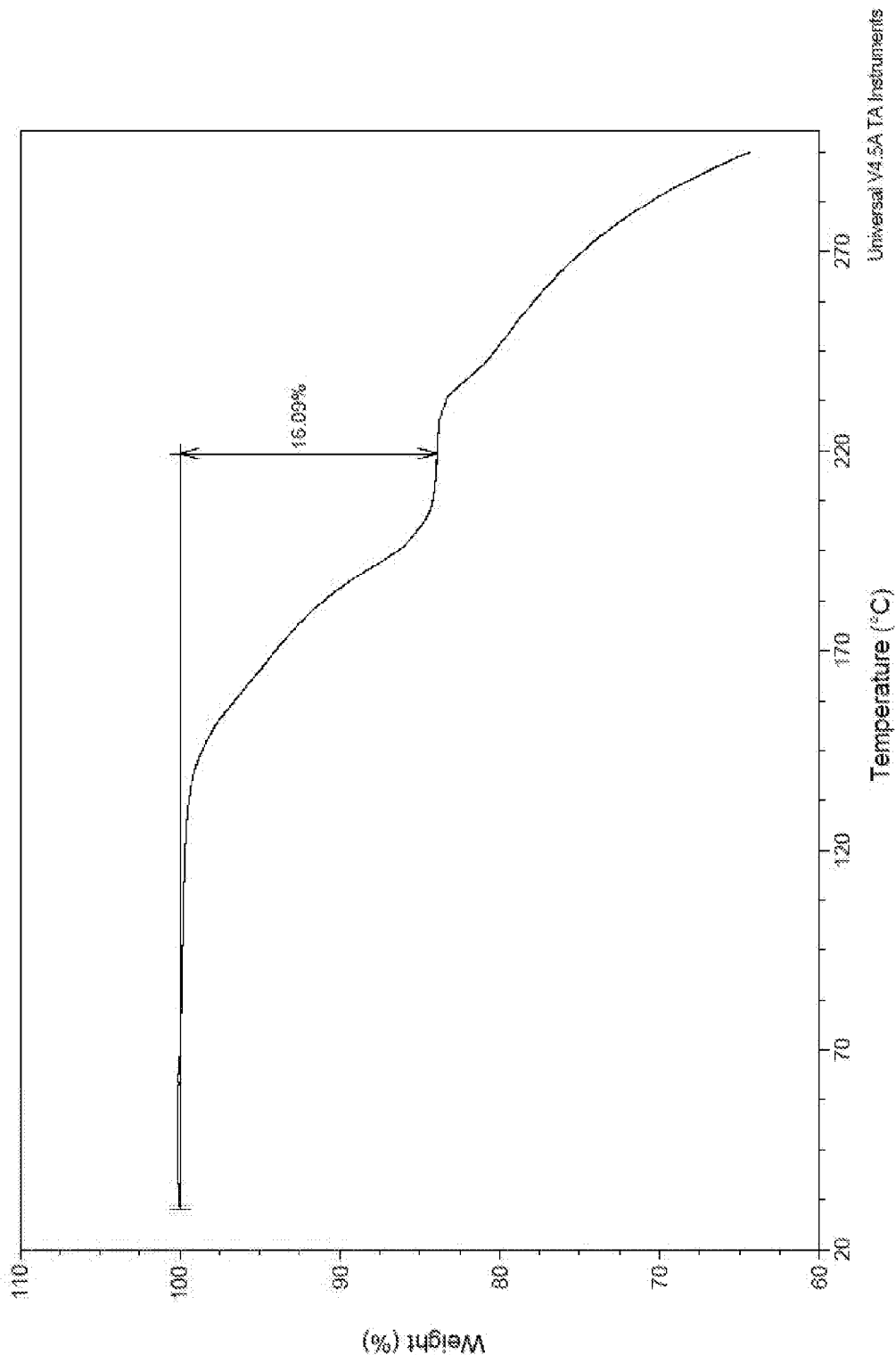
FIG. 12 provides a thermogravimetric analysis (TGA) diagram of crystalline form IV of the compound of Formula VI.
Figure 13:
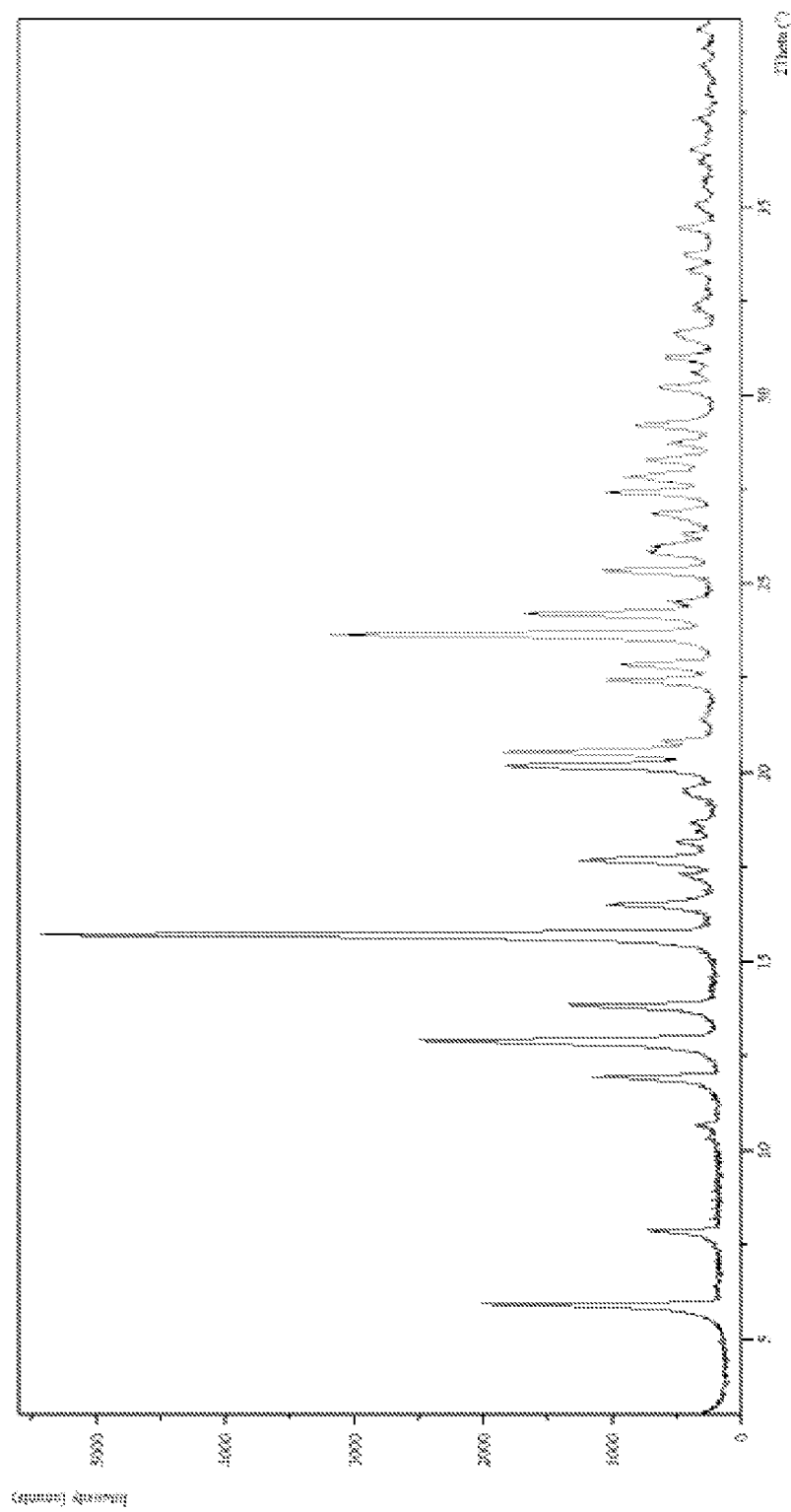
FIG. 13 provides an X-ray powder diffraction (XRPD) pattern of crystalline form V of the compound of Formula VI.
Figure 14:
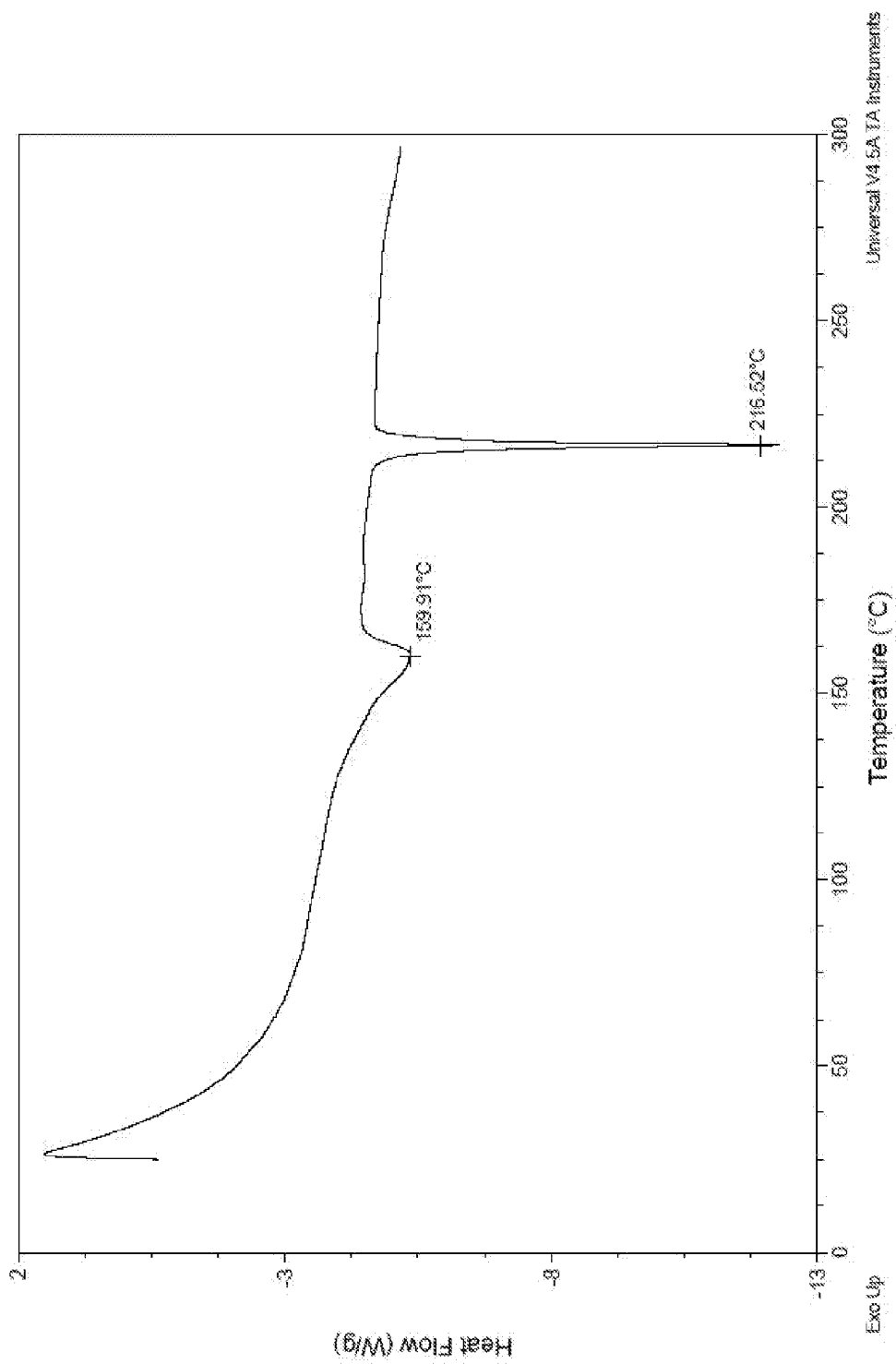
FIG. 14 provides a differential scanning calorimetry (DSC) curve of crystalline form V of the compound of Formula VI.
Figure 15:
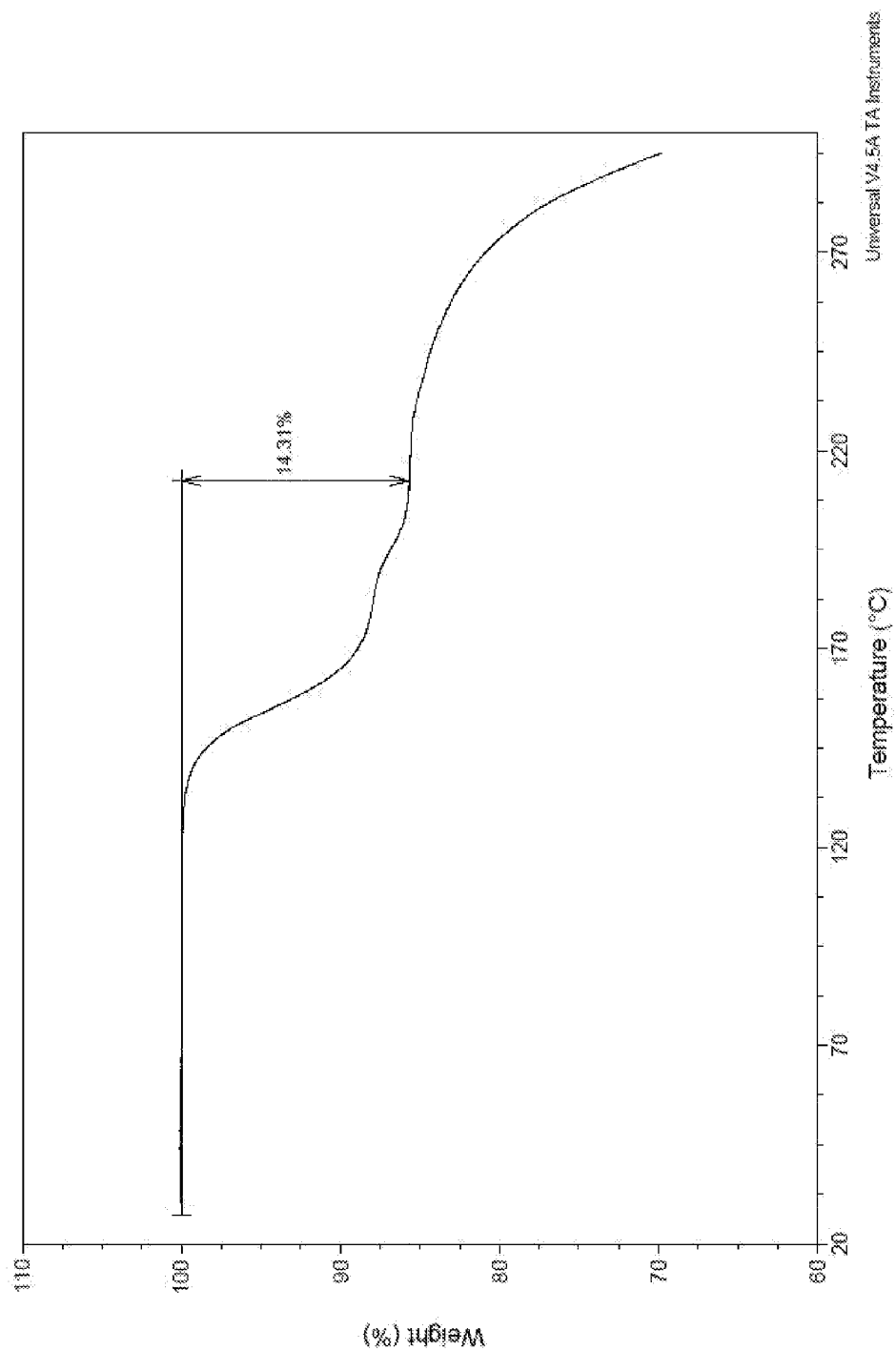
FIG. 15 provides a thermogravimetric analysis (TGA) diagram of crystalline form V of the compound of Formula VI.
Figure 16:
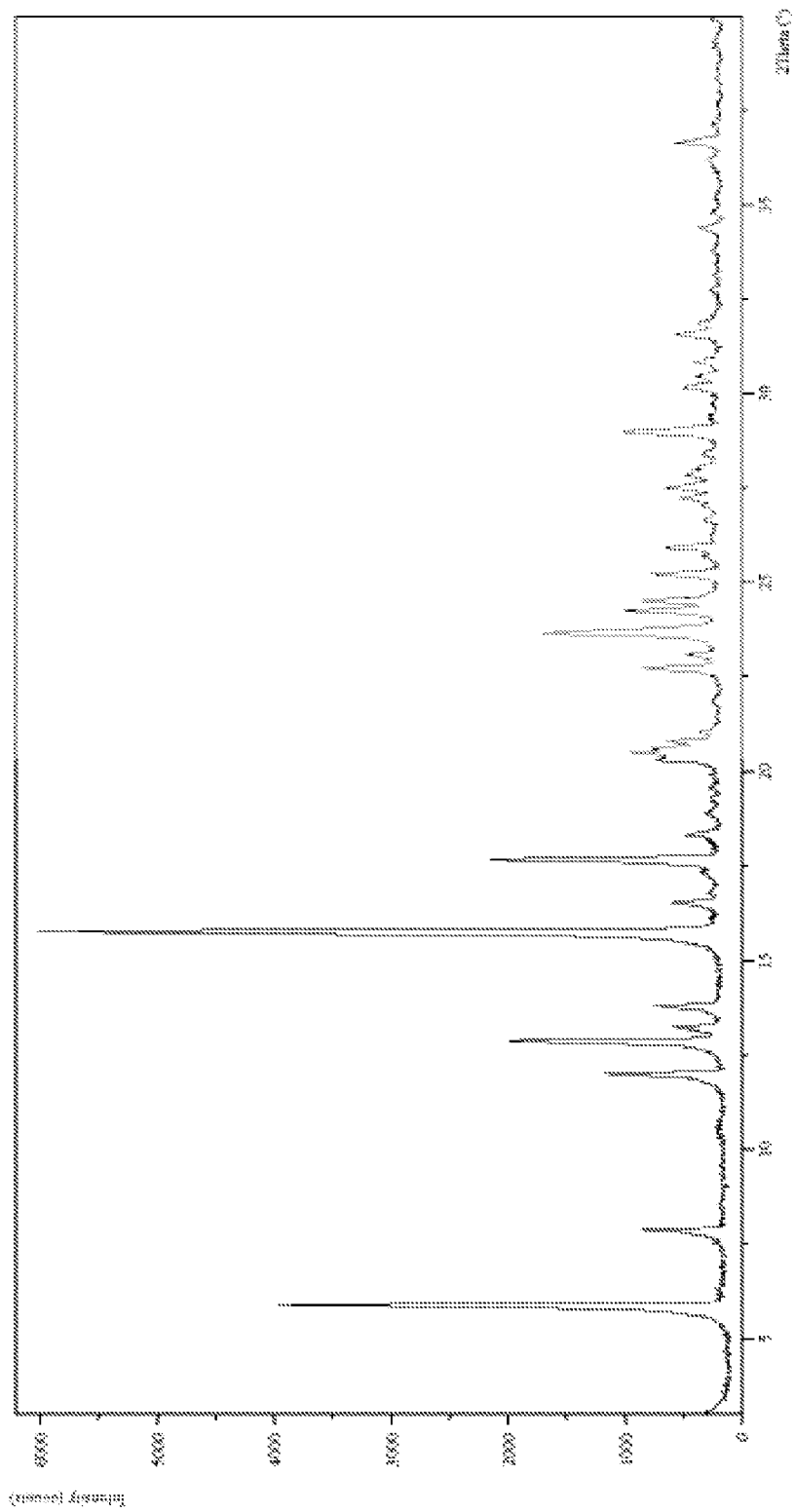
FIG. 16 provides an X-ray powder diffraction (XRPD) pattern of crystalline form VI of the compound of Formula VI.
Figure 17:
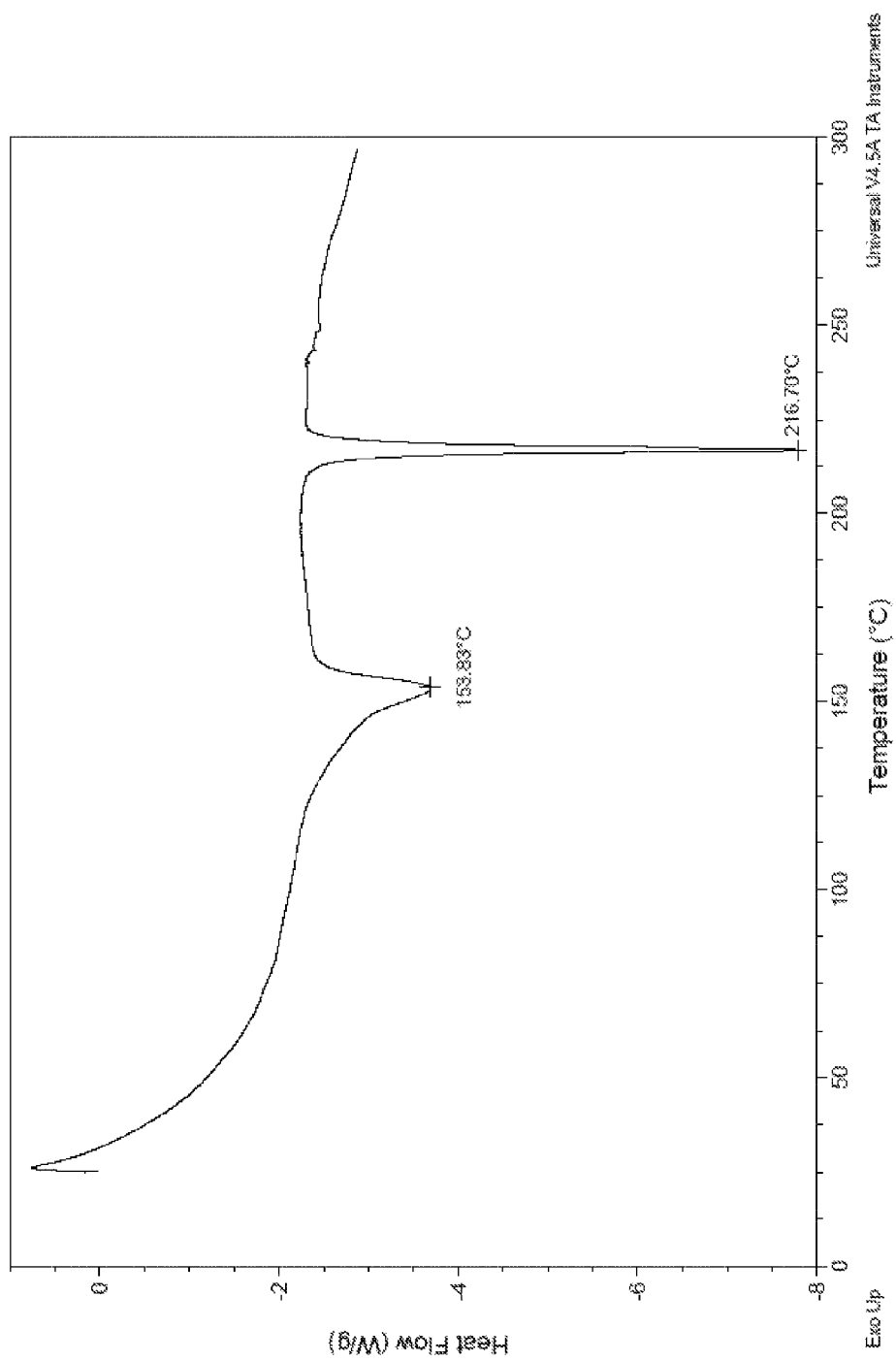
FIG. 17 provides a differential scanning calorimetry (DSC) curve of crystalline form VI of the compound of Formula VI.
Figure 18:
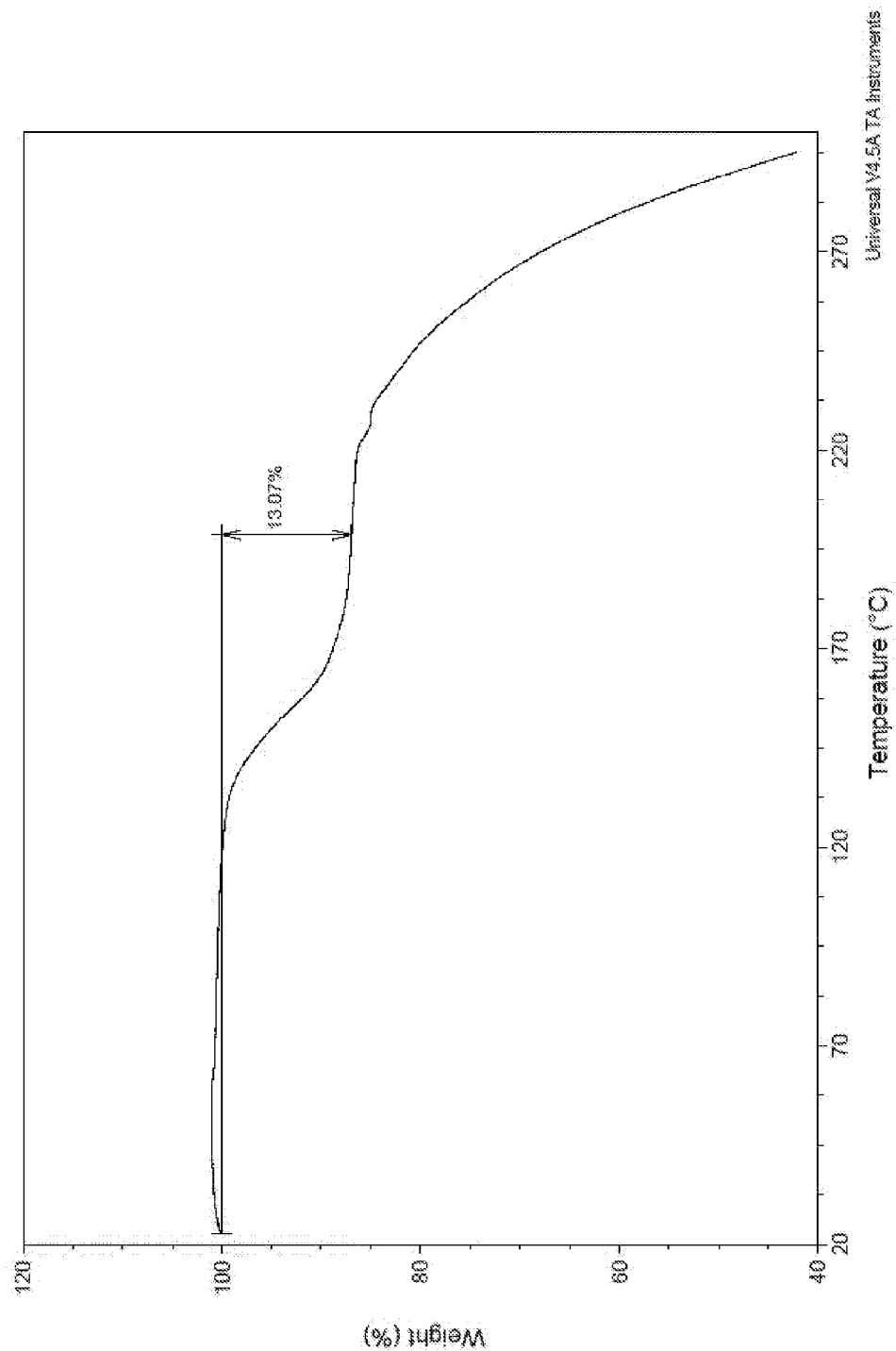
FIG. 18 provides a thermogravimetric analysis (TGA) diagram of crystalline form VI of the compound of Formula VI.

Generally, the compounds disclosed herein may be prepared by methods described herein, wherein the substituents are as defined for Formula (I) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

The X-ray powder diffraction (XRPD) analysis method of the present invention comprises recording an X-ray powder diffraction diagram on a PAN alytical Empyrean X-ray diffractometer using Cu-Kα radiation (45 KV, 40 mA). A thin layer is prepared from powder sample on the single-crystal silicon wafer, and a sample spinner is used. The angular range extends from 3° to 40° in 2θ with a 0.0168° step size in 2θ. Data are collected by Data Collector software, and processed by High Score Plus software, read by Data Viewer software.

Differential Scanning calorimetry (DSC): Differential scanning calorimetry thermogram is recorded on a TA Q2000 instrument with a thermoanalysis controller. The data are collected and analyzed by TA Instruments Thermal Solutions software. About 1-5 mg sample is weighed accurately in special aluminium pans with a cover lid. The scan rate is 10° C./minute and the sample is heated from ambient temperature to 250° C. During the experiment, the DSC room was purged with dry nitrogen.

Thermogravimetric Analysis (TGA): Thermogravimetric curve is recorded on a TA Q500 instrument with a thermoanalysis controller. The data are collected and analyzed by TA Instruments Thermal Solutions software. About 10 mg sample is weighed accurately in platinum sample pans. The scan rate is 10° C./minute and the sample is heated from ambient temperature to 300° C. During the experiment, the TGA oven chamber was purged with dry nitrogen.

The solubility of the compound disclosed herein is measured by Aglient 1200 high performance liquid chromatography with VWD detector. The chromatographic column model is Waters Xbridge-C18 (4.6×150 mm, 5 μm), the detection wavelength is 250 nm, the flow rate is 1.0 mL/min, the column temperature is 35° C., the mobile phase is acetonitrile-water (V/V=40/60).

The hygroscopicity disclosed herein is detected on a DVS INT-Std dynamic vapor and gas absorption analyzer (England Surface Measurement Systems Company) under the humidity ranged from 0% to 95%, the airflow rate is 200 mL/min, the temperature is 25° C., and one test point is provided per rising 5% humidity.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1H$ NMR spectra were obtained by using $CDCl_3$, DMSO-$d_6$, $CD_3OD$ or $d_6$-acetone as solvents (reported in ppm), and TMS (0 ppm) or chloroform (7.25 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constants, when given, were reported in Hertz (Hz).

Low-resolution mass spectral (MS) data were determined by an Agilent 6320 Series LC-MS spectrometer equipped with a G1312A binary pump and a G1316A TCC (column was operated at 30° C.). G1329A autosampler and G1315B DAD detector were applied in the analysis, and an ESI source was used in the LC-MS spectrometer.

Low-resolution mass spectral (MS) data were determined by an Agilent 6120 Series LC-MS spectrometer equipped with a G1311A quaternary pump and a G1316A TCC (column was operated at 30° C.). G1329A autosampler and G1315D DAD detector were applied in the analysis, and an ESI source was used on the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were showed in Table 1.

TABLE 1

| Time (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micron). The run time was 10 min, and the flow rate was 0.6 mL/min. The elution was performed with a gradient of 5 to 95% phase A (0.1% formic acid in $CH_3CN$) in phase B (0.1% formic acid in $H_2O$). Column was operated at 40° C.

Purities of compounds were assessed by high performance liquid chromatography (HPLC) (ZORBAX Eclipse Plus C18 column, 2.1×30 mm, 5 micron). The flow rate was 1 mL/min, and the column was operated at 35° C. The HPLC peaks were recorded by UV-Vis wavelength at 226 nm and 290 nm. The mobile phases was phase A (100 mM $NaClO_4$+

10% ACN solution, adjusting to pH 2.5 with HClO$_4$) and phase B (acetonitrile). The gradient elution conditions were showed in Table 2.

TABLE 2

| Time (min) | Phase A % | Phase B % |
|---|---|---|
| 0-4 | 77.8-58 | 22.2-42 |
| 4-9 | 58 | 42 |
| 9-15 | 58-33.3 | 42-66.7 |
| 15-20 | 33.3 | 66.7 |
| 20-20.1 | 33.3-77.8 | 66.7-22.2 |
| 20.1-25 | 77.8 | 22.2 |

The following abbreviations are used throughout the specification:
t-BuOK potassium tert-butoxide
CHCl$_3$ chloroform
CDCl$_3$ chloroform-d
CD$_3$OD methyl alcohol-d$_4$
LiOH.H$_2$O lithium hydroxide monohydrate
CDI 1,1'-carbonyldiimidazole
DMF N,N-dimethylformamide
DMAP 4-dimethylaminopyridine
DIPEA N,N-diisopropylethylamine
DMSO-d$_6$ dimethylsulfoxide-d$_6$
DMSO dimethylsulfoxide
EDC, EDCI N-(3-dimethylaminopropyl)-N'-ethylcarbodiimide hydrochloride
H$_2$ hydrogen
H$_2$O$_2$ hydrogen peroxide
mL, ml milliliter
N$_2$ nitrogen
PdCl$_2$(PPh$_3$)$_2$ bis(triphenylphosphine)palladium(II) chloride
PPh$_3$ triphenylphosphine
Pd/C Palladium on activated carbon
RT, rt room temperature
Rt retention time
NIS N-iodosuccinimide
H$_2$O water
TFA trifluoroacetic acid
TEA triethylamine
HOAT 1-hydroxy-7-azabenzotriazole
DCM dichloromethane
PE petroleum ether
MeOH methanol
EtOAc ethyl acetate

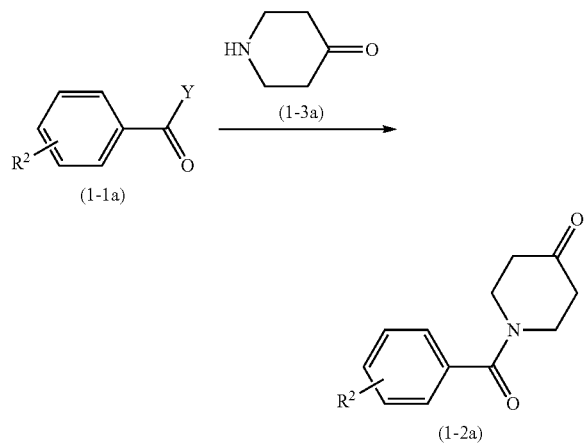

The intermedia (1-2a) disclosed herein can be prepared by the process illustrated in scheme 1 of intermedia: condensation reaction of compound (1-1a) with compound (1-3a) in the present of condensating agents of EDCI and HOAT can give the intermedia (1-2a). This reaction can be carried out in the presence of an alkali, the alkali includes, but is not limited to, sodium hydride and diisopropylethylamine. Wherein Y is an easy leaving group, such as halogen, hydroxy and the like; R$^2$ is as defined herein.

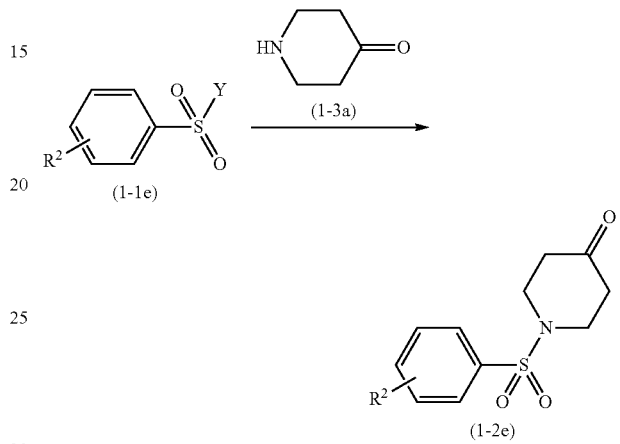

The intermedia (1-2e) disclosed herein can be prepared by the process illustrated in scheme 2 of intermedia: condensation reaction of compound (1-1e) with compound (1-3a) in the present of a condensating agent can give the intermedia (1-2e). Wherein Y is an easy leaving group, such as halogen, hydroxy and the like; R$^2$ is as defined herein.

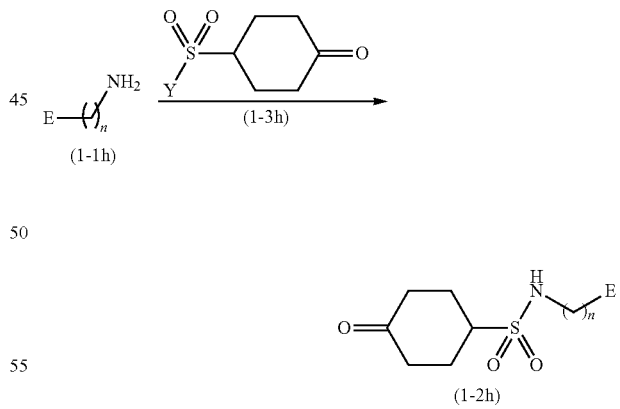

The intermedia (1-2h) disclosed herein can be prepared by the process illustrated in scheme 3 of intermedia: condensation reaction of compound (1-1h) with compound (1-3h) in the present of condensating agents of EDCI and HOAT can give the intermedia (1-2h). This reaction can be carried out in the presence of an alkali, the alkali includes, but is not limited to, sodium hydride and diisopropylethylamine. Wherein Y is an easy leaving group, such as halogen, hydroxy and the like; each n and E is as defined herein.

Scheme 4 of intermedia

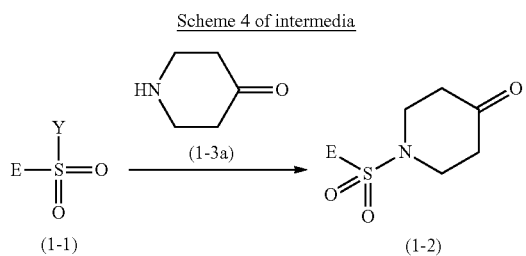

The intermedia (1-2) disclosed herein can be prepared by the process illustrated in scheme 4 of intermedia: condensation reaction of compound (1-1) with compound (1-3a) in the present of a condensating agent can give the intermedia (1-2). Wherein Y is an easy leaving group, such as halogen, hydroxy and the like; E is as defined herein.

Scheme 5 of intermedia

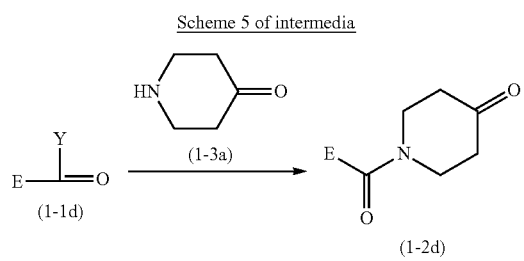

The intermedia (1-2d) disclosed herein can be prepared by the process illustrated in scheme 5 of intermedia: condensation reaction of compound (1-1d) with compound (1-3a) in the present of condensating agents of EDCI and HOAT can give the intermedia (1-2d). This reaction can be carried out in the presence of an alkali, the alkali includes, but is not limited to, sodium hydride and diisopropylethylamine. Wherein Y is an easy leaving group, such as halogen, hydroxy and the like; E is as defined herein.

Scheme 6 of intermedia

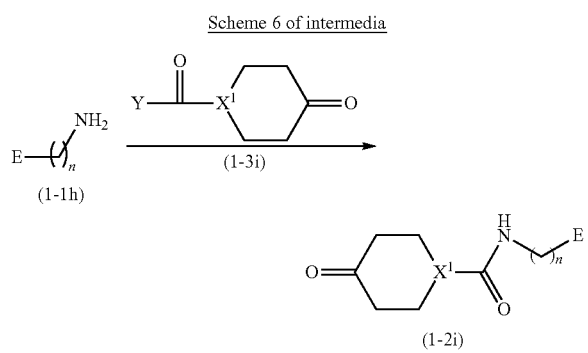

The intermedia (1-2i) disclosed herein can be prepared by the process illustrated in scheme 6 of intermedia. Condensation reaction of compound (1-1h) with compound (1-3i) in the present of condensating agent of EDCI and HOAT can give the intermedia (1-2i). This reaction can be carried out in the presence of an alkali, the alkali includes, but is not limited to, sodium hydride and diisopropylethylamine. Wherein Y is an easy leaving group, such as halogen, hydroxy and the like; each n and E is as defined herein.

Scheme 1

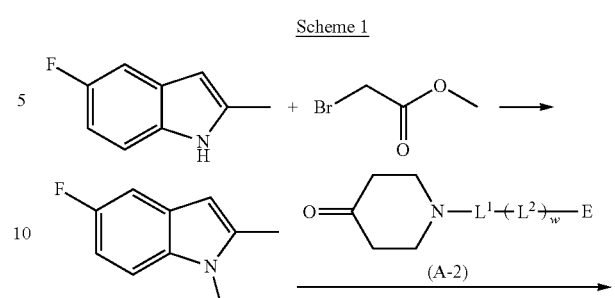

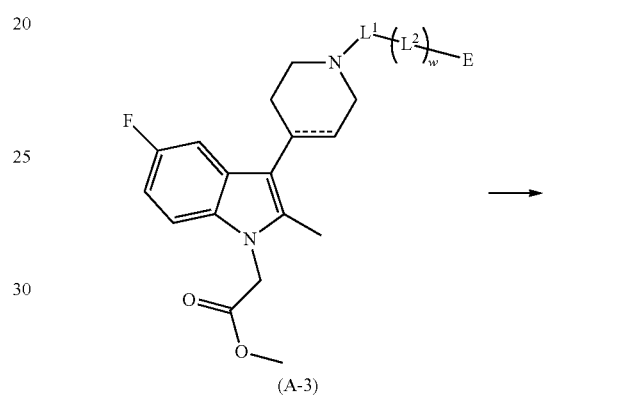

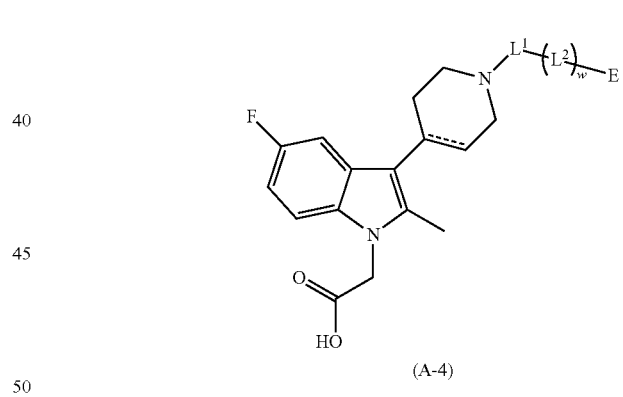

Compound (A-4) disclosed herein can be prepared by the process illustrated in scheme 1. Wherein $L^1$, $L^2$, w and E are as defined herein, and ---- can be a single bond or double bond. Nucleophilic substitution reaction of 5-fluoro-2-methylindole with methyl bromoacetate in the present of a base (the base includes, but is not limited to, sodium hydride, sodium hydroxide, etc.) can give the compound (A-1); compound (A-1) can react with compound (A-2) in the present of TFA and triethyl silicane to afford compound (A-3), and compound (A-3) can be further hydrolysed in the present of a base (the base includes, but is not limited to, sodium hydroxide, potassium hydroxide or lithium hydrate), after working up in the present of an acid (the acid includes, but is not limited to hydrochloric acid), the target compound (A-4) is obtained.

Scheme 2

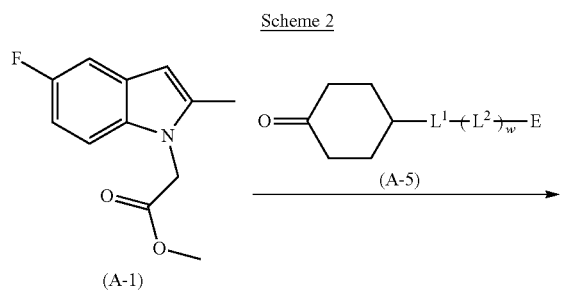

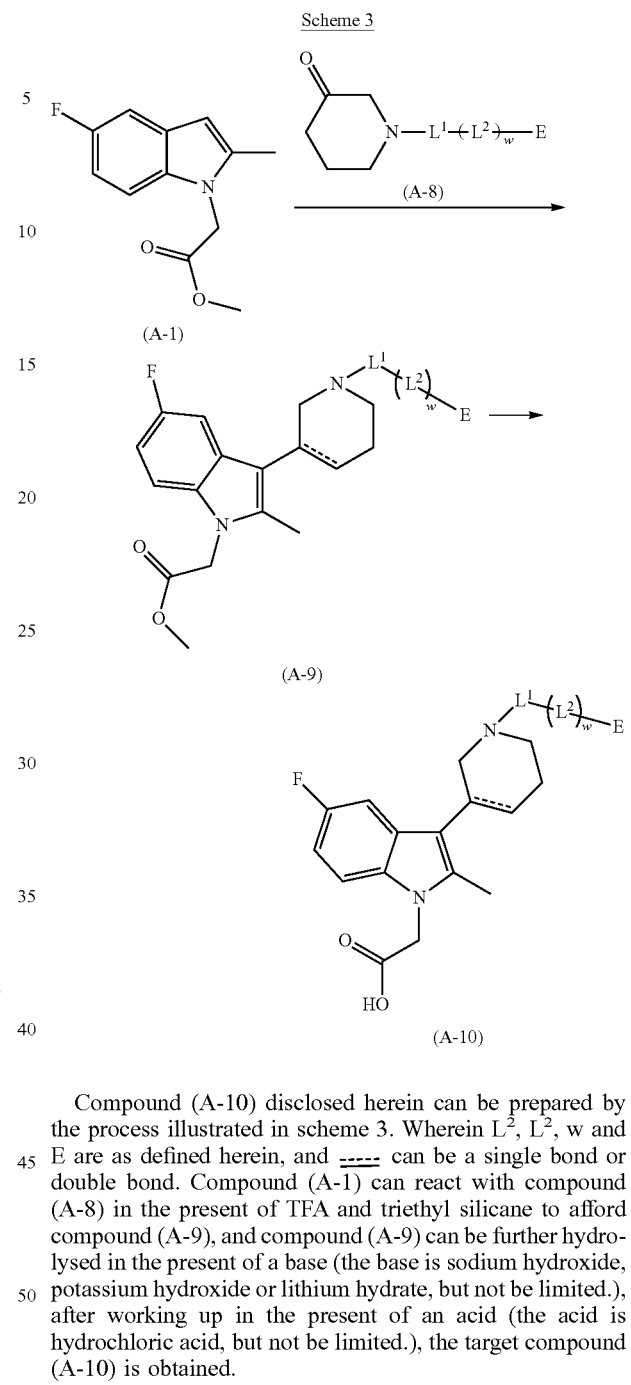

Compound (A-7) disclosed herein can be prepared by the process illustrated in scheme 2. Wherein $L^1$, $L^2$, w and E are as defined herein. Compound (A-1) can react with compound (A-5) in the present of TFA and triethyl silicane to afford compound (A-6), and compound (A-6) can be further hydrolysed in the present of a base (the base includes, but is not limited to, sodium hydroxide, potassium hydroxide or lithium hydrate), after working up in the present of an acid (the acid includes, but is not limited to hydrochloric acid), the target compound (A-7) is obtained.

Compound (A-10) disclosed herein can be prepared by the process illustrated in scheme 3. Wherein $L^2$, $L^2$, w and E are as defined herein, and ---- can be a single bond or double bond. Compound (A-1) can react with compound (A-8) in the present of TFA and triethyl silicane to afford compound (A-9), and compound (A-9) can be further hydrolysed in the present of a base (the base is sodium hydroxide, potassium hydroxide or lithium hydrate, but not be limited.), after working up in the present of an acid (the acid is hydrochloric acid, but not be limited.), the target compound (A-10) is obtained.

Scheme 4

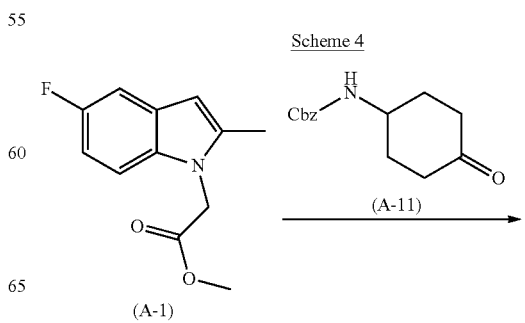

91

-continued

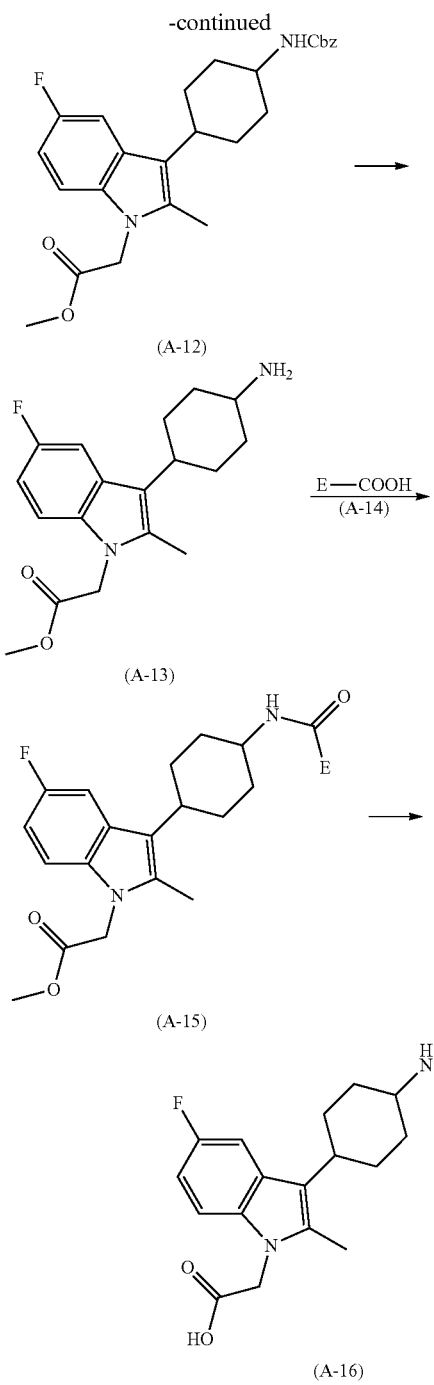

(A-12)

E—COOH
(A-14)

(A-13)

(A-15)

(A-16)

Compound (A-16) disclosed herein can be prepared by the process illustrated in scheme 4. Wherein E is as defined herein. Compound (A-1) can react with compound (A-11) in the present of TFA and triethyl silicane to afford compound (A-12), compound (A-12) can undergo reduction reaction catalyzed by palladium reagent (palladium reagent is Pd/C or Pd, but not be limited.) to give compound (A-13); condensation reaction of compound (A-13) with compound (A-14) in the present of a condensating agent (condensating agent is EDCI or HOAT, but not be limited.) to give compound (A-15); and compound (A-15) can be further hydrolysed in the present of a base (the base is sodium hydroxide, potassium hydroxide or lithium hydrate, but not be limited.), after working up in the present of an acid (the acid is hydrochloric acid, but not be limited.), the target compound (A-10) is obtained.

92

Scheme 5

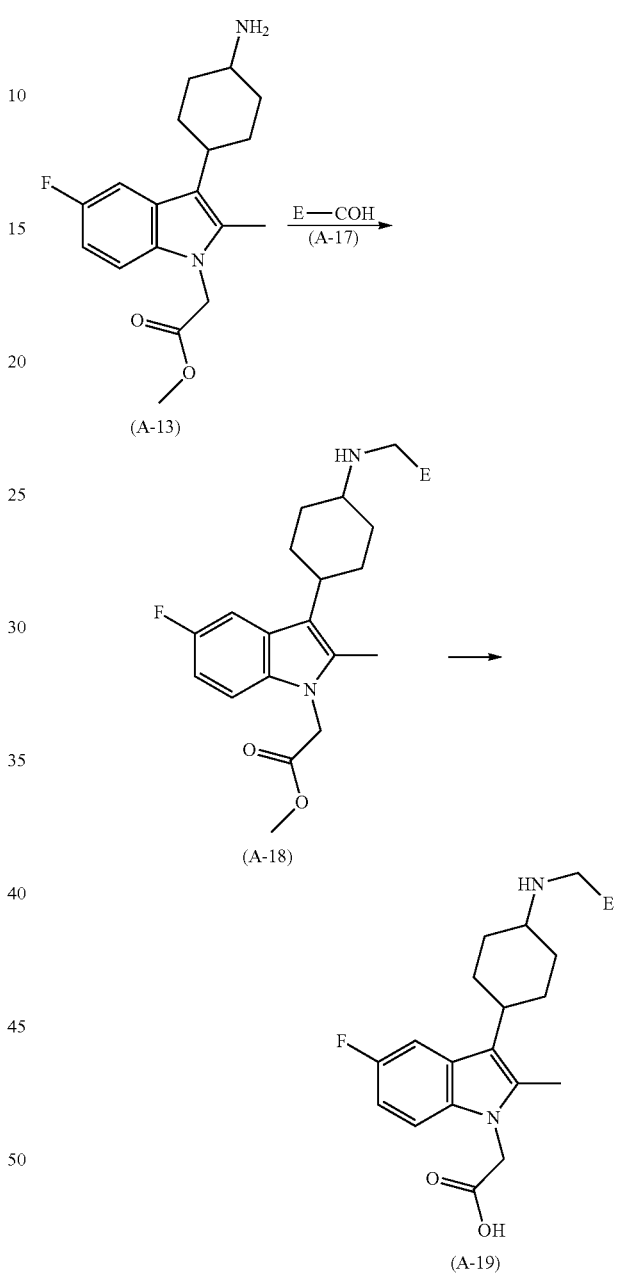

(A-13)

E—COH
(A-17)

(A-18)

(A-19)

Compound (A-19) disclosed herein can be prepared by the process illustrated in scheme 5. Wherein E is as defined herein. Reductive amination reaction of compound (A-13) with compound (A-17) to give compound (A-18) (reducing reagent can be STAB, sodium borohydride or sodium cyanoborohydride, but not be limited.), and compound (A-18) can be further hydrolysed in the present of a base (the base is sodium hydroxide, potassium hydroxide or lithium hydrate, but not be limited.), after post-processing in the present of an acid (the acid is hydrochloric acid, but not be limited.), the target compound (A-19) is obtained.

Scheme 6

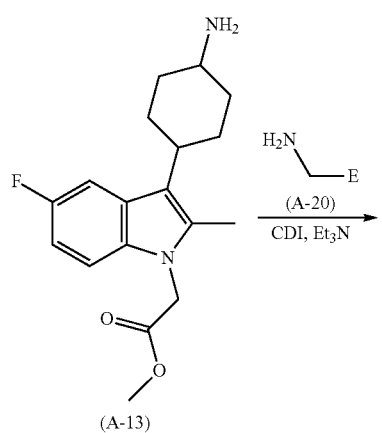
(A-13)

H2N—E
(A-20)
———————→
CDI, Et3N

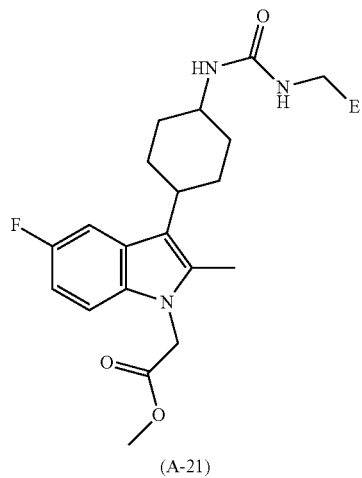
(A-21)

↓

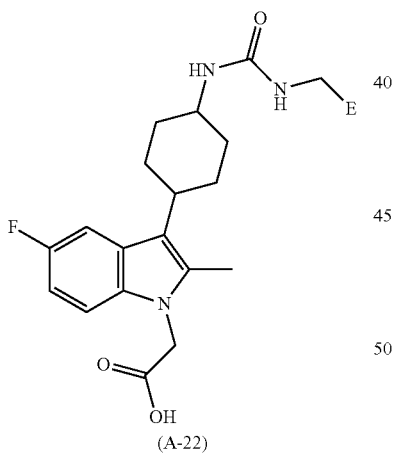
(A-22)

Compound (A-22) disclosed herein can be prepared by the process illustrated in scheme 6. Wherein E is as defined herein. Compound (A-13) can react with compound (A-20) under the action of activation reagent CDI to afford compound (A-21) in an alkaline medium (the alkaline can be, but not limited to triethylamine), and compound (A-21) can be further hydrolysed in the present of a base (the base is sodium hydroxide, potassium hydroxide or lithium hydrate, but not be limited.), after working up in the present of an acid (the acid is hydrochloric acid, but not be limited.), the target compound (A-22) is obtained.

Scheme 7

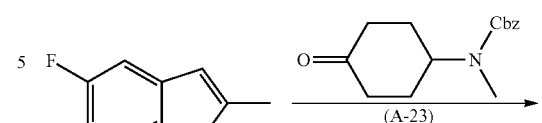
(A-1)

(A-23)
————→

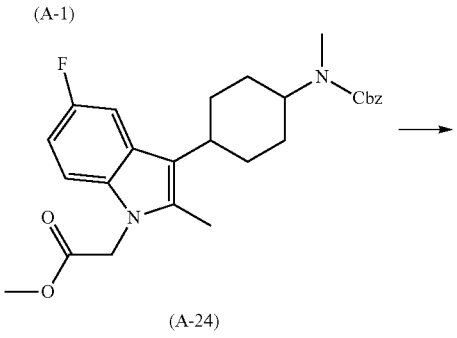
(A-24)

→

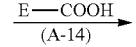
(A-25)

E—COOH
(A-14)
————→

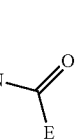
(A-26)

→

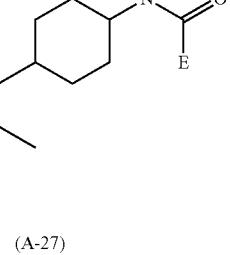
(A-27)

Compound (A-27) disclosed herein can be prepared by the process illustrated in scheme 7. Wherein E is as defined herein. Compound (A-1) can react with compound (A-23) in the present of TFA and triethyl silicane to afford compound (A-24), compound (A-24) can undergo reduction reaction catalyzed by palladium reagent (palladium reagent is Pd/C or Pd, but not be limited.) to give compound (A-25); condensation reaction of compound (A-25) with compound (A-14) in the present of a condensating agent (condensating agent is EDCI and/or HOAT, but not be limited.) to give compound (A-26); and compound (A-26) can be further hydrolysed in the present of a base (the base is sodium hydroxide, potassium hydroxide or lithium hydrate, but not be limited.), after working up in the present of an acid (the acid is hydrochloric acid, but not be limited.), the target compound (A-27) is obtained.

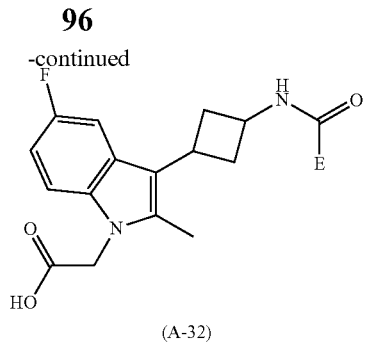

(A-32)

Compound (A-32) disclosed herein can be prepared by the process illustrated in scheme 8. Wherein E is as defined herein. Compound (A-1) can react with compound (A-28) in the present of TFA and triethyl silicane to afford compound (A-29), compound (A-29) can undergo reduction reaction catalyzed by palladium reagent (palladium reagent is Pd/C or Pd, but not be limited.) to give compound (A-30); condensation reaction of compound (A-30) with compound (A-14) in the present of a condensating agent (condensating agent is EDCI and/or HOAT, but not be limited.) to give compound (A-31); and compound (A-31) can be further hydrolysed in the present of a base (the base is sodium hydroxide, potassium hydroxide or lithium hydrate, but not be limited.), after working up in the present of an acid (the acid is hydrochloric acid, but not be limited.), the target compound (A-32) is obtained.

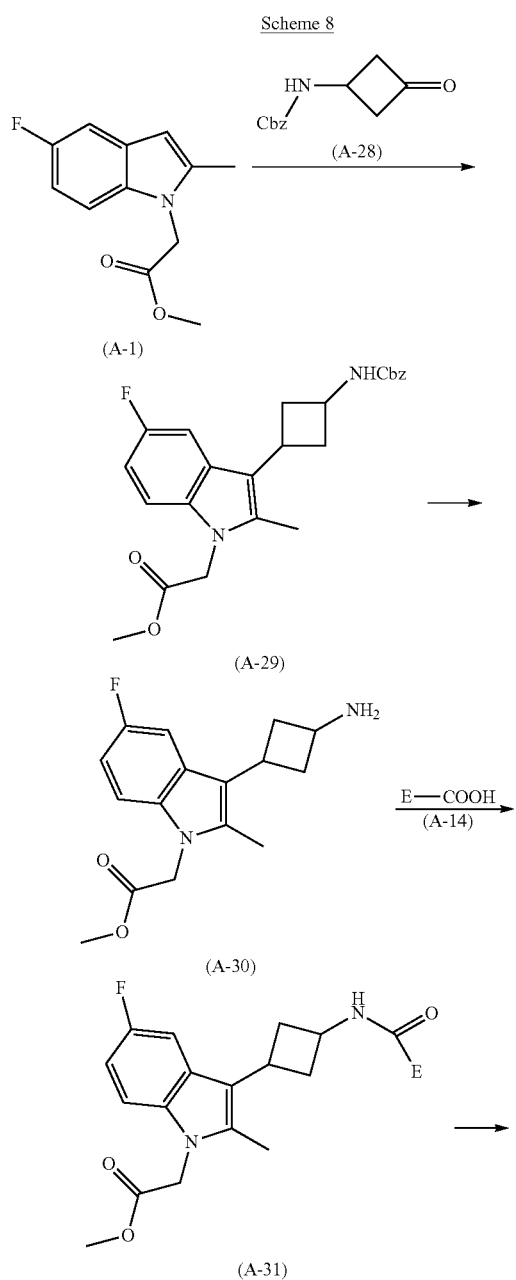

Scheme 8

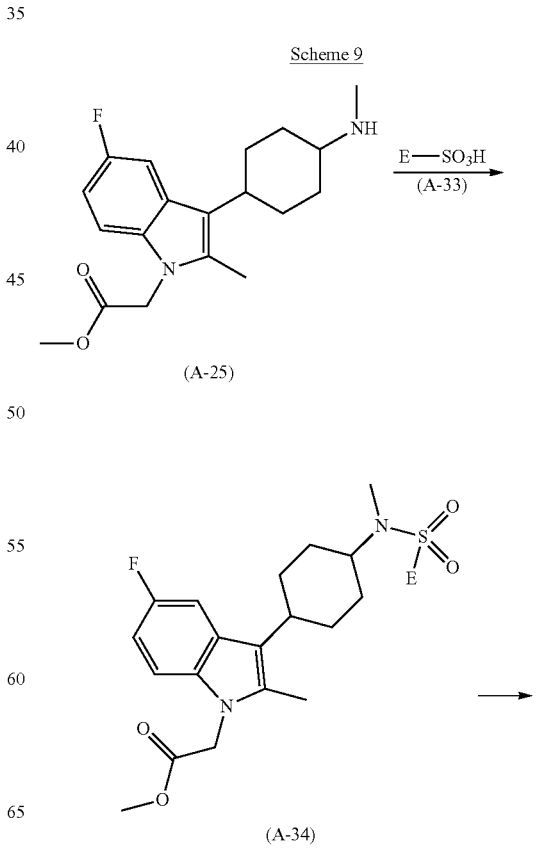

Scheme 9

-continued

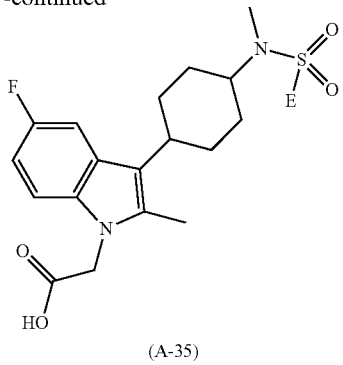

(A-35)

Compound (A-35) disclosed herein can be prepared by the process illustrated in scheme 9, wherein E is as defined herein. Condensation reaction of compound (A-25) with compound (A-33) to give compound (A-34); and compound (A-34) can be further hydrolysed in the present of a base (the base is sodium hydroxide, potassium hydroxide or lithium hydrate, but not be limited.), after post-processing in the present of an acid (the acid is hydrochloric acid, but not be limited.) the target compound (A-35) is obtained.

The following examples disclosed herein are presented to further describe the invention. However, these examples should not be used to limit the scope of the invention.

EXAMPLE

Example 1: 2-(5-fluoro-3-(1-(4-flurobenzoyl)piperidin-4-yl)-2-methyl-1H-indol-1-yl)acetic acid

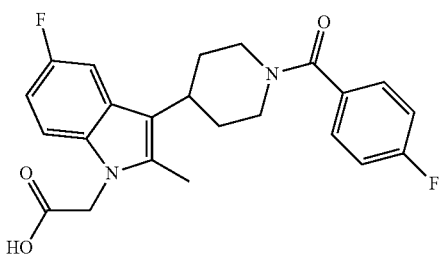 [SMILES: Cc1c(C2CCN(C(=O)c3ccc(F)cc3)CC2)c2cc(F)ccc2n1CC(=O)O]

Step 1) methyl 2-(5-fluoro-2-methyl-1H-indol-1-yl)acetate

To a solution of 5-fluoro-2-methylindole (3 g, 20.11 mmol) and sodium hydride (0.97 g, 24.13 mmol) in DMF (20 mL) was added methyl bromoacetate (2.3 mL, 24.13 mmol) dropwise. The mixture was stirred for 24 h at rt, after removing the solvent, the residue was diluted with water (20 mL) and then extracted with EtOAc (15 mL×2). The combined organic layers were dried over anhydrous $Na_2SO_4$ and concentrated. The residue was purified by silica gel chromatography eluted with PE/EtOAc (V/V)=20/1 to give a white solid product (2.47 g, 55%).

$^1$H NMR (600 MHz, $CDCl_3$): δ ppm 7.20 (dd, $J_1$=9.5 Hz, $J_2$=2.4 Hz, 1H), 7.09 (dd, $J_1$=8.8 Hz, $J_2$=4.2 Hz, 1H), 6.91 (td, $J_1$=9.1 Hz, $J_2$=2.4 Hz, 1H), 6.29 (s, 1H), 4.80 (s, 2H), 3.77 (s, 3H), 2.41 (s, 3H); and MS-ESI: m/z 222.2 [M+H]$^+$.

Step 2) 1-(4-fluorobenzoyl)piperidin-4-one

To a solution of 4-fluorobenzoic acid (422 mg, 3.01 mmol), 4-piperidone hydrochloride (340 mg, 2.51 mmol), EDCI (721 mg, 3.76 mmol) and HOAT (853 mg, 6.27 mmol) in DCM (20 mL) was added DIPEA (1.8 mL, 10.03 mmol) at 0° C. The mixture was stirred for 23 h at rt and then washed with water (15 mL). The organic layer was dried over anhydrous $Na_2SO_4$ and concentrated. The residue was purified by silica gel chromatography eluted with PE/EtOAc (V/V)=2/1 to give a white solid product (520 mg, 93%).

$^1$H NMR (400 MHz, $CDCl_3$): δ ppm 7.47-7.51 (m, 2H), 7.15 (t, J=8.6 Hz, 2H), 3.87 (m, 4H), 2.50 (m, 4H); and MS-ESI: m/z 222.1 [M+H]$^+$.

Step 3) methyl 2-(5-fluoro-3-(1-(4-flurobenzoyl)piperidin-4-yl)-2-methyl-1H-indol-1-yl)acetate To a solution of methyl 2-(5-fluoro-2-methyl-1H-indol-1-yl))acetate (224 mg, 1.01 mmol) and 1-(4-fluoro-benzoyl)-piperidin-4-one (200 mg, 0.92 mmol) in DCM (20 mL) were added triethyl silicane (0.81 mL, 5.06 mmol) and TFA (0.22 mL, 2.95 mmol) dropwise respectively at 0° C. The mixture was stirred for 20 h at rt. After removing the solvent, the residue was diluted with saturated aqueous sodium bicarbonate solution (25 mL) and then extracted with EtOAc (15 mL×2). The combined organic layers were dried over anhydrous $Na_2SO_4$ and concentrated. The residue was purified by silica gel chromatography eluted with PE/EtOAc (V/V)=2/1 to give a white solid product (369 mg, 94%).

$^1$H NMR (400 MHz, $CDCl_3$): δ ppm 7.51-7.54 (m, 2H), 7.28-7.31 (m, 1H), 7.15 (t, J=8.7 Hz, 2H), 7.10 (dd, $J_1$=8.8 Hz, $J_2$=4.3 Hz, 1H), 6.91 (td, $J_1$=9.0 Hz, $J_2$=2.4 Hz, 1H), 4.79 (s, 2H), 3.78 (s, 3H), 2.98-3.06 (m, 1H), 2.38 (s, 3H), 2.07-2.14 (m, 2H), 1.75-1.95 (m, 2H), 1.64 (s, 2H); and MS-ESI: and m/z 427.2 [M+H]$^+$.

Step 4) 2-(5-fluoro-3-(1-(4-fluorobenzoyl)piperidin-4-yl)-2-methyl-1H-indol-1-yl)acetic acid To a solution of methyl 2-(5-fluoro-3-(1-(4-flurobenzoyl)piperidin-4-yl)-2-methyl-1H-indol-1-yl)acetate (357 mg, 0.84 mmol) in a mixed solvent of THF (16 mL) and water (8 mL) was added sodium hydroxide (167 mg, 4.18 mmol). The mixture was stirred for 3 h at 60° C. After adjusting the mixture to pH 1 with concentrated hydrochloric acid (2 mL), the resulting mixture was extracted with EtOAc (10 mL×3). The combined organic layers were dried over anhydrous $Na_2SO_4$ and concentrated to give a light yellow solid product (135 mg, 39%).

$^1$H NMR (600 MHz, $d_6$-DMSO): δ ppm 7.57-7.59 (m, 2H), 7.43 (d, J=10.2 Hz, 1H), 7.34 (dd, $J_1$=8.7 Hz, $J_2$=4.4 Hz, 1H), 7.29 (t, J=8.7 Hz, 2H), 6.86-6.89 (m, 1H), 4.93 (s, 2H), 3.42 (m, 4H), 3.05-3.09 (m, 1H), 2.86-2.93 (m, 1H), 2.31 (s, 3H), 2.02-2.04 (m, 2H), 1.60-1.71 (m, 2H);

$^{13}$C NMR (150 MHz, $d_6$-DMSO): δ ppm 171.0, 168.7, 163.7, 158.0, 135.0, 133.7, 129.9, 126.7, 115.9, 114.6, 110.4, 44.9, 34.6, 10.7; and MS-ESI: m/z 413.2 [M+H]$^+$.

Example 2: 2-(3-(1-(1-naphthoyl)piperidin-4-yl)-5-fluoro-2-methyl-1H-indol-1-yl)acetic

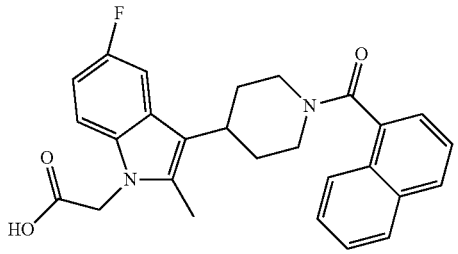 [SMILES: Cc1c(C2CCN(C(=O)c3cccc4ccccc34)CC2)c2cc(F)ccc2n1CC(=O)O]

Step 1) 1-(1-naphthoyl)piperidin-4-one

By using 4-piperidone hydrochloride (300 mg, 2.21 mmol), 1-naphthoic acid (457 mg, 2.66 mmol), EDCI (636 mg, 3.32 mmol), HOAT (753 mg, 5.53 mmol), DCM (20 mL) and DIPEA (1.5 mL, 8.85 mmol) and according to the method described in step 2) of example 1 to prepare the title compound as a white solid (560 mg, 99%).

$^1$H NMR (400 MHz, CDCl$_3$): δ ppm 7.87-7.95 (m, 3H), 7.49-7.60 (m, 4H), 4.23 (t, J=6.0 Hz, 2H), 3.52 (t, J=6.2 Hz, 2H), 2.70 (t, J=6.3 Hz, 2H), 2.31-2.34 (m, 2H); and MS-ESI: m/z 254.2 [M+H]$^+$.

Step 2) methyl 2-(3-(1-(1-naphthoyl)piperidin-4-yl)-5-fluoro-2-methyl-1H-indol-1-yl)acetate By using methyl 2-(5-fluoro-2-methyl-1H-indol-1-yl)acetate (192 mg, 0.87 mmol), 1-(1-naphthoyl)piperidin-4-one (200 mg, 0.79 mmol), DCM (20 mL), triethyl silicane (0.69 mL, 4.34 mmol) and trifluoroacetic acid (0.19 mL, 2.53 mmol) at 0° C. and according to the method described in step 3) of example 1 to prepare the title compound as a white solid (296 mg, 81%).

$^1$H NMR (400 MHz, CDCl$_3$): δ ppm 8.16-8.19, 7.84-7.87 (m, m, 0.5H, 0.5H), 7.91-7.93 (m, 2H), 7.72-7.76, 7.44-7.46 (m, m, 0.5H, 0.5H), 7.51-7.62 (m, 3H), 7.31-7.39 (m, 1H), 7.07-7.11 (m, 1H), 6.92 (t, J=8.9 Hz, 1H), 5.19-5.21 (m, 1H), 4.77-4.81 (m, 2H), 3.76-3.78 (m, 3H), 3.55-3.58 (m, 1H), 3.06-3.16 (m, 1H), 2.93-3.03 (m, 2H), 2.34-2.37 (m, 3H), 2.25-2.32 (m, 1H), 1.95-2.03 (m, 2H); and MS-ESI: m/z 459.3 [M+H]$^+$.

Step 3) 2-(3-(1-(1-naphthoyl)piperidin-4-yl)-5-fluoro-2-methyl-1H-indol-1-yl)acetic acid By using a solution of methyl 2-(3-(1-(1-naphthoyl)piperidin-4-yl)-5-fluoro-2-methyl-1H-indol-1-yl)acetate (287 mg, 0.63 mmol) in a mixed solvent of THF (16 mL) and water (8 mL), sodium hydroxide (125 mg, 3.13 mmol), concentrated hydrochloric acid (2 mL) and EtOAc (10 mL×3) to extract and according to the method described in step 4) of example 1 to prepare the title compound as a light red solid (270 mg, 97%), and then the crude product was purified by prep-HPLC to give a yellow solid (110 mg, 39.8%).

$^1$H NMR (600 MHz, CD$_3$OD): δ ppm 8.09 (d, J=8.3 Hz, 1H), 7.94-7.97 (m, 2H), 7.73 (t, J=7.4 Hz, 1H), 7.55-7.60 (m, 3H), 7.42 (d, J=6.2 Hz, 1H), 7.29 (t, J=7.9 Hz, 1H), 7.14-7.15 (m, 1H), 6.80-6.84 (m, 1H), 4.97-5.01 (m, 1H), 4.82 (s, 2H), 3.36-3.40 (m, 1H), 2.99-3.14 (m, 3H), 2.30-2.32 (m, 3H), 2.21-2.27 (m, 1H), 1.82-1.97 (m, 2H), 1.30-1.35 (m, 1H);

$^{13}$C NMR (150 MHz, CD$_3$OD): δ ppm 171.1, 170.2, 158.1, 134.2, 133.5, 129.1, 128.9, 128.4, 126.9, 126.7, 126.5, 123.1, 114.1, 109.2, 42.7, 42.7, 31.5, 9.1; and MS-ESI: m/z 445.3 [M+H]$^+$.

Example 3: 2-(3-(4-(1-naphthamido)cyclohexyl)-5-fluoro-2-methyl-1H-indol-1-yl)acetic acid

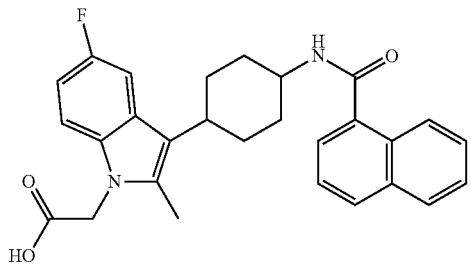 [SMILES: Cc1c(C2CCC(NC(=O)c3cccc4ccccc34)CC2)c2cc(F)ccc2n1CC(=O)O]

Step 1) N-(4-oxocyclohexyl)-1-naphthamide

By using 4-aminocyclohexanone hydrochloride (261 mg, 1.74 mmol), 1-naphthoic acid (250 mg, 1.45 mmol), EDCI (418 mg, 2.18 mmol), HOAT (494 mg, 3.63 mmol), DCM (20 mL) and DIPEA (1.0 mL, 5.81 mmol) and according to the method described in step 2) of example 1 to prepare the title compound as a white solid (338 mg, 87%).

$^1$H NMR (400 MHz, CDCl$_3$): δ ppm 8.26-8.29 (m, 1H), 7.94 (d, J=8.2 Hz, 1H), 7.88-7.91 (m, 1H), 7.53-7.60 (m, 3H), 7.45-7.49 (m, 1H), 6.09 (d, J=7.2 Hz, 1H), 4.52-4.59 (m, 1H), 2.42-2.56 (m, 6H), 1.76-1.85 (m, 2H); and MS-ESI: m/z 268.3 [M+H]$^+$.

Step 2) methyl 2-(3-(4-(1-naphthamido)cyclohexyl)-5-fluoro-2-methyl-1H-indol-1-yl)acetate By using methyl 2-(5-fluoro-2-methyl-1H-indol-1-yl)acetate (191 mg, 0.86 mmol), N-(4-oxocyclohexyl)-1-naphthamide (210 mg, 0.79 mmol), DCM (20 mL), triethyl silicane (0.69 mL, 4.32 mmol) and trifluoroacetic acid (0.19 mL, 2.51 mmol) and according to the method described in step 3) of example 1 to prepare the title compound as a white solid (213 mg, 57%).

$^1$H NMR (400 MHz, CDCl$_3$): δ ppm 8.42 (d, J=8.4 Hz, 1H), 7.99 (d, J=8.2 Hz, 1H), 7.94 (d, J=7.8 Hz, 1H), 7.78 (dd, J$_1$=7.0 Hz, J$_2$=1.1 Hz, 1H), 7.62-7.66 (m, 1H), 7.56-7.61 (m, 2H), 7.26 (dd, J$_1$=10.1 Hz, J$_2$=2.4 Hz, 1H), 7.08 (dd, J$_1$=8.8 Hz, J$_2$=4.3 Hz, 1H), 6.88 (td, J$_1$=9.0 Hz, J$_2$=2.4 Hz, 1H), 6.36 (d, J=6.6 Hz, 1H), 4.78 (s, 2H), 4.56-4.58 (m, 1H), 3.77 (s, 3H), 2.83-2.90 (m, 1H), 2.36 (s, 3H), 2.23-2.26 (m, 2H), 2.09-2.20 (m, 2H), 1.88-1.93 (m, 2H), 1.80-1.84 (m, 2H); and MS-ESI: m/z 473.3 [M+H]$^+$.

Step 3) 2-(3-(4-(1-naphthamido)cyclohexyl)-5-fluoro-2-methyl-1H-indol-1-yl)acetic acid By using a solution of methyl 2-(3-(4-(1-naphthamido)cyclohexyl)-5-fluoro-2-methyl-1H-indol-1-yl)acetate (213 mg, 0.45 mmol) in a mixed solvent of THF (14 mL) and water (7 mL), sodium hydroxide (90 mg, 2.25 mmol), concentrated hydrochloric acid (2 mL) and EtOAc (10 mL×3) to extract and according to the method described in step 4) of example 1 to prepare the title compound as a white solid (110 mg, 50%).

$^1$H NMR (600 MHz, CD$_3$OD): δ ppm 8.24 (d, J=8.3 Hz, 1H), 8.03 (d, J=8.2 Hz, 1H), 7.98 (d, J=7.9 Hz, 1H), 7.71 (d, J=6.9 Hz, 1H), 7.57-7.62 (m, 3H), 7.42 (dd, J$_1$=10.3 Hz, J$_2$=2.2 Hz, 1H), 7.17 (dd, J$_1$=8.7 Hz, J$_2$=4.3 Hz, 1H), 6.80-6.83 (m, 1H), 2.89-2.91 (m, 1H), 2.37 (s, 3H), 2.26-2.33 (m, 4H), 1.88-1.92 (m, 2H), 1.68-1.71 (m, 2H);

$^{13}$C NMR (150 MHz, CD$_3$OD): δ ppm 171.3, 158.1, 135.2, 133.8, 133.6, 130.2, 129.7, 128.1, 126.7, 126.0, 124.9, 124.7, 116.3, 108.6, 107.7, 56.7, 48.5, 45.6, 29.9, 27.0, 17.0, 9.0; and MS-ESI: m/z 459.3 [M+H]$^+$.

Example 4: 2-(5-fluoro-2-methyl-3-(1-(quinoline-2-carbonyl)piperidin-4-yl)-1H-indol-1-yl)acetic acid hydrochloride

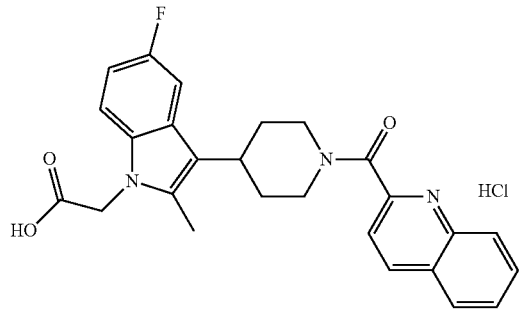 [SMILES: Cc1c(C2CCN(C(=O)c3ccc4ccccc4n3)CC2)c2cc(F)ccc2n1CC(=O)O ; Cl]

Step 1) benzyl 4-oxopiperidine-1-carboxylate

To a solution of piperidin-4-one hydrochloride (680 mg, 5.02 mmol) in DCM (5 mL) was added DIPEA (4.3 mL, 25.07 mmol) at rt. After stirring for 10 min, benzyl chloroformate (2.0 mL, 15.04 mmol) was added to the mixture at 0° C. The mixture was stirred at rt for 3 h and washed with saturated aqueous sodium bicarbonate solution (20 mL). The organic layer was dried over anhydrous Na$_2$SO$_4$ and concentrated. The residue was purified by silica gel chromatography eluted with PE/EtOAc (V/V)=6/1 to give colorless liquid (1.1 g, 94%).

$^1$H NMR (600 MHz, CDCl$_3$): δ ppm 7.32-7.38 (m, 5H), 5.18 (s, 2H), 3.78-3.80 (m, 4H), 2.46 (br.s, 4H); and MS-ESI: m/z 256.05 [M+Na]$^+$.

Step 2) benzyl 4-(5-fluoro-1-(2-methoxy-2-oxo-ethyl)-2-methyl-1H-indol-3-yl)piperidine-1-carboxylate To a solution of methyl 2-(5-fluoro-2-methyl-1H-indol-1-yl))acetate (300 mg, 1.36 mmol) and benzyl 4-oxopiperidine-1-carboxylate (316 mg, 1.36 mmol) in DCM (10 mL) were added triethyl silicane (1.2 mL, 7.46 mmol) and TFA (0.33 mL, 4.34 mmol) dropwise respectively at 0° C. The mixture was stirred for 2 h at rt and washed with saturated aqueous ammonium chloride solution (15 mL). The organic layer was dried over anhydrous Na$_2$SO$_4$ and concentrated. The residue was purified by silica gel chromatography eluted with PE/EtOAc (V/V)=3/1 to give a white solid product (586 mg, 98%).

$^1$H NMR (400 MHz, CDCl$_3$): δ ppm 7.31-7.42 (m, 5H), 7.24-7.27 (m, 1H), 7.06 (dd, J=8.8, 4.3 Hz, 1H), 6.87 (td, J=9.0, 2.2 Hz, 1H), 5.20 (s, 2H), 4.75 (s, 2H), 4.37 (br.s, 2H), 3.75 (s, 3H), 2.85-2.91 (m, 3H), 2.33 (s, 3H), 2.02-2.12 (m, 2H), 1.72-1.76 (m, 2H); and MS-ESI: m/z 439.30 [M+H]$^+$.

Step 3) methyl 2-(5-fluoro-2-methyl-3-(piperidin-4-yl)-1H-indol-1-yl)acetate

To a solution of benzyl 4-(5-fluoro-1-(2-methoxy-2-oxo-ethyl)-2-methyl-1H-indol-3-yl)piperidine-1-carboxylate (580 mg, 1.33 mmol) in MeOH (10 mL) was added Pd/C (60 mg) at rt. The mixture was stirred under hydrogen for 3 h at rt, and then filtered. The filtrate was concentrated to give a light yellow solid product (400 mg, 99%).

$^1$H NMR (400 MHz, CDCl$_3$): δ ppm 9.76 (br.s, 1H), 7.55-7.58 (m, 1H), 7.05 (dd, J=8.8, 4.4 Hz, 1H), 6.87 (td, J=8.9, 2.1 Hz, 1H), 4.75 (s, 2H), 3.74 (s, 3H), 3.68-3.72 (m, 2H), 2.97-3.11 (m, 3H), 2.64-2.74 (m, 2H), 2.38 (s, 3H), 1.92-1.95 (m, 2H); and MS-ESI: m/z 305.20 [M+H]$^+$.

Step 4) methyl 2-(5-fluoro-2-methyl-3-(1-(quinoline-2-carbonyl)piperidin-4-yl)-1H-indol-1-yl)acetate To a solution of quinoline-2-carboxylic acid (135 mg, 0.79 mmol), methyl 2-(5-fluoro-2-methyl-3-(piperidin-4-yl)-1H-indol-1-yl)acetate (200 mg, 0.66 mmol), EDCI (188 mg, 0.99 mmol) and HOAT (134 mg, 0.99 mmol) in DCM (10 mL) was added DIPEA (0.35 mL, 1.97 mmol) dropwise at 0° C. The mixture was stirred for 5 h at rt, and then washed with water (10 mL×3). The organic layer was dried over anhydrous Na$_2$SO$_4$ and concentrated. The residue was purified by silica gel chromatography eluted with PE/EtOAc (V/V)=2/3 to give a white solid product (215 mg, 71%).

$^1$H NMR (600 MHz, CDCl$_3$): δ ppm 8.30 (d, J=8.3 Hz, 1H), 8.14 (d, J=8.6 Hz, 1H), 7.87 (d, J=8.1 Hz, 1H), 7.76-7.78 (m, 2H), 7.59-7.62 (m, 1H), 7.36-7.38 (m, 1H), 7.07 (dd, J=8.9, 4.3 Hz, 1H), 6.89 (td, J=9.0, 2.4 Hz, 1H), 5.01-5.04 (m, 1H), 4.77 (s, 2H), 4.18-4.21 (m, 1H), 3.75 (s, 3H), 3.26-3.31 (m, 1H), 3.02-3.08 (m, 1H), 2.95-3.00 (m, 1H), 2.37 (s, 3H), 2.12-2.31 (m, 2H), 1.92-1.94 (m, 2H), 1.71-1.73 (m, 2H); and MS-ESI: m/z 460.90 [M+H]$^+$.

Step 5) 2-(5-fluoro-2-methyl-3-(1-(quinoline-2-carbonyl)piperidin-4-yl)-1H-indol-1-yl)acetic acid hydrochloride A solution of methyl 2-(5-fluoro-2-methyl-3-(1-(quinoline-2-carbonyl)piperidin-4-yl)-1H-indol-1-yl)acetate (205 mg, 0.45 mmol) and LiOH.H$_2$O (93 mg, 2.23 mmol) in a mixed solvent of THF (5 mL) and water (3 mL) was stirred for 30 min at 45° C. After adjusting the mixture to pH 1 with hydrochloric acid (1.0 mol/L), the resulting mixture was extracted with EtOAc (10 mL×3). The combined organic layers were dried over anhydrous Na$_2$SO$_4$ and concentrated to give a white solid product (210 mg, 98%).

$^1$H NMR (600 MHz, d$_6$-DMSO): δ ppm 8.58 (d, J=8.5 Hz, 1H), 8.08 (d, J=8.3 Hz, 2H), 7.86 (t, J=7.8 Hz, 1H), 7.80 (d, J=8.4 Hz, 1H), 7.70 (t, J=7.6 Hz, 1H), 7.42-7.44 (m, 1H), 7.33-7.35 (m, 1H), 6.86-6.90 (m, 1H), 4.93 (s, 2H), 4.73-4.75 (m, 1H), 4.01-4.07 (m, 1H), 3.24-3.29 (m, 1H), 3.11-3.17 (m, 1H), 2.97-3.01 (m, 1H), 2.32 (s, 3H), 2.05-2.08 (m, 2H), 1.78-1.80 (m, 1H), 1.56-1.58 (m, 1H); and MS-ESI: m/z 446.90 [M+H—HCl]$^+$.

Example 5: 2-(5-fluoro-2-methyl-3-(1-(quinoline-2-carbonyl)-1,2,3,6-tetrahydropyridin-4-yl)-1H-indol-1-yl)acetic acid hydrochloride

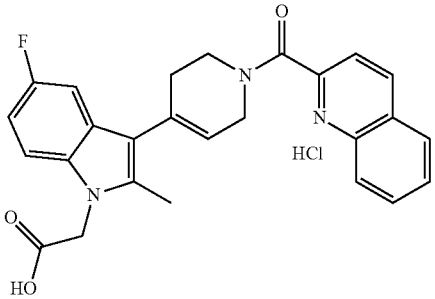 [SMILES: Cc1c(C2=CCN(C(=O)c3ccc4ccccc4n3)CC2)c2cc(F)ccc2n1CC(=O)O ; Cl]

Step 1) 1-(quinolin-2-carbonyl)piperidin-4-one

By using quinoline-2-carboxylic acid (500 mg, 2.89 mmol), piperidin-4-one hydrochloride (344 mg, 3.46 mmol), EDCI (830 mg, 4.33 mmol), HOAT (982 mg, 7.22 mmol), DCM (20 mL) and DIPEA (2.0 mL, 11.54 mmol) and according to the method described in step 2) of example 1 to prepare the title compound as a white solid (532 mg, 72%).

$^1$H NMR (400 MHz, CDCl$_3$): δ ppm 8.32 (d, J=8.4 Hz, 1H), 8.10 (d, J=8.4 Hz, 1H), 7.90 (d, J=8.2 Hz, 1H), 7.84 (d, J=8.4 Hz, 1H), 7.78-7.82 (m, 1H), 7.63-7.67 (m, 1H), 4.15 (t, J=6.3 Hz, 2H), 4.03 (t, J=6.1 Hz, 2H), 2.69 (t, J=6.3 Hz, 4H); and
MS-ESI: m/z 255.2 [M+H]$^+$.

Step 2) methyl 2-(5-fluoro-2-methyl-3-(1-(quinoline-2-carbonyl)-1,2,3,6-tetrahydropyridin-4-yl)-1H-indol-1-yl)acetate By using a solution of methyl 2-(5-fluoro-2-methyl-1H-indol-1-yl)acetate (240 mg, 1.08 mmol) and 1-(quinolin-2-carbonyl)piperidin-4-one (250 mg, 0.98 mmol) in DCM (20 mL), triethyl silicane (0.86 mL, 5.41 mmol) and TFA (0.23 mL, 3.15 mmol) and according to the method described in step 3) of example 1 to prepare the title compound as a white solid (375 mg, 83%).

$^1$H NMR (600 MHz, CDCl$_3$): δ ppm 8.32 (d, J=8.3 Hz, 1H), 8.15-8.18 (m, 1H), 7.90 (d, J=8.0 Hz, 1H), 7.79-7.82 (m, 2H), 7.63-7.67 (m, 1H), 7.22 (d, J=9.7 Hz, 1H), 7.06-7.10 (m, 1H), 6.91-6.94 (m, 1H), 4.80-4.82 (m, 2H), 4.55-4.56 (m, 1H), 4.43-4.44 (m, 1H), 4.14-4.15, 4.02-4.04 (m, m, 1.5H, 0.5H), 3.90-3.91 (m, 1H), 3.77-3.79 (m, 3H), 2.69-2.71 (m, 3H), 2.38-2.43 (m, 3H); and
MS-ESI: m/z 458.1 [M+H]$^+$.

Step 3) 2-(5-fluoro-2-methyl-3-(1-(quinoline-2-carbonyl)-1,2,3,6-tetrahydropyridin-4-yl)-1H-indol-1-yl)acetic acid hydrochloride To a solution of methyl 2-(5-fluoro-2-methyl-3-(1-(quinoline-2-carbonyl)-1,2,3,6-tetrahydropyridin-4-yl)-1H-indol-1-yl) acetate (369 mg, 0.80 mmol) in a mixed solvent of THF (16 mL) and water (8 mL) was added sodium hydroxide (161 mg, 4.01 mmol). The mixture was stirred at 50° C. for 3 h and the THF was removed. The aqueous layer was washed with PE (10 mL) and then adjusted with concentrated hydrochloric acid (2 mL) to pH 1. Some solid precipitated out and then the mixture was filtered. The filter cake was washed with water (10 mL×3) and dried to give the title compound as a gray solid (290 mg, 75%).

$^1$H NMR (600 MHz, d$_6$-DMSO): δ ppm 8.53 (d, J=7.7 Hz, 1H), 8.05-8.08 (m, 2H), 7.84-7.85 (m, 1H), 7.75-7.76 (m, 1H), 7.69-7.70 (m, 1H), 7.38-7.39 (m, 1H), 7.27 (d, J=9.1 Hz, 1H), 6.91-6.92 (m, 1H), 4.97 (s, 2H), 4.40 (m, 1H), 4.22 (m, 1H), 3.99 (m, 1H), 3.18 (m, 1H), 2.51-2.60 (m, 3H), 2.31-2.35 (m, 3H);
$^{13}$C NMR (150 MHz, d$_6$-DMSO): δ ppm 170.8, 167.6, 158.5, 157.0, 154.8, 137.9, 133.4, 130.8, 120.8, 114.4, 110.7, 108.9, 49.1, 45.1, 42.6, 30.3, 11.5; and
MS-ESI: m/z 444.1 [M−HCl+H]$^+$.

Example 6: 2-(5-fluoro-2-methyl-3-(4-(quinoline-2-carboxamido)cyclohexyl)-1H-indol-1-yl)acetic acid hydrochloride (6a) and 2-(5-fluoro-2-methyl-3-(4-(quinoline-2-carboxamido)cyclohexyl)-1H-indol-1-yl)acetic acid hydrochloride (6b)

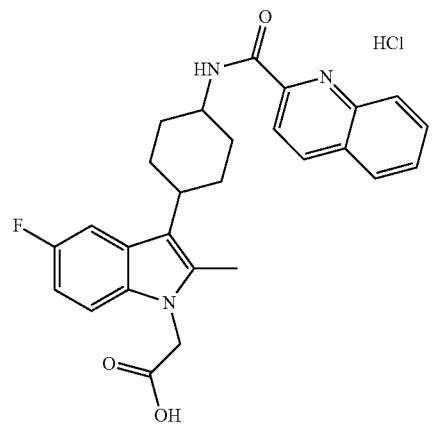 [SMILES: Cc1c(C2CCC(NC(=O)c3ccc4ccccc4n3)CC2)c2cc(F)ccc2n1CC(=O)O ; Cl]

Step 1) N-(4-oxocyclohexyl)quinoline-2-carboxamide

By using quinoline-2-carboxylic acid (250 mg, 1.44 mmol), 4-aminocyclohexanone hydrochloride (259 mg, 1.73 mmol), EDCI (415 mg, 2.16 mmol), HOAT (491 mg, 3.61 mmol), DCM (20 mL) and DIPEA (1.0 mL, 5.77 mmol) and according to the method described in step 2) of example 1 to prepare the title compound as a white solid (330 mg, 85%).

$^1$H NMR (600 MHz, CDCl$_3$): δ ppm 8.34-8.36 (m, 2H), 8.31-8.33 (m, 1H), 8.13 (d, J=8.5 Hz, 1H), 7.91 (d, J=8.2 Hz, 1H), 7.79-7.81 (m, 1H), 7.64-7.67 (m, 1H), 4.50-4.55 (m, 1H), 2.52-2.61 (m, 4H), 2.41-2.44 (m, 2H), 1.95-2.01 (m, 2H); and
MS-ESI: m/z 269.2 [M+H]$^+$.

Step 2) methyl 2-(5-fluoro-2-methyl-3-(4-(quinoline-2-carboxamido)cyclohexyl)-1H-indol-1-yl)acetate (6a-1) and methyl 2-(5-fluoro-2-methyl-3-(4-(quinoline-2-carboxamido)cyclohexyl)-1H-indol-1-yl)acetate (6b-1)

To a solution of methyl 2-(5-fluoro-2-methyl-1H-indol-1-yl))acetate (227 mg, 1.02 mmol) and N-(4-oxocyclohexyl)quinoline-2-carboxamide (250 mg, 0.93 mmol) in DCM (20 mL) were added triethyl silicane (0.82 mL, 5.12 mmol) and TFA (0.22 mL, 2.98 mmol) dropwise respectively at 0° C. The mixture was stirred for 3 h at rt. After removing the solvent, the residue was diluted with saturated sodium bicarbonate solution (15 mL) and then extracted with EtOAc (15 mL×2). The combined organic layers were dried over anhydrous Na$_2$SO$_4$ and concentrated. The residue was purified by silica gel chromatography eluted with PE/EtOAc (V/V)=2/1 to give compound (6b-1) as a yellow solid (251 mg, 57%) and compound (6a-1) as a white solid product (109 mg, 24%).

Compound 6b-1: MS-ESI: m/z 474.1 [M+H]$^+$.

Compound 6a-1: $^1$H NMR (400 MHz, CDCl$_3$): δ ppm 8.33-8.39 (m, 2H), 8.23 (d, J=8.4 Hz, 1H), 8.17 (d, J=8.4 Hz, 1H), 7.92 (d, J=8.0 Hz, 1H), 7.78-7.82 (m, 1H), 7.63-7.67 (m, 1H), 7.38 (dd, J$_1$=10.1 Hz, J$_2$=2.3 Hz, 1H), 7.09 (dd, J$_1$=8.8 Hz, J$_2$=4.3 Hz, 1H), 6.91 (td, J$_1$=9.0 Hz, J$_2$=2.4 Hz, 1H), 4.79 (s, 2H), 4.18-4.24 (m, 1H), 3.77 (s, 3H), 2.81-2.87 (m, 1H), 2.39 (s, 3H), 2.32-2.35 (m, 2H), 2.12-2.22 (m, 2H), 1.94-1.97 (m, 2H), 1.60-1.64 (m, 2H); and MS-ESI: m/z 474.1 [M+H]$^+$.

Step 3) 2-(5-fluoro-2-methyl-3-(4-(quinoline-2-carboxamido)cyclohexyl)-1H-indol-1-yl)acetic acid hydrochloride (6a)

To a solution of methyl 2-(5-fluoro-2-methyl-3-(4-(quinoline-2-carboxamido)cyclohexyl)-1H-indol-1-yl)acetate (6a-1) (96 mg, 0.20 mmol) in a mixed solvent of THF (10 mL) and water (5 mL) was added sodium hydroxide (41 mg, 1.01 mmol). The mixture was stirred for 1.5 h at 50° C. After adjusting the mixture to pH about 1 with hydrochloric acid (1 mol/L), the resulting mixture was extracted with EtOAc (15 mL×3). The combined organic layers were dried over anhydrous Na$_2$SO$_4$ and concentrated to give compound (6a) as a yellow solid (93 mg, 92.6%). Rt of HPLC was 19.02 min.

$^1$H NMR (600 MHz, d$_6$-DMSO): δ ppm 8.63 (d, J=8.5 Hz, 1H), 8.57 (d, J=8.5 Hz, 1H), 8.20 (d, J=8.5 Hz, 2H), 8.09 (d, J=8.0 Hz, 1H), 7.88 (t, J=7.6 Hz, 1H), 7.73 (t, J=7.4 Hz, 1H), 7.45 (dd, J$_1$=10.5 Hz, J$_2$=2.2 Hz, 1H), 7.33 (dd, J$_1$=8.8 Hz, J$_2$=4.6 Hz, 1H), 6.86-6.89 (m, 1H), 4.93 (s, 2H), 4.11-4.15 (m, 1H), 2.78-2.82 (m, 1H), 2.31 (s, 3H), 2.04-2.10 (m, 4H), 1.72-1.76 (m, 2H), 1.66-1.70 (m, 2H);

$^{13}$C NMR (150 MHz, d$_6$-DMSO): δ ppm 171.0, 163.6, 157.9, 156.4, 150.8, 138.4, 134.6, 133.7, 130.9, 129.7, 129.3, 128.5, 119.2, 115.7, 110.3, 108.2, 55.4, 48.5, 45.0, 31.7, 30.9, 10.7; and MS-ESI: m/z 460.3 [M+H—HCl]$^+$.

Step 4) 2-(5-fluoro-2-methyl-3-(4-(quinoline-2-carboxamido)cyclohexyl)-1H-indol-1-yl)acetic acid hydrochloride (6b)

To a solution of methyl 2-(5-fluoro-2-methyl-3-(4-(quinoline-2-carboxamido)cyclohexyl)-1H-indol-1-yl)acetate (6b-1) (251 mg, 0.53 mmol) in a mixed solvent of THF (14 mL) and water (7 mL) was added sodium hydroxide (41 mg, 1.01 mmol). The mixture was stirred for 3 h at 50° C. THF was removed and the residue was adjusted to pH about 1 with hydrochloric acid (1 mol/L). The resulting mixture was filtered. The filter cake was suck dried to give compound (6b) as a yellow solid (244 mg, 92.9%). Rt of HPLC was 7.77 min.

$^1$H NMR (600 MHz, CD$_3$OD): δ ppm 8.51 (d, J=8.4 Hz, 1H), 8.34 (d, J=8.4 Hz, 1H), 8.25 (d, J=8.4 Hz, 1H), 8.02 (d, J=8.1 Hz, 1H), 7.88 (t, J=7.5 Hz, 1H), 7.72 (t, J=7.5 Hz, 1H), 7.53-7.51 (m, 1H), 7.21 (dd, J$_1$=8.7 Hz, J$_2$=4.3 Hz, 1H), 6.87-6.84 (m, 1H), 4.87 (s, 2H), 4.43-4.42 (m, 1H), 3.00-2.95 (m, 1H), 2.39 (s, 3H), 2.34-2.28 (m, 2H), 2.14-2.12 (m, 2H), 1.94-1.89 (m, 2H), 1.78-1.76 (m, 2H); and MS-ESI: m/z 460.1 [M+H—HCl]$^+$.

Example 7: 2-(5-fluoro-2-methyl-3-(1-(quinoline-2-carbonyl)-1,2,5,6-tetrahydropyridin-3-yl)-1H-indol-1-yl)acetic acid hydrochloride

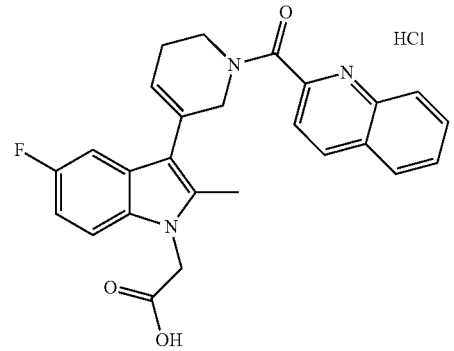 [SMILES: Cc1c(C2=CCCN(C(=O)c3ccc4ccccc4n3)C2)c2cc(F)ccc2n1CC(=O)O ; Cl]

Step 1) 1-(quinoline-2-carbonyl)piperidin-3-one

By using quinoline-2-carboxylic acid (350 mg, 2.02 mmol), piperidin-3-one hydrochloride (330 mg, 2.42 mmol), EDCI (581 mg, 3.03 mmol), HOAT (688 mg, 5.05 mmol), DCM (20 mL) and DIPEA (1.4 mL, 8.08 mmol) and according to the method described in step 2) of example 1 to prepare the title compound as yellow oil (269 mg, 52%).

$^1$H NMR (400 MHz, CDCl$_3$): δ ppm 8.29-8.32 (m, 1H), 8.11 (t, J=8.7 Hz, 1H), 7.89 (t, 7.7 Hz, 1H), 7.77-7.82 (m, 2H), 7.62-7.67 (m, 1H), 4.44 (d, J=9.4 Hz, 2H), 4.04 (t, J=5.8 Hz, 1H), 3.91 (t, J=5.9 Hz, 1H), 2.62-2.66 (m, 2H), 2.13-2.23 (m, 2H); and MS-ESI: m/z 255.3 [M+H]$^+$.

Step 2) methyl 2-(5-fluoro-2-methyl-3-(1-(quinoline-2-carbonyl)-1,2,5,6-tetrahydropyridin-3-yl)-1H-indol-1-yl)acetate By using a solution of methyl 2-(5-fluoro-2-methyl-1H-indol-1-yl)acetate (254 mg, 1.15 mmol) and 1-(quinolin-2-carbonyl)piperidin-3-one (266 mg, 1.05 mmol) in DCM (20 mL), triethyl silicane (0.92 mL, 5.75 mmol) and TFA (0.25 mL, 3.35 mmol) and according to the method described in step 3) of example 1 to prepare the title compound as a yellow solid (250 mg, 52%).

$^1$H NMR (600 MHz, CDCl$_3$): δ ppm 8.27 (d, J=8.4 Hz, 1H), 8.22 (d, J=8.4 Hz, 1H), 7.84 (d, J=8.3 Hz, 1H), 7.77-7.80 (m, 2H), 7.60-7.63 (m, 1H), 7.33 (dd, J$_1$=9.6 Hz, J$_2$=2.4 Hz, 1H), 7.00-7.02 (m, 2H), 6.86 (td, J$_1$=9.0 Hz, J$_2$=2.5 Hz, 1H), 4.72 (s, 2H), 4.08-4.10 (m, 2H), 3.97-3.98 (m, 1H), 3.71 (s, 3H), 2.57-2.59 (m, 2H), 2.37 (s, 3H), 2.21-2.25 (m, 2H); and MS-ESI: m/z 458.3 [M+H]$^+$.

Step 3) 2-(5-fluoro-2-methyl-3-(1-(quinoline-2-carbonyl)-1,2,5,6-tetrahydropyridin-3-yl)-1H-indol-1-yl)acetic acid hydrochloride By using a solution of methyl 2-(5-fluoro-2-methyl-3-(1-(quinoline-2-carbonyl)-1,2,5,6-tetrahydropyridin-3-yl)-1H- indol-1-yl) acetate (250 mg, 0.54 mmol) in a mixed solvent of THF (14 mL) and water (7 mL), sodium hydroxide (109 mg, 2.72 mmol), hydrochloric acid (1 mol/L) and EtOAc (15 mL×3) to extract and according to the method described in step 4) of example 1 to prepare the title compound as a red solid (242 mg, 92.4%).

$^1$H NMR (600 MHz, d$_6$-DMSO): δ ppm 8.52 (d, J=8.5 Hz, 1H), 8.11 (d, J=8.2 Hz, 1H), 8.02 (d, J=8.1 Hz, 1H), 7.82-7.84 (m, 1H), 7.77 (d, J=8.5 Hz, 1H), 7.68 (t, J=7.4 Hz, 1H), 7.29-7.32 (m, 1H), 7.25 (dd, J$_1$=9.9 Hz, J$_2$=2.1 Hz, 1H), 6.84 (td, J$_1$=9.1 Hz, J$_2$=2.2 Hz, 1H), 4.88 (s, 2H), 3.93-3.95 (m, 2H), 3.75-3.77 (m, 1H), 3.58-3.60 (m, 1H), 2.52-2.53 (m, 1H), 2.25 (s, 3H), 2.08-2.10 (m, 2H);

$^{13}$C NMR (150 MHz, d$_6$-DMSO): δ ppm 170.8, 166.2, 158.4, 156.9, 153.9, 138.2, 138.0, 135.8, 133.5, 133.3, 131.0, 129.5, 128.5, 128.3, 128.2, 125.5, 121.5, 117.6, 113.6, 113.0, 110.7, 67.5, 60.2, 45.0, 25.6, 11.5; and MS-ESI: m/z 444.3 [M+H—HCl]$^+$.

Example 8: 2-(5-fluoro-2-methyl-3-(1-(quinolin-2-yl)methyl-1,2,3,6-tetrahydropyridin-4-yl)-1H-indol-1-yl)acetic acid dihydrochloride

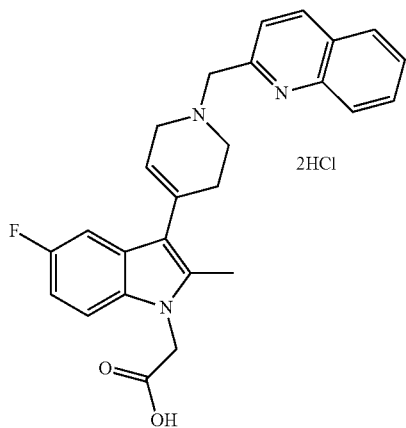 [SMILES: Cc1c(C2=CCN(Cc3ccc4ccccc4n3)CC2)c2cc(F)ccc2n1CC(=O)O ; "2HCl"]

Step 1) 1-((quinolin-2-yl)methyl)piperidin-4-one

To a solution of quinoline-2-formaldehyde (500 mg, 3.18 mmol), sodium triacetoxyborohydride (1.21 g, 5.73 mmol) in anhydrous DCM was added 1,4-dioxa-8-azaspiro[4.5]decane (0.73 mL, 5.73 mmol) dropwise at 0° C. The mixture was stirred for 3 h at rt and washed with aqueous sodium hydroxide solution (15 mL). The organic layer was dried over anhydrous Na$_2$SO$_4$ and concentrated. The residue was purified by silica gel chromatography eluted with DCM/MeOH (V/V)=40/1 to give the compound named 8-((quinoline-2-yl)methyl)-1,4-dioxa-8-azaspiro[4.5]decane as yellow oil (733 mg, 81%).

$^1$H NMR (400 MHz, CDCl$_3$): δ ppm 8.12 (d, J=8.4 Hz, 1H), 8.07 (d, J=8.5 Hz, 1H), 7.79 (d, J=8.1 Hz, 1H), 7.68-7.70 (m, 1H), 7.65 (d, J=8.5 Hz, 1H), 7.48-7.52 (m, 1H), 3.95 (s, 4H), 3.86 (s, 2H), 2.64 (t, J=5.4 Hz, 4H), 1.78 (t, J=5.6 Hz, 4H); and MS-ESI: m/z 285.3 [M+H]$^+$.

To 8-((quinolin-2-yl)methyl)-1,4-dioxa-8-azaspiro[4.5]decane (300 mg, 1.06 mmol) was added concentrated hydrochloric acid (6 mL) and glacial acetic acid (6 mL). The mixture was refluxed for 3.5 h at 100° C. Sodium hydroxide solid was added into the system in an ice-bath to obtain an alkaline solution. The mixture was extracted with EtOAc (15 mL×2). The combined organic layers were dried over anhydrous Na$_2$SO$_4$ and concentrated. The residue was purified by silica gel chromatography eluted with DCM/MeOH (V/V)=40/1 to give a yellow oily product (215 mg, 84%).

$^1$H NMR (400 MHz, CDCl$_3$): δ ppm 8.17 (d, J=8.5 Hz, 1H), 8.09 (d, J=8.5 Hz, 1H), 7.82 (d, J=8.1 Hz, 1H), 7.71-7.73 (m, 1H), 7.68 (d, J=8.6 Hz, 1H), 7.52-7.55 (m, 1H), 3.98 (s, 2H), 2.88 (t, J=6.1 Hz, 4H), 2.50 (t, J=6.1 Hz, 4H); and MS-ESI: m/z 241.1 [M+H]$^+$.

Step 2) methyl 2-(5-fluoro-2-methyl-3-(1-(quinolin-2-yl)-1,2,3,6-tetrahydropyridin-4-yl)-1H-indol-1-yl)acetate By using methyl 2-(5-fluoro-2-methyl-1H-indol-1-yl)acetate (214 mg, 0.97 mmol), 1-(quinolin-2-ylmethyl)piperidin-4-one (211 mg, 0.88 mmol), DCM (20 mL), triethyl silicane (0.77 mL, 4.83 mmol) and TFA (0.21 mL, 2.81 mmol) and according to the method described in step 3) of example 1 to prepare the title compound as yellow thick oil (203 mg, 52%).

$^1$H NMR (600 MHz, CDCl$_3$): δ ppm 8.19 (d, J=8.5 Hz, 1H), 8.13 (d, J=8.5 Hz, 1H), 7.84 (d, J=8.0 Hz, 1H), 7.77 (d, J=8.5 Hz, 1H), 7.72-7.75 (m, 1H), 7.54-7.56 (m, 1H), 7.26 (dd, J$_1$=9.8 Hz, J$_2$=2.4 Hz, 1H), 7.08 (dd, J$_1$=8.8 Hz, J$_2$=4.2 Hz, 1H), 6.90 (td, J$_1$=9.0 Hz, J$_2$=2.4 Hz, 1H), 5.71 (s, 1H), 4.79 (s, 2H), 4.04 (s, 2H), 3.76 (s, 3H), 3.35-3.36 (m, 2H), 2.86 (t, J=5.6 Hz, 2H), 2.57-2.59 (m, 2H), 2.40 (s, 3H); and MS-ESI: m/z 444.0 [M+H]$^+$.

Step 3) 2-(5-fluoro-2-methyl-3-(1-((quinolin-2-yl)methyl)-1,2,3,6-tetrahydropyridin-4-yl)-1H-indol-1-yl)acetic acid dihydrochloride By using a solution of methyl 2-(5-fluoro-2-methyl-3-(1-(quinolin-2-yl)-1,2,3,6-tetrahydropyridin-4-yl)-1H-indol-1-yl)acetate (195 mg, 0.44 mmol) in a mixed solvent of THF (14 mL) and water (7 mL), lithium hydroxide monohydrate (92 mg, 2.20 mmol) and according to the method described in step 4) of example 1 to prepare the title compound as a yellow solid (164 mg, 74.4%).

$^1$H NMR (600 MHz, d$_6$-DMSO): δ ppm 8.53 (d, J=8.3 Hz, 1H), 8.12 (d, J=8.3 Hz, 1H), 8.07 (d, J=7.9 Hz, 1H), 7.85-7.88 (m, 2H), 7.70 (t, J=7.2 Hz, 1H), 7.39-7.41 (m, 1H), 7.34 (d, J=9.4 Hz, 1H), 6.91-6.94 (m, 1H), 5.64 (s, 1H), 4.99 (s, 2H), 4.83 (s, 2H), 4.04 (s, 2H), 2.82 (m, 2H), 2.35 (s, 3H);

$^{13}$C NMR (150 MHz, d$_6$-DMSO): 170.7, 158.6, 157.1, 147.3, 138.1, 136.4, 133.4, 130.8, 129.2, 128.6, 127.9, 126.9, 122.6, 118.9, 113.2, 110.8, 109.0, 59.4, 55.3, 50.8, 49.5, 45.1, 26.8, 11.4; and MS-ESI: m/z 430.0 [M+H-2HCl]$^+$.

Example 9: 2-(3-(1-((2,4-difluorobenzyl)carbamoyl)-1,2,3,6-tetrahydropyridin-4-yl)-5-fluoro-2-methyl-1H-indol-1-yl)acetic acid (9a) and 2-(3-(1-((2,4-difluorobenzyl)carbamoyl)piperidin-4-yl)-5-fluoro-2-methyl-1H-indol-1-yl)acetic acid (9b)

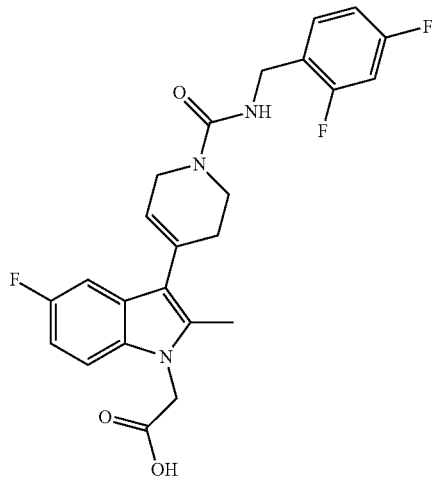

9a

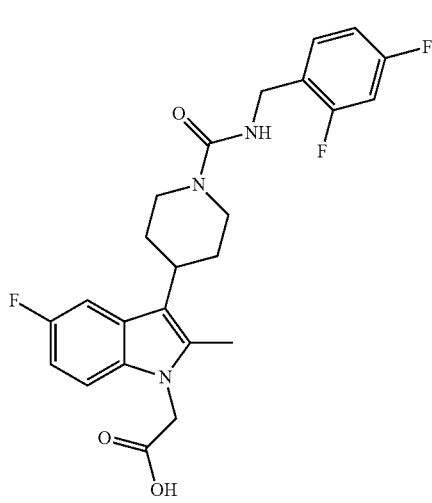

9b

Step 1) N-(2,4-difluorobenzyl)-4-oxopiperidine-1-carboxamide

To a solution of CDI (555 mg, 3.32 mmol) in anhydrous DMF (10 mL) were added TEA (0.77 mL, 5.53 mmol) and 2,4-difluorobenzylamine (0.32 mL, 2.66 mmol) dropwise respectively. After stirring for 30 min at rt, and piperidone hydrochloride (300 mg, 2.21 mmol) was added to the mixture. The resulting mixture was stirred at 70° C. in a sealing tube for 5 h and then the solvent was removed. The residue was diluted with water (10 mL), the resulting mixture was extracted with EtOAc (10 mL×3). The combined organic layers were dried over anhydrous $Na_2SO_4$ and concentrated. The residue was purified by silica gel chromatography eluted with DCM/MeOH (V/V)=40/1 to give a colorless oily product (484 mg, 81%).

$^1$H NMR (400 MHz, $CDCl_3$): δ ppm 7.34-7.40 (m, 1H), 6.76-6.86 (m, 2H), 5.05-5.07 (m, 1H), 4.43 (d, J=5.7 Hz, 2H), 3.69 (t, J=6.2 Hz, 4H), 2.48 (t, J=6.2 Hz, 4H); and MS-ESI: m/z 269.2 [M+H]$^+$.

Step 2) methyl 2-(3-(1-((2,4-difluorobenzyl)carbamoyl)-1,2,3,6-tetrahydropyridin-4-yl)-5-fluoro-2-methyl-1H-indol-1-yl)acetate (9a-1) and methyl 2-(3-(1-((2,4-difluorobenzyl)carbamoyl)piperidin-4-yl)-5-fluoro-2-methyl-1H-indol-1-yl)acetate (9b-1)

To a solution of methyl 2-(5-fluoro-2-methyl-1H-indol-1-yl))acetate (210 mg, 0.94 mmol) and N-(2,4-difluorobenzyl)-4-oxopiperidin-1-formamide (230 mg, 0.86 mmol) in DCM (20 mL) were added triethyl silicane (0.75 mL, 4.72 mmol) and TFA (0.20 mL, 2.74 mmol) dropwise respectively at 0° C. The mixture was stirred for 5 h at rt and washed with saturated aqueous sodium hydroxide solution (15 mL). The combined organic layers were dried over anhydrous $Na_2SO_4$ and the solvent was removed. The residue was purified by silica gel chromatography eluted with DCM/MeOH (V/V)=100/1 to give a white solid product (315 mg, 77%), which was a mixture of compound (9a-1) and (9b-1).

$^1$H NMR (400 MHz, $CDCl_3$): δ ppm 7.40-7.46 (m, 1H), 7.22-7.25, 7.13-7.16 (m, m, 0.5H, 0.5H), 7.04-7.08 (m, 1H), 6.78-6.92 (m, 3H), 5.68 (s, 0.5H), 4.89-4.96 (m, 1H), 4.78 (s, 2H), 4.47-4.50 (m, 2H), 4.09-4.15 (m, 1H), 3.73 (s, 3H), 3.67 (t, J=5.6 Hz, 1H), 2.85-2.93 (m, 1H), 2.52-2.55 (m, 1H), 2.34 (s, 3H), 2.00-2.10 (m, 2H), 1.73-1.77 (m, 1H); and MS-ESI: m/z 472.3 [M+H]$^+$, 474.3 [M+H]$^+$.

Step 3) 2-(3-(1-((2,4-difluorobenzyl)carbamoyl)-1,2,3,6-tetrahydropyridin-4-yl)-5-fluoro-2-methyl-1H-indol-1-yl)acetic acid (9a) and 2-(3-(1-((2,4-difluorobenzyl)carbamoyl)piperidin-4-yl)-5-fluoro-2-methyl-1H-indol-1-yl)acetic acid (9b)

To a solution of the above mixture of methyl 2-(3-(1-((2,4-difluorobenzyl)carbamoyl)-1,2,3,6-tetrahydropyridin-4-yl)-5-fluoro-2-methyl-1H-indol-1-yl)acetate (9a-1) and methyl 2-(3-(1-((2,4-difluorobenzyl)carbamoyl)piperidin-4-yl)-5-fluoro-2-methyl-1H-indol-1-yl)acetate (9b-1) (306 mg, 0.65 mmol) in a mixed solvent of THF (18 mL) and water (9 mL) was added lithium hydroxide monohydrate (136 mg, 3.23 mmol). The mixture was stirred for 1.5 h at 45° C. After adjusting to pH about 1 with hydrochloric acid (1 mol/L), the resulting mixture was extracted with EtOAc (10 mL×5). The combined organic layers were dried over anhydrous $Na_2SO_4$ and the solvent was removed to give a brown solid product (266 mg, 89%), which was a mixture of compound 9a and 9b. The mixture was separated by prep-HPLC to give compound 9a as a lavender solid (70 mg, 93.64%) and compound 9b as a light yellow solid (72 mg, 99.19%).

Compound 9a: $^1$H NMR (400 MHz, $CDCl_3$:$CD_3OD$=3:1): δ ppm 7.13-7.19 (m, 1H), 6.88-6.91 (m, 2H), 6.61-6.65 (m, 2H), 6.55-6.58 (m, 1H), 5.46 (m, 1H), 4.56 (s, 2H), 4.17 (s, 2H), 3.84 (m, 2H), 3.44 (t, J=5.5 Hz, 2H), 2.30 (m, 2H), 2.13 (s, 3H);

$^{13}$C NMR (100 MHz, $CDCl_3$: $CD_3OD$=3:1): δ ppm 159.2, 156.9, 134.6, 133.0, 131.2, 130.5, 128.3, 127.3, 122.2, 115.0, 111.1, 110.8, 110.0, 109.1, 104.0, 103.7, 44.6, 43.5, 40.5, 37.7, 29.8, 10.7; and MS-ESI: m/z 458.3 [M+H]$^+$.

Compound 9b: $^1$H NMR (600 MHz, $CD_3OD$: $CDCl_3$=3:1): δ ppm 7.43-7.47 (m, 1H), 7.26 (dd, $J_1$=10.2 Hz, $J_2$=2.2 Hz, 1H), 7.17 (dd, $J_1$=8.8 Hz, $J_2$=4.3 Hz, 1H), 6.95 (td, $J_1$=8.3 Hz, $J_2$=1.7 Hz, 1H), 6.86-6.90 (m, 2H), 4.85 (s, 2H), 4.48 (s, 2H), 4.22-4.24 (m, 2H), 3.01-3.04 (m, 1H), 2.95-2.99 (m, 2H), 2.39 (s, 3H), 2.09-2.16 (m, 2H), 1.77-1.79 (m, 2H);
$^{13}$C NMR (150 MHz, CD$_3$OD: CDCl$_3$=3:1): δ ppm 171.1, 161.5, 159.9, 158.5, 156.6, 133.8, 130.2, 126.8, 114.8, 110.9, 110.7, 109.0, 108.3, 104.0, 45.1, 44.3, 37.6, 31.5, 9.7; and
MS-ESI: m/z 460.0 [M+H]$^+$.

Example 10: 2-(5-fluoro-3-(4-(5-fluoro-1-naphthamido)cyclohexyl)-2-methyl-1H-indol-1-yl)acetic acid

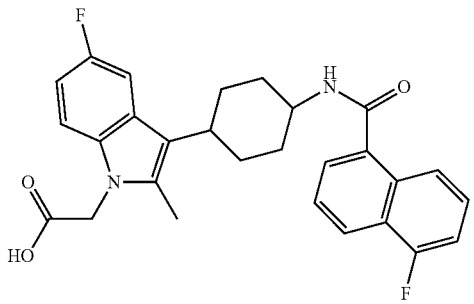 [SMILES: Cc1c(C2CCC(NC(=O)c3cccc4c(F)cccc34)CC2)c2cc(F)ccc2n1CC(=O)O]

Step 1) methyl 2-(3-(4-(((benzyloxy)carbonyl)amino)cyclohexyl)-5-fluoro-2-methyl-1H-indol-1-yl)acetate By using a solution of methyl 2-(5-fluoro-2-methyl-1H-indol-1-yl)acetate (984 mg, 4.45 mmol) and benzyl (4-oxo-cyclohexyl)carbamate (1.00 g, 4.04 mmol) in DCM (10 mL), triethyl silicane (3.55 mL, 22.20 mmol) and TFA (0.96 mL, 12.90 mmol) and according to the method described in step 2) of example 4 to prepare the title compound as a white solid (960 mg, 52%).
$^1$H NMR (400 MHz, CDCl$_3$): δ ppm 7.32-7.44 (m, 5H), 7.25-7.28 (m, 1H), 7.05 (dd, J$_1$=8.8 Hz, J$_2$=4.4 Hz, 1H), 6.87 (td, J$_1$=9.0 Hz, J$_2$=2.4 Hz, 1H), 5.16 (s, 2H), 4.75 (s, 2H), 4.00-4.04 (m, 1H), 3.74 (s, 3H), 2.72-2.78 (m, 1H), 2.32 (s, 3H), 1.92-2.04 (m, 4H), 1.67-1.74 (m, 4H); and
MS-ESI: m/z 453.1 [M+H]$^+$.

Step 2) methyl 2-(3-(4-aminocyclohexyl)-5-fluoro-2-methyl-1H-indol-1-yl) acetate By using a solution of methyl 2-(3-(4-(((benzyloxy)carbonyl)amino)cyclohexyl)-5-fluoro-2-methyl-1H-indol-1-yl) acetate (937 mg, 2.07 mmol) in methanol (15 mL) and Pd/C (94 mg) under H$_2$ and according to the method described in step 3) of example 4 to prepare the title compound as a white solid (618 mg, 93%).
$^1$H NMR (400 MHz, CDCl$_3$): δ ppm 7.39 (dd, J$_1$=10.2 Hz, J$_2$=2.3 Hz, 1H), 7.05 (dd, J$_1$=8.8 Hz, J$_2$=4.4 Hz, 1H), 6.86 (td, J$_1$=9.0 Hz, J$_2$=2.4 Hz, 1H), 4.75 (s, 2H), 3.74 (s, 3H), 3.33-3.35 (m, 1H), 2.68-2.75 (m, 1H), 2.34 (s, 3H), 2.18-2.28 (m, 2H), 1.81-1.85 (m, 2H), 1.68-1.74 (m, 2H), 1.56-1.60 (m, 2H); and
MS-ESI: m/z 319.3 [M+H]$^+$.

Step 3) methyl 2-(5-fluoro-3-(4-(5-fluoro-1-naphthamido)cyclohexyl)-2-methyl-1H-indol-1-yl)acetate To a solution of methyl 2-(3-(4-aminocyclohexyl)-5-fluoro-2-methyl-1H-indol-1-yl) acetate (170 mg, 0.53 mmol), 5-fluoro-1-naphthoic acid (122 mg, 0.64 mmol), EDCI (154 mg, 0.80 mmol), HOAT (182 mg, 1.34 mmol) in DCM (15 mL) was added DIPEA (0.37 mL, 2.14 mmol) at 0° C., and then the mixture was reacted according to the method described in step 4) of example 4 to prepare the title compound as a white solid (163 mg, 62%).
$^1$H NMR (400 MHz, CDCl$_3$): δ ppm 8.25 (d, J=8.4 Hz, 1H), 8.16 (d, J=8.6 Hz, 1H), 7.80 (d, J=6.4 Hz, 1H), 7.62 (t, J=7.7 Hz, 1H), 7.51-7.57 (m, 1H), 7.20-7.23 (m, 2H), 7.06 (dd, 8.8 Hz, J$_2$=4.4 Hz, 1H), 6.86 (td, J$_1$=9.0 Hz, J$_2$=2.4 Hz, 1H), 6.33 (d, J=6.5 Hz, 1H), 4.76 (s, 2H), 4.52-4.54 (m, 1H), 3.74 (s, 3H), 2.81-2.87 (m, 1H), 2.34 (s, 3H), 2.20-2.23 (m, 2H), 2.06-2.13 (m, 2H), 1.78-1.90 (m, 4H); and
MS-ESI: m/z 491.0 [M+H]$^+$.

Step 4) 2-(5-fluoro-3-(4-(5-fluoro-1-naphthamido)cyclohexyl)-2-methyl-1H-indol-1-yl)acetic acid By using a solution of methyl 2-(5-fluoro-3-(4-(5-fluoro-1-naphthamido)cyclohexyl)-2-methyl-1H-indol-1-yl)acetate (159 mg, 0.32 mmol) in a mixed solvent of THF (10 mL) and water (5 mL), lithium hydroxide monohydrate (68 mg, 1.62 mmol) and according to the method described in step 5) of example 4 to prepare the title compound as a yellow solid (133 mg, 86%).
$^1$H NMR (600 MHz, CD$_3$OD): δ ppm 8.22 (d, J=8.3 Hz, 1H), 8.04 (d, J=8.5 Hz, 1H), 7.76-7.77 (m, 1H), 7.65 (t, J=7.7 Hz, 1H), 7.52-7.55 (m, 1H), 7.39 (d, J=10.2 Hz, 1H), 7.23-7.26 (m, 1H), 7.12 (dd, J$_1$=8.6 Hz, J$_2$=4.2 Hz, 1H), 6.80 (t, J=8.1 Hz, 1H), 4.38-4.39 (m, 1H), 2.85-2.89 (m, 1H), 2.35 (s, 3H), 2.23-2.30 (m, 4H), 1.84-1.89 (m, 2H), 1.69-1.71 (m, 2H);
$^{13}$C NMR (150 MHz, CD$_3$OD): δ ppm 171.2, 170.7, 157.9, 135.0, 133.5, 131.6, 127.1, 126.7, 126.0, 125.3, 121.9, 120.8, 116.4, 109.5, 108.7, 107.8, 104.4, 45.7, 44.2, 36.2, 30.0, 27.1, 9.5; and
MS-ESI: m/z 477.3 [M+H]$^+$.

Example 11: sodium 2-(5-fluoro-2-methyl-3-(4-((quinolin-2-ylmethyl)amino)cyclohexyl)-1H-indol-1-yl)acetate

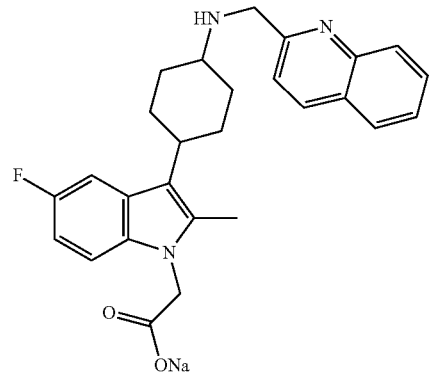

Step 1) methyl 2-(5-fluoro-2-methyl-3-(4-((quinolin-2-ylmethyl)amino)cyclohexyl)-1H-indol-1-yl)acetate To a mixture of sodium triacetoxyborohydride (324 mg, 1.53 mmol) and quinoline-2-carbaldehyde (240 mg, 1.53 mmol) in DCM (20 mL) was added methyl 2-(3-(4-aminocyclohexyl)-5-fluoro-2-methyl-1H-indol-1-yl)acetate (270 mg, 0.85 mmol) at 0° C. The mixture was stirred at rt for 22 h and then washed with aqueous sodium hydroxide solution (10 mL×2). The organic layer was dried over anhydrous Na$_2$SO$_4$ and concentrated. The residue was purified by silica gel chromatography eluted with DCM/MeOH (V/V)=30/1 to give the title compound as a yellow solid (70 mg, 17%).

$^1$H NMR (400 MHz, CDCl$_3$): δ ppm 8.17 (d, J=8.4 Hz, 1H), 8.11 (d, J=8.4 Hz, 1H), 7.82 (d, J=8.0 Hz, 1H), 7.68-7.72 (m, 1H), 7.66 (d, J=8.4 Hz, 1H), 7.49-7.56 (m, 2H), 7.05 (dd, 8.8 Hz, J$_2$=4.3 Hz, 1H), 6.87 (td, J$_1$=9.0 Hz, J$_2$=2.4 Hz, 1H), 4.75 (s, 2H), 4.17 (s, 2H), 3.74 (s, 3H), 3.10-3.12 (m, 1H), 2.73-2.80 (m, 1H), 2.36-2.43 (m, 2H), 2.34 (s, 3H), 1.98-2.01 (m, 2H), 1.62-1.68 (m, 2H), 1.51-1.54 (m, 2H); and MS-ESI: m/z 460.1 [M+H]$^+$.

Step 2) sodium 2-(5-fluoro-2-methyl-3-(4-((quinolin-2-yl)methyl)amino)cyclohexyl)-1H-indol-1-yl)acetate To a solution of methyl 2-(5-fluoro-2-methyl-3-(4-((quinolin-2-ylmethyl)amino)cyclohexyl)-1H-indol-1-yl)acetate (70 mg, 0.15 mmol) in a mixed solvent of THF (8 mL) and water (4 mL) was added lithium hydroxide monohydrate (32 mg, 0.76 mmol). The mixture was stirred for 2.5 h at 45° C. After adjusting the mixture to pH about 13 with sodium hydroxide. The resulting mixture was extracted with EtOAc (10 mL×2). The combined organic layers were dried over anhydrous Na$_2$SO$_4$ and concentrated to give the title compound as a yellow solid (65 mg, 95%).

$^1$H NMR (600 MHz, CDCl$_3$): δ ppm 7.97 (d, J=8.3 Hz, 1H), 7.94 (d, J=8.3 Hz, 1H), 7.62 (d, J=8.0 Hz, 1H), 7.54 (t, J=7.4 Hz, 1H), 7.29-7.36 (m, 4H), 6.87-6.90 (m, 1H), 6.57 (t, J=7.7 Hz, 1H), 4.36 (s, 2H), 3.81 (s, 2H), 2.80 (br.s, 1H), 2.48-2.53 (m, 1H), 2.05-2.11 (m, 4H), 2.03 (s, 3H), 1.66-1.68 (m, 2H), 1.33-1.37 (m, 2H);

$^{13}$C NMR (150 MHz, CDCl$_3$): δ ppm 176.2, 156.2, 147.4, 136.5, 134.0, 133.2, 129.5, 128.8, 127.5, 126.1, 120.6, 115.9, 107.9, 51.4, 47.0, 35.9, 31.9, 29.7, 11.4; and MS-ESI: m/z 446.3 [M+2H—Na]$^+$.

Example 12: 2-(5-fluoro-2-methyl-3-(4-(quinoline-3-carboxamido)cyclohexyl)-1H-indol-1-yl)acetic acid hydrochloride Step 1) methyl 2-(5-fluoro-2-methyl-3-(4-(quinoline-3-carboxamido)cyclohexyl)-1H-indol-1-yl)acetate By using a solution of methyl 2-(3-(4-aminocyclohexyl)-5-fluoro-2-methyl-1H-indol-1-yl)acetate (180 mg, 0.57 mmol), quinoline-3-carboxylic acid (118 mg, 0.68 mmol), EDCI (163 mg, 0.85 mmol) and HOAT (192 mg, 1.41 mmol) in DCM (20 mL) and DIPEA (0.39 mL, 2.26 mmol), and according to the method described in step 4) of example 4 to prepare the title compound as a white solid (191 mg, 71%).

$^1$H NMR (400 MHz, CDCl$_3$): δ ppm 9.37 (s, 1H), 8.63 (s, 1H), 8.18 (d, J=8.4 Hz, 1H), 8.00 (d, J=8.0 Hz, 1H), 7.83 (t, J=8.3 Hz, 1H), 7.65 (t, J=7.2 Hz, 1H), 7.33 (dd, J$_1$=10.1 Hz, J$_2$=2.3 Hz, 1H), 7.08 (dd, J$_1$=8.8 Hz, J$_2$=4.4 Hz, 1H), 6.89 (td, J$_1$=9.0 Hz, J$_2$=2.4 Hz, 1H), 6.63 (d, J=6.4 Hz, 1H), 4.77 (s, 2H), 4.49-4.53 (m, 1H), 3.75 (s, 3H), 2.84-2.90 (m, 1H), 2.36 (s, 3H), 2.09-2.21 (m, 4H), 1.81-1.89 (m, 4H); and MS-ESI: m/z 474.1 [M+H]$^+$.

Step 2) 2-(5-fluoro-2-methyl-3-(4-(quinoline-3-carboxamido)cyclohexyl)-1H-indol-1-yl)acetic acid hydrochloride By using a solution of methyl 2-(5-fluoro-2-methyl-3-(4-(quinoline-3-carboxamido)cyclohexyl)-1H-indol-1-yl)acetate (188 mg, 0.40 mmol) in a mixed solvent of THF (10 mL) and water (5 mL) and lithium hydroxide monohydrate (83 mg, 1.99 mmol), and according to the method described in step 5) of example 4 to prepare the title compound as a yellow solid (170 mg, 86.4%).

$^1$H NMR (600 MHz, d$_6$-DMSO): δ ppm 9.33 (s, 1H), 8.92 (s, 1H), 8.79 (d, J=5.7 Hz, 1H), 8.15 (t, J=7.9 Hz, 2H), 7.91 (t, J=7.6 Hz, 1H), 7.75 (t, J=7.5 Hz, 1H), 7.59 (dd, J$_1$=10.2 Hz, J$_2$=2.1 Hz, 1H), 7.32 (dd, J$_1$=8.8 Hz, J$_2$=4.6 Hz, 1H), 6.88 (td, J$_1$=9.2 Hz, J$_2$=2.2 Hz, 1H), 4.92 (s, 2H), 4.24-4.26 (m, 1H), 2.81-2.86 (m, 1H), 2.32 (s, 3H), 2.28-2.34 (m, 2H), 2.09-2.11 (m, 2H), 1.75-1.80 (m, 2H), 1.53-1.55 (m, 2H);

$^{13}$C NMR (150 MHz, d$_6$-DMSO): δ ppm 171.0, 165.9, 157.8, 149.5, 148.2, 136.8, 134.6, 133.7, 131.8, 129.5, 128.7, 128.0, 127.1, 116.4, 110.3, 108.1, 45.3, 45.0, 35.9, 30.4, 27.5, 10.6; and MS-ESI: m/z 460.0 [M+H—HCl]$^+$.

Example 13: 2-(5-fluoro-2-methyl-3-(4-(quinoline-4-carboxamido)cyclohexyl)-1H-indol-1-yl)acetic acid hydrochloride

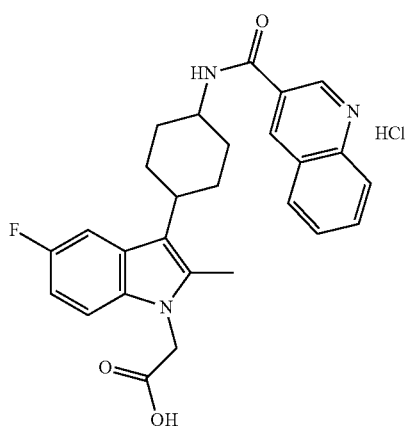 [SMILES: Cc1c(C2CCC(NC(=O)c3cnc4ccccc4c3)CC2)c2cc(F)ccc2n1CC(=O)O ; Cl]

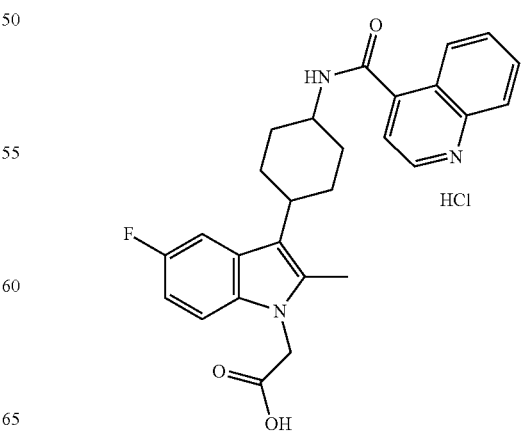

Step 1) methyl 2-(5-fluoro-2-methyl-3-(4-(quinoline-4-carboxamido)cyclohexyl)-1H-indol-1-yl)acetate By using a solution of methyl 2-(3-(4-aminocyclohexyl)-5-fluoro-2-methyl-1H-indol-1-yl)acetate (170 mg, 0.53 mmol), quinoline-4-carboxylic acid (111 mg, 0.64 mmol), EDCI (154 mg, 0.80 mmol) and HOAT (182 mg, 1.34 mmol) in DCM (12 mL), and DIPEA (0.37 mL, 2.14 mmol) and according to the method described in step 4) of example 4 to prepare the title compound as a white solid (185 mg, 73%).

$^1$H NMR (400 MHz, CDCl$_3$): δ ppm 8.98 (d, J=4.3 Hz, 1H), 8.29 (d, J=8.4 Hz, 1H), 8.18 (d, J=8.4 Hz, 1H), 7.79 (t, J=8.2 Hz, 1H), 7.67 (t, J=7.6 Hz, 1H), 7.53 (d, J=4.3 Hz, 1H), 7.21 (dd, J$_1$=10.0 Hz, J$_2$=2.3 Hz, 1H), 7.06 (dd, J$_1$=8.8 Hz, J$_2$=4.4 Hz, 1H), 6.85 (td, J$_1$=9.0 Hz, J$_2$=2.4 Hz, 1H), 6.48 (d, J=6.0 Hz, 1H), 4.75 (s, 2H), 4.53-4.54 (m, 1H), 3.74 (s, 3H), 2.82-2.88 (m, 1H), 2.33 (s, 3H), 2.20-2.24 (m, 2H), 2.04-2.13 (m, 2H), 1.87-1.91 (m, 2H), 1.79-1.83 (m, 2H); and MS-ESI: m/z 474.0 [M+H]$^+$.

Step 2) 2-(5-fluoro-2-methyl-3-(4-(quinoline-4-carboxamido)cyclohexyl)-1H-indol-1-yl)acetic acid hydrochloride By using a solution of methyl 2-(5-fluoro-2-methyl-3-(4-(quinoline-4-carboxamido)cyclohexyl)-1H-indol-1-yl)acetate (181 mg, 0.38 mmol) in a mixed solvent of THF (10 mL) and water (5 mL), and lithium hydroxide monohydrate (80 mg, 1.91 mmol) and according to the method described in step 5) of example 4 to prepare the title compound as a yellow solid (101 mg, 53.3%).

$^1$H NMR (400 MHz, d$_6$-DMSO): δ ppm 9.04-9.08 (m, 2H), 8.13 (t, J=9.8 Hz, 2H), 7.86 (t, J=7.4 Hz, 1H), 7.70 (t, J=7.4 Hz, 1H), 7.62 (d, J=4.0 Hz, 1H), 7.45 (d, J=10.4 Hz, 1H), 7.29 (dd, J$_1$=8.6 Hz, J$_2$=4.4 Hz, 1H), 6.82 (t, J=8.5 Hz, 1H), 4.90 (s, 2H), 4.30-4.34 (m, 1H), 2.78-2.84 (m, 1H), 2.29 (s, 3H), 2.17-2.23 (m, 2H), 2.06-2.10 (m, 2H), 1.77-1.84 (m, 2H), 1.51-1.54 (m, 2H);

$^{13}$C NMR (100 MHz, d$_6$-DMSO): δ ppm 171.0, 167.0, 158.2, 150.4, 147.7, 144.4, 134.6, 133.7, 130.6, 129.3, 128.0, 125.7, 125.0, 119.6, 116.4, 110.2, 108.1, 45.0, 36.0, 30.6, 27.5, 10.6; and MS-ESI: m/z 460.0 [M+H—HCl]$^+$.

Example 14: 2-(5-fluoro-2-methyl-3-(4-(quinoxaline-2-carboxamido)cyclohexyl)-1H-indol-1-yl)acetic acid hydrochloride Step 1) methyl 2-(5-fluoro-2-methyl-3-(4-(quinoxaline-2-carboxamido)cyclohexyl)-1H-indol-1-yl)acetate By using a solution of methyl 2-(3-(4-aminocyclohexyl)-5-fluoro-2-methyl-1H-indol-1-yl) acetate (170 mg, 0.53 mmol), quinoxaline-2-carboxylic acid (112 mg, 0.64 mmol), EDCI (154 mg, 0.80 mmol) and HOAT (182 mg, 1.34 mmol) in DCM (20 mL), and DIPEA (0.37 mL, 2.14 mmol) and according to the method described in step 4) of example 4 to prepare the title compound as a light yellow solid (193 mg, 76%).

$^1$H NMR (400 MHz, CDCl$_3$): δ ppm 9.73 (s, 1H), 8.68 (d, J=8.2 Hz, 1H), 8.35-8.38 (m, 1H), 8.19-8.23 (m, 1H), 7.87-7.93 (m, 2H), 7.52 (dd, J$_1$=10.1 Hz, J$_2$=2.3 Hz, 1H), 7.09 (dd, J$_1$=8.8 Hz, J$_2$=4.4 Hz, 1H), 6.87-6.92 (m, 1H), 4.78 (s, 2H), 4.55-4.57 (m, 1H), 3.75 (s, 3H), 2.82-2.91 (m, 1H), 2.37 (s, 3H), 2.25-2.33 (m, 2H), 2.14-2.17 (m, 2H), 1.85-1.96 (m, 2H), 1.79-1.82 (m, 2H); and MS-ESI: m/z 475.3 [M+H]$^+$.

Step 2) 2-(5-fluoro-2-methyl-3-(4-(quinoxaline-2-carboxamido)cyclohexyl)-1H-indol-1-yl)acetic acid hydrochloride By using a solution of methyl 2-(5-fluoro-2-methyl-3-(4-(quinoxaline-2-carboxamido)cyclohexyl)-1H-indol-1-yl)acetate (187 mg, 0.39 mmol) in a mixed solvent of THF (10 mL) and water (5 mL), and lithium hydroxide monohydrate (83 mg, 1.97 mmol) and according to the method described in step 5) of example 4 to obtain the crude product as a yellow solid (181 mg, 92.5%, HPLC: 76.8%), then the crude product was purified by prep-HPLC to give the title compound as a yellow solid (108 mg, 55.1%).

$^1$H NMR (400 MHz, CD$_3$OD): δ ppm 9.59 (s, 1H), 8.67 (d, J=8.2 Hz, 1H), 8.29-8.32 (m, 1H), 8.12-8.14 (m, 1H), 7.83-7.88 (m, 2H), 7.42 (dd, J$_1$=10.2 Hz, J$_2$=2.1 Hz, 1H), 7.05 (dd, J$_1$=8.8 Hz, J$_2$=4.4 Hz, 1H), 6.80 (td, J$_1$=9.0 Hz, J$_2$=2.2 Hz, 1H), 4.68 (s, 2H), 4.42-4.44 (m, 1H), 2.78-2.84 (m, 1H), 2.30 (s, 3H), 2.13-2.23 (m, 2H), 2.04-2.08 (m, 2H), 1.79-1.82 (m, 2H), 1.70-1.75 (m, 2H);

$^{13}$C NMR (150 MHz, CD$_3$OD): δ ppm 171.0, 162.5, 158.2, 143.7, 143.3, 140.5, 133.5, 131.9, 131.1, 130.1, 128.9, 126.8, 116.3, 109.1, 108.4, 104.5, 60.5, 44.7, 30.4, 26.8, 10.3; and MS-ESI: m/z 461.3 [M+H—HCl]$^+$.

Example 15: 2-(5-fluoro-3-(4-(5-fluoro-1H-indole-2-carboxamido)cyclohexyl)-2-methyl-1H-indol-1-yl)acetic acid hydrochloride

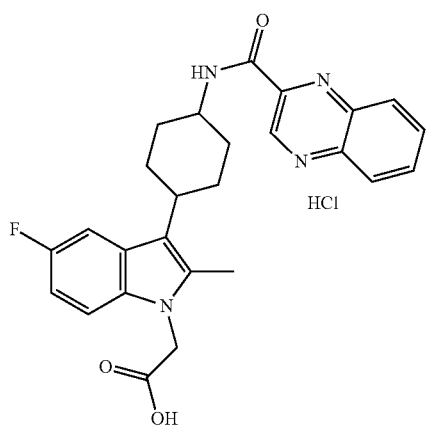 [SMILES: Cc1c(C2CCC(NC(=O)c3cnc4ccccc4n3)CC2)c2cc(F)ccc2n1CC(=O)O ; Cl]

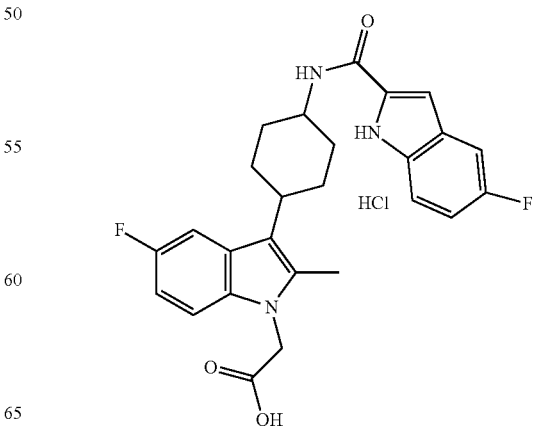

Step 1) methyl 2-(5-fluoro-3-(4-(5-fluoro-1H-indole-2-carboxamido)cyclohexyl)-2-methyl-1H-indol-1-yl)acetate By using a solution of methyl 2-(3-(4-aminocyclohexyl)-5-fluoro-2-methyl-1H-indol-1-yl) acetate (150 mg, 0.47 mmol), 5-fluoro-1H-indole-2-carboxylic acid (101 mg, 0.57 mmol), EDCI (136 mg, 0.71 mmol) and HOAT (160 mg, 1.18 mmol) in DCM (12 mL), and DIPEA (0.33 mL, 1.88 mmol) and according to the method described in step 4) of example 4 to prepare the title compound as a light yellow solid (149 mg, 65%).

$^1$H NMR (400 MHz, CDCl$_3$): δ ppm 7.38-7.41 (m, 1H), 7.35-7.37 (m, 1H), 7.31 (dd, J$_1$=10.1 Hz, J$_2$=2.3 Hz, 1H), 7.04-7.10 (m, 2H), 6.98 (s, 1H), 6.90 (td, J$_1$=9.0 Hz, J$_2$=2.4 Hz, 1H), 6.53 (d, J=7.0 Hz, 1H), 4.77 (s, 2H), 4.44-4.48 (m, 1H), 3.76 (s, 3H), 2.81-2.86 (m, 1H), 2.36 (s, 3H), 2.06-2.17 (m, 4H), 1.78-1.87 (m, 4H); and MS-ESI: m/z 480.3 [M+H]$^+$.

Step 2) 2-(5-fluoro-3-(4-(5-fluoro-1H-indole-2-carboxamido)cyclohexyl)-2-methyl-1H-indol-1-yl)acetic acid hydrochloride By using a solution of methyl 2-(5-fluoro-3-(4-(5-fluoro-1H-indole-2-carboxamido)cyclohexyl)-2-methyl-1H-indol-1-yl)acetate (145 mg, 0.30 mmol) in a mixed solvent of THF (10 mL) and water (5 mL), and lithium hydroxide monohydrate (63 mg, 1.51 mmol) and according to the method described in step 5) of example 4 to prepare the title compound as a white solid (137 mg, 90.3%).

$^1$H NMR (400 MHz, d$_6$-DMSO): δ ppm 11.70 (s, 1H), 8.29 (d, J=5.6 Hz, 1H), 7.50 (dd, J$_1$=10.6 Hz, J$_2$=2.3 Hz, 1H), 7.41-7.49 (m, 3H), 7.31 (dd, J$_1$=8.9 Hz, J$_2$=4.6 Hz, 1H), 7.06 (td, 9.3 Hz, J$_2$=2.5 Hz, 1H), 6.86 (td, J$_1$=9.1 Hz, J$_2$=2.3 Hz, 1H), 4.91 (s, 2H), 4.16-4.19 (m, 1H), 2.78-2.84 (m, 1H), 2.30 (s, 3H), 2.23-2.26 (m, 2H), 2.07-2.10 (m, 2H), 1.71-1.78 (m, 2H), 1.50-1.53 (m, 2H);

$^{13}$C NMR (100 MHz, d$_6$-DMSO): δ ppm 170.8, 161.3, 158.8, 134.2, 133.6, 127.7, 126.9, 116.5, 113.8, 112.1, 110.0, 108.1, 107.9, 105.7, 44.9, 35.9, 30.4, 27.4, 10.6; and MS-ESI: m/z 466.0 [M+H—HCl]$^+$.

Example 16: 2-(3-(4-(3-(2,4-difluorobenzyl)ureido)cyclohexyl)-5-fluoro-2-methyl-1H-indol-1-yl)acetic acid

Step 1): methyl 2-(3-(4-(3-(2,4-difluorobenzyl)ureido)cyclohexyl)-5-fluoro-2-methyl-1H-indol-1-yl)acetate To a solution of CDI (107 mg, 0.64 mmol) in anhydrous THF (5 mL) was added triethylamine (0.19 mL, 1.34 mmol) dropwise at rt, and then a solution of (2,4-difluorophenyl)methanamine (0.08 mL, 0.64 mmol) in anhydrous THF (3 mL) was added dropwise slowly. The mixture was stirred at rt for 40 min, then methyl 2-(3-(4-aminocyclohexyl)-5-fluoro-2-methyl-1H-indol-1-yl)acetate (170 mg, 0.53 mmol) was added. The resulting mixture was refluxed at 75° C. for 5 h and washed with dilute hydrochloric acid (10 mL×2). The organic layer was dried over anhydrous Na$_2$SO$_4$ and concentrated. The residue was purified by silica gel chromatography eluted with PE/EtOAc (V/V)=2/1 to give the title compound as a yellow solid (50 mg, 19%).

$^1$H NMR (400 MHz, CDCl$_3$): δ ppm 7.35-7.41 (m, 1H), 7.27-7.30 (m, 1H), 7.05 (dd, J$_1$=8.8 Hz, J$_2$=4.4 Hz, 1H), 6.76-6.88 (m, 3H), 5.02-5.07 (m, 1H), 4.96-4.97 (m, 1H), 4.75 (s, 2H), 4.42 (d, J=5.2 Hz, 2H), 4.04 (m, 1H), 3.74 (s, 3H), 2.69-2.72 (m, 1H), 2.31 (s, 3H), 1.93-1.98 (m, 4H), 1.67-1.72 (m, 4H); and
MS-ESI: m/z 488.4 [M+H]$^+$.

Step 2) 2-(3-(4-(3-(2,4-difluorobenzyl)ureido)cyclohexyl)-5-fluoro-2-methyl-1H-indol-1-yl)acetic acid By using a solution of methyl 2-(3-(4-(3-(2,4-difluorobenzyl)ureido)cyclohexyl)-5-fluoro-2-methyl-1H-indol-1-yl)acetate (48 mg, 0.10 mmol) in a mixed solvent of THF (8 mL) and water (4 mL), and lithium hydroxide monohydrate (21 mg, 0.49 mmol) and according to the method described in step 5) of example 4 to prepare the title compound as a light yellow solid (36 mg, 77%).

$^1$H NMR (600 MHz, CD$_3$OD): δ ppm 7.41-7.45 (m, 2H), 7.17 (dd, J$_1$=8.8 Hz, J$_2$=4.4 Hz, 1H), 6.93-6.97 (m, 2H), 6.82 (td, J$_1$=9.1 Hz, J$_2$=2.4 Hz, 1H), 4.86 (s, 2H), 4.40 (s, 2H), 4.00-4.02 (m, 1H), 2.79-2.84 (m, 1H), 2.35 (s, 3H), 2.06-2.13 (m, 2H), 1.93-1.95 (m, 2H), 1.72-1.78 (m, 2H), 1.62-1.64 (m, 2H);

$^{13}$C NMR (150 MHz, CD$_3$OD): δ ppm 171.4, 161.7, 159.1, 158.1, 156.6, 133.7, 130.3, 127.1, 116.2, 110.8, 110.6, 108.7, 107.7, 104.0, 44.3, 31.1, 26.9, 9.0; and
MS-ESI: m/z 474.0 [M+H]$^+$.

Example 17: 2-(5-fluoro-2-methyl-3-(4-(N-methylquinoline-2-carboxamido)cyclohexyl)-1H-indol-1-yl)acetic acid hydrochloride (17a) and 2-(5-fluoro-2-methyl-3-(4-(N-methylquinoline-2-carboxamido)cyclohexyl)-1H-indol-1-yl)acetic acid hydrochloride (17b)

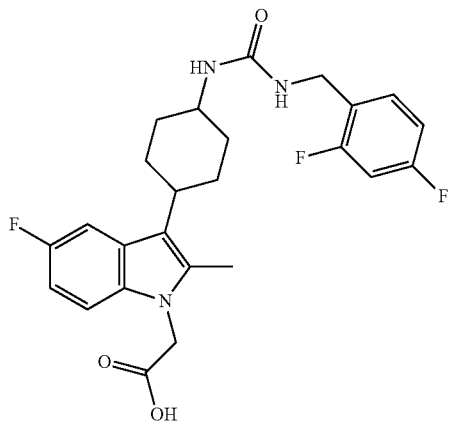 [SMILES: Cc1c(C2CCC(NC(=O)NCc3ccc(F)cc3F)CC2)c2cc(F)ccc2n1CC(=O)O]

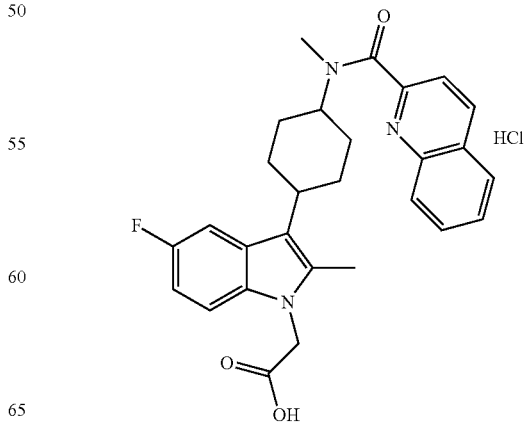

Step 1) methyl 2-(3-(4-(((benzyloxy)carbonyl) (methyl)amino)cyclohexyl)-5-fluoro-2-methyl-1H-indol-1-yl) acetate By using methyl 2-(5-fluoro-2-methyl-1H-indol-1-yl)acetate (270 mg, 1.2 mmol), benzyl methyl(4-oxocyclohexyl) carbamate (290 mg, 1.1 mmol), DCM (10 mL), triethyl silicane (1.0 mL, 6.1 mmol) and TFA (0.26 mL, 3.2 mmol) and according to the method described in step 2) of example 4 to prepare the title compound as a light green solid (490 mg, 94%).

$^1$H NMR (400 MHz, CDCl$_3$)): δ ppm 7.37-7.43 (m, 4H), 7.34-7.36 (m, 1H), 7.29-7.32 (m, 1H), 7.05-7.09 (m, 1H), 6.87-6.92 (m, 1H), 5.19 (s, 2H), 4.78 (s, 2H), 4.29-4.32 (m, 1H), 3.76 (s, 3H), 3.12 (s, 2H), 2.94-2.99 (m, 1H), 2.90 (m, 1H), 2.36 (s, 3H), 2.17-2.28 (m, 2H), 2.00-2.06 (m, 2H), 1.88-1.92 (m, 1H), 1.78-1.85 (m, 3H); and MS-ESI: m/z 467.10 [M+H]$^+$.

Step 2) methyl 2-(5-fluoro-2-methyl-3-(4-(methylamino)cyclohexyl)-1H-indol-1-yl)acetate By using a mixture of methyl 2-(3-(4-(((benzyloxy)carbonyl)(methyl)amino)cyclohexyl)-5-fluoro-2-methyl-1H-indol-1-yl)acetate (490 mg, 2.9 mmol) and 10% Pd/C (50 mg, 0.02 mmol) in methanol (10 mL) and according to the method described in step 3) of example 4 to prepare the title compound as a light yellow solid (300 mg, 86%).

$^1$H NMR (400 MHz, CDCl$_3$)): δ ppm 7.39 (dd, J$_1$=10.2 Hz, J$_2$=2.3 Hz, 1H), 7.02-7.06 (m, 1H), 6.85 (td, J$_1$=9.0 Hz, J$_2$=2.2 Hz, 1H), 4.74 (s, 2H), 3.74 (s, 3H), 2.80-2.83 (m, 1H), 2.69-2.75 (m, 1H), 2.47 (s, 3H), 2.33 (s, 3H), 2.07-2.11 (m, 2H), 1.83-1.99 (m, 2H), 1.50-1.62 (m, 4H); and MS-ESI: m/z 333.10 [M+H]$^+$.

Step 3) methyl 2-(5-fluoro-2-methyl-3-(4-(N-methylquinoline-2-carboxamido)cyclohexyl)-1H-indol-1-yl)acetate By using methyl 2-(5-fluoro-2-methyl-3-(4-(methylamino)cyclohexyl)-1H-indol-1-yl)acetate (150 mg, 0.45 mmol), quinoline-2-carboxylic acid (94 mg, 0.54 mmol), EDCI (130 mg, 0.68 mmol), HOAT (154 mg, 1.13 mmol), DCM (14 mL) and DIPEA (0.32 mL, 1.81 mmol) and according to the method described in step 4) of example 4 to prepare the title compound as a white solid (195 mg, 88%).

$^1$H NMR (400 MHz, CDCl$_3$): δ ppm 8.27 (d, J=8.4 Hz, 1H), 8.14 (d, J=8.4 Hz, 1H), 7.86 (d, J=8.0 Hz, 1H), 7.77 (t, J=7.0 Hz, 1H), 7.67 (d, J=8.4 Hz, 1H), 7.61 (t, J=7.3 Hz, 1H), 7.06 (dd, J$_1$=8.8 Hz, J$_2$=4.4 Hz, 1H), 6.87 (td, J$_1$=9.0 Hz, J$_2$=2.3 Hz, 1H), 4.76 (s, 2H), 3.74 (s, 3H), 3.23 (s, 3H), 2.36-2.28 (m, 5H), 2.19-2.10 (m, 2H), 1.95-1.75 (m, 4H); and MS-ESI: m/z 488.4 [M+H]$^+$.

Step 4) 2-(5-fluoro-2-methyl-3-(4-(N-methylquinoline-2-carboxamido)cyclohexyl)-1H-indol-1-yl)acetic acid hydrochloride By using a solution of methyl 2-(5-fluoro-2-methyl-3-(4-(N-methylquinoline-2-carboxamido)cyclohexyl)-1H-indol-1-yl)acetate (194 mg, 0.40 mmol) in a mixed solvent of THF (10 mL) and water (5 mL), and lithium hydroxide monohydrate (83 mg, 1.99 mmol) and according to the method described in step 5) of example 4 to obtain the crude product as a yellow solid (163 mg, 86%). The crude product was purified by prep-HPLC to give compound 17b as a yellow solid (100 mg, HPLC: 87.78%, Rt: 11.33 min) and compound 17a as a red solid (20 mg, HPLC: 96.70%, Rt: 10.65 min).

Compound 17b: $^1$H NMR (400 MHz, CDCl$_3$): δ ppm 8.41 (s, 1H), 8.27 (s, 1H), 7.93 (d, J=8.2 Hz, 1H), 7.85 (t, J=7.4 Hz, 1H), 7.71-7.64 (m, 2H), 7.23-7.20 (m, 1H), 7.05 (dd, J$_1$=8.8 Hz, J$_2$=4.4 Hz, 1H), 6.83 (t, J=8.8 Hz, 1H), 4.74 (s, 2H), 3.11 (s, 3H), 2.98-2.94 (m, 1H), 2.40-2.36 (m, 1H), 2.30 (br.s, 3H), 2.30-2.15 (m, 4H), 1.88-1.76 (m, 4H); and MS-ESI: m/z 474.3 [M+H—HCl]$^+$.

Example 18: methyl 2-(3-(4-(1,8-naphthyridine-2-carboxamido)cyclohexyl)-5-fluoro-2-methyl-1H-indol-1-yl)acetate (18a) and methyl 2-(3-(4-(1,8-naphthyridine-2-carboxamido)cyclohexyl)-5-fluoro-2-methyl-1H-indol-1-yl)acetate (18b)

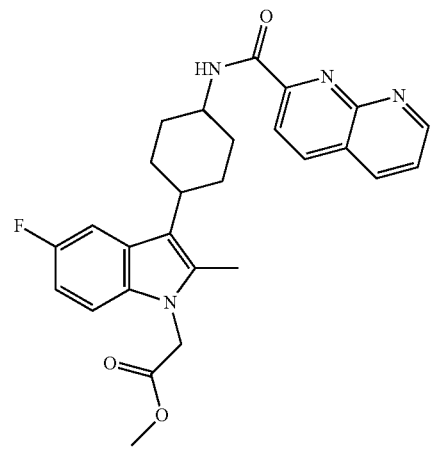 [SMILES: COC(=O)Cn1c(C)c(C2CCC(NC(=O)c3ccc4cccnc4n3)CC2)c2cc(F)ccc21]

By using methyl 2-(3-(4-aminocyclohexyl)-5-fluoro-2-methyl-1H-indol-1-yl) acetate (250 mg, 0.79 mmol), 1,8-naphthyridine-2-carboxylic acid (164 mg, 0.94 mmol), EDCI (226 mg, 1.18 mmol), HOAT (267 mg, 1.96 mmol), DCM (15 mL) and DIPEA (0.55 mL, 3.14 mmol) and according to the method described in step 4) of example 4 to obtain the crude product. The crude product was purified by silica gel chromatography eluted with PE/EtOAc (V/V)=1/2 to give compound 18a (158 mg, 42%) as yellow thick oil and compound 18b (80 mg, 22%) as a white solid.

Compound 18b: $^1$H NMR (400 MHz, CDCl$_3$): δ ppm 9.21 (dd, J$_1$=4.1, J$_2$=1.8 Hz, 1H), 8.51 (d, J=8.3 Hz, 1H), 8.40 (d, J=8.4 Hz, 1H), 8.35 (d, J=8.5 Hz, 1H), 8.31 (dd, J$_1$=8.2, J$_2$=1.8 Hz, 1H), 7.60 (dd, J$_1$=8.2, J$_2$=4.2 Hz, 1H), 7.36 (dd, J$_1$=10.2, J$_2$=2.3 Hz, 1H), 7.06 (dd, J$_1$=8.8, J$_2$=4.3 Hz, 1H), 6.88 (td, J$_1$=8.9, J$_2$=2.3 Hz, 1H), 4.77 (s, 2H), 4.23-4.16 (m, 1H), 3.74 (s, 3H), 2.82-2.75 (m, 1H), 2.37 (s, 3H), 2.27-2.25 (m, 2H), 2.19-2.08 (m, 2H), 1.93-1.90 (m, 2H), 1.58-1.54 (m, 2H); and MS-ESI: m/z 475.3 [M+H]$^+$.

Compound 18a: $^1$H NMR (400 MHz, CDCl$_3$): δ ppm 9.23 (dd, J$_1$=4.1 Hz, J$_2$=1.9 Hz, 1H), 8.79 (d, J=6.3 Hz, 1H), 8.49 (d, J=8.3 Hz, 1H), 8.41 (d, J=8.3 Hz, 1H), 8.30 (dd, J$_1$=8.2 Hz, J$_2$=1.8 Hz, 1H), 7.60 (dd, J$_1$=8.2 Hz, J$_2$=4.2 Hz, 1H), 7.36 (dd, J$_1$=10.1 Hz, J$_2$=2.3 Hz, 1H), 7.03 (dd, J$_1$=8.8 Hz, J$_2$=4.3 Hz, 1H), 6.82 (td, J$_1$=9.0 Hz, J$_2$=2.3 Hz, 1H), 4.75 (s, 2H), 4.39-4.41 (m, 1H), 3.73 (s, 3H), 2.89-2.83 (m, 1H), 2.37 (s, 3H), 2.29-2.18 (m, 4H), 1.88-1.79 (m, 4H); and MS-ESI: m/z 475.2 [M+H]$^+$.

Example 19: 2-(3-(4-(1,8-naphthyridine-2-carboxamido)cyclohexyl)-5-fluoro-2-methyl-1H-indol-1-yl)acetic acid hydrochloride

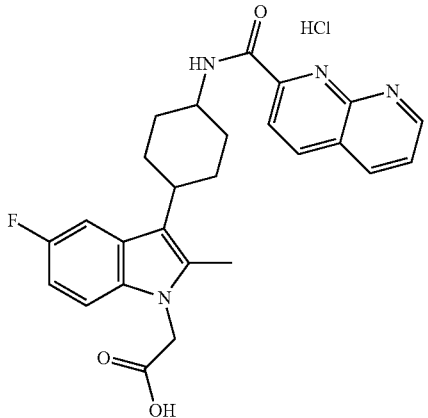 [SMILES: Cc1c(C2CCC(NC(=O)c3ccc4cccnc4n3)CC2)c2cc(F)ccc2n1CC(=O)O ; Cl]

To a solution of methyl 2-(3-(4-(1,8-naphthyridine-2-carboxamido)cyclohexyl)-5-fluoro-2-methyl-1H-indol-1-yl)acetate (18a) (152 mg, 0.32 mmol) in a mixed solvent of THF (8 mL) and water (4 mL) was added lithium hydroxide monohydrate (67 mg, 1.60 mmol). The mixture was stirred for 2 h at 45° C. After adjusting to pH about 1 with hydrochloric acid (1 mol/L), the resulting mixture was extracted with EtOAc (10 mL×2). The combined organic layers were concentrated to give a yellow solid product (70 mg, 44%, HPLC Rt: 9.13 min).

$^1$H NMR (600 MHz, d$_6$-DMSO): δ ppm 9.24 (s, 1H), 8.90 (br.s, 1H), 8.73 (d, J=7.3 Hz, 1H), 8.61 (d, J=6.5 Hz, 1H), 8.30 (d, J=7.2 Hz, 1H), 7.77 (s, 1H), 7.36-7.32 (m, 2H), 6.84-6.81 (m, 1H), 4.92 (s, 2H), 4.28 (m, 1H), 4.06-4.03 (m, 2H), 2.93-2.88 (m, 1H), 2.34 (s, 3H), 2.13-2.11 (m, 2H), 1.84-1.80 (m, 2H), 1.65-1.64 (m, 2H);

$^{13}$C NMR (150 MHz, d$_6$-DMSO): δ ppm 171.0, 163.5, 157.8, 155.3, 154.3, 153.3, 140.5, 138.1, 134.7, 133.6, 124.4, 119.8, 116.0, 110.4, 108.2, 64.6, 44.6, 35.5, 30.3, 10.8; and MS-ESI: m/z 461.2 [M+H—HCl]$^+$.

Example 20: 2-(3-(4-(1,8-naphthyridine-2-carboxamido)cyclohexyl)-5-fluoro-2-methyl-1H-indol-1-yl)acetic acid hydrochloride

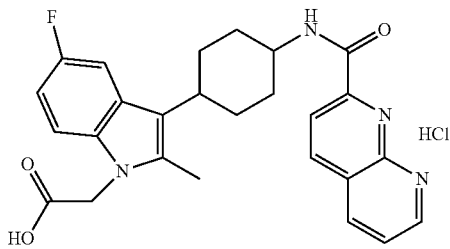 [SMILES: Cc1c(C2CCC(NC(=O)c3ccc4cccnc4n3)CC2)c2cc(F)ccc2n1CC(=O)O ; Cl]

To a solution of methyl 2-(3-(4-(1,8-naphthyridine-2-carboxamido)cyclohexyl)-5-fluoro-2-methyl-1H-indol-1-yl)acetate (18b) (80 mg, 0.17 mmol) in a mixed solvent of THF (8 mL) and water (4 mL) was added lithium hydroxide monohydrate (35 mg, 0.84 mmol). The mixture was stirred for 2 h at 45° C. After adjusting to pH about 1 with hydrochloric acid (1 mol/L), the resulting mixture was extracted with EtOAc (10 mL×2). The combined organic layers were concentrated to give a yellow solid product (70 mg, 83.6%, HPLC Rt: 9.30 min).

$^1$H NMR (600 MHz, d$_6$-DMSO): δ ppm 9.22-9.21 (m, 1H), 8.69 (t, J=8.8 Hz, 2H), 8.59 (dd, J$_1$=8.1 Hz, J$_2$=1.6 Hz, 1H), 8.30 (d, J=8.3 Hz, 1H), 7.75 (dd, J$_1$=8.1 Hz, J$_2$=4.1 Hz, 1H), 7.45 (dd, J$_1$=10.5 Hz, J$_2$=2.1 Hz, 1H), 7.33 (dd, J$_1$=8.8 Hz, J$_2$=4.5 Hz, 1H), 6.87 (td, J$_1$=9.0 Hz, J$_2$=2.2 Hz, 1H), 4.92 (s, 2H), 4.15-4.12 (m, 1H), 2.82-2.78 (m, 1H), 2.31 (s, 3H), 2.10-2.05 (m, 4H), 1.77-1.70 (m, 4H);

$^{13}$C NMR (150 MHz, d$_6$-DMSO): δ ppm 171.0, 163.3, 157.9, 155.2, 154.4, 153.4, 140.2, 138.1, 134.6, 133.7, 124.3, 123.9, 120.1, 115.6, 110.3, 108.2, 64.6, 48.7, 45.0, 33.2, 30.9, 10.7; and MS-ESI: m/z 461.2 [M+H—HCl]$^+$.

Example 21: 2-(5-fluoro-2-methyl-3-(3-(quinoline-2-carboxamido)cyclobutyl)-1H-indol-1-yl)acetic acid hydrochloride

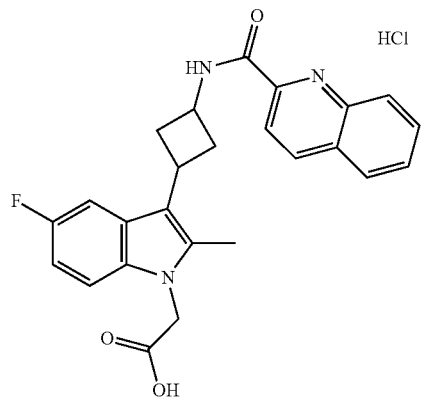 [SMILES: Cc1c(C2CC(NC(=O)c3ccc4ccccc4n3)C2)c2cc(F)ccc2n1CC(=O)O ; Cl]

Step 1) benzyl (3-oxocyclobutyl)carbamate

By using a solution of 3-aminocyclobutanone hydrochloride (500 mg, 4.11 mmol) in DCM (20 mL), DIPEA (3.6 mL, 20.56 mmol) and benzyl chloroformate (1.7 mL, 12.34 mmol) and according to the method described in step 1) of example 4 to prepare the title compound as a white solid (617 mg, 68%).

$^1$H NMR (400 MHz, CDCl$_3$): δ ppm 7.37-7.33 (m, 5H), 5.22 (br.s, 1H), 5.12 (s, 2H), 4.34-4.30 (m, 1H), 3.44-3.37 (m, 2H), 3.09-3.05 (m, 2H); and MS-ESI: m/z 220.0 [M+H]$^+$.

Step 2) methyl 2-(3-(3-(((benzyloxy)carbonyl)amino)cyclobutyl)-5-fluoro-2-methyl-1H-indol-1-yl)acetate By using a solution of methyl 2-(5-fluoro-2-methyl-1H-indol-1-yl)acetate (278 mg, 1.25 mmol) and benzyl (3-oxocyclobutyl)carbamate (250 mg, 1.14 mmol) in DCM (16 mL), triethyl silicane (1.00 mL, 6.27 mmol) and TFA (0.27 mL, 3.65 mmol) and according to the method described in step 2) of example 4 to prepare the title compound as a yellow solid (276 mg, 57%).

$^1$H NMR (400 MHz, CDCl$_3$): δ ppm 7.38-7.36 (m, 4H), 7.35-7.32 (m, 1H), 7.29 (dd, J$_1$=10.2 Hz, J$_2$=1.9 Hz, 1H), 7.05 (dd, $J_1$=8.8 Hz, $J_2$=4.3 Hz, 1H), 6.88 (td, $J_1$=9.0 Hz, $J_2$=2.4 Hz, 1H), 5.11 (s, 2H), 5.06-5.04 (m, 1H), 4.73 (s, 2H), 4.25-4.19 (m, 1H), 3.74 (s, 3H), 3.33-3.29 (m, 1H), 2.86-2.84 (m, 2H), 2.36-2.31 (m, 2H), 2.28 (s, 3H); and MS-ESI: m/z 425.3 [M+H]$^+$.

Step 3) methyl 2-(3-(3-aminocyclobutyl)-5-fluoro-2-methyl-1H-indol-1-yl)acetate

By using a solution of methyl 2-(3-(3-(((benzyloxy)carbonyl)amino)cyclobutyl)-5-fluoro-2-methyl-1H-indol-1-yl) acetate (615 mg, 1.45 mmol) in a mixed solvent of methanol (8 mL) and DCM (6 mL), and Pd/C (62 mg) and according to the method described in step 3) of example 4 to prepare the title compound as a yellow solid (365 mg, 86%).

$^1$H NMR (400 MHz, CD$_3$OD): δ ppm 7.47 (dd, $J_1$=10.2 Hz, $J_2$=2.4 Hz, 1H), 7.20 (dd, $J_1$=8.8 Hz, $J_2$=4.4 Hz, 1H), 6.86 (td, $J_1$=9.1 Hz, $J_2$=2.4 Hz, 1H), 4.95 (s, 2H), 3.75 (s, 3H), 3.72-3.68 (m, 1H), 3.53-3.48 (m, 1H), 2.83-2.73 (m, 2H), 2.56-2.48 (m, 2H), 2.32 (s, 3H); and MS-ESI: m/z 291.0 [M+H]$^+$.

Step 4) methyl 2-(5-fluoro-2-methyl-3-(3-(quinoline-2-carboxamido)cyclobutyl)-1H-indol-1-yl)acetate By using methyl 2-(3-(3-aminocyclobutyl)-5-fluoro-2-methyl-1H-indol-1-yl) acetate (180 mg, 0.62 mmol), quinoline-2-carboxylic acid (129 mg, 0.74 mmol), EDCI (178 mg, 0.93 mmol), HOAT (211 mg, 1.55 mmol), DCM (15 mL) and DIPEA (0.43 mL, 2.48 mmol) and according to the method described in step 4) of example 4 to prepare the title compound as a white solid (172 mg, 62%).

$^1$H NMR (400 MHz, CDCl$_3$): δ ppm 8.49 (d, J=7.9 Hz, 1H), 8.32 (s, 2H), 8.16 (d, J=8.5 Hz, 1H), 7.88 (d, J=8.2 Hz, 1H), 7.80-7.76 (m, 1H), 7.62 (t, J=7.5 Hz, 1H), 7.40 (dd, $J_1$=10.0 Hz, $J_2$=2.3 Hz, 1H), 7.08 (dd, $J_1$=8.8 Hz, $J_2$=4.3 Hz, 1H), 6.90 (td, $J_1$=9.0 Hz, $J_2$=2.4 Hz, 1H), 4.77 (s, 2H), 4.74-4.68 (m, 1H), 3.76 (s, 3H), 3.51-3.44 (m, 1H), 3.07-3.01 (m, 2H), 2.62-2.54 (m, 2H), 2.34 (s, 3H); and MS-ESI: m/z 446.1 [M+H]$^+$.

Step 5) 2-(5-fluoro-2-methyl-3-(3-(quinoline-2-carboxamido)cyclobutyl)-1H-indol-1-yl)acetic acid hydrochloride By using a solution of methyl 2-(5-fluoro-2-methyl-3-(3-(quinoline-2-carboxamido)cyclobutyl)-1H-indol-1-yl)acetate (167 mg, 0.37 mmol) in a mixed solvent of THF (8 mL) and water (4 mL), lithium hydroxide monohydrate (87 mg, 1.87 mmol) and according to the method described in step 5) of example 4 to prepare the title compound as a white solid (141 mg, 80.5%).

$^1$H NMR (600 MHz, d$_6$-DMSO): δ ppm 9.43 (d, J=8.3 Hz, 1H), 8.56 (d, J=8.5 Hz, 1H), 8.23 (d, J=8.5 Hz, 1H), 8.16 (d, J=8.5 Hz, 1H), 8.08 (d, J=8.1 Hz, 1H), 7.88 (t, J=7.3 Hz, 1H), 7.81 (dd, $J_1$=10.5 Hz, $J_2$=2.2 Hz, 1H), 7.73 (t, J=7.4 Hz, 1H), 7.34 (dd, $J_1$=8.8 Hz, $J_2$=4.5 Hz, 1H), 6.89 (td, $J_1$=9.2 Hz, $J_2$=2.2 Hz, 1H), 4.93 (s, 2H), 4.56-4.52 (m, 1H), 3.61-3.59 (m, 1H), 2.77-2.72 (m, 2H), 2.66-2.62 (m, 2H), 2.31 (s, 3H);

$^{13}$C NMR (150 MHz, d$_6$-DMSO): δ ppm 171.0, 164.3, 158.1, 156.6, 151.1, 146.6, 138.2, 135.4, 133.7, 130.9, 129.7, 129.2, 128.5, 128.4, 127.5, 127.4, 119.4, 113.0, 110.3, 108.4, 104.7, 60.2, 44.9, 40.4, 29.5, 10.7; and MS-ESI: m/z 432.2 [M+H—HCl]$^+$.

Example 22: 2-(3-(3-(1,8-naphthyridine-2-carboxamido)cyclobutyl)-5-fluoro-2-methyl-1H-indol-1-yl)acetic acid hydrochloride

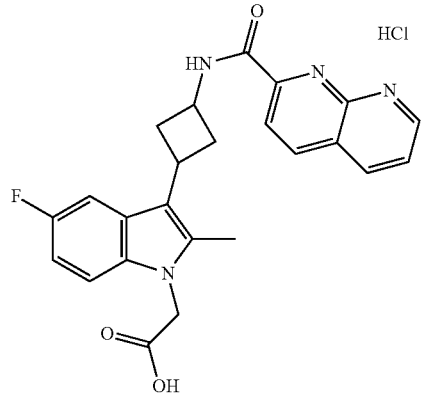 [SMILES: Cc1c(C2CC(NC(=O)c3ccc4cccnc4n3)C2)c2cc(F)ccc2n1CC(=O)O ; Cl]

Step 1) methyl 2-(3-(3-(1,8-naphthyridine-2-carboxamido)cyclobutyl)-5-fluoro-2-methyl-1H-indol-1-yl)acetate By using methyl 2-(3-(3-aminocyclobutyl)-5-fluoro-2-methyl-1H-indol-1-yl)acetate (172 mg, 0.59 mmol), 1,8-naphthyridine-2-carboxylic acid (124 mg, 0.71 mmol), EDCI (170 mg, 0.89 mmol), HOAT (202 mg, 1.48 mmol), DCM (15 mL) and DIPEA (0.41 mL, 2.37 mmol) and according to the method described in step 4) of example 4 to prepare the title compound as a yellow solid (150 mg, 56%).

$^1$H NMR (400 MHz, CDCl$_3$): δ ppm 9.20 (dd, $J_1$=4.2 Hz, $J_2$=1.9 Hz, 1H), 8.64 (d, J=7.5 Hz, 1H), 8.47 (d, J=8.3 Hz, 1H), 8.39 (d, J=8.4 Hz, 1H), 8.30 (dd, $J_1$=8.2 Hz, $J_2$=1.8 Hz, 1H), 7.59 (dd, $J_1$=8.2 Hz, $J_2$=4.2 Hz, 1H), 7.39 (dd, $J_1$=9.9 Hz, $J_2$=2.3 Hz, 1H), 7.06 (dd, $J_1$=8.8 Hz, $J_2$=4.3 Hz, 1H), 6.89 (td, $J_1$=9.0 Hz, $J_2$=2.4 Hz, 1H), 4.76 (s, 2H), 4.69-4.63 (m, 1H), 3.75 (s, 3H), 3.51-3.42 (m, 1H), 3.00-2.94 (m, 2H), 2.63-2.56 (m, 2H), 2.35 (s, 3H); and MS-ESI: m/z 447.9 [M+H]$^+$.

Step 2) 2-(3-(3-(1,8-naphthyridine-2-carboxamido)cyclobutyl)-5-fluoro-2-methyl-1H-indol-1-yl)acetic acid hydrochloride By using a solution of methyl 2-(3-(3-(1, 8-naphthyridine-2-carboxamido)cyclobutyl)-5-fluoro-2-methyl-1H-indol-1-yl)acetate (143 mg, 0.32 mmol) in a mixed solvent of THF (8 mL) and water (4 mL), and lithium hydroxide monohydrate (67 mg, 1.60 mmol) and according to the method described in step 5) of example 4 to prepare the title compound as a red solid (120 mg, 80%).

$^1$H NMR (600 MHz, d$_6$-DMSO): δ ppm 9.60 (d, J=8.2 Hz, 1H), 9.25-9.24 (m, 1H), 8.71 (d, J=8.3 Hz, 1H), 8.67-8.65 (m, 1H), 8.29 (d, J=8.3 Hz, 1H), 7.84 (dd, $J_1$=10.5 Hz, $J_2$=1.8 Hz, 1H), 7.80 (dd, $J_1$=8.1 Hz, $J_2$=4.2 Hz, 1H), 7.34 (dd, $J_1$=8.8 Hz, $J_2$=4.5 Hz, 1H), 6.89 (td, $J_1$=9.2 Hz, $J_2$=2.0 Hz, 1H), 4.92 (s, 2H), 4.57-4.53 (m, 1H), 3.39-3.35 (m, 1H), 2.79-2.74 (m, 2H), 2.63-2.61 (m, 2H), 2.31 (s, 3H);

$^{13}$C NMR (150 MHz, d$_6$-DMSO): δ ppm 170.9, 164.0, 158.1, 156.6, 154.7, 154.2, 153.8, 140.1, 139.0, 135.5, 133.7, 127.5, 124.3, 124.0, 120.7, 112.9, 110.3, 108.4, 104.7, 44.9, 42.4, 36.9, 25.9, 10.6; and MS-ESI: m/z 433.3 [M+H—HCl]+.

Example 23: 2-(3-(1-(1-naphthoyl)-1,2,5,6-tetrahydropyridin-3-yl)-5-fluoro-2-methyl-1H-indol-1-yl)acetic acid

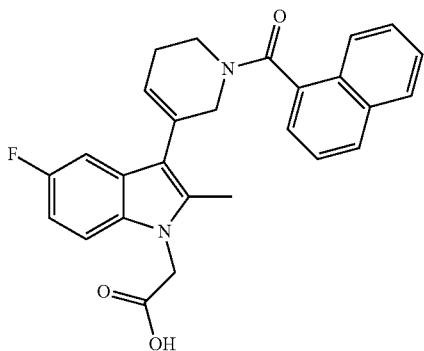 [SMILES: Cc1c(C2=CCCN(C(=O)c3cccc4ccccc34)C2)c2cc(F)ccc2n1CC(=O)O]

Step 1) 1-(1-naphthoyl)piperidin-3-one

By using 1-naphthoic acid (350 mg, 2.03 mmol), piperidin-3-one hydrochloride (331 mg, 2.44 mmol), EDCI (585 mg, 3.05 mmol), HOAT (692 mg, 5.08 mmol), DCM (20 mL) and DIPEA (1.4 mL, 8.13 mmol) and according to the method described in step 2) of example 1 to prepare the title compound as colorless thick oil (380 mg, 73%).

$^1$H NMR (400 MHz, CDCl$_3$): δ ppm 7.90-7.94 (m, 2H), 7.73-7.83 (m, 1H), 7.48-7.57 (m, 3H), 7.39-7.46 (m, 1H), 4.53 (m, 1H), 4.10-4.15 (m, 1H), 3.78-3.79 (m, 1H), 3.40 (m, 1H), 2.58 (t, J=6.8 Hz, 2H), 2.19-2.22 (m, 1H), 1.88-1.89 (m, 1H); and MS-ESI: m/z 254.2 [M+H]+.

Step 2) methyl 2-(3-(1-(1-naphthoyl)-1,2,5,6-tetrahydropyridin-3-yl)-5-fluoro-2-methyl-1H-indol-1-yl)acetate By using methyl 2-(5-fluoro-2-methyl-1H-indol-1-yl)acetate (346 mg, 1.56 mmol), 1-(1-naphthoyl)piperidin-3-one (360 mg, 1.42 mmol), DCM (20 mL), triethyl silicane (1.25 mL, 7.81 mmol) and TFA (0.34 mL, 4.55 mmol) and according to the method described in step 3) of example 1 to prepare the title compound as a yellow solid (390 mg, 59%).

$^1$H NMR (400 MHz, CDCl$_3$): δ ppm 7.91-7.94 (m, 1H), 7.87-7.90 (m, 2H), 7.57-7.59 (m, 1H), 7.50-7.55 (m, 3H), 6.96 (dd, J$_1$=8.8 Hz, J$_2$=4.2 Hz, 1H), 6.86 (dd, J$_1$=9.7 Hz, J$_2$=2.4 Hz, 1H), 6.81 (td, J$_1$=9.0 Hz, J$_2$=2.5 Hz, 1H), 6.17 (s, 1H), 4.63 (s, 2H), 4.17-4.20 (m, 1H), 3.70 (s, 3H), 2.51-2.58 (m, 3H), 2.18-2.24 (m, 2H), 1.98 (s, 3H); and MS-ESI: m/z 457.3 [M+H]+.

Step 3) 2-(3-(1-(1-naphthoyl)-1,2,5,6-tetrahydropyridin-3-yl)-5-fluoro-2-methyl-1H-indol-1-yl)acetic acid By using a solution of methyl 2-(3-(1-(1-naphthoyl)-1,2,5,6-tetrahydropyridin-3-yl)-5-fluoro-2-methyl-1H-indol-1-yl)acetate (383 mg, 0.84 mmol) in a mixed solvent of THF (14 mL) and water (7 mL), and sodium hydroxide (167 mg, 4.20 mmol) and according to the method described in step 4) of example 1 to prepare the title compound as a yellow solid (360 mg, 97%).

$^1$H NMR (600 MHz, d$_6$-DMSO): δ ppm 8.03-8.04 (m, 1H), 7.99-8.00 (m, 1H), 7.80-7.81 (m, 1H), 7.59-7.65 (m, 3H), 7.55-7.57 (m, 1H), 7.23-7.26 (m, 1H), 6.77-6.80 (m, 2H), 5.95 (s, 1H), 4.80 (s, 2H), 3.98-4.10 (m, 2H), 3.19-3.30 (m, 2H), 2.43-2.51 (m, 3H), 2.08-2.12 (m, 2H);

$^{13}$C NMR (150 MHz, d$_6$-DMSO): δ ppm 172.5, 170.9, 158.3, 135.6, 134.2, 133.5, 133.3, 129.8, 129.3, 129.0, 127.9, 127.1, 125.8, 125.2, 125.0, 124.7, 122.7, 113.8, 112.7, 110.6, 45.6, 27.0, 10.9; and MS-ESI: m/z 443.3 [M+H]+.

Example 24: 2-(5-fluoro-3-(1-((4-fluorophenyl)sulfonyl)piperidin-4-yl)-2-methyl-1H-indol-1-yl)acetic acid

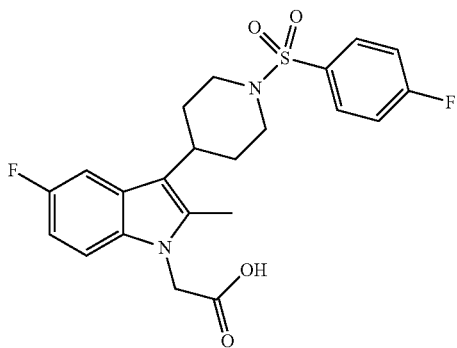 [SMILES: Cc1c(C2CCN(S(=O)(=O)c3ccc(F)cc3)CC2)c2cc(F)ccc2n1CC(=O)O]

Step 1) 1-((4-fluorophenyl)sulfonyl)piperidin-4-one

To a solution of 4-fluorobenzenesulfonic acid (300 mg, 1.71 mmol) in DCM (5 mL) was added thionyl chloride (300 mg, 2.55 mmol) at rt. After stirring for 10 min, DMF (1 mL) was added to the mixture. The mixture was stirred at rt for 1 h and concentrated. To a solution of piperidin-4-one hydrochloride (230 mg, 1.71 mmol) and triethylamine (690 mg, 6.82 mmol) in DCM (5 mL) was added the above residue at 0° C. The resulting mixture was stirred at rt for 1 h and concentrated. The residue was washed with water (15 mL) and filtered under vacuum to give the title compound as a white solid (300 mg, 68%).

$^1$H NMR (400 MHz, CDCl$_3$): δ ppm 7.80-7.84 (m, 2H), 7.21-7.26 (m, 2H), 3.40 (t, J=6.2 Hz, 4H), 2.55 (t, J=6.2 Hz, 4H); and MS-ESI: m/z 258.10 [M+H]+.

Step 2) methyl 2-(5-fluoro-3-(1-((4-fluorophenyl)sulfonyl)piperidin-4-yl)-2-methyl-1H-indol-1-yl)acetate To a solution of methyl 2-(5-fluoro-2-methyl-1H-indol-1-yl))acetate (285 mg, 1.28 mmol) and 1-((4-fluorophenyl)sulfonyl)piperidin-4-one (300 mg, 1.17 mmol) in DCM (10 mL) were added triethyl silicane (1.0 mL, 6.41 mmol) and TFA (0.28 mL, 3.73 mmol) dropwise respectively at 0° C. The mixture was stirred for 2 h at rt and washed with saturated aqueous sodium bicarbonate solution (10 mL), the water phase was extracted with DCM (10 mL×3). The combined organic layers were dried over anhydrous Na$_2$SO$_4$ and concentrated. The residue was purified by silica gel chromatography eluted with PE/EtOAc (V/V)=2/1 to give a white solid product (200 mg, 37%).

$^1$H NMR (400 MHz, CDCl$_3$): δ ppm 7.83-7.87 (m, 2H), 7.24-7.28 (m, 2H), 7.17 (dd, J=10.0, 2.5 Hz, 1H), 7.05 (dd, J=8.9, 4.3 Hz, 1H), 6.87 (td, J=9.0, 2.4 Hz, 1H), 4.73 (s, 2H), 3.98-4.01 (m, 2H), 3.74 (s, 3H), 2.61-2.70 (m, 1H), 2.38-2.45 (m, 2H), 2.27 (s, 3H), 2.17-2.25 (m, 2H), 1.75-1.81 (m, 2H); and MS-ESI: m/z 463.05 [M+H]$^+$.

Step 3) 2-(5-fluoro-3-(1-((4-fluorophenyl)sulfonyl)piperidin-4-yl)-2-methyl-1H-indol-1-yl)acetic acid A solution of methyl 2-(5-fluoro-3-(1-((4-fluorophenyl)sulfonyl)piperidin-4-yl)-2-methyl-1H-indol-1-yl)acetate (200 mg, 0.42 mmol) and sodium hydroxide (85 mg, 2.12 mmol) in a mixed solvent of THF (5 mL) and water (5 mL) was stirred for 2 h at 50° C. After adjusting to pH 1 with hydrochloric acid (1.0 mol/L), the resulting mixture was extracted with EtOAc (10 mL×3). The combined organic layers were dried over anhydrous Na$_2$SO$_4$ and concentrated. The residue was washed with a mixed solvent of EtOAc and PE (V/V=3/1) and dried to give a white solid product (110 mg, 57%).

$^1$H NMR (400 MHz, d$_6$-DMSO): δ ppm 12.96 (br.s 1H), 7.89-7.93 (m, 2H), 7.51-7.56 (m, 2H), 7.32 (dd, J=8.9, 4.5 Hz, 1H), 7.07 (dd, J=10.4, 2.3 Hz, 1H), 6.85 (td, J=9.1, 2.3 Hz, 1H), 4.89 (s, 2H), 3.83-3.86 (m, 2H), 2.77-2.83 (m, 1H), 2.47-2.53 (m, 2H), 2.22 (s, 3H), 1.94-2.03 (m, 2H), 1.63-1.66 (m, 2H);

$^{13}$C NMR (150 MHz, d$_6$-DMSO) δ ppm 170.9, 165.9, 164.2, 157.8, 156.3, 135.1, 133.6, 133.4, 131.1, 126.6, 117.2, 114.1, 110.5, 108.1, 103.8, 47.2, 44.9, 33.20, 30.9, 10.5; and MS-ESI: m/z 449.10 [M+H]$^+$.

Example 25: 2-(3-(4-((2,4-difluorobenzyl)carbamoyl)cyclohexyl)-5-fluoro-2-methyl-1H-indol-1-yl)acetic acid

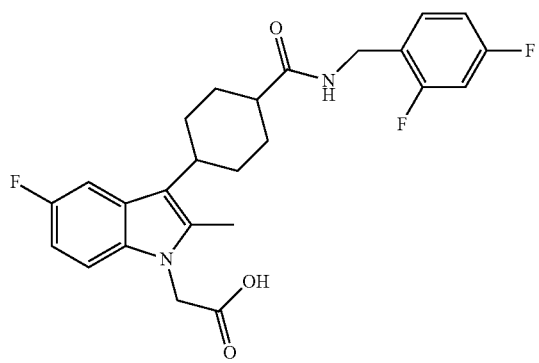 [SMILES: Cc1c(C2CCC(C(=O)NCc3ccc(F)cc3F)CC2)c2cc(F)ccc2n1CC(=O)O]

Step 1)
N-(2,4-difluorobenzyl)-4-oxocyclohexanecarboxamide

To a solution of 4-oxocyclohexanecarboxylic acid (300 mg, 2.11 mmol), (2,4-difluorophenyl)methanamine (360 mg, 2.53 mmol), EDCI (800 mg, 4.22 mmol) and HOAT (576 mg, 4.22 mmol) in DCM (10 mL) was added DIPEA (1.1 mL, 6.33 mmol) dropwise at 0° C. The mixture was stirred for 10 h at rt and then washed with water (15 mL). The organic layer was dried over anhydrous Na$_2$SO$_4$ and concentrated. The residue was purified by silica gel chromatography eluted with PE/EtOAc (V/V)=2/1 to give a white solid product (430 mg, 76%).

$^1$H NMR (400 MHz, CDCl$_3$): δ ppm 7.29-7.35 (m, 1H), 6.78-6.87 (m, 2H), 5.94 (br.s, 1H), 4.46 (d, J=5.9 Hz, 2H), 2.49-2.57 (m, 3H), 2.28-2.36 (m, 2H), 2.11-2.18 (m, 2H), 1.95-2.05 (m, 2H); and MS-ESI: m/z 268.10 [M+H]$^+$.

Step 2) methyl 2-(3-(4-((2,4-difluorobenzyl)carbamoyl)cyclohexyl)-5-fluoro-2-methyl-1H-indol-1-yl)acetate To a solution of methyl 2-(5-fluoro-2-methyl-1H-indol-1-yl))acetate (270 mg, 1.24 mmol) and N-(2,4-difluorobenzyl)-4-oxocyclohexanecarboxamide (300 mg, 1.12 mmol) in DCM (10 mL) were added triethyl silicane (1.0 mL, 6.17 mmol) and TFA (0.23 mL, 3.59 mmol) dropwise respectively at 0° C. The mixture was stirred for 2 h at rt and washed with saturated aqueous sodium bicarbonate solution (10 mL), and the water phase was extracted with DCM (10 mL×3). The combined organic layers were dried over anhydrous Na$_2$SO$_4$ and concentrated. The residue was purified by silica gel chromatography eluted with PE/EtOAc (V/V)=2/1 to give a white solid product (200 mg, 37%).

$^1$H NMR (400 MHz, CDCl$_3$): δ ppm 7.42-7.48 (m, 1H), 7.23-7.26 (m, 1H), 7.01-7.04 (m, 1H), 6.78-6.90 (m, 3H), 6.01-6.05 (m, 1H), 4.73 (s, 2H), 4.55 (d, J=5.9 Hz, 2H), 3.73 (s, 3H), 2.70-2.77 (m, 1H), 2.58-2.63 (m, 1H), 2.29 (s, 3H), 2.09-2.22 (m, 4H), 1.61-1.75 (m, 4H); and MS-ESI: m/z 473.30 [M+H]$^+$.

Step 3) 2-(3-(4-((2,4-difluorobenzyl)carbamoyl)cyclohexyl)-5-fluoro-2-methyl-1H-indol-1-yl)acetic acid A solution of methyl 2-(3-(4-((2,4-difluorobenzyl)carbamoyl)cyclohexyl)-5-fluoro-2-methyl-1H-indol-1-yl)acetate (200 mg, 0.42 mmol) and sodium hydroxide (85 mg, 2.12 mmol) in a mixed solvent of THF (5 mL) and water (5 mL) was stirred for 2 h at 50° C. After adjusting the pH of mixture to 1 with hydrochloric acid (1.0 mol/L), the resulting mixture was extracted with EtOAc (10 mL×3). The combined organic layers were dried over anhydrous Na$_2$SO$_4$ and concentrated to give a white solid product (180 mg, 93%).

$^1$H NMR (600 MHz, d$_6$-DMSO): δ ppm 8.31-8.34 (m, 1H), 7.37-7.43 (m, 1H), 7.18-7.28 (m, 3H), 7.00-7.04 (m, 1H), 6.81-6.85 (m, 1H), 4.87 (s, 2H), 4.34 (s, 2H), 2.70-2.74 (m, 1H), 2.58-2.61 (m, 1H), 2.23 (s, 3H), 2.15-2.21 (m, 2H), 2.05-2.07 (m, 2H), 1.57-1.64 (m, 2H), 1.40-1.44 (m, 2H);

$^{13}$C NMR (100 MHz, d$_6$-DMSO) δ ppm 175.4, 171.1, 158.1, 155.8, 134.2, 133.6, 130.9, 126.8, 123.3, 116.6, 111.7, 110.3, 108.1, 107.8, 104.3, 104.0, 103.7, 44.9, 37.8, 35.9, 28.7, 10.4; and MS-ESI: m/z 459.10 [M+H]$^+$.

Example 26: 2-(5-fluoro-2-methyl-3-(4-(quinoline-5-carboxamido)cyclohexyl)-1H-indol-1-yl)acetic acid hydrochloride (26a) and 2-(5-fluoro-2-methyl-3-(4-(quinoline-5-carboxamido)cyclohexyl)-1H-indol-1-yl)acetic acid hydrochloride (26b)

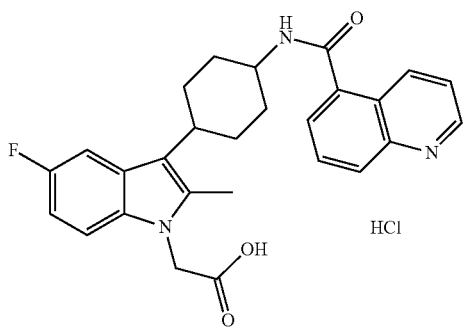 [SMILES: Cc1c(C2CCC(NC(=O)c3cccc4ncccc34)CC2)c2cc(F)ccc2n1CC(=O)O ; Cl]

Step 1) methyl 2-(5-fluoro-2-methyl-3-(4-(quinoline-5-carboxamido)cyclohexyl)-1H-indol-1-yl)acetate (26-1a) and (26-1b)

To a solution of methyl 2-(3-(4-aminocyclohexyl)-5-fluoro-2-methyl-1H-indol-1-yl) acetate (180 mg, 0.58 mmol), quinoline-5-carboxylic acid (100 mg, 0.58 mmol), EDCI (220 mg, 1.15 mmol) and HOAT (120 mg, 0.87 mmol) in DCM (25 mL) was added DIPEA (0.3 mL, 1.73 mmol) dropwise at 0° C. The mixture was stirred for 10 h at rt and washed with water (10 mL×3). The organic layer was dried over anhydrous $Na_2SO_4$ and concentrated. The residue was purified by silica gel chromatography eluted with PE/EtOAc (V/V)=1/2 to give compound 26-1a (100 mg, 36%) and compound 26-1b (100 mg, 36%) as white solids.

Compound 26-1a: $^1$H NMR (400 MHz, $CDCl_3$): δ ppm 8.97-8.99 (m, 1H), 8.80 (d, J=8.5 Hz, 1H), 8.23 (d, J=8.2 Hz, 1H), 7.76-7.83 (m, 2H), 7.51 (dd, J=8.6, 4.2 Hz, 1H), 7.22-7.26 (m, 1H), 7.24 (dd, J=8.0, 2.3 Hz, 1H), 7.07 (dd, J=8.8, 4.3 Hz, 1H), 6.85 (td, J=9.0, 2.3 Hz, 1H), 6.42 (d, J=6.7 Hz, 1H), 4.76 (s, 2H), 4.49-4.54 (m, 1H), 3.74 (s, 3H), 2.82-2.88 (m, 1H), 2.34 (s, 3H), 2.19-2.22 (m, 2H), 2.03-2.14 (m, 2H), 1.79-1.90 (m, 4H); and MS-ESI: m/z 474.30 $[M+H]^+$.

Compound 26-1b: $^1$H NMR (400 MHz, $CDCl_3$): δ ppm 8.93-8.95 (m, 1H), 8.76 (d, J=8.6 Hz, 1H), 8.16-8.19 (m, 1H), 7.66-7.71 (m, 2H), 7.47 (dd, J=8.6, 4.2 Hz, 1H), 7.31 (dd, J=10.2, 2.3 Hz, 1H), 7.04 (dd, J=8.8, 4.3 Hz, 1H), 6.86 (td, J=8.9, 2.4 Hz, 1H), 5.94 (d, J=8.1 Hz, 1H), 4.74 (s, 2H), 4.18-4.26 (m, 1H), 3.73 (s, 3H), 2.73-2.79 (m, 1H), 2.33 (s, 3H), 2.30-2.34 (m, 2H), 2.08-2.19 (m, 2H), 1.88-1.92 (m, 2H), 1.38-1.48 (m, 2H); and MS-ESI: m/z 474.10 $[M+H]^+$.

Step 2) 2-(5-fluoro-2-methyl-3-(4-(quinoline-5-carboxamido)cyclohexyl)-1H-indol-1-yl)acetic acid hydrochloride (26a)

A solution of methyl 2-(5-fluoro-2-methyl-3-(4-(quinoline-5-carboxamido)cyclohexyl)-1H-indol-1-yl)acetate (26-1a) (95 mg, 0.20 mmol) and sodium hydroxide (42 mg, 1.0 mmol) in a mixed solvent of THF (5 mL) and water (3 mL) was stirred for 1 h at 50° C. After adjusting to pH 1 with hydrochloric acid (1.0 mol/L), the resulting mixture was extracted with EtOAc (10 mL×3). The combined organic layers were dried over anhydrous $Na_2SO_4$ and concentrated to give a white solid product (85 mg, 85.5%, HPLC Rt: 5.07 min).

$^1$H NMR (600 MHz, $d_6$-DMSO): δ ppm 8.91-8.96 (m, 2H), 8.55 (d, J=8.3 Hz, 1H), 8.14 (d, J=8.3 Hz, 1H), 7.85 (t, J=7.6 Hz, 1H), 7.76 (d, J=6.8 Hz, 1H), 7.58-7.60 (m, 1H), 7.49 (d, J=10.1 Hz, 1H), 7.25-7.29 (m, 1H), 6.83 (t, J=8.3 Hz, 1H), 4.88 (s, 2H), 4.29-4.32 (m, 1H), 2.78-2.82 (m, 1H), 2.29 (s, 3H), 2.20-2.29 (m, 2H), 2.05-2.09 (m, 2H), 1.76-1.81 (m, 2H), 1.51-1.53 (m, 2H); and MS-ESI: m/z 460.00 $[M+H-HCl]^+$.

Step 3) 2-(5-fluoro-2-methyl-3-(4-(quinoline-5-carboxamido)cyclohexyl)-1H-indol-1-yl)acetic acid hydrochloride (26b)

A solution of methyl 2-(5-fluoro-2-methyl-3-(4-(quinoline-5-carboxamido)cyclohexyl)-1H-indol-1-yl)acetate (26-1b) (95 mg, 0.20 mmol) and sodium hydroxide (45 mg, 1.10 mmol) in a mixed solvent of THF (5 mL) and water (3 mL) was stirred for 1 h at 50° C. After adjusting to pH 1 with hydrochloric acid (1.0 mol/L), the resulting mixture was extracted with EtOAc (10 mL×3). The combined organic layers were dried over anhydrous $Na_2SO_4$ and concentrated to give a white solid product (95 mg, 90.8%, HPLC Rt: 5.11 min).

$^1$H NMR (600 MHz, $d_6$-DMSO): δ ppm 9.19-9.26 (m, 2H), 8.85 (d, J=7.6 Hz, 1H), 8.44 (d, J=8.5 Hz, 1H), 8.09-8.12 (m, 1H), 7.99-8.03 (m, 2H), 7.44 (d, J=10.5 Hz, 1H), 7.32 (dd, J=8.9, 4.2 Hz, 1H), 6.85-6.88 (m, 1H), 4.92 (s, 2H), 4.07-4.14 (m, 1H), 2.75-2.79 (m, 1H), 2.30 (s, 3H), 2.03-2.13 (m, 4H), 1.75-1.77 (m, 2H), 1.53-1.59 (m, 2H); and MS-ESI: m/z 460.00 $[M+H-HCl]^+$.

Example 27: 2-(5-fluoro-3-(4-(4-fluorophenylsulfonamido)cyclohexyl)-2-methyl-1H-indol-1-yl)acetic acid (27a) and 2-(5-fluoro-3-(4-(4-fluorophenylsulfonamido)cyclohexyl)-2-methyl-1H-indol-1-yl)acetic acid (27b)

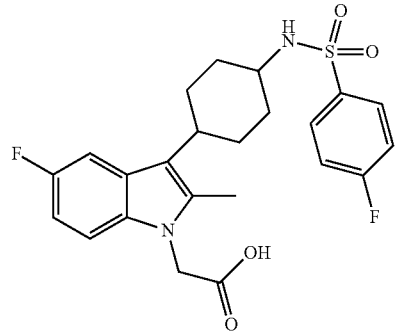 [SMILES: Cc1c(C2CCC(NS(=O)(=O)c3ccc(F)cc3)CC2)c2cc(F)ccc2n1CC(=O)O]

Step 1) 4-fluoro-N-(4-oxocyclohexyl)benzenesulfonamide

By using 4-fluorobenzenesulfonic acid (300 mg, 1.70 mmol), DCM (5 mL), thionyl chloride (300 mg, 2.55 mmol), DMF (1 mL), 4-aminocyclohexanone hydrochloride (310 mg, 2.04 mmol) and a solution of triethylamine (690 mg, 6.82 mmol) in DCM (5 mL) and according to the method described in step 1) of example 24 to give the title compound as a white solid (180 mg, 39%).

$^1$H NMR (400 MHz, CDCl$_3$): δ ppm 7.91-7.95 (m, 2H), 7.22 (t, J=8.5 Hz, 2H), 4.84-4.90 (m, 1H), 3.56-3.65 (m, 1H), 2.28-2.43 (m, 4H), 2.03-2.10 (m, 2H), 1.71-1.80 (m, 2H); and MS-ESI: m/z 272.20 [M+H]$^+$.

Step 2) methyl 2-(5-fluoro-3-(4-(4-fluorophenylsulfonamido)cyclohexyl)-2-methyl-1H-indol-1-yl)acetate (27-1a) and methyl 2-(5-fluoro-3-(4-(4-fluorophenylsulfonamido)cyclohexyl)-2-methyl-1H-indol-1-yl)acetate (27-1b)

To a solution of methyl 2-(5-fluoro-2-methyl-1H-indol-1-yl))acetate (160 mg, 0.73 mmol) and 4-fluoro-N-(4-oxocyclohexyl)benzenesulfonamide (180 mg, 0.66 mmol) in DCM (10 mL) were added triethyl silicane (0.6 mL, 3.65 mmol) and TFA (0.16 mL, 2.12 mmol) dropwise respectively at 0° C. The mixture was stirred for 2 h at rt and washed with saturated aqueous sodium bicarbonate solution (10 mL), and the water phase was extracted with DCM (10 mL×3). The combined organic layers were dried over anhydrous Na$_2$SO$_4$ and concentrated. The residue was purified by silica gel chromatography eluted with PE/EtOAc (V/V)=3/1 to give compound 27-1a (102 mg, 32%) as a white solid and compound 27-1b (100 mg, 32%) as a white solid.

Compound 27-1a: $^1$H NMR (600 MHz, CDCl$_3$): δ ppm 7.97-7.99 (m, 2H), 7.22 (dd, J=10.0, 2.4 Hz, 1H), 7.18-7.21 (m, 2H), 7.04 (dd, J=8.8, 4.3 Hz, 1H), 6.86 (td, J=9.0, 2.4 Hz, 1H), 4.88 (d, J=5.4 Hz, 1H), 4.73 (s, 2H), 3.73 (s, 3H), 3.64-3.67 (m, 1H), 2.65-2.69 (m, 1H), 2.28 (s, 3H), 1.90-1.97 (m, 2H), 1.82-1.85 (m, 2H), 1.56-1.64 (m, 4H); and MS-ESI: m/z 477.00 [M+H]$^+$.

Compound 27-1b: $^1$H NMR (600 MHz, CDCl$_3$): δ ppm 7.94-7.97 (m, 2H), 7.21-7.24 (m, 3H), 7.04 (dd, J=8.8, 4.3 Hz, 1H), 6.85 (td, J=9.0, 2.4 Hz, 1H), 4.73 (s, 2H), 4.50 (d, J=7.6 Hz, 1H), 3.73 (s, 3H), 3.25-3.30 (m, 1H), 2.60-2.66 (m, 1H), 2.28 (s, 3H), 1.98-2.02 (m, 2H), 1.87-1.94 (m, 2H), 1.75-1.80 (m, 2H), 1.29-1.37 (m, 2H); and MS-ESI: m/z 477.00 [M+H]$^+$.

Step 3) 2-(5-fluoro-3-(4-(4-fluorophenylsulfonamido)cyclohexyl)-2-methyl-1H-indol-1-yl)acetic acid (27a)

A solution of methyl 2-(5-fluoro-3-(4-(4-fluorophenylsulfonamido)cyclohexyl)-2-methyl-1H-indol-1-yl)acetate (27-1a) (90 mg, 0.19 mmol) and sodium hydroxide (79 mg, 1.89 mmol) in a mixed solvent of THF (5 mL) and water (3 mL) was stirred for 1 h at 50° C. After adjusting to pH 1 with hydrochloric acid (1.0 mol/L), the resulting mixture was extracted with EtOAc (10 mL×3). The combined organic layers were dried over anhydrous Na$_2$SO$_4$ and concentrated to give a white solid product (70 mg, 80%, HPLC Rt: 7.59 min).

Compound 27a: $^1$H NMR (600 MHz, d$_6$-DMSO): δ ppm δ ppm 7.95-8.00 (m, 3H), 7.52 (d, J=9.5 Hz, 1H), 7.40-7.48 (m, 2H), 7.25-7.30 (m, 1H), 6.83-6.89 (m, 1H), 4.87 (s, 2H), 3.35 (s, 1H), 2.63-2.68 (m, 1H), 2.24 (s, 3H), 2.06-2.12 (m, 2H), 1.62-1.69 (m, 2H), 1.51-1.58 (m, 2H), 1.32-1.40 (m, 2H); and MS-ESI: m/z 463.30 [M+H]$^+$.

Step 4) 2-(5-fluoro-3-(4-(4-fluorophenylsulfonamido)cyclohexyl)-2-methyl-1H-indol-1-yl)acetic acid (27b)

A solution of methyl 2-(5-fluoro-3-(4-(4-fluorophenylsulfonamido)cyclohexyl)-2-methyl-1H-indol-1-yl)acetate (27-1b) (90 mg, 0.19 mmol) and sodium hydroxide (79 mg, 1.89 mmol) in a mixed solvent of THF (5 mL) and water (3 mL) was stirred for 1 h at 50° C. After adjusting to pH 1 with hydrochloric acid (1.0 mol/L), the resulting mixture was extracted with EtOAc (10 mL×3). The combined organic layers were dried over anhydrous Na$_2$SO$_4$ and concentrated to give a white solid product (80 mg, 92%, HPLC Rt: 7.20 min).

Compound 27b: $^1$H NMR (600 MHz, d$_6$-DMSO): δ ppm 7.92-7.95 (m, 2H), 7.73 (d, J=7.4 Hz, 1H), 7.43 (t, J=8.7 Hz, 2H), 7.37 (d, J=9.3 Hz, 1H), 7.24-7.27 (m, 1H), 6.82 (t J=8.3 Hz, 1H), 4.85 (s, 2H), 3.21-3.28 (m, 1H), 2.59-2.63 (m, 1H), 2.22 (s, 3H), 1.81-1.87 (m, 2H), 1.72-1.74 (m, 2H), 1.55-1.57 (m, 2H), 1.31-1.36 (m, 2H); and MS-ESI: m/z 463.30 [M+H]$^+$.

Example 28: 2-(5-fluoro-3-(4-(4-fluoro-N-methylphenylsulfonamido)cyclohexyl)-2-methyl-1H-indol-1-yl) acetic acid

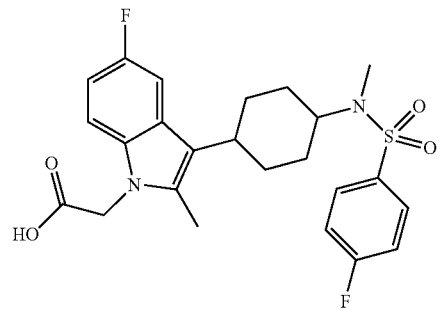 [SMILES: Cc1c(C2CCC(N(C)S(=O)(=O)c3ccc(F)cc3)CC2)c2cc(F)ccc2n1CC(=O)O]

Step 1) methyl 2-(5-fluoro-3-(4-(4-fluoro-N-methylphenylsulfonamido)cyclohexyl)-2-methyl-1H-indol-1-yl) acetate To a solution of 4-fluorobenzenesulfonic acid (110 mg, 0.61 mmol) in DCM (5 mL) was added thionyl chloride (120 mg, 0.93 mmol) at rt. After stirring for 10 min, DMF (1 mL) was added to the mixture. The mixture was stirred at rt for 1 h and concentrated. To a solution of methyl 2-(5-fluoro-2-methyl-3-(4-(methylamino)cyclohexyl)-1H-indol-1-yl) acetate (136 mg, 0.41 mmol) and triethylamine (250 mg, 2.43 mmol) in DMF (5 mL) was added the above residue at 0° C. The resulting mixture was stirred at rt for 3 h and concentrated. The residue was diluted with water (15 mL) and extracted with EtOAc (10 mL×3). The combined organic layers were dried over anhydrous Na$_2$SO$_4$ and concentrated. The residue was purified by silica gel chromatography eluted with PE/EtOAc (V/V)=1/1 to give the title compound as a white solid (180 mg, 90%).

$^1$H NMR (400 MHz, CDCl$_3$): δ ppm 7.86-7.92 (m, 2H), 7.20-7.25 (m, 3H), 7.07 (dd, J=8.8, 4.4 Hz, 1H), 6.86-6.92 (m, 1H), 4.77 (s, 2H), 3.97-4.02 (m, 1H), 3.76 (s, 3H), 2.98 (s, 2H), 2.91-2.97 (m, 1H), 2.84 (s, 1H), 2.32-2.34 (m, 3H), 2.14-2.22 (m, 2H), 1.91-2.02 (m, 2H), 1.66-1.82 (m, 4H); and MS-ESI: m/z 491.95 [M+H]$^+$.

Step 2) 2-(5-fluoro-3-(4-(4-fluoro-N-methylphenylsulfonamido)cyclohexyl)-2-methyl-1H-indol-1-yl) acetic acid To a solution of methyl 2-(5-fluoro-3-(4-(4-fluoro-N-methylphenylsulfonamido)cyclohexyl)-2-methyl-1H-indol- 1-yl)acetate (180 mg, 0.37 mmol) in a mixed solvent of THF (5 mL) and water (3 mL) was added lithium hydroxide monohydrate (80 mg, 1.83 mmol). The mixture was stirred for 1 h at 45° C. After adjusting to pH 1 with hydrochloric acid (1.0 mol/L), the resulting mixture was extracted with EtOAc (5 mL×3). The combined organic layers were dried over anhydrous $Na_2SO_4$ and concentrated to give a light yellow solid product (158 mg, 90%).

$^1$H NMR (400 MHz, $d_6$-DMSO): δ ppm 7.89-8.00 (m, 2H), 7.44-7.50 (m, 2H), 7.28-7.34 (m, 1H), 7.19-7.23 (m, 1H), 6.83-6.89 (m, 1H), 4.89-4.91 (m, 2H), 3.74-3.78 (m, 1H), 3.57-3.62 (m, 1H), 2.90 (s, 2H), 2.74 (s, 1H), 2.25-2.27 (m, 3H), 1.98-2.11 (m, 2H), 1.85-1.91 (m, 1H), 1.74-1.78 (m, 1H), 1.55-1.63 (m, 4H); and MS-ESI: m/z 477.00 [M+H]$^+$.

Example 29 2-(3-(4-(2,4-difluorophenylsulfonamido)cyclohexyl)-5-fluoro-2-methyl-1H-indol-1-yl)acetic acid (29a) and 2-(3-(4-(2,4-difluorophenylsulfonamido)cyclohexyl)-5-fluoro-2-methyl-1H-indol-1-yl)acetic acid (29b)

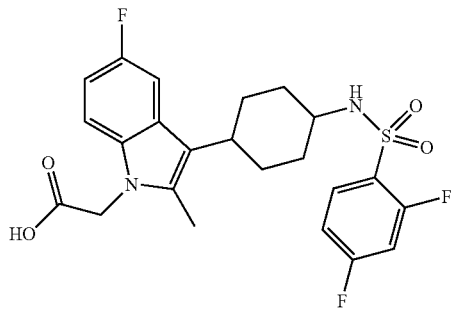 [SMILES: Cc1c(C2CCC(NS(=O)(=O)c3ccc(F)cc3F)CC2)c2cc(F)ccc2n1CC(=O)O]

Step 1) methyl 2-(3-(4-(2,4-difluorophenylsulfonamido)cyclohexyl)-5-fluoro-2-methyl-1H-indol-1-yl)acetate (29-1a) and methyl 2-(3-(4-(2,4-difluorophenylsulfonamido)cyclohexyl)-5-fluoro-2-methyl-1H-indol-1-yl)acetate (29-1b)

To a solution of 2,4-difluorobenzenesulfonic acid (170 mg, 0.85 mmol) in DCM (10 mL) was added thionyl chloride (134 mg, 1.13 mmol) at rt. After stirring for 10 min, DMF (1 mL) was added to the mixture. The mixture was stirred at rt for 1 h and concentrated. To a solution of methyl 2-(3-(4-aminocyclohexyl)-5-fluoro-2-methyl-1H-indol-1-yl)acetate (180 mg, 0.57 mmol) and triethylamine (0.48 mL, 3.39 mmol) in DMF (5 mL) was added the above residue at 0° C. The resulting mixture was stirred at rt for 3 h and concentrated. The residue was diluted with water (15 mL) and extracted with EtOAc (10 mL×3). The combined organic layers were dried over anhydrous $Na_2SO_4$ and concentrated. The residue was purified by silica gel chromatography eluted with PE/EtOAc (V/V)=3/1 to give compound 29-1a (25 mg, 9%) as a white solid and compound (29-1b) (21 mg, 7%) as a white solid.

Compound 29-1a: $^1$H NMR (600 MHz, CDCl$_3$): δ ppm 7.94-7.98 (m, 1H), 7.27 (dd, J=7.7, 2.4 Hz, 1H), 7.04-7.07 (m, 1H), 6.99-7.01 (m, 2H), 6.88 (td, J=9.0, 2.4 Hz, 1H), 5.08 (d, J=5.4 Hz, 1H), 4.75 (s, 2H), 3.74 (s, 3H), 3.71-3.75 (m, 1H), 2.66-2.71 (m, 1H), 2.31 (s, 3H), 1.93-2.01 (m, 2H), 1.86-1.88 (m, 2H), 1.61-1.66 (m, 4H); and MS-ESI: m/z 495.75 [M+H]$^+$.

Compound 29-1b: $^1$H NMR (600 MHz, CDCl$_3$): δ ppm 7.98-8.02 (m, 1H), 7.20 (dd, J=10.1, 2.4 Hz, 1H), 7.02-7.06 (m, 2H), 6.96-7.00 (m, 1H), 6.85 (td, J=9.0, 2.4 Hz, 1H), 4.73 (s, 2H), 4.72 (d, J=6.4 Hz, 1H), 3.73 (s, 3H), 3.28-3.35 (m, 1H), 2.62-2.67 (m, 1H), 2.28 (s, 3H), 2.00-2.03 (m, 2H), 1.87-1.94 (m, 2H), 1.77-1.79 (m, 2H), 1.35-1.41 (m, 2H); and MS-ESI: m/z 495.70 [M+H]$^+$.

Step 2) 2-(3-(4-(2,4-difluorophenylsulfonamido)cyclohexyl)-5-fluoro-2-methyl-1H-indol-1-yl)acetic acid (29a)

A solution of methyl 2-(3-(4-(2,4-difluorophenylsulfonamido)cyclohexyl)-5-fluoro-2-methyl-1H-indol-1-yl)acetate (29-1a) (60 mg, 0.12 mmol) and LiOH.H$_2$O (25 mg, 0.61 mmol) in a mixed solvent of THF (5 mL) and water (3 mL) was stirred for 30 min at 45° C. After adjusting to pH 1 with hydrochloric acid (1.0 mol/L), the resulting mixture was extracted with EtOAc (10 mL×3). The combined organic layers were dried over anhydrous $Na_2SO_4$ and concentrated to give a white solid product (56 mg, 94%, HPLC Rt: 7.55 min).

Compound 29a: $^1$H NMR (600 MHz, $d_6$-DMSO): δ ppm 8.42 (d, J=6.2 Hz, 1H), 7.91-7.95 (m, 1H), 7.60 (dd, J=10.7, 2.4 Hz, 1H), 7.49-7.53 (m, 1H), 7.27-7.30 (m, 2H), 6.86 (td, J=9.2, 2.4 Hz, 1H), 4.89 (s, 2H), 3.47-3.50 (m, 1H), 2.64-2.68 (m, 1H), 2.25 (s, 3H), 2.09-2.16 (m, 2H), 1.69-1.71 (m, 2H), 1.59-1.63 (m, 2H), 1.35-1.37 (m, 2H);

$^{13}$C NMR (100 MHz, $d_6$-DMSO) δ ppm 170.9, 156.0, 134.5, 133.6, 132.3, 126.9, 116.2, 112.7, 110.1, 108.1, 106.3, 104.9, 60.2, 48.5, 44.9, 35.7, 31.5, 26.7, 21.2, 14.5, 10.4; and MS-ESI: m/z 481.80 [M+H]$^+$.

Step 3) 2-(3-(4-(2,4-difluorophenylsulfonamido)cyclohexyl)-5-fluoro-2-methyl-1H-indol-1-yl)acetic acid (29b)

A solution of methyl 2-(3-(4-(2,4-difluorophenylsulfonamido)cyclohexyl)-5-fluoro-2-methyl-1H-indol-1-yl)acetate (29-1b) (50 mg, 0.1 mmol) and LiOH.H$_2$O (22 mg, 0.5 mmol) in a mixed solvent of THF (5 mL) and water (3 mL) was stirred for 1 h at 50° C. After adjusting to pH 1 with hydrochloric acid (1.0 mol/L), the resulting mixture was extracted with EtOAc (10 mL×3). The combined organic layers were dried over anhydrous $Na_2SO_4$ and concentrated to give a white solid product (45 mg, 93%, HPLC Rt: 7.29 min).

Compound 29b: $^1$H NMR (600 MHz, $d_6$-DMSO): δ ppm 8.06 (d, J=7.8 Hz, 1H), 7.91-7.95 (m, 1H), 7.51-7.56 (m, 1H), 7.37 (dd, J=10.6, 2.5 Hz, 1H), 7.27-7.31 (m, 2H), 6.82 (td, J=9.1, 2.5 Hz, 1H), 4.87 (s, 2H), 3.32-3.48 (m, 1H), 2.59-2.64 (m, 1H), 2.23 (s, 3H), 1.82-1.89 (m, 2H), 1.75-1.78 (m, 2H), 1.56-1.59 (m, 2H), 1.38-1.45 (m, 2H); and MS-ESI: m/z 481.80 [M+H]$^+$.

Example 30: 2-(5-fluoro-3-(2-((4-fluorophenyl)sulfonyl)octahydrocyclopenta[c]pyrrol-5-yl)-2-methyl-1H-indol-1-yl)acetic acid

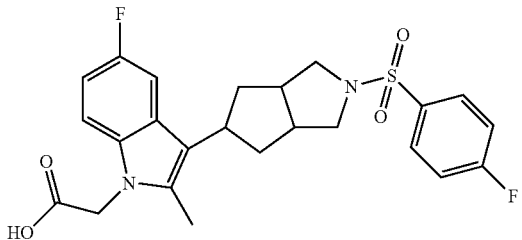 [SMILES: Cc1c(C2CC3CN(S(=O)(=O)c4ccc(F)cc4)CC3C2)c2cc(F)ccc2n1CC(=O)O]

Step 1) benzyl 5-(5-fluoro-1-(2-methoxy-2-oxoethyl)-2-methyl-1H-indol-3-yl)hexahydrocyclopenta[c]pyrrole-2(1H)-carboxylate By using methyl 2-(5-fluoro-2-methyl-1H-indol-1-yl)acetate (1.3 g, 5.90 mmol), benzyl 5-oxohexahydrocyclopenta[c]pyrrole-2(1H)-carboxylate (1.0 g, 3.9 mmol), DCM (20 mL), triethyl silicane (3.4 mL, 21.0 mmol) and TFA (0.92 mL, 12.0 mmol) and according to the method described in step 2) of example 4 to prepare the title compound as a white solid (717 mg, 40%).

$^1$H NMR (400 MHz, CDCl$_3$) δ ppm 7.27-7.42 (m, 5H), 7.21 (dd, J=10.0, 2.4 Hz, 1H), 7.05 (dd, J=8.8, 4.3 Hz, 1H), 6.87 (td, J=9.0, 2.4 Hz, 1H), 5.19 (d, J=2.8 Hz, 2H), 4.75 (s, 1H), 3.74 (s, 3H), 3.61-3.68 (m, 2H), 3.47-3.58 (m, 2H), 3.23-3.32 (m, 1H), 2.76-2.83 (m, 2H), 2.31 (s, 3H), 2.14-2.21 (m, 2H), 1.85-1.96 (m, 2H); and MS-ESI: m/z 465.25 [M+H]$^+$.

Step 2) methyl 2-(5-fluoro-2-methyl-3-(octahydrocyclopenta[c]pyrrol-5-yl)-1H-indol-1-yl)acetate By using benzyl 5-(5-fluoro-1-(2-methoxy-2-oxoethyl)-2-methyl-1H-indol-3-yl)hexahydrocyclopenta[c]pyrrole-2(1H)-carboxylate (720 mg, 1.6 mmol), methanol (10 mL) and Pd/C (51 mg) and according to the method described in step 3) of example 4 to prepare the title compound as light yellow thick oil (400 mg, 93%).

$^1$H NMR (400 MHz, CDCl$_3$) δ ppm 7.28 (dd, J=8.0, 2.3 Hz, 1H), 7.05 (dd, J=8.8, 4.4 Hz, 1H), 6.86 (td, J=9.0, 2.3 Hz, 1H), 4.74 (s, 2H), 3.74 (s, 3H), 3.09-3.18 (m, 1H), 2.85-2.92 (m, 4H), 2.65-2.71 (m, 2H), 2.33 (s, 3H), 2.12-2.19 (m, 2H), 1.68-1.77 (m, 2H); and MS-ESI: m/z 331.10 [M+H]$^+$.

Step 3) methyl 2-(5-fluoro-3-(2-((4-fluorophenyl)sulfonyl)octahydrocyclopenta[c]pyrrol-5-yl)-2-methyl-1H-indol-1-yl)acetate To a solution of methyl 2-(5-fluoro-2-methyl-3-(octahydrocyclopenta[c]pyrrol-5-yl)-1H-indol-1-yl)acetate (200 mg, 0.61 mmol) in DMF (10 mL) were added triethylamine (0.22 mL, 1.6 mmol) and 4-fluorobenzene-1-sulfonyl chloride (110 mg, 0.57 mmol) at 0° C. The mixture was stirred at rt for 3 h and concentrated. The residue was diluted with water (15 mL) and extracted with EtOAc (15 mL×2). The combined organic layers were dried over anhydrous Na$_2$SO$_4$ and concentrated. The residue was purified by silica gel chromatography eluted with PE/EtOAc (V/V)=2/1 to give the title compound as a white solid (217 mg, 79%).

$^1$H NMR (400 MHz, CDCl$_3$) δ ppm 7.90-7.93 (m, 2H), 7.24-7.28 (m, 2H), 7.14 (dd, J=10.0, 2.3 Hz, 1H), 7.05 (dd, J=8.9, 4.3 Hz, 1H), 6.88 (td, J=9.0, 2.3 Hz, 1H), 4.74 (s, 2H), 3.74 (s, 3H), 3.25-3.27 (m, 2H), 3.10-3.18 (m, 1H), 3.05-3.09 (m, 2H), 2.69-2.75 (m, 2H), 2.30 (s, 3H), 2.09-2.20 (m, 2H), 1.81-1.89 (m, 2H); and MS-ESI: m/z 489.20 [M+H]$^+$.

Step 4) 2-(5-fluoro-3-(2-((4-fluorophenyl)sulfonyl)octahydrocyclopenta[c]pyrrol-5-yl)-2-methyl-1H-indol-1-yl)acetic acid By using a mixture of methyl 2-(5-fluoro-3-(2-((4-fluorophenyl)sulfonyl)octahydrocyclopenta[c]pyrrol-5-yl)-2-methyl-1H-indol-1-yl)acetate (212 mg, 0.43 mmol) and lithium hydroxide monohydrate (65 mg, 1.55 mmol) in a mixed solvent of THF (5 mL) and water (5 mL) and according to the method described in step 5) of example 4 to prepare the title compound as a yellow solid (196 mg, 95%).

$^1$H NMR (400 MHz, d$_6$-DMSO) δ ppm 7.89-7.93 (m, 2H), 7.50 (t, J=8.7 Hz, 2H), 7.34 (dd, J=8.8, 4.5 Hz, 1H), 7.08 (dd, J=8.5, 2.3 Hz, 1H), 6.88 (td, J=8.2, 2.3 Hz, 1H), 4.90 (s, 2H), 3.37 (s, 3H), 3.16-3.19 (m, 3H), 2.92-2.95 (m, 2H), 2.65-2.72 (m, 2H), 2.23 (s, 3H), 2.03-2.11 (m, 2H), 1.66-1.75 (m, 2H); and MS-ESI: m/z 475.20 [M+H]$^+$.

Example 31: 2-(5-fluoro-3-(1-((3-fluorophenyl)sulfonyl)piperidin-4-yl)-2-methyl-1H-indol-1-yl)acetic acid

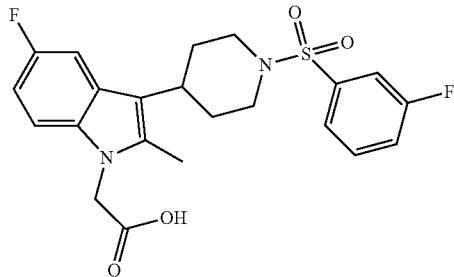 [SMILES: Cc1c(C2CCN(S(=O)(=O)c3cccc(F)c3)CC2)c2cc(F)ccc2n1CC(=O)O]

Step 1) 1-((3-fluorophenyl)sulfonyl)piperidin-4-one

By using piperidin-4-one hydrochloride (500 mg, 3.68 mmol), DMF (10 mL), TEA (1.4 mL, 10.0 mmol) and 3-fluorobenzene-1-sulfonyl chloride (624 mg, 3.21 mmol) and according to the method described in step 2) of example 1 to prepare the title compound as a white solid (625 mg, 74%).

$^1$H NMR (400 MHz, CDCl$_3$): δ ppm 7.49-7.61 (m, 3H), 7.58-7.63 (m, 1H), 7.31-7.35 (m, 1H), 3.44 (t, J=6.2 Hz, 4H), 2.56 (t, J=6.2 Hz, 4H); and MS-ESI: m/z 258.30 [M+H]$^+$.

Step 2) methyl 2-(5-fluoro-3-(1-((3-fluorophenyl)sulfonyl)piperidin-4-yl)-2-methyl-1H-indol-1-yl)acetate By using methyl 2-(5-fluoro-2-methyl-1H-indol-1-yl)acetate (283 mg, 1.28 mmol), 1-((3-fluorophenyl)sulfonyl)

piperidin-4-one (300 mg, 1.17 mmol), DCM (10 mL), triethyl silicane (1.05 mL, 6.59 mmol) and TFA (0.29 mL, 3.90 mmol) and according to the method described in step 2) of example 24 to prepare the title compound as a white solid (492 mg, 91%).

$^1$H NMR (400 MHz, CDCl$_3$) δ ppm 7.54-7.64 (m, 3H), 7.35 (td, J=8.2, 1.6 Hz, 1H), 7.13 (dd, J=10.0, 2.3 Hz, 1H), 7.05 (dd, J=8.8, 4.3 Hz, 1H), 6.87 (td, J=9.0, 2.3 Hz, 1H), 4.73 (s, 2H), 4.00-4.03 (m, 2H), 3.74 (s, 3H), 2.63-2.70 (m, 1H), 2.44-2.51 (m, 2H), 2.27 (s, 3H), 2.16-2.26 (m, 2H), 1.76-1.80 (m, 2H); and MS-ESI: m/z 463.20 [M+H]$^+$.

Step 3) 2-(5-fluoro-3-(1-((3-fluorophenyl)sulfonyl)piperidin-4-yl)-2-methyl-1H-indol-1-yl)acetic acid By using a mixture of methyl 2-(5-fluoro-3-(1-((3-fluorophenyl)sulfonyl)piperidin-4-yl)-2-methyl-1H-indol-1-yl)acetate (491 mg, 1.06 mmol) and lithium hydroxide monohydrate (156 mg, 3.7 mmol) in a mixed solvent of THF (5 mL) and water (5 mL) and according to the method described in step 3) of example 24 to prepare the title compound as a white solid (371 mg, 78%).

$^1$H NMR (600 MHz, CDCl$_3$) δ ppm 7.63 (d, J=7.8 Hz, 1H), 7.53-7.59 (m, 2H), 7.35 (td, J=8.2, 1.7 Hz, 1H), 7.14 (dd, J=9.9, 2.2 Hz, 1H), 7.05 (dd, J=8.8, 4.2 Hz, 1H), 6.87 (td, J=8.9, 2.2 Hz, 1H), 4.76 (s, 2H), 3.99-4.01 (m, 2H), 2.63-2.68 (m, 1H), 2.46 (t, J=11.3 Hz, 2H), 2.27 (s, 3H), 2.16-2.23 (m, 2H), 1.75-1.77 (m, 2H);

$^{13}$C NMR (150 MHz, CDCl$_3$): δ ppm 184.9, 172.6, 163.3, 161.6, 158.4, 156.8, 138.8, 133.3, 130.9, 126.8, 123.3, 120.0, 119.9, 115.0, 114.8, 114.8, 109.3, 108.8, 104.6, 47.2, 44.4, 34.1, 30.8, 10.5; and MS-ESI: m/z 449.50 [M+H]$^+$.

Example 32: 2-(5-fluoro-3-(3-(4-fluorophenylsulfonamido)cyclobutyl)-2-methyl-1H-indol-1-yl)acetic acid

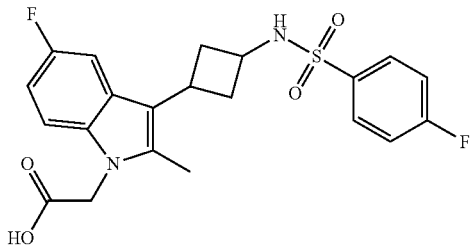 [SMILES: Cc1c(C2CC(NS(=O)(=O)c3ccc(F)cc3)C2)c2cc(F)ccc2n1CC(=O)O]

Step 1) methyl 2-(5-fluoro-3-(3-(4-fluorophenylsulfonamido)cyclobutyl)-2-methyl-1H-indol-1-yl)acetate By using 4-fluorobenzenesulfonic acid (186 mg, 1.05 mmol), DCM (10 mL), thionyl chloride (165 mg, 1.38 mmol), DMF (6 mL), methyl 2-(3-(3-aminocyclobutyl)-5-fluoro-2-methyl-1H-indol-1-yl)acetate (200 mg, 0.69 mmol) and triethylamine (0.36 mL, 2.59 mmol) and according to the method described in step 1) of example 28 to give the title compound as a white solid (105 mg, 34%).

$^1$H NMR (400 MHz, CDCl$_3$): δ ppm 7.91-7.95 (m, 2H), 7.14-7.21 (m, 3H), 7.03 (dd, J=8.8, 4.3 Hz, 1H), 6.86 (td, J=9.0, 2.4 Hz, 1H), 4.83 (d, J=8.4 Hz, 1H), 4.71 (s, 2H), 3.80-3.87 (m, 1H), 3.74 (s, 3H), 3.20-3.29 (m, 1H), 2.26-2.78 (m, 2H), 2.23 (s, 3H), 2.19-2.27 (m, 2H); and MS-ESI: m/z 449.20 [M+H]+.

Step 2) 2-(5-fluoro-3-(3-(4-fluorophenylsulfonamido)cyclobutyl)-2-methyl-1H-indol-1-yl)acetic acid By using a mixture of methyl 2-(5-fluoro-3-(3-(4-fluorophenyl sulfonamido)cyclobutyl)-2-methyl-1H-indol-1-yl)acetate (95 mg, 0.21 mmol) and lithium hydroxide monohydrate (45 mg, 1.06 mmol) in a mixed solvent of THF (5 mL) and water (3 mL) and according to the method described in step 2) of example 28 to prepare the title compound as a white solid (91 mg, 99%).

$^1$H NMR (400 MHz, d$_6$-DMSO): δ ppm 8.33 (d, J=9.1 Hz, 1H), 7.89-7.92 (m, 2H), 7.56-7.59 (m, 1H), 7.43 (t, J=8.8 Hz, 2H), 7.29 (dd, J=8.8, 4.5 Hz, 1H), 6.86 (td, J=9.2, 2.3 Hz, 1H), 4.85 (s, 2H), 4.01-4.07 (m, 1H), 3.12-3.18 (m, 1H), 2.18-2.29 (m, 4H), 2.16 (s, 3H);

$^{13}$C NMR (100 MHz, CDCl$_3$) δ ppm 170.4, 168.2, 165.4, 162.92, 158.0, 155.7, 138.1, 134.9, 133.2, 129.5, 126.6, 116.4, 111.98, 110.0, 109.9, 108.0, 107.7, 103.8, 103.6, 64.2, 54.8, 44.4, 37.0, 30.1, 24.9, 18.5, 13.4, 10.0; and MS-ESI: m/z 435.20 [M+H]$^+$.

Example 33: 2-(5-fluoro-3-(1-((2,4-difluorophenyl)sulfonyl)piperidin-4-yl)-2-methyl-1H-indol-1-yl)acetic acid

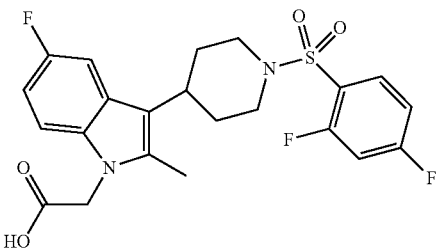 [SMILES: Cc1c(C2CCN(S(=O)(=O)c3ccc(F)cc3F)CC2)c2cc(F)ccc2n1CC(=O)O]

Step 1) methyl 2-(5-fluoro-3-(1-((2,4-difluorophenyl)sulfonyl)piperidin-4-yl)-2-methyl-1H-indol-1-yl)acetate By using 2,4-difluorobenzenesulfonic acid (237 mg, 1.22 mmol), DCM (5 mL), thionyl chloride (240 mg, 2.02 mmol), DMF (1 mL), methyl 2-(5-fluoro-2-methyl-3-(piperidin-4-yl)-1H-indol-1-yl)acetate (255 mg, 0.84 mmol) and a solution of triethylamine (1.2 mL, 8.6 mmol) in DCM (10 mL) and according to the method described in step 1) of example 28 to give the title compound as a white solid (174 mg, 43%).

$^1$H NMR (400 MHz, CDCl$_3$): δ ppm 7.90-7.96 (m, 1H), 7.16 (dd, J=10.0, 2.2 Hz, 1H), 7.00-7.07 (m, 3H), 6.88 (td, J=8.9, 2.2 Hz, 1H), 4.74 (s, 2H), 4.04-4.07 (m, 2H), 3.74 (s, 3H), 2.66-2.78 (m, 3H), 2.30 (s, 3H), 2.15-2.26 (m, 2H), 1.78-1.81 (m, 2H); and MS-ESI: m/z 481.80 [M+H]$^+$.

Step 2) 2-(5-fluoro-3-(1-((2,4-difluorophenyl)sulfonyl)piperidin-4-yl)-2-methyl-1H-indol-1-yl)acetic acid By using a mixture of methyl 2-(5-fluoro-3-(1-((2,4-difluorophenyl)sulfonyl)piperidin-4-yl)-2-methyl-1H-indol- 1-yl)acetate (170 mg, 0.35 mmol) and lithium hydroxide monohydrate (147 mg, 3.5 mmol) in a mixed solvent of THF (10 mL) and water (5 mL) and according to the method described in step 2) of example 28 to prepare the title compound as a white solid (158 mg, 95%).

$^1$H NMR (600 MHz, d$_6$-DMSO): δ ppm 7.92-7.96 (m, 1H), 7.63-7.67 (m, 1H), 7.37-7.39 (m, 1H), 7.32 (dd, J=8.8, 4.5 Hz, 1H), 7.05 (dd, J=10.3, 1.9 Hz, 1H), 6.86 (td, J=9.2, 2.2 Hz, 1H), 4.90 (s, 2H), 3.85-3.87 (m, 2H), 2.86-2.91 (m, 1H), 2.74 (t, J=12.0 Hz, 2H), 2.23 (s, 3H), 1.94-2.01 (m, 2H);

$^{13}$C NMR (150 MHz, d$_6$-DMSO) δ ppm 170.9, 166.5, 164.8, 160.4, 158.7, 156.3, 135.1, 133.6, 126.6, 122.3, 114.1, 113.1, 110.5, 108.3, 106.9, 103.6, 67.4, 60.2, 46.8, 44.9, 33.1, 31.1, 25.5, 21.2, 14.5, 10.5, 9.3; and MS-ESI: m/z 467.25 [M+H]$^+$.

Example 34: 2-(5-fluoro-3-(1-((4-chloro-2-fluorophenyl)sulfonyl)piperidin-4-yl)-2-methyl-1H-indol-1-yl) acetic acid

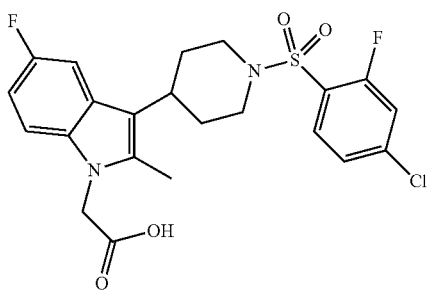 [SMILES: Cc1c(C2CCN(S(=O)(=O)c3ccc(Cl)cc3F)CC2)c2cc(F)ccc2n1CC(=O)O]

Step 1) 1-((4-chloro-2-fluorophenyl)sulfonyl)piperidin-4-one

By using a solution of piperidin-4-one hydrochloride (500 mg, 3.71 mmol), DMF (10 mL), TEA (0.8 mL, 6.0 mmol) and 4-chloro-2-fluorobenzene-1-sulfonyl chloride (700 mg, 3.06 mmol) and according to the method described in step 2) of example 1 to prepare the title compound as a white solid (764 mg, 80%).

$^1$H NMR (400 MHz, CDCl$_3$): δ ppm 7.84 (t, J=8.0 Hz, 1H), 7.25-7.31 (m, 2H), 3.59 (t, J=6.0 Hz, 4H), 2.56 (t, J=6.2 Hz, 4H); and MS-ESI: m/z 292.15 [M+H]$^+$.

Step 2) methyl 2-(5-fluoro-3-(1-((4-chloro-2-fluorophenyl)sulfonyl)piperidin-4-yl)-2-methyl-1H-indol-1-yl) acetate By using methyl 2-(5-fluoro-2-methyl-1H-indol-1-yl)acetate (171 mg, 0.77 mmol), 1-((4-chloro-2-fluorophenyl)sulfonyl)piperidin-4-one (200 mg, 0.69 mmol), DCM (10 mL), triethyl silicane (0.6 mL, 4.0 mmol) and trifluoroacetic acid (0.18 mL, 2.4 mmol) and according to the method described in step 2) of example 24 to prepare the title compound as a white solid (207 mg, 60%).

$^1$H NMR (400 MHz, CDCl$_3$): δ ppm 7.85 (t, J=7.8 Hz, 1H), 7.31 (d, J=8.5 Hz, 2H), 7.18 (dd, J=10.0, 2.3 Hz, 1H), 7.05 (dd, J=8.8, 4.3 Hz, 1H), 6.88 (td, J=9.0, 2.3 Hz, 1H), 4.74 (s, 2H), 4.03-4.07 (m, 2H), 3.74 (s, 3H), 2.66-2.78 (m, 3H), 2.30 (s, 3H), 2.16-2.26 (m, 2H), 1.78-1.82 (m, 2H); and MS-ESI: m/z 497.15 [M+H]$^+$.

Step 3) 2-(5-fluoro-3-(1-((4-chloro-2-fluorophenyl)sulfonyl)piperidin-4-yl)-2-methyl-1H-indol-1-yl) acetic acid By using a mixture of methyl 2-(5-fluoro-3-(1-((4-chloro-2-fluorophenyl)sulfonyl)piperidin-4-yl)-2-methyl-1H-indol-1-yl)acetate (200 mg, 0.41 mmol) and lithium hydroxide monohydrate (96 mg, 2.29 mmol) in a mixed solvent of THF (5 mL) and water (5 mL) and according to the method described in step 3) of example 24 to prepare the title compound as a white solid (193 mg, 99%).

$^1$H NMR (600 MHz, d$_6$-DMSO): δ ppm 7.85 (t, J=7.8 Hz, 2H), 7.58 (d, J=8.5 Hz, 1H), 7.32 (dd, J=10.0, 2.3 Hz, 1H), 7.10 (dd, J=8.8, 4.3 Hz, 1H), 6.86 (td, J=9.0, 2.3 Hz, 1H), 4.90 (s, 2H), 3.84-3.87 (m, 2H), 2.86-2.92 (m, 1H), 2.71-2.76 (m, 2H), 2.23 (s, 3H), 1.95-2.02 (m, 2H), 1.65-1.71 (m, 2H);

$^{13}$C NMR (150 MHz, d$_6$-DMSO) δ ppm 170.9, 159.6, 157.9, 156.3, 139.9, 135.1, 133.6, 132.6, 126.6, 124.5, 118.9, 114.1, 110.5, 108.3, 103.8, 46.8, 44.9, 33.1, 31.1, 10.5; and MS-ESI: m/z 483.10[M+H]$^+$.

Example 35: 2-(5-fluoro-3-(1-((2-chloro-4-fluorophenyl)sulfonyl)piperidin-4-yl)-2-methyl-1H-indol-1-yl) acetic acid

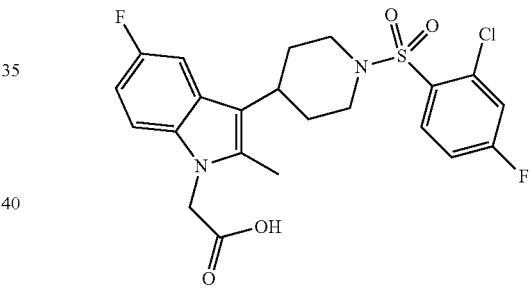

Step 1) 1-((2-chloro-4-fluorophenyl)sulfonyl)piperidin-4-one

By using a solution of piperidin-4-one hydrochloride (500 mg, 3.71 mmol), DMF (10 mL), TEA (0.8 mL, 6.0 mmol) and 2-chloro-4-fluorobenzene-1-sulfonyl chloride (700 mg, 3.06 mmol) and according to the method described in step 2) of example 1 to prepare the title compound as a white solid (636 mg, 67%).

$^1$H NMR (400 MHz, CDCl$_3$): δ ppm 8.12-8.16 (m, 1H), 7.29 (dd, J=8.1, 2.5 Hz, 1H), 7.11-7.16 (m, 1H), 3.65 (t, J=6.1 Hz, 4H), 2.57 (t, J=6.2 Hz, 4H); and MS-ESI: m/z 292.20 [M+H]+.

Step 2) methyl 2-(5-fluoro-3-(1-((2-chloro-4-fluorophenyl)sulfonyl)piperidin-4-yl)-2-methyl-1H-indol-1-yl) acetate By using methyl 2-(5-fluoro-2-methyl-1H-indol-1-yl)acetate (171 mg, 0.77 mmol), 1-((2-chloro-4-fluorophenyl)sulfonyl)piperidin-4-one (200 mg, 0.69 mmol), DCM (10 mL), triethyl silicane (0.6 mL, 4.0 mmol) and TFA (0.18 mL, 2.4 mmol) and according to the method described in step 2) of example 24 to prepare the title compound as a white solid (292 mg, 86%).

$^1$H NMR (400 MHz, CDCl$_3$): δ ppm 8.12-8.16 (m, 1H), 7.34 (dd, J=8.2, 2.5 Hz, 1H), 7.18 (dd, J=10.0, 2.3 Hz, 1H), 7.10-7.15 (m, 1H), 7.05 (dd, J=8.8, 4.3 Hz, 1H), 6.87 (td, J=9.0, 2.4 Hz, 1H), 4.75 (s, 2H), 4.00-4.04 (m, 2H), 3.74 (s, 3H), 2.75-2.92 (m, 3H), 2.31 (s, 3H), 2.13-2.24 (m, 2H), 1.75-1.80 (m, 2H); and MS-ESI: m/z 497.10 [M+H]+.

Step 3) 2-(5-fluoro-3-(1-((2-chloro-4-fluorophenyl)sulfonyl)piperidin-4-yl)-2-methyl-1H-indol-1-yl)acetic acid By using a mixture of methyl 2-(5-fluoro-3-(1-((2-chloro-4-fluorophenyl)sulfonyl)piperidin-4-yl)-2-methyl-1H-indol-1-yl)acetate (285 mg, 0.57 mmol) and lithium hydroxide monohydrate (186 mg, 4.43 mmol) in a mixed solvent of THF (5 mL) and water (5 mL) and according to the method described in step 3) of example 24 to prepare the title compound as a white solid (254 mg, 94%).

$^1$H NMR (600 MHz, d$_6$-DMSO): δ ppm 8.12-8.14 (m, 1H), 7.80 (dd, J=8.2, 2.5 Hz, 1H), 7.48 (dd, J=10.0, 2.3 Hz, 1H), 7.30-7.34 (m, 1H), 7.05 (dd, J=8.8, 4.3 Hz, 1H), 6.86 (td, J=9.0, 2.4 Hz, 1H), 4.90 (s, 2H), 3.86-3.90 (m, 2H), 2.89-2.96 (m, 3H), 2.24 (s, 3H), 1.93-2.01 (m, 2H), 1.65-1.68 (m, 2H);

$^{13}$C NMR (150 MHz, d$_6$-DMSO) δ ppm 170.9, 165.3, 163.6, 157.8, 156.3, 135.1, 134.6, 133.6, 133.3, 126.6, 120.4, 115.7, 114.2, 110.6, 108.3, 103.7, 46.7, 44.9, 33.2, 31.3, 10.6; and MS-ESI: m/z 483.10[M+H]$^+$.

Example 36: 2-(5-fluoro-3-(1-((2,4-dichlorophenyl)sulfonyl)piperidin-4-yl)-2-methyl-1H-indol-1-yl)acetic acid

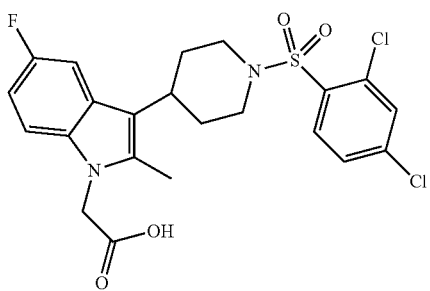 [SMILES: Cc1c(C2CCN(S(=O)(=O)c3ccc(Cl)cc3Cl)CC2)c2cc(F)ccc2n1CC(=O)O]

Step 1)
1-((2,4-dichlorophenyl)sulfonyl)piperidin-4-one

By using a solution of piperidin-4-one hydrochloride (264 mg, 1.95 mmol), DMF (10 mL), TEA (0.8 mL, 6.0 mmol) and 2,4-dichlorobenzene-1-sulfonyl chloride (440 mg, 1.79 mmol) and according to the method described in step 2) of example 1 to prepare the title compound as a white solid (533 mg, 88%).

$^1$H NMR (400 MHz, CDCl$_3$): δ ppm 8.05 (d, J=8.5 Hz, 1H), 7.56 (d, J=2.0 Hz, 1H), 7.41 (dd, J=8.5, 2.0 Hz, 1H), 3.65 (t, J=6.1 Hz, 4H), 2.57 (t, J=6.2 Hz, 4H).

MS-ESI: m/z 308.20 [M+H]$^+$.

Step 2) methyl 2-(5-fluoro-3-(1-((2,4-dichlorophenyl)sulfonyl)piperidin-4-yl)-2-methyl-1H-indol-1-yl)acetate By using methyl 2-(5-fluoro-2-methyl-1H-indol-1-yl)acetate (160 mg, 0.73 mmol), 1-((2,4-dichlorophenyl)sulfonyl)piperidin-4-one (200 mg, 0.65 mmol), DCM (10 mL), triethyl silicane (0.6 mL, 4.0 mmol) and TFA (0.16 mL, 2.2 mmol) and according to the method described in step 2) of example 24 to prepare the title compound as a white solid (314 mg, 94%).

$^1$H NMR (400 MHz, CDCl$_3$): δ ppm 8.05 (d, J=8.5 Hz, 1H), 7.61 (d, J=2.0 Hz, 1H), 7.40 (dd, J=8.5, 2.0 Hz, 1H), 7.19 (dd, J=10.0, 2.3 Hz, 1H), 7.05 (dd, J=8.8, 4.3 Hz, 1H), 6.88 (td, J=9.0, 2.3 Hz, 1H), 4.75 (s, 2H), 4.00-4.04 (m, 2H), 3.74 (s, 3H), 2.70-2.92 (m, 3H), 2.31 (s, 3H), 2.13-2.24 (m, 2H), 1.75-1.80 (m, 2H); and MS-ESI: m/z 513.40 [M+H]$^+$.

Step 3) 2-(5-fluoro-3-(1-((2,4-dichlorophenyl)sulfonyl)piperidin-4-yl)-2-methyl-1H-indol-1-yl)acetic acid By using a mixture of methyl 2-(5-fluoro-3-(1-((2,4-dichlorophenyl)sulfonyl)piperidin-4-yl)-2-methyl-1H-indol-1-yl)acetate (300 mg, 0.58 mmol) and lithium hydroxide monohydrate (146 mg, 3.46 mmol) in a mixed solvent of THF (5 mL) and water (5 mL) and according to the method described in step 2) of example 24 to prepare the title compound as a white solid (287 mg, 98%).

$^1$H NMR (400 MHz, d$_6$-DMSO): δ ppm 8.05 (d, J=8.6 Hz, 1H), 7.97 (d, J=2.0 Hz, 1H), 7.70 (dd, J=8.6, 2.0 Hz, 1H), 7.30 (dd, J=8.8, 4.5 Hz, 1H), 7.08 (dd, J=10.4, 2.1 Hz, 1H), 6.84 (td, J=9.1, 2.4 Hz, 1H), 4.82 (s, 2H), 3.86-3.89 (m, 2H), 2.89-3.00 (m, 3H), 2.24 (s, 3H), 1.93-2.01 (m, 2H), 1.65-1.69 (m, 2H);

$^{13}$C NMR (100 MHz, d$_6$-DMSO) δ ppm 170.9, 158.1, 155.8, 138.9, 135.6, 133.6, 132.6, 128.5, 126.6, 114.0, 110.5, 108.2, 107.9, 103.6, 46.7, 45.4, 33.2, 31.4, 10.6; and MS-ESI: m/z 499.30 [M+H]+.

Example 37: 2-(5-fluoro-3-(1-((4-hydroxyphenyl)sulfonyl)piperidin-4-yl)-2-methyl-1H-indol-1-yl)acetic acid

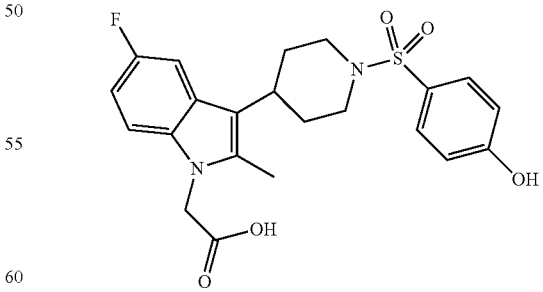

Step 1)
1-((4-hydroxyphenyl)sulfonyl)piperidin-4-one

To a solution of 4-hydroxybenzenesulfonic acid (1.0 g, 5.7 mmol) in DCM (10 mL) was added thionyl chloride (0.62 mL, 8.6 mmol) at rt. After stirring for 30 min, DMF (5 mL) was added to the mixture at 0° C. The mixture was stirred at rt for 1 h and concentrated. To a solution of piperidin-4-one hydrochloride (1.2 g, 8.6 mmol) and triethylamine (7.2 mL, 51.6 mmol) in anhydrous DMF (20 mL) was added the above residue at 0° C. The resulting mixture was stirred at rt for 3 h and concentrated. The residue was diluted with water (15 mL) and extracted with EtOAc (10 mL×3). The combined organic layers were dried over anhydrous $Na_2SO_4$ and concentrated. The residue was purified by silica gel chromatography eluted with PE/EtOAc (V/V)=3/1 to give the title compound as a white solid (190 mg, 14%).

$^1$H NMR (400 MHz, $d_6$-DMSO): δ ppm 7.62 (d, J=8.8 Hz, 2H), 6.95 (d, J=8.7 Hz, 2H), 3.24 (t, J=6.0 Hz, 4H), 2.41 (t, J=6.2 Hz, 4H); and MS-ESI: m/z 256.25 [M+H]$^+$.

Step 2) methyl 2-(5-fluoro-3-(1-((4-hydroxyphenyl)sulfonyl)piperidin-4-yl)-2-methyl-1H-indol-1-yl)acetate By using methyl 2-(5-fluoro-2-methyl-1H-indol-1-yl)acetate (185 mg, 0.84 mmol), 1-((4-hydroxyphenyl)sulfonyl)piperidin-4-one (190 mg, 0.74 mmol), DCM (10 mL), triethyl silicane (0.65 mL, 4.1 mmol) and TFA (0.18 mL, 2.4 mmol) and according to the method described in step 2) of example 24 to prepare the title compound as a white solid (314 mg, 92%).

$^1$H NMR (400 MHz, CDCl$_3$): δ ppm 7.73 (d, J=8.7 Hz, 2H), 7.15 (dd, J=10.1, 2.3 Hz, 1H), 7.04 (dd, J=8.8, 4.3 Hz, 1H), 6.98 (d, J=8.7 Hz, 2H), 6.87 (td, J=9.0, 2.3 Hz, 1H), 5.84 (br.s, 1H), 4.73 (s, 2H), 3.96-3.99 (m, 2H), 3.76 (s, 3H), 2.62-2.68 (m, 1H), 2.41-2.46 (m, 2H), 2.27 (s, 3H), 2.14-2.24 (m, 2H), 1.73-1.76 (m, 2H), 1.42 (d, J=6.0 Hz, 6H); and MS-ESI: m/z 461.40 [M+H]$^+$.

Step 3) 2-(5-fluoro-3-(1-((4-hydroxyphenyl)sulfonyl)piperidin-4-yl)-2-methyl-1H-indol-1-yl)acetic acid By using a mixture of methyl 2-(5-fluoro-3-(1-((4-hydroxyphenyl)sulfonyl)piperidin-4-yl)-2-methyl-1H-indol-1-yl)acetate (280 mg, 0.3 mmol) and lithium hydroxide monohydrate (128 mg, 3.04 mmol) in a mixed solvent of THF (5 mL) and water (5 mL) and according to the method described in step 3) of example 24 to prepare the title compound as a white solid (263 mg, 97%).

$^1$H NMR (400 MHz, $d_6$-DMSO): δ ppm 10.53 (br.s, 1H), 7.63 (d, J=8.6 Hz, 2H), 7.31 (dd, J=8.8, 4.5 Hz, 1H), 7.19 (dd, J=10.4, 1.9 Hz, 1H), 6.99 (d, J=8.6 Hz, 2H), 6.85 (td, J=12.6, 5.5 Hz, 1H), 4.89 (s, 2H), 3.74-3.78 (m, 2H), 2.73-2.79 (m, 1H), 2.34-2.40 (m, 2H), 2.22 (s, 3H), 1.96-2.06 (m, 2H), 1.64-1.67 (m, 2H);

$^{13}$C NMR (150 MHz, $d_6$-DMSO) δ ppm 170.9, 162.1, 157.8, 156.3, 135.1, 133.5, 130.3, 126.75, 126.6, 116.2, 114.2, 110.5, 108.3, 103.9, 60.2, 47.3, 44.8, 33.2, 31.1, 21.2, 14.5, 10.6; and MS-ESI: m/z 447.20 [M+H]$^+$.

Example 38: 2-(5-fluoro-3-(1-((4-isopropoxyphenyl)sulfonyl)piperidin-4-yl)-2-methyl-1H-indol-1-yl)acetic acid

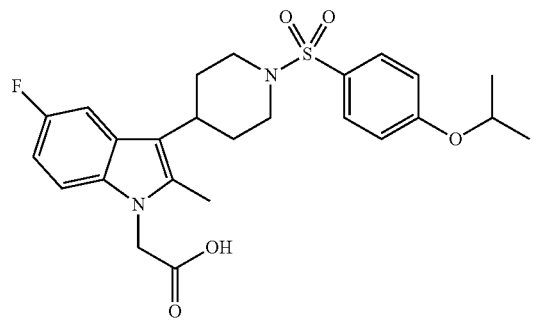 [SMILES: Cc1c(C2CCN(S(=O)(=O)c3ccc(OC(C)C)cc3)CC2)c2cc(F)ccc2n1CC(=O)O]

Step 1) 4-isopropoxybenzenesulfonic acid

A mixture of 4-hydroxybenzenesulfonic acid (2.0 g, 12 mmol), sodium hydroxide (960 mg, 24 mmol), 2-bromopropane (3.0 g, 24 mmol) and anhydrous DMF (15 mL) in a 50 mL of sealing tube was stirred at 80° C. for 24 h and then concentrated. The residue was diluted with water (25 mL) and extracted with EtOAc (10 mL×3) to remove impurities. The water phase was adjusting with hydrochloric acid (1.0 mol/L) to pH 6 and concentrated to give the title compound as a white solid (1.8 g, 68%).

$^1$H NMR (400 MHz, D$_2$O): δ ppm 7.64 (d, J=8.6 Hz, 2H), 6.92 (d, J=8.6 Hz, 2H), 4.65-4.74 (m, 1H), 1.29 (d, J=6.7 Hz, 3H), 1.24 (d, J=6.4 Hz, 3H); and MS-ESI: m/z 215.20 [M−H]$^−$.

Step 2) 1-((4-isopropoxyphenyl)sulfonyl)piperidin-4-one

By using 4-isopropoxybenzenesulfonic acid (1.0 g, 4.6 mmol), DCM (10 mL), thionyl chloride (0.5 mL, 7.0 mmol), DMF (5 mL), piperidin-4-one hydrochloride (932 mg, 6.9 mmol) and a solution of triethylamine (4.0 mL, 28 mmol) in anhydrous DMF (20 mL) and according to the method described in step 1) of example 37 to give the title compound as a white solid (327 mg, 25%).

$^1$H NMR (400 MHz, CDCl$_3$): δ ppm 7.70 (d, J=8.9 Hz, 2H), 6.96 (d, J=8.9 Hz, 2H), 4.60-4.66 (m, 1H), 3.38 (t, J=6.2 Hz, 4H), 2.53 (t, J=6.2 Hz, 4H), 1.37 (d, J=6.1 Hz, 6H); and MS-ESI: m/z 298.30 [M+H]$^+$.

Step 3) methyl 2-(5-fluoro-3-(1-((4-isopropoxyphenyl)sulfonyl)piperidin-4-yl)-2-methyl-1H-indol-1-yl)acetate By using methyl 2-(5-fluoro-2-methyl-1H-indol-1-yl)acetate (110 mg, 0.48 mmol), 1-((4-isopropoxyphenyl)sulfonyl)piperidin-4-one (130 mg, 0.44 mmol), DCM (10 mL), triethyl silicane (0.4 mL, 3.0 mmol) and TFA (0.1 mL, 1.0 mmol) and according to the method described in step 2) of example 24 to prepare the title compound as a white solid (160 mg, 73%).

$^1$H NMR (400 MHz, CDCl$_3$): δ ppm 7.76 (d, J=8.8 Hz, 2H), 7.23 (dd, J=10.0, 2.3 Hz, 1H), 7.05-7.08 (m, 1H), 7.02 (d, J=8.9 Hz, 2H), 6.89 (td, J=9.0, 2.4 Hz, 1H), 4.76 (s, 2H), 4.65-4.71 (m, 1H), 3.97-4.01 (m, 2H), 3.76 (s, 3H), 2.64-

2.70 (m, 1H), 2.39-2.45 (m, 2H), 2.29 (s, 3H), 2.20-2.27 (m, 2H), 1.75-1.81 (m, 2H), 1.42 (d, J=6.0 Hz, 6H); and
MS-ESI: m/z 503.505 [M+H]$^+$.

Step 4) 2-(5-fluoro-3-(1-((4-isopropoxyphenyl)sulfonyl)piperidin-4-yl)-2-methyl-1H-indol-1-yl)acetic acid By using a mixture of methyl 2-(5-fluoro-3-(1-((4-isopropoxyphenyl)sulfonyl)piperidin-4-yl)-2-methyl-1H-indol-1-yl)acetate (150 mg, 0.3 mmol) and lithium hydroxide monohydrate (63 mg, 1.5 mmol) in a mixed solvent of THF (5 mL) and water (5 mL) and according to the method described in step 3) of example 24 to prepare the title compound as a white solid (142 mg, 97%).

$^1$H NMR (400 MHz, d$_6$-DMSO): δ ppm 7.71 (d, J=8.8 Hz, 2H), 7.31 (dd, J=8.8, 4.5 Hz, 1H), 7.11 (dd, J=9.0, 4.3 Hz, 1H), 7.16 (d, J=9.0 Hz, 2H), 6.89 (td, J=9.2, 2.3 Hz, 1H), 4.89 (s, 2H), 4.73-4.79 (m, 1H), 3.77-3.81 (m, 2H), 2.75-2.81 (m, 1H), 2.39-2.45 (m, 2H), 2.22 (s, 3H), 1.96-2.04 (m, 2H), 1.64-1.68 (m, 2H), 1.31 (d, J=6.0 Hz, 6H);

$^{13}$C NMR (100 MHz, d$_6$-DMSO) δ 170.8, 161.5, 155.9, 135.1, 133.6, 130.1, 127.7, 126.7, 116.0, 114.2, 110.1, 108.3, 103.9, 70.4, 47.2, 44.9, 33.3, 31.1, 22.1, 10.6; and
MS-ESI: m/z 489.45 [M+H]$^+$.

Example 39: 2-(5-fluoro-3-(1-((2-fluorophenyl)sulfonyl)piperidin-4-yl)-2-methyl-1H-indol-1-yl)acetic acid

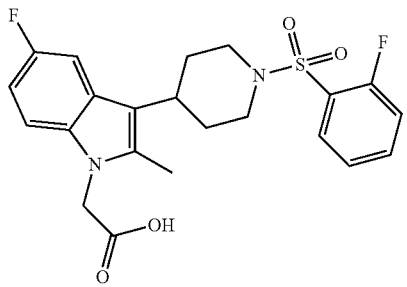 [SMILES: Cc1c(C2CCN(S(=O)(=O)c3ccccc3F)CC2)c2cc(F)ccc2n1CC(=O)O]

Step 1) 1-((2-fluorophenyl)sulfonyl)piperidin-4-one

By using a solution of piperidin-4-one hydrochloride (500 mg, 3.68 mmol), DMF (10 mL), TEA (1.4 mL, 10.0 mmol) and 2-fluorobenzene-1-sulfonyl chloride (580 mg, 2.98 mmol) and according to the method described in step 2) of example 1 to prepare the title compound as a white solid (693 mg, 83%).

$^1$H NMR (400 MHz, CDCl$_3$): δ ppm 7.88-7.92 (m, 1H), 7.58-7.63 (m, 1H), 7.31 (t, J=7.7 Hz, 1H), 7.22 (t, J=9.0 Hz, 1H), 3.59 (t, J=6.1 Hz, 4H), 2.56 (t, J=6.2 Hz, 4H); and
MS-ESI: m/z 258.25 [M+H]$^+$.

Step 2) methyl 2-(5-fluoro-3-(1-((2-fluorophenyl) sulfonyl)piperidin-4-yl)-2-methyl-1H-indol-1-yl) acetate By using methyl 2-(5-fluoro-2-methyl-1H-indol-1-yl)acetate (180 mg, 0.81 mmol), 1-((2-fluorophenyl)sulfonyl) piperidin-4-one (200 mg, 0.78 mmol), DCM (10 mL), triethyl silicane (0.64 mL, 4.0 mmol) and TFA (0.18 mL, 2.4 mmol) and according to the method described in step 2) of example 24 to prepare the title compound as a white solid (294 mg, 84%).

$^1$H NMR (400 MHz, CDCl$_3$): δ ppm 7.90-7.94 (m, 1H), 7.59-7.63 (m, 1H), 7.26-7.34 (m, 2H), 7.12 (dd, J=10.0, 2.3 Hz, 1H), 7.05 (dd, J=8.8, 4.3 Hz, 1H), 6.87 (td, J=9.0, 2.4 Hz, 1H), 4.73 (s, 2H), 4.07-4.10 (m, 2H), 3.74 (s, 3H), 2.69-2.75 (m, 3H), 2.29 (s, 3H), 2.13-2.25 (m, 2H), 1.75-1.80 (m, 2H); and
MS-ESI: m/z 463.35 [M+H]$^+$.

Step 3) 2-(5-fluoro-3-(1-((2-fluorophenyl)sulfonyl) piperidin-4-yl)-2-methyl-1H-indol-1-yl)acetic acid By using a mixture of methyl 2-(5-fluoro-3-(1-(2-fluorophenyl)sulfonyl)piperidin-4-yl)-2-methyl-1H-indol-1-yl)acetate (290 mg, 0.62 mmol) and lithium hydroxide monohydrate (133 mg, 3.14 mmol) in a mixed solvent of THF (5 mL) and water (5 mL) and according to the method described in step 3) of example 24 to prepare the title compound as a white solid (276 mg, 98%).

$^1$H NMR (400 MHz, d$_6$-DMSO): δ ppm 7.78-7.89 (m, 2H), 7.52-7.57 (m, 1H), 7.48 (t, J=7.6 Hz, 1H), 7.32 (dd, J=8.8, 4.5 Hz, 1H), 7.07 (dd, J=10.3, 2.0 Hz, 1H), 6.85 (td, J=9.1, 2.3 Hz, 1H), 4.90 (s, 2H), 3.86-3.90 (m, 2H), 2.85-2.91 (m, 1H), 2.70-2.76 (m, 2H), 2.23 (s, 3H), 1.93-2.03 (m, 2H), 1.65-1.69 (m, 2H);

$^{13}$C NMR (150 MHz, d$_6$-DMSO) δ ppm 170.9, 159.5, 157.9, 156.3, 136.4, 135.1, 133.6, 131.4, 126.6, 125.7, 118.2, 114.2, 110.5, 108.3, 103.8, 46.8, 44.9, 33.1, 31.1, 10.6; and
MS-ESI: m/z 449.40 [M+H]$^+$.

Example 40: 2-(5-fluoro-3-(1-((4-fluorophenyl)sulfonyl)piperidin-3-yl)-2-methyl-1H-indol-1-yl)acetic acid

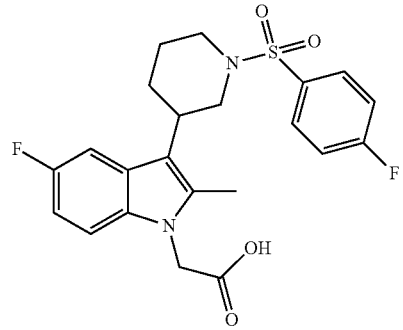 [SMILES: Cc1c(C2CCCN(S(=O)(=O)c3ccc(F)cc3)C2)c2cc(F)ccc2n1CC(=O)O]

Step 1) piperidin-3-one hydrochloride

To a solution of tert-butyl 3-oxopiperidine-1-carboxylate (2.5 g, 13 mmol) in DCM (5 mL) was added a HCl solution in EtOAc (4 M, 10 mL). The mixture was stirred at rt for 1.5 h and concentrated to give the title compound as a yellow solid (1.8 g, 100%).
MS-ESI: m/z 100.25 [M+H—HCl]$^+$.

Step 2) 1-((4-fluorophenyl)sulfonyl)piperidin-3-one

By using a solution of piperidin-3-one hydrochloride (800 mg, 5.9 mmol), DMF (5 mL), TEA (2.6 mL, 19.0 mmol) and 4-fluorobenzene-1-sulfonyl chloride (870 mg, 4.5 mmol) and according to the method described in step 2) of example 1 to prepare the title compound as a white solid (514 mg, 33%).

$^1$H NMR (400 MHz, CDCl$_3$): δ ppm 7.78-7.82 (m, 2H), 7.21-7.26 (m, 2H), 3.62 (s, 2H), 3.31 (t, J=6.9 Hz, 2H), 2.39 (t, J=6.9 Hz, 2H), 2.00-2.06 (m, 2H); and MS-ESI: m/z 258.25 [M+H]$^+$.

Step 3) methyl 2-(5-fluoro-3-(1-((4-fluorophenyl)sulfonyl)piperidin-3-yl)-2-methyl-1H-indol-1-yl)acetate By using methyl 2-(5-fluoro-2-methyl-1H-indol-1-yl)acetate (96 mg, 0.43 mmol), 1-((4-fluorophenyl)sulfonyl)piperidin-3-one (100 mg, 0.39 mmol), DCM (5 mL), triethyl silicane (0.4 mL, 3.0 mmol) and trifluoroacetic acid (0.1 mL, 1.0 mmol) and according to the method described in step 2) of example 24 to prepare the title compound as a white solid (83 mg, 46%).

$^1$H NMR (400 MHz, CDCl$_3$): δ ppm 7.74-7.78 (m, 2H), 7.18-7.26 (m, 2H), 7.06-7.09 (m, 2H), 6.86 (td, J=9.0, 2.4 Hz, 1H), 4.76 (s, 2H), 3.93-3.96 (m, 1H), 3.79-3.83 (m, 1H), 3.76 (s, 3H), 3.06-3.14 (m, 1H), 2.62 (t, J=11.6 Hz, 1H), 2.34 (s, 3H), 2.30-2.37 (m, 1H), 1.86-1.91 (m, 4H); and MS-ESI: m/z 463.20 [M+H]$^+$.

Step 4) 2-(5-fluoro-3-(1-((4-fluorophenyl)sulfonyl)piperidin-3-yl)-2-methyl-1H-indol-1-yl)acetic acid By using a mixture of methyl 2-(5-fluoro-3-(1-((4-fluorophenyl)sulfonyl)piperidin-3-yl)-2-methyl-1H-indol-1-yl)acetate (80 mg, 0.17 mmol) and lithium hydroxide monohydrate (57 mg, 1.36 mmol) in a mixed solvent of THF (5 mL) and water (5 mL) and according to the method described in step 3) of example 24 to prepare the title compound as a white solid (73 mg, 94%).

$^1$H NMR (600 MHz, d$_6$-DMSO): δ ppm 7.82-7.84 (m, 2H), 7.45-7.48 (m, 2H), 7.33-7.35 (m, 1H), 7.28-7.30 (m, 1H), 6.85 (td, J=9.0, 2.4 Hz, 1H), 4.93 (s, 2H), 3.74-3.76 (m, 1H), 3.53-3.55 (m, 1H), 3.00-3.04 (m, 1H), 2.66 (t, J=11.3 Hz, 1H), 2.50-2.55 (m, 1H), 2.28 (s, 3H), 1.92-1.92 (m, 1H), 1.81-1.84 (m, 1H), 1.65-1.70 (m, 2H).

$^{13}$C NMR (150 MHz, d$_6$-DMSO) δ 170.92, 165.8, 164.1, 157.9, 156.4, 135.9, 133.6, 130.9, 126.5, 117.13, 116.9, 111.9, 110.6, 108.4, 104.4, 67.4, 50.7, 46.1, 44.9, 34.9, 30.8, 29.1, 25.6, 10.6; and MS-ESI: m/z 449.20 [M+H]$^+$.

Example 41: 2-(5-fluoro-2-methyl-3-(1-((4-(trifluoromethyl)phenyl)sulfonyl)piperidin-4-yl)-1H-indol-1-yl)acetic acid Step 1) 1-((4-(trifluoromethyl)phenyl)sulfonyl)piperidin-4-one By using a solution of piperidin-3-one hydrochloride (500 mg, 3.70 mmol), DMF (5 mL), TEA (1.4 mL, 10.0 mmol) and 4-(trifluoromethyl)benzene-1-sulfonyl chloride (724 mg, 2.96 mmol) and according to the method described in step 2) of example 1 to prepare the title compound as a white solid (753 mg, 75%).

$^1$H NMR (400 MHz, CDCl$_3$): δ ppm 7.94 (d, J=8.2 Hz, 2H), 7.83 (d, J=8.4 Hz, 2H), 3.45 (t, J=6.9 Hz, 4H), 2.57 (t, J=6.9 Hz, 4H); and MS-ESI: m/z 308.30 [M+H]$^+$.

Step 2) methyl 2-(5-fluoro-2-methyl-3-(1-((4-(trifluoromethyl)phenyl)sulfonyl)piperidin-4-yl)-1H-indol-1-yl)acetate By using methyl 2-(5-fluoro-2-methyl-1H-indol-1-yl)acetate (160 mg, 0.72 mmol), 1-((4-(trifluoromethyl)phenyl)sulfonyl)piperidin-4-one (200 mg, 0.65 mmol), DCM (10 mL), triethyl silicane (0.6 mL, 4.0 mmol) and TFA (0.16 mL, 2.2 mmol) and according to the method described in step 2) of example 24 to prepare the title compound as a white solid (258 mg, 77%).

$^1$H NMR (400 MHz, CDCl$_3$): δ ppm 7.96 (d, J=8.2 Hz, 2H), 7.85 (d, J=8.2 Hz, 2H), 7.20 (dd, J=10.0, 2.3 Hz, 1H), 7.05 (dd, J=8.8, 4.3 Hz, 1H), 6.88 (td, J=9.0, 2.3 Hz, 1H), 4.74 (s, 2H), 4.01-4.04 (m, 2H), 3.74 (s, 3H), 2.64-2.70 (m, 1H), 2.41-2.47 (m, 2H), 2.27 (s, 3H), 2.19-2.30 (m, 2H), 1.79-1.82 (m, 2H); and MS-ESI: m/z 513.20 [M+H]$^+$.

Step 3) 2-(5-fluoro-2-methyl-3-(1-((4-(trifluoromethyl)phenyl)sulfonyl)piperidin-4-yl)-1H-indol-1-yl)acetic acid By using a mixture of methyl 2-(5-fluoro-2-methyl-3-(1-((4-(trifluoromethyl)phenyl)sulfonyl)piperidin-4-yl)-1H-indol-1-yl)acetate (250 mg, 0.49 mmol) and lithium hydroxide monohydrate (106 mg, 2.53 mmol) in a mixed solvent of THF (5 mL) and water (5 mL) and according to the method described in step 3) of example 24 to prepare the title compound as a white solid (230 mg, 94%).

$^1$H NMR (600 MHz, d$_6$-DMSO): 8.06-8.09 (m, 4H), 7.31-7.33 (m, 1H), 7.10 (d, J=10.2 Hz, 1H), 6.85 (td, J=9.0, 2.0 Hz, 1H), 4.89 (s, 2H), 3.87-3.89 (m, 2H), 2.81-2.85 (m, 1H), 2.53-2.57 (m, 2H), 2.21 (s, 3H), 1.96-2.02 (m, 2H), 1.65-1.67 (m, 2H);

$^{13}$C NMR (150 MHz, d$_6$-DMSO) δ ppm 170.9, 157.8, 156.3, 140.8, 135.1, 133.5, 133.3, 128.9, 127.1, 126.6, 124.8, 123.0, 114.1, 110.5, 108.3, 103.8, 67.4, 47.2, 44.8, 33.0, 31.0, 25.5, 10.5; and MS-ESI: m/z 499.15 [M+H]$^+$.

Example 42: 2-(5-fluoro-2-methyl-3-(1-(naphthalen-1-ylsulfonyl)piperidin-4-yl)-1H-indol-1-yl)acetic acid

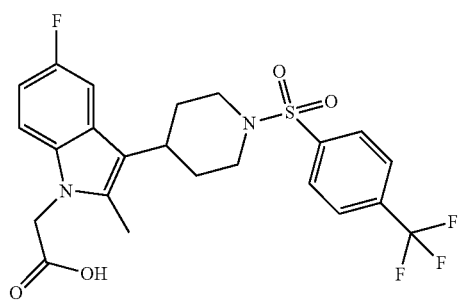 [SMILES: Cc1c(C2CCN(S(=O)(=O)c3ccc(C(F)(F)F)cc3)CC2)c2cc(F)ccc2n1CC(=O)O]

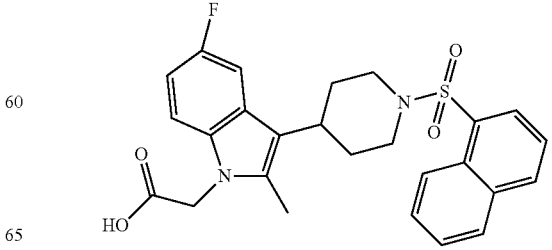

Step 1) methyl 2-(5-fluoro-2-methyl-3-(1-(naphthalen-1-ylsulfonyl)piperidin-4-yl)-1H-indol-1-yl)acetate To a solution of methyl 2-(5-fluoro-2-methyl-3-(piperidin-4-yl)-1H-indol-1-yl)acetate (250 mg, 0.82 mmol) in DCM (10 mL) was added TEA (0.69 mL, 4.93 mmol) at 20° C., and then a solution of naphthalene-1-sulfonyl chloride (745 mg, 3.29 mmol) in DCM (6 mL) was added at 0° C. The mixture was stirred for 3 h at rt and washed with water (10 mL×3). The organic layer was dried over anhydrous $Na_2SO_4$ and concentrated. The residue was purified by silica gel chromatography eluted with a gradient of PE/EtOAc ((V/V)=3/1, 2/1) to give a white solid product (307 mg, 75%).

$^1$H NMR (400 MHz, $CDCl_3$): δ ppm 8.87 (d, J=8.6 Hz, 1H), 8.30 (d, J=7.3 Hz, 1H), 8.12 (d, J=8.2 Hz, 1H), 7.99 (d, J=8.1 Hz, 1H), 7.74-7.70 (m, 1H), 7.64 (t, J=7.5 Hz, 1H), 7.59 (t, J=7.8 Hz, 1H), 7.01 (dd, $J_1$=8.8 Hz, $J_2$=4.3 Hz, 1H), 6.92 (dd, $J_1$=10.0 Hz, $J_2$=2.3 Hz, 1H), 6.84 (td, $J_1$=9.0 Hz, $J_2$=2.4 Hz, 1H), 4.71 (s, 2H), 4.08-4.05 (m, 2H), 3.72 (s, 3H), 2.76-2.65 (m, 3H), 2.23 (s, 3H), 2.11-2.01 (m, 2H), 1.71-1.68 (m, 2H); and MS-ESI: m/z 495.3 [M+H]$^+$.

Step 2) 2-(5-fluoro-2-methyl-3-(1-(naphthalen-1-ylsulfonyl)piperidin-4-yl)-1H-indol-1-yl)acetic acid To a solution of methyl 2-(5-fluoro-2-methyl-3-(1-(naphthalen-1-ylsulfonyl)piperidin-4-yl)-1H-indol-1-yl)acetate (292 mg, 0.59 mmol) in a mixed solvent of THF (10 mL) and water (5 mL) was added lithium hydroxide monohydrate (124 mg, 2.95 mmol). The mixture was stirred for 1.5 h at 45° C. After adjusting to pH 1 with hydrochloric acid (1 N), the resulting mixture was extracted with EtOAc (10 mL×2) and the combined organic layers were concentrated to give a white solid product (260 mg, 91%).

$^1$H NMR (600 MHz, $CD_3OD$): δ ppm 8.84 (d, J=8.5 Hz, 1H), 8.30 (d, J=7.0 Hz, 1H), 8.23 (d, J=8.0 Hz, 1H), 8.07 (d, J=8.0 Hz, 1H), 7.75 (t, J=7.4 Hz, 1H), 7.69-7.65 (m, 2H), 7.13-7.11 (m, 1H), 6.82-6.77 (m, 2H), 4.81 (s, 2H), 4.03-4.01 (m, 2H), 2.85-2.78 (m, 3H), 2.21 (s, 3H), 1.99-1.93 (m, 2H), 1.62-1.60 (m, 2H);

$^{13}$C NMR (150 MHz, $CD_3OD$): δ ppm 171.1, 158.1, 134.7, 133.8, 130.1, 129.0, 124.0, 114.2, 108.9, 107.9, 46.1, 43.9, 33.8, 30.7, 8.9; and MS-ESI: m/z 481.3 [M+H]+.

Example 43: 2-(5-fluoro-2-methyl-3-(4-(picolinamido)cyclohexyl)-1H-indol-1-yl)acetic acid hydrochloride (43a) and 2-(5-fluoro-2-methyl-3-(4-(picolinamido)cyclohexyl)-1H-indol-1-yl)acetic acid hydrochloride (43b)

Step 1) methyl 2-(5-fluoro-2-methyl-3-(4-(picolinamido)cyclohexyl)-1H-indol-1-yl)acetate By using methyl 2-(3-(4-aminocyclohexyl)-5-fluoro-2-methyl-1H-indol-1-yl) acetate (280 mg, 0.88 mmol), picolinic acid (130 mg, 1.05 mmol), EDCI (253 mg, 1.32 mmol), HOAT (300 mg, 2.20 mmol), DCM (15 mL) and DIPEA (0.61 mL, 3.52 mmol) and according to the method described in step 4) of example 4 to prepare the title compound as a white solid (302 mg, 79%).

$^1$H NMR (400 MHz, $CDCl_3$): δ ppm 8.84 (d, J=7.6 Hz, 1H), 8.75 (d, J=4.3 Hz, 1H), 8.23 (d, J=7.8 Hz, 1H), 7.88 (td, $J_1$=7.7 Hz, $J_2$=1.6 Hz, 1H), 7.55 (dd, $J_1$=10.4 Hz, $J_2$=2.3 Hz, 1H), 7.50-7.46 (m, 1H), 7.07 (dd, $J_1$=8.9 Hz, $J_2$=4.4 Hz, 1H), 6.91-6.86 (m, 1H), 4.76 (s, 2H), 4.46-4.44 (m, 1H), 3.75 (s, 3H), 2.89-2.84 (m, 1H), 2.35 (s, 3H), 2.26-2.22 (m, 2H), 2.13-2.10 (m, 2H), 1.82-1.72 (m, 4H); and MS-ESI: m/z 424.3 [M+H]$^+$.

Step 2) 2-(5-fluoro-2-methyl-3-(4-(picolinamido)cyclohexyl)-1H-indol-1-yl)acetic acid hydrochloride By using a solution of methyl 2-(5-fluoro-2-methyl-3-(4-(picolinamido)cyclohexyl)-1H-indol-1-yl)acetate (292 mg, 0.69 mmol) in a mixed solvent of THF (10 mL) and water (5 mL), lithium hydroxide monohydrate (145 mg, 3.45 mmol) and according to the method described in step 5) of example 4 to obtain a crude product as a white solid (268 mg, 87%). The crude product was separated to give compound (43a) as a pompadour solid (50 mg, HPLC: 94.01%) and compound (43b) as a light yellow solid (150 mg, HPLC: 96.42%).

Compound (43a): $^1$H NMR (600 MHz, $CD_3OD$): δ ppm 8.56-8.55 (m, 1H), 8.15 (d, J=7.5 Hz, 1H), 7.87 (t, J=7.4 Hz, 1H), 7.46-7.44 (m, 1H), 7.29 (d, J=9.7 Hz, 1H), 7.06 (dd, $J_1$=8.7 Hz, $J_2$=4.2 Hz, 1H), 6.84-6.81 (m, 1H), 4.72 (s, 2H), 4.08-4.06 (m, 1H), 2.79-2.74 (m, 1H), 2.33 (s, 3H), 2.20-2.19 (m, 2H), 2.11-2.05 (m, 2H), 1.88-1.86 (m, 2H), 1.54-1.48 (m, 2H);

$^{13}$C NMR (150 MHz, $CD_3OD$): δ ppm 171.0, 164.0, 158.2, 156.7, 149.6, 148.1, 137.7, 133.5, 133.3, 127.0, 126.4, 122.2, 115.9, 108.9, 108.5, 108.3, 104.6, 44.6, 35.8, 33.5, 31.3, 29.6, 10.3; and MS-ESI: m/z 410.9 [M+H—HCl]$^+$.

Compound (43b): $^1$H NMR (400 MHz, $d_6$-DMSO): δ ppm 8.75 (d, J=4.3 Hz, 1H), 8.72 (d, J=7.3 Hz, 1H), 8.11-8.04 (m, 2H), 7.69 (t, J=5.5 Hz, 1H), 7.46-7.43 (m, 1H), 7.34 (dd, 8.8 Hz, $J_2$=4.5 Hz, 1H), 6.90-6.85 (m, 1H), 4.91 (s, 2H), 4.24-4.21 (m, 1H), 2.91-2.85 (m, 1H), 2.30 (s, 3H), 2.15-2.08 (m, 2H), 2.03-1.99 (m, 2H), 1.80-1.74 (m, 2H), 1.61-1.58 (m, 2H);

$^{13}$C NMR (100 MHz, $d_6$-DMSO): δ ppm 170.9, 163.3, 158.2, 155.9, 150.5, 148.9, 138.6, 134.6, 133.8, 127.2, 122.1, 116.1, 110.5, 108.2, 108.0, 104.2, 45.0, 44.0, 34.9, 30.0, 26.9, 10.5; and MS-ESI: m/z 410.9 [M+H—HCl]$^+$.

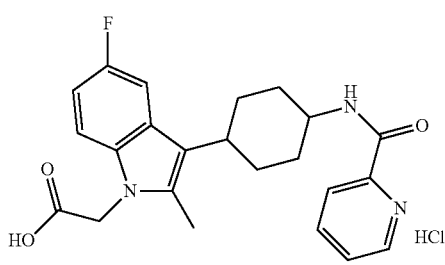 [SMILES: Cc1c(C2CCC(NC(=O)c3ccccn3)CC2)c2cc(F)ccc2n1CC(=O)O ; Cl]

Example 44: 2-(5-fluoro-3-(4-(4-fluoropicolinamido)cyclohexyl)-2-methyl-1H-indol-1-yl)acetic acid hydrochloride

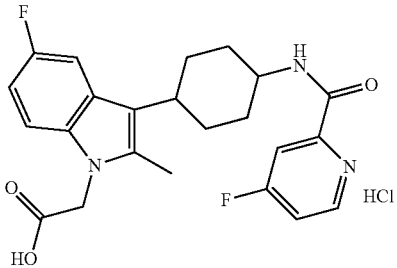 [SMILES: Cc1c(C2CCC(NC(=O)c3cc(F)ccn3)CC2)c2cc(F)ccc2n1CC(=O)O ; Cl]

Step 1) methyl 2-(5-fluoro-3-(4-(4-fluoropicolinamido)cyclohexyl)-2-methyl-1H-indol-1-yl)acetate By using methyl 2-(3-(4-aminocyclohexyl)-5-fluoro-2-methyl-1H-indol-1-yl) acetate (277 mg, 0.87 mmol), 4-fluoropicolinic acid (147 mg, 1.04 mmol), EDCI (250 mg, 1.31 mmol), HOAT (296 mg, 2.18 mmol), DCM (15 mL) and DIPEA (0.61 mL, 3.48 mmol) and according to the method described in step 1) of example 4 to prepare the title compound as a white solid (130 mg, 33%).

$^1$H NMR (600 MHz, CDCl$_3$): δ ppm 8.76 (d, J=7.7 Hz, 1H), 8.74-8.72 (m, 1H), 7.96 (dd, J$_1$=9.2 Hz, J$_2$=2.5 Hz, 1H), 7.53 (dd, J$_1$=10.4 Hz, J$_2$=2.4 Hz, 1H), 7.22-7.20 (m, 1H), 7.07 (dd, J$_1$=8.8 Hz, J$_2$=4.4 Hz, 1H), 6.88 (td, J$_1$=9.0 Hz, J$_2$=2.4 Hz, 1H), 4.77 (s, 2H), 4.45-4.43 (m, 1H), 3.75 (s, 3H), 2.87-2.82 (m, 1H), 2.35 (s, 3H), 2.24-2.17 (m, 2H), 2.11-2.09 (m, 2H), 1.82-1.73 (m, 4H); and MS-ESI: m/z 442.3 [M+H]$^+$.

Step 2) 2-(5-fluoro-3-(4-(4-fluoropicolinamido)cyclohexyl)-2-methyl-1H-indol-1-yl)acetic acid hydrochloride By using a solution of methyl 2-(5-fluoro-3-(4-(4-fluoropicolinamido)cyclohexyl)-2-methyl-1H-indol-1-yl)acetate (120 mg, 0.27 mmol) in a mixed solvent of THF (8 mL) and water (4 mL), lithium hydroxide monohydrate (57 mg, 1.36 mmol) and according to the method described in step 5) of example 4 to obtain the product as a white solid (89 mg, 70%).

$^1$H NMR (600 MHz, d$_6$-DMSO): δ ppm 8.76-8.74 (m, 1H), 8.71 (d, J=7.4 Hz, 1H), 7.84 (dd, J$_1$=9.4 Hz, J$_2$=2.5 Hz, 1H), 7.51-7.49 (m, 1H), 7.41 (dd, J$_1$=10.5 Hz, J$_2$=2.2 Hz, 1H), 7.24 (dd, J$_1$=8.8 Hz, J$_2$=4.5 Hz, 1H), 6.83 (td, J$_1$=9.1 Hz, J$_2$=2.3 Hz, 1H), 4.86 (s, 2H), 4.24-4.23 (m, 1H), 2.90-2.84 (m, 1H), 2.28 (s, 3H), 2.13-2.06 (m, 2H), 2.02-1.99 (m, 2H), 1.79-1.74 (m, 2H), 1.61-1.59 (m, 2H);

$^{13}$C NMR (150 MHz, d$_6$-DMSO): δ ppm 170.7, 169.0, 162.2, 157.9, 156.3, 153.9, 151.7, 134.4, 133.7, 126.7, 116.0, 114.4, 110.0, 109.7, 107.9, 104.0, 44.5, 44.1, 34.9, 29.8, 26.7, 9.8; and MS-ESI: m/z 428.9 [M+H—HCl]$^+$.

Example 45: 2-(5-fluoro-3-(1-((4-fluorophenoxy)carbonyl)piperidin-4-yl)-2-methyl-1H-indol-1-yl)acetic acid

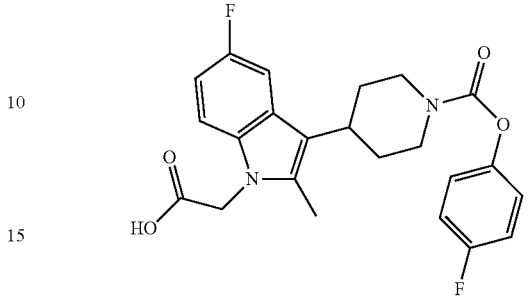

Step 1) 4-fluorophenyl 4-(5-fluoro-1-(2-methoxy-2-oxoethyl)-2-methyl-1H-indol-3-yl)piperidine-1-carboxylate To a solution of CDI (569 mg, 3.29 mmol) in anhydrous THF (4 mL) was added triethylamine (0.23 mL, 1.64 mmol) dropwise at 18° C., and then 4-fluorophenol (368 mg, 3.29 mmol) was added dropwise slowly. The mixture was stirred at 50° C. for 50 min, then a solution of methyl 2-(5-fluoro-2-methyl-3-(piperidin-4-yl)-1H-indol-1-yl)acetate (250 mg, 0.82 mmol) in anhydrous THF (10 mL) was added. The resulting mixture was refluxed at 75° C. for 21 h and washed with dilute hydrochloric acid (10 mL×3) until the water phase was acid. The waster phase was extracted with EtOAc (15 mL×2). The combined organic layers were dried over anhydrous Na$_2$SO$_4$ and concentrated. The residue was purified by silica gel chromatography eluted with PE/EtOAc (V/V)=3/1 to give the title compound as a white solid (160 mg, 44%).

$^1$H NMR (600 MHz, CDCl$_3$): δ ppm 7.31 (dd, J$_1$=10.0 Hz, J$_2$=2.3 Hz, 1H), 7.15-7.12 (m, 2H), 7.09-7.05 (m, 3H), 6.89 (td, J$_1$=8.9 Hz, J$_2$=2.3 Hz, 1H), 4.77 (s, 2H), 4.50-4.42 (m, 2H), 3.76 (s, 3H), 3.12-3.07 (m, 1H), 2.98-2.92 (m, 2H), 2.37 (s, 3H), 2.21-2.14 (m, 2H), 1.84-1.82 (m, 2H); and MS-ESI: m/z 443.9 [M+H]$^+$.

Step 2) 2-(5-fluoro-3-(1-((4-fluorophenoxy)carbonyl)piperidin-4-yl)-2-methyl-1H-indol-1-yl)acetic acid To a solution of 4-fluorophenyl 4-(5-fluoro-1-(2-methoxy-2-oxoethyl)-2-methyl-1H-indol-3-yl)piperidine-1-carboxylate (156 mg, 0.35 mmol) in a mixed solvent of THF (8 mL) and water (4 mL) was added lithium hydroxide monohydrate (74 mg, 1.76 mmol). The mixture was stirred for 2 h at 45° C. After adjusting to pH 1 with hydrochloric acid (1 mol/L), the resulting mixture was extracted with EtOAc (10 mL×2). The combined organic layers were concentrated to give a light yellow solid product (150 mg, 99%).

$^1$H NMR (600 MHz, d$_6$-DMSO): δ ppm 7.36 (d, J=9.4 Hz, 1H), 7.34-7.32 (m, 1H), 7.22-7.20 (m, 4H), 6.86 (t, J=7.9 Hz, 1H), 4.92 (s, 2H), 4.35-4.30 (m, 1H), 4.21-4.19 (m, 1H), 4.05-4.02 (m, 1H), 3.06-3.00 (m, 2H), 2.33 (s, 3H), 2.11-2.02 (m, 2H), 1.72-1.70 (m, 2H);

$^{13}$C NMR (150 MHz, d$_6$-DMSO): δ ppm 170.9, 160.5, 158.9, 157.9, 156.4, 153.3, 147.9, 135.0, 133.7, 126.7, 124.2, 116.2, 116.0, 114.6, 110.4, 108.3, 104.2, 60.2, 55.3, 44.9, 34.2, 10.7; and MS-ESI: m/z 427.9 [M−H]$^-$.

Example 46: 2-(5-fluoro-2-methyl-3-(1-(phenylsulfonyl)piperidin-4-yl)-1H-indol-1-yl)acetic acid

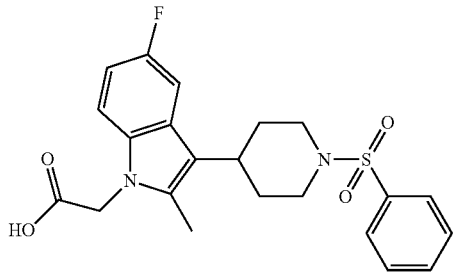 [SMILES: Cc1c(C2CCN(S(=O)(=O)c3ccccc3)CC2)c2cc(F)ccc2n1CC(=O)O]

Step 1) methyl 2-(5-fluoro-2-methyl-3-(1-(phenylsulfonyl)piperidin-4-yl)-1H-indol-1-yl)acetate To a solution of methyl 2-(5-fluoro-2-methyl-3-(piperidin-4-yl)-1H-indol-1-yl)acetate (250 mg, 0.82 mmol) in DCM (10 mL) was added TEA (0.69 mL, 4.93 mmol) at 18° C., and then a solution of benzenesulfonyl chloride (0.42 mL, 3.29 mmol) in DCM (6 mL) was added at 0° C. The mixture was stirred for 4.5 h at rt and washed with saturated aqueous sodium chloride solution (10 mL×3). The organic layer was dried over anhydrous $Na_2SO_4$ and concentrated. The residue was purified by silica gel chromatography eluted with a gradient of PE/EtOAc (V/V)=4/1 and 2/1 to give a white solid product (272 mg, 74%).

$^1$H NMR (400 MHz, $CDCl_3$): δ ppm 7.86-7.84 (m, 2H), 7.67-7.63 (m, 1H), 7.60-7.57 (m, 2H), 7.12 (dd, $J_1$=10.0 Hz, $J_2$=2.3 Hz, 1H), 7.04 (dd, $J_1$=8.8 Hz, $J_2$=4.3 Hz, 1H), 6.86 (td, $J_1$=9.0 Hz, $J_2$=2.3 Hz, 1H), 4.73 (s, 2H), 4.04-4.01 (m, 2H), 3.73 (s, 3H), 2.68-2.61 (m, 1H), 2.48-2.41 (m, 2H), 2.27 (s, 3H), 2.22-2.15 (m, 2H), 1.77-1.73 (m, 2H); and MS-ESI: m/z 445.8 [M+H]$^+$.

Step 2) 2-(5-fluoro-2-methyl-3-(1-(phenylsulfonyl)piperidin-4-yl)-1H-indol-1-yl)acetic acid To a solution of methyl 2-(5-fluoro-2-methyl-3-(1-(phenylsulfonyl)piperidin-4-yl)-1H-indol-1-yl)acetate (262 mg, 0.59 mmol) in a mixed solvent of THF (10 mL) and water (5 mL) was added lithium hydroxide monohydrate (124 mg, 2.95 mmol). The mixture was stirred for 2 h at 45° C. After adjusting to pH 1 with hydrochloric acid (1 mol/L), the resulting mixture was extracted with EtOAc (10 mL×2) and the combined organic layers were concentrated to give a white solid product (243 mg, 95%).

$^1$H NMR (600 MHz, $d_6$-DMSO): δ ppm 7.83 (d, J=7.1 Hz, 2H), 7.77-7.75 (m, 1H), 7.70 (t, J=6.9 Hz, 2H), 7.32-7.30 (m, 1H), 7.07 (d, J=9.7 Hz, 1H), 6.85 (t, J=8.3 Hz, 1H), 4.89 (s, 2H), 3.86-3.84 (m, 2H), 2.80-2.76 (m, 1H), 2.48-2.46 (m, 2H), 2.21 (s, 3H), 2.01-1.95 (m, 2H), 1.65-1.63 (m, 2H);

$^{13}$C NMR (150 MHz, $d_6$-DMSO): δ ppm 172.5, 157.9, 136.9, 135.1, 133.6, 130.0, 127.9, 126.7, 114.2, 110.5, 108.3, 103.9, 55.4, 47.3, 44.9, 31.0, 10.6; and MS-ESI: m/z 431.3 [M+H]+.

Example 47: 2-(3-(1-((4-chlorophenyl)sulfonyl)piperidin-4-yl)-5-fluoro-2-methyl-1H-indol-1-yl)acetic acid

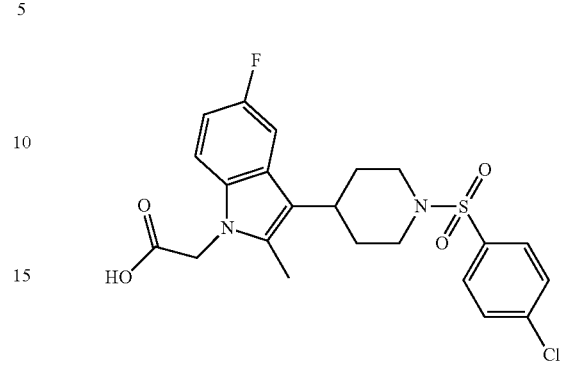

Step 1) methyl 2-(3-(1-((4-chlorophenyl)sulfonyl)piperidin-4-yl)-5-fluoro-2-methyl-1H-indol-1-yl)acetate To a solution of methyl 2-(5-fluoro-2-methyl-3-(piperidin-4-yl)-1H-indol-1-yl)acetate (250 mg, 0.82 mmol) in DCM (10 mL) was added TEA (0.69 mL, 4.93 mmol) at 20° C., and then a solution of 4-chlorobenzene-1-sulfonyl chloride (693 mg, 3.29 mmol) in DCM (6 mL) was added at 0° C. The mixture was stirred for 5 h at rt and washed with saturated aqueous ammonium chloride solution (10 mL×3). The organic layer was dried over anhydrous $Na_2SO_4$ and concentrated. The residue was purified by silica gel chromatography eluted with PE/EtOAc (V/V)=4/1 to give a white solid product (282 mg, 71%).

$^1$H NMR (400 MHz, $CDCl_3$): δ ppm 7.77 (d, J=8.5 Hz, 2H), 7.55 (d, J=8.5 Hz, 2H), 7.19 (dd, $J_1$=10.0 Hz, $J_2$=2.3 Hz, 1H), 7.05 (dd, $J_1$=8.8 Hz, $J_2$=4.3 Hz, 1H), 6.87 (td, $J_1$=9.0 Hz, $J_2$=2.4 Hz, 1H), 4.74 (s, 2H), 4.00-3.97 (m, 2H), 3.74 (s, 3H), 2.69-2.62 (m, 1H), 2.44-2.38 (m, 2H), 2.27 (s, 3H), 2.25-2.18 (m, 2H), 1.80-1.77 (m, 2H); and MS-ESI: m/z 479.8 [M+H]$^+$.

Step 2) 2-(3-(1-((4-chlorophenyl)sulfonyl)piperidin-4-yl)-5-fluoro-2-methyl-1H-indol-1-yl)acetic acid To a solution of methyl 2-(3-(1-((4-chlorophenyl)sulfonyl)piperidin-4-yl)-5-fluoro-2-methyl-1H-indol-1-yl)acetate (278 mg, 0.58 mmol) in a mixed solvent of THF (10 mL) and water (5 mL) was added lithium hydroxide monohydrate (122 mg, 2.90 mmol). The mixture was stirred for 2 h at 45° C. After adjusting to pH 1 with hydrochloric acid (1 mol/L), the resulting mixture was extracted with EtOAc (10 mL×2) and the combined organic layers were concentrated to give a white solid product (267 mg, 98%).

$^1$H NMR (600 MHz, $d_6$-DMSO): δ ppm 7.80 (d, J=8.4 Hz, 2H), 7.69 (d, J=8.4 Hz, 2H), 7.23 (dd, $J_1$=8.8 Hz, $J_2$=4.4 Hz, 1H), 7.08 (dd, $J_1$=10.2 Hz, $J_2$=1.9 Hz, 1H), 6.80 (td, $J_1$=9.1 Hz, $J_2$=2.0 Hz, 1H), 4.84 (s, 2H), 3.85-3.83 (m, 2H), 2.78-2.74 (m, 1H), 2.48-2.45 (m, 2H), 2.20 (s, 3H), 2.03-1.97 (m, 2H), 1.66-1.64 (m, 2H);

$^{13}$C NMR (150 MHz, $d_6$-DMSO): δ ppm 170.7, 157.9, 138.6, 135.6, 135.0, 133.5, 129.8, 129.6, 114.1, 110.1, 108.2, 103.8, 54.7, 44.5, 33.3, 30.9, 10.0; and MS-ESI: m/z 465.8 [M+H]$^+$.

Example 48: the Crystalline Form I of 2-(5-fluoro-3-(1-((4-fluorophenyl)sulfonyl)piperidin-4-yl)-2-methyl-1H-indol-1-yl)acetic acid

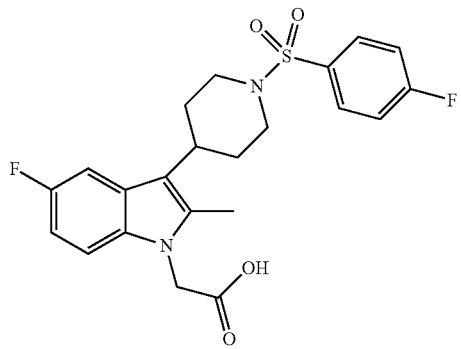 [SMILES: Cc1c(C2CCN(S(=O)(=O)c3ccc(F)cc3)CC2)c2cc(F)ccc2n1CC(=O)O]

Step 1) Preparation of the Crystalline Form I

The preparation method was described in example 24.

Step 2) Identification of Crystalline Form I (1) The XRPD pattern of crystalline form I was analyzed and identified by using Empyrean X-ray powder diffraction (XRPD) with Cu-Kα radiation, having the following characteristic peaks expressed in degrees 2θ at 3.80°, 7.69°, 8.56°, 9.72°, 10.57°, 12.77°, 13.20°, 13.66°, 14.05°, 15.46°, 15.80°, 16.09°, 16.87°, 17.24°, 17.79°, 18.16°, 18.53°, 18.90°, 19.27°, 19.57°, 20.19°, 20.69°, 20.91°, 21.84°, 22.62°, 22.98°, 23.31°, 23.84°, 24.47°, 25.51°, 25.75°, 26.18°, 26.65°, 27.54°, 28.11°, 28.39°, 28.68°, 28.99°, 29.27°, 29.56°, 29.87°, 30.57°, 30.98°, 31.25°, 32.14°, 32.69°, 32.90°, 33.72°, 34.23° and 34.76°. The error margin in 2θ of the characteristic peaks was ±0.2°.

(2) The DSC thermogram of crystalline form I was analyzed and identified by using TA Q2000 differential scanning calorimetry (DSC) with a scan rate of 10° C./minute, comprising endothermic peaks at 123.99° C. and 217.23° C. The error margin in the melting peaks was ±3° C.

(3) The TGA curve of crystalline form I was analyzed and identified by using TA Q500 thermal gracity analysis (TGA) with a scan rate of 10° C./minute, the weight loss ratio was 3.991%.

Example 49: The Crystalline Form II of 2-(5-fluoro-3-(1-((4-fluorophenyl)sulfonyl)piperidin-4-yl)-2-methyl-1H-indol-1-yl)acetic acid Step 1) Preparation of the Crystalline Form II Method one: A mixture of 2-(5-fluoro-3-(1-((4-fluorophenyl)sulfonyl)piperidin-4-yl)-2-methyl-1H-indol-1-yl)acetic acid (106 mg) and ethanol (9.0 mL) was heated at 80° C. until the solid dissolved completely, keeping the temperature at 80° C. for 80 min and then stopping heating. The mixture was cooled naturally to rt and filtered under vacuum. The filter cake was washed with ethanol (2.0 mL×2) and dried in vacuum at rt to give a white powder solid (80 mg, 75%).

Method two: A mixture of 2-(5-fluoro-3-(1-((4-fluorophenyl)sulfonyl)piperidin-4-yl)-2-methyl-1H-indol-1-yl)acetic acid (63 mg) and ethanol (4.0 mL) was heated at 80° C. until the solid dissolved completely, keeping the temperature at 80° C. for 30 min and then stopping heating. The mixture was cooled rapidly to 0° C. After 4 hours of cooling crystallization, the mixture was filter under vacuum. The filter cake was washed with ethanol (1.0 mL×2) and dried in vacuum at rt to give a white powder solid (57 mg, 90.5%).

Step 2) Identification of Crystalline Form II (1) The XRPD pattern of crystalline form II was analyzed and identified by using Empyrean X-ray powder diffraction (XRPD) with Cu-Kα radiation, having the following characteristic peaks expressed in degrees 2θ at 5.96°, 7.94°, 10.52°, 10.95°, 12.09°, 13.17°, 14.14°, 14.79°, 15.96°, 16.85°, 17.68°, 17.97°, 18.41°, 19.28°, 19.96°, 20.63°, 20.77°, 21.20°, 22.02°, 22.84°, 23.28°, 24.07°, 24.64°, 24.99°, 25.81°, 26.43°, 26.69°, 26.98°, 27.41°, 27.93°, 28.48°, 28.99°, 29.77°, 30.95°, 31.74°, 32.21°, 33.17°, 34.14°, 34.53°, 35.24°, 36.30°, 37.19°, 38.61° and 39.57°. The error margin in 2θ of the characteristic peaks was ±0.2°.

(2) The DSC thermogram of crystalline form II was analyzed and identified by using TA Q2000 differential scanning calorimetry (DSC) with a scan rate of 10° C./minute, comprising endothermic peaks at 142.11° C. and 215.90° C. The error margin in the melting peaks was ±3° C.

(3) The TGA curve of crystalline form II was analyzed and identified by using TA Q500 thermal gracity analysis (TGA) with a scan rate of 10° C./minute, the weight loss ratio was 9.054%.

Example 50: The Crystalline Form III of 2-(5-fluoro-3-(1-((4-fluorophenyl)sulfonyl)piperidin-4-yl)-2-methyl-1H-indol-1-yl)acetic acid Step 1) Preparation of the Crystalline Form III A mixture of 2-(5-fluoro-3-(1-((4-fluorophenyl)sulfonyl)piperidin-4-yl)-2-methyl-1H-indol-1-yl)acetic acid (57 mg) and N,N-dimethylformamide (1.0 mL) was stirred at rt for 15 min until the solid dissolved completely, and then to the mixture was added water (0.4 mL) dropwise. After 4 hours of crystallization at rt, the mixture was filter under vacuum. The filter cake was washed with water (1.0 mL×2) and dried in vacuum at rt to give a white powder solid (56 mg, 98.2%).

Step 2) Identification of Crystalline Form III (1) The XRPD pattern of crystalline form III was analyzed and identified by using Empyrean X-ray powder diffraction (XRPD) with Cu-Kα radiation, having the following characteristic peaks expressed in degrees 2θ at 5.77°, 7.79°, 10.51°, 12.00°, 12.76°, 13.33°, 13.94°, 15.67°, 16.20°, 16.85°, 17.44°, 18.28°, 19.06°, 19.65°, 20.02°, 20.89°, 21.16°, 22.79°, 23.07°, 23.28°, 23.92°, 24.62°, 25.31°, 26.39°, 26.95°, 27.26°, 27.55°, 28.14°, 29.23°, 29.82°, 30.85°, 31.66°, 32.04°, 33.45°, 34.10°, 35.13°, 35.64°, 36.51°, 37.19° and 37.97°. The error margin in 2θ of the characteristic peaks was ±0.2°.

(2) The DSC thermogram of crystalline form III was analyzed and identified by using TA Q2000 differential scanning calorimetry (DSC) with a scan rate of 10° C./minute, comprising an endothermic peak at 152.50° C. The error margin in the melting peaks was ±3° C.

(3) The TGA curve of crystalline form III was analyzed and identified by using TA Q500 thermal gracity analysis (TGA) with a scan rate of 10° C./minute, the weight loss ratio was 13.58%.

Example 51: The Crystalline Form IV of 2-(5-fluoro-3-(1-((4-fluorophenyl)sulfonyl)piperidin-4-yl)-2-methyl-1H-indol-1-yl)acetic acid Step 1) Preparation of the Crystalline Form IV A mixture of 2-(5-fluoro-3-(1-((4-fluorophenyl)sulfonyl)piperidin-4-yl)-2-methyl-1H-indol-1-yl)acetic acid (55.5 mg) and dimethylsulfoxide (1.0 mL) was stirred at rt for 15 min until the solid dissolved completely, and then to the mixture was added water (1.0 mL) dropwise. After 4 hours of crystallization at rt, the mixture was filter under vacuum. The filter cake was washed with water (1.0 mL×2) and dried in vacuum to give a white powder solid (44.5 mg, 80.2%).

Step 2) Identification of Crystalline Form IV (1) The XRPD pattern of crystalline form IV was analyzed and identified by using Empyrean X-ray powder diffraction (XRPD) with Cu-Kα radiation, having the following characteristic peaks expressed in degrees 2θ at 6.11°, 8.05°, 10.54°, 10.87°, 12.16°, 13.24°, 14.13°, 15.12°, 16.09°, 16.83°, 17.42°, 18.19°, 18.93°, 19.72°, 19.98°, 20.57°, 20.98°, 21.76°, 23.10°, 23.68°, 24.11°, 24.43°, 24.82°, 25.93°, 26.30°, 26.60°, 26.85°, 27.27°, 27.52°, 27.96°, 28.46°, 29.01°, 29.29°, 30.04°, 30.94°, 31.69°, 32.43°, 33.12°, 34.18°, 34.72°, 35.49°, 35.89°, 36.37°, 36.99°, 37.41°, 37.97° and 38.70°. The error margin in 2θ of the characteristic peaks was ±0.2°.

(2) The DSC thermogram of crystalline form IV was analyzed and identified by using TA Q2000 differential scanning calorimetry (DSC) with a scan rate of 10° C./minute, comprising an endothermic peak at 185.0° C. The error margin in the melting peaks was ±3° C.

(3) The TGA curve of crystalline form IV was analyzed and identified by using TA Q500 thermal gracity analysis (TGA) with a scan rate of 10° C./minute, the weight loss ratio was 16.09%.

Example 52: The Crystalline Form V of 2-(5-fluoro-3-(1-((4-fluorophenyl)sulfonyl)piperidin-4-yl)-2-methyl-1H-indol-1-yl)acetic acid Step 1) Preparation of the Crystalline Form V A mixture of 2-(5-fluoro-3-(1-((4-fluorophenyl)sulfonyl)piperidin-4-yl)-2-methyl-1H-indol-1-yl)acetic acid (398 mg) and t-butanol (50.0 mL) was heated at 80° C. until the solid dissolved completely, keeping the temperature at 80° C. for 5 hours and then stopping heating. The mixture was cooled naturally to rt and filtered under vacuum. The filter cake was dried in vacuum at rt to give a white powder solid (365 mg, 91.7%).

Step 2) Identification of Crystalline Form V (1) The XRPD pattern of crystalline form V was analyzed and identified by using Empyrean X-ray powder diffraction (XRPD) with Cu-Kα radiation, having the following characteristic peaks expressed in degrees 2θ at 5.88°, 7.83°, 10.51°, 11.91°, 12.86°, 13.81°, 15.68°, 16.49°, 17.26°, 17.69°, 18.15°, 19.52°, 20.17°, 20.50°, 20.79°, 22.39°, 22.81°, 23.60°, 24.17°, 24.49°, 25.31°, 25.88°, 26.82°, 27.40°, 27.83°, 28.28°, 28.70°, 29.19°, 30.18°, 30.60°, 30.97°, 31.58°, 32.36°, 33.69°, 34.42°, 35.03°, 36.52° and 37.29°. The error margin in 2θ of the characteristic peaks was ±0.2°.

(2) The DSC thermogram of crystalline form V was analyzed and identified by using TA Q2000 differential scanning calorimetry (DSC) with a scan rate of 10° C./minute, comprising endothermic peaks at 159.91° C. and 216.52° C. The error margin in the melting peaks was ±3° C.

(3) The TGA curve of crystalline form V was analyzed and identified by using TA Q500 thermal gracity analysis (TGA) with a scan rate of 10° C./minute, the weight loss ratio was 14.31%.

Example 53: The Crystalline Form VI of 2-(5-fluoro-3-(1-((4-fluorophenyl)sulfonyl)piperidin-4-yl)-2-methyl-1H-indol-1-yl)acetic acid Step 1) Preparation of the Crystalline Form VI A mixture of 2-(5-fluoro-3-(1-((4-fluorophenyl)sulfonyl)piperidin-4-yl)-2-methyl-1H-indol-1-yl)acetic acid (312.4 mg) and isopropanol (50 mL) was heated at 70° C. until the solid dissolved completely, keeping the temperature at 70° C. for 30 min and then stopping heating. The mixture was cooled slowly to rt. After 4 hours of crystallization, the mixture was filtered under vacuum. The filter cake was washed with isopropanol (2.0 mL×2) and dried in a vacuum at rt to give a white powder solid (296.5 mg, 94.9%).

Step 2) Identification of Crystalline Form VI (1) The XRPD pattern of crystalline form VI was analyzed and identified by using Empyrean X-ray powder diffraction (XRPD) with Cu-Kα radiation, having the following characteristic peaks expressed in degrees 2θ at 5.84°, 7.83°, 11.96°, 12.83°, 13.20°, 13.76°, 15.72°, 16.49°, 17.63°, 18.30°, 18.87°, 19.55°, 20.43°, 20.74°, 20.98°, 22.67°, 23.03°, 23.62°, 24.20°, 24.46°, 25.18°, 25.88°, 26.62°, 27.17°, 27.47°, 27.84°, 28.36°, 28.94°, 30.12°, 30.41°, 30.79°, 31.52°, 31.80°, 32.70°, 34.33°, 36.11° and 36.62°. The error margin in 2θ of the characteristic peaks was ±0.2°.

(2) The DSC thermogram of crystalline form VI was analyzed and identified by using TA Q2000 differential scanning calorimetry (DSC) with a scan rate of 10° C./minute, comprising endothermic peaks at 153.83° C. and 216.70° C. The error margin in the melting peaks was ±3° C.

(3) The TGA curve of crystalline form V was analyzed and identified by using TA Q500 thermal gracity analysis (TGA) with a scan rate of 10° C./minute, the weight loss ratio was ±13.07%.

Figure 19:
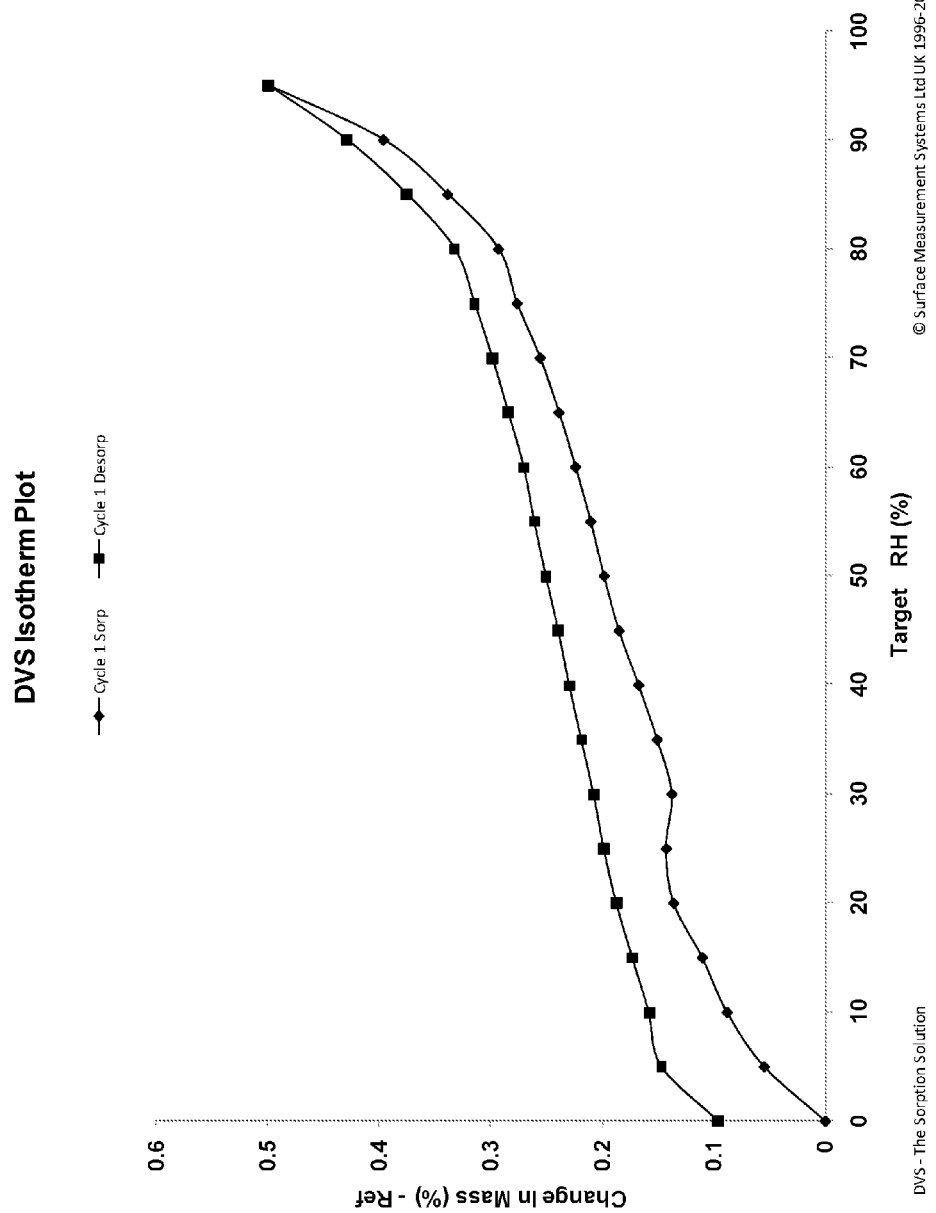
FIG. 19 provides a dynamic vapor sorption (DVS) profile of Form I of the compound of Formula VI

Example 54: The Hygroscopicity Test of the Crystalline Form of 2-(5-fluoro-3-(1-((4-fluorophenyl)sulfonyl)piperidin-4-yl)-2-methyl-1H-indol-1-yl) acetic acid An appropriate amount of test sample was sampled, and the hygroscopicity of the test sample was detected on a dynamic vapor sorption instrument. The experiment results are as shown in table 7; the dynamic vapor sorption profiles of the crystalline form I of the compound represented by Formula (VI) is substantial the same as shown in FIG. 19.

TABLE 7

The hygroscopicity tests of the crystalline form I of the compound represented by Formula VI

| Test sample | Weigh increase rate % under RH 80% | Weigh increase rate % under RH 95% |
|---|---|---|
| Crystalline form I | 0.293 | 0.499 |

Conclusion: As can be seen in table 7 and FIG. 19, the crystalline form I has 0.293% of weigh increase under relative humidity (RH) 80%, which belongs to Slight hygroscopicity according to the definition standard of hygroscopic weight gain, i.e. the crystalline form I is not easy to deliquesce under high humidity conditions, which is convenience for long storage of the drugs.

The hygroscopic features and definition of hygroscopic weight gain are summarized in table 8 (deriving from Chinese Pharmacopoeia 2010, appendix XIX J: Guideline on pharmaceutical hygroscopicity test, test conditions: 25° C.±1° C., Relative Humidity 80%).

TABLE 8

The hygroscopic features and definition of hygroscopic weight gain

| Hygroscopic features | Hygroscopic weight gain |
|---|---|
| Deliquescence | absorbing enough water to form liquid |
| High hygroscopicity | the weight increase of the hygroscopicity is no less than 15% |
| Having hygroscopicity | the weight increase of the hygroscopicity is between 15% and 2% |
| Slight hygroscopicity | the weight increase of the hygroscopicity is between 2% and 0.2% |
| No or almost no hygroscopicity | the weight increase of the hygroscopicity is less than 0.2% |

BIOLOGICAL ASSAY

Biologic Example 1: Pharmacological Activity In Vitro of the Compound of the Invention 1. Preparation of the Solution The test compound was weighed accurately and then dissolved in a suitable amount of DMSO to prepare a stock solution at a concentration of 10 mM; after clear and transparent, the stock solution was subpackaged and cryostoraged at −20° C. for use. Before testing, the test compound was diluted with balanced salt solution (HBSS buffer, containing 4-(2-hydroxyethyl)piperazine-1-ethanesulfonicacid) at a concentration of 20 mM) to 5 times testing concentration.

2. Detection of FLIPR (Real-Time Fluorescence Imaging Analysis)

CHO-K1/G cells with stable expression of CRTH2 receptor were prepared to 5 times testing concentration and seeded into 384-microwell plate, and incubated in an incubator at 37° C./5% $CO_2$. After incubating for 18 hours, to the cells in 384-microwell plate was added 20 μL of dye followed by the addition of 10 μL of prepared test compound solution. And then the cell plate was incubated in the incubator at 37° C./5% $CO_2$ for 1 hour, at last which was balanced at rt for 15 min. After adding 12.5 μL of positive agonist (PGD2) at a concentration of 5 times $EC_{80}$ to each well of the cell plate, the RFU (fluorescence intensity) value of the test compound was detected.

3. Data Analysis

The data were recorded from ScreenWorks (version 3.1), and collected and analyzed by using Excel and GraphPad Prism 6 software to calculate the values of $IC_{50}$.

TABLE 3 inhibitory activity against CRTH2

| Example | $IC_{50}$ (nM) |
|---|---|
| 2 | 673.7 |
| 3 | 265 |
| 4 | 306 |
| 6a | 200 |
| 7 | 776 |
| 8 | 657 |
| 9a | 192 |
| 10 | 545 |
| 16 | 969 |
| 17a | 600 |
| 17b | 97.2 |
| 20 | 39.8 |
| 21 | 185 |
| 23 | 866 |
| 24 | 148 |
| 26b | 83.9 |
| 27b | 57.3 |
| 28 | 138 |
| 29b | 79.5 |
| 32 | 33.7 |
| 33 | 80.4 |
| 34 | 211 |
| 35 | 333 |
| 36 | 422 |
| 37 | 137 |
| 39 | 106 |
| 40 | 17.4 |
| 42 | 283 |
| 46 | 317 |
| 47 | 139 |
| Control compound | 6190 |

Structure of the control compound:

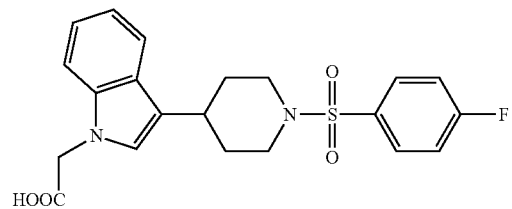 [SMILES: O=C(O)Cn1cc(C2CCN(S(=O)(=O)c3ccc(F)cc3)CC2)c2ccccc21]

Conclusion: The data listed in table 3 indicated that the most compounds of the invention have better inhibitory activities against CRTH2 and obviously better than the control compound.

Biologic Example 2: Detection of Pharmacodynamics Activity In Vivo

The experiment purpose was to assess the drug efficacy of the test compound in OVA (ovalbumin)-induced asthmatic model in rats.

Test Method

1. Sensitization Process

Grouping the animal randomly to control group, model group and administered group. At the first, second and third day, the control group was administered with 1 mL of PBS (phosphate buffer solution) by intraperitoneal injection, and the model group and administered group were administered with a sensitization solution (prepared by mixing 6 mL of 1% OVA in phosphate buffer solution and 54 mL of alum solution at a ratio of 1:9) by intraperitoneal injection per day (1 mL per rat).

2. Administration and Attacking Process

From the nineteenth day, the administered group was administered with the test compound at a certain dose by gavage, and the control group and model group was administered with the menstruum at a corresponding dose by gavage, once a day for three days. After 1 hour of administering each day, attacking the model group and administered group with 1% OVA in phosphate buffer solution and the control group with phosphate buffer solution for 20 min.

3. Detection of Index and Collection of Sample:

At the twenty-third day, the animals were anesthetized with 1% pentobarbital sodium (60 mg/Kg) by intraperitoneal injection. The blood samples were collected from aorta abdominalis under pentobarbital sodium anaesthesia into EDTA-K2 tubes. After tracheal intubation was performed, the lung of the animals were lavaged with 3 mL of PBS containing 1% FBS (Fetal Bovine Serum) once, and then lavaged with 5 mL of PBS containing 1% FBS at least two times; the volume of the combined lavage solutions were adjusted to 15 mL. The total cells in the lavage solution were counted by using a hemacytometer and a Trypan blue staining method and then white blood cells in the lavage solution were counted differentially.

4. Conclusion:

TABLE 4

The results of the count of white blood cells

| Group/Example | Total number of white cells (×10⁵/mL) | Eosinophilic granulocyte Number(×10⁵/mL) | Inhibition ratio |
|---|---|---|---|
| Control group | 56.100 | 13.77 | 100% |
| Model group | 352.280 | 222.700 | 0 |
| OC000459 | 269.925 | 161.62 | 29.24% |
| Example 6a | 247.350 | 153.75 | 33% |
| Example 24 | 272.775 | 145.82 | 36.8% |
| Example 27b | 277.800 | 142.17 | 38.55% |

Structure of OC000459:

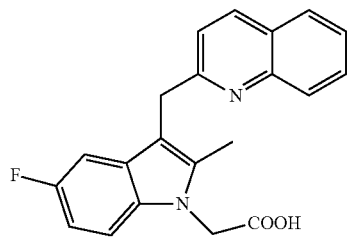 [SMILES: Cc1c(Cc2ccc3ccccc3n2)c2cc(F)ccc2n1CC(=O)O]

The results indicated that the compounds of the invention have inhibitory effect on total number of white blood cells and the number of eosinophilic granulocyte, and play a role in reducing inflammation degree and lessening disease.

Biologic Example 3: Detection Method of LC/MS/MS

The analysis was performed using a 4000 QTRAPP series LC/MS/MS mass spectrometer equipped with Agilent 1200 dual injection pumps, 1290 automatic sampler, column oven and ESI source, detecting by the negative ion MRM mode. Waters Xbridge C18 column was used in the analysis, and the mobile phase consisted of phase (A) (2 mM ammonium formate+0.1% aqueous ammonia solution) and phase (B) (2 mM ammonium formate+0.1% ammonia methanol solution), the flow rate was 0.4 mL/min, column temperature was 40° C., the amount of injection was 3 μL.

Biologic Example 4: Metabolic Stability Detection of the Compound in Liver Microsomal A mixture of the compound and human liver microsomal, a mixture of the compound and dog liver microsomal, or a mixture of the compound and rat liver microsomal were separately incubated at 37° C., under a condition of pH7.4. The sample concentrations at various incubative times were detected by LC/MS/MS (the method described in biologic example 3), speed constant was obtained by plotting "Log [drug concentration]" to "incubative time" in GraphPad Prism 5.01, and the drug half-life and intrinsic clearance rate were calculated; metabolic stability of the compound in liver microsomal were evaluated based on the drug half-life and intrinsic clearance rate. The results were as shown in table 5:

TABLE 5

Stability data of the compound of the invetion in liver microsomal

| | Human | | Rat | | Dog | |
|---|---|---|---|---|---|---|
| Example No. | Drug half-life (min) | Clearance rate (ml/min/kg) | Drug half-life (min) | Clearance rate (ml/min/kg) | Drug half-life (min) | Clearance rate (ml/min/kg) |
| 24 | 681.60 | 2.55 | 180.10 | 13.79 | 2525.00 | 1.37 |

The results indicated that the compounds of the invention have an advantage in stability in liver microsomal in various species, and have a lower clearance rate.

Biological Example 5: Detection of PK

The male Beagle dogs or rats were administered with the compound of the invention by intravenous injection (0.4 mg/Kg) and gavage (1 mg/Kg) respectively, the blood samples were collected at the time point of 0.083, 0.25, 0.5, 1, 2, 4, 6, 8, 10, 24 and 36 h and then centrifuged to obtain plasma samples. The compound concentrations in plasma samples at various times were detected by LC/MS/MS (the method described in biologic example 3), the main pharmacokinetic parameters were calculated, and pharmacokinetic properties of the compounds of the invention in Beagle dogs or rats were evaluated. The results were as shown in table 6:

TABLE 6

Pharmacokinetic parameters of the compounds of the invention in Beagle dogs or rats

| Example No. | Species | Drug-delivery way | $T_{1/2}$ (h) | Cmax (ng/mL) | AUClast (h*ng/mL) | AUCinf (h*ng/mL) |
|---|---|---|---|---|---|---|
| 6a | Rats | i.v. | 1.57 | 2020 | 2680 | 2780 |
| | | p.o. | 2.86 | 2110 | 5670 | 5940 |
| 24 | Rats | i.v. | 3.40 | 757 | 991 | 1030 |
| | | p.o. | 4.37 | 393 | 1710 | 1890 |
| 24 | Dogs | i.v. | 4.72 | 3210 | 5400 | 5500 |
| | | p.o. | 10.8 | 1160 | 6600 | 6920 |
| 27b | Rats | i.v. | 1.58 | 802 | 883 | 920 |
| | | p.o. | 1.33 | 631 | 1600 | 1640 |

TABLE 6-continued

Pharmacokinetic parameters of the compounds of the invention in Beagle dogs or rats

| Example No. | Species | Drug-delivery way | $T_{1/2}$ (h) | Cmax (ng/mL) | AUClast (h*ng/mL) | AUCinf (h*ng/mL) |
|---|---|---|---|---|---|---|
| 33 | Rats | i.v. | 4.5 | 1300 | 2440 | 2500 |
|  |  | p.o. | 4.52 | 1960 | 4090 | 4270 |

The results indicated that the compound of the invention have a higher exposure level.

Biological Example 6: Study of Eosinophilia in Airway of Wistar Rats Induced by DK-PGD2

Purpose: evaluation of inhibitory effects of the compounds on the total number of white blood cells and eosinophilia in airway of Wistar rats induced by DK-PGD2.

Process: observation on the drug therapeutic effect through preventive medication. Specific operation: After 0.5 h of administering a preventive dose, the administered group and model group were induced eosinophilia with 100 μL of DK-PGD2 by spray injection through airway of rats, the blank group was spray injected with a corresponding dose of normal saline; after 24 h of molding, the rats were killed by bloodletting from aorta abdominalis, exposing the airway and the chest, performing the trachea cannula, and the bronchial pulmonary alveoli were lavaged with 8 mL of 1% BSA in PBS in twice, the bronchoalveolar lavage fluids (BALF) were collected and placed in an ice-bath; after smear, the cells were differential counted. The concentration of DK-PGD2 mother liquor was 10 mg/mL, which was diluted 5 folds to get 2 mg/mL. Specific results were shown in table 9:

TABLE 9

The effects of the compounds on the total number of white blood cells and the number of eosinophilic granulocyte in BALF

| Groups | Dosage mg/Kg | The total number of white blood cells | Eosinophilic granulocyte C ($10^5$/ml) | Inhibition rate |
|---|---|---|---|---|
| The blank group | / | 1.115 ± 0.17## | 0.0059 ± 0.0001## | 100% |
| The model group | / | 3.189 ± 0.32 | 0.3935 ± 0.08 | / |
| OC000459 | 10 | 2.427 ± 0.25# | 0.1192 ± 0.03## | 70.77% |
| Example 6a | 10 | 1.634 ± 0.30## | 0.0568 ± 0.02## | 86.85% |
| Example 24 | 10 | 1.881 ± 0.26## | 0.0804 ± 0.02## | 80.77% |
| Example 27b | 10 | 1.986 ± 0.28## | 0.09597 ± 0.04## | 76.76% |

Note:
Comparing with the model group, #means P < 0.05, ##means P < 0.01. According to statistical analysis based on the experimental data, the total number of white blood cells, the number of eosinophilic granulocytes of the model group are obviously much morethan those of the blank group, which indicates statistically significant (p) differences between groups, and the number of eosinophilic granulocytes in airway of Wistar rats can increase significantly induced with DK-PGD2 by spray injection, the molding is available in the assay.

Examples 6a, 24 and 27b have better inhibitory effects on the increase of the total number of white blood cells and the number of eosinophilic granulocytes in airway of Wistar rats induced by DK-PGD2, the inhibitory effects of which on the total number of white blood cells and the number of eosinophilic granulocytes are stronger than those of OC000459.

What is claimed is:

1. A compound having Formula (I) or a stereoisomer, a geometric isomer, a tautomer, or a pharmaceutically acceptable salt thereof,

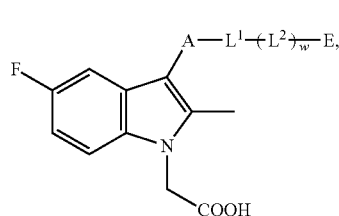

wherein
A is 6- to 9-membered heterocyclylene, 4-membered heterocyclylene, spiro heterobicyclylene, fused heterobicyclylene, bridged heterobicyclylene, spiro bicyclylene, fused bicyclylene, bridged bicyclylene, cycloalkylene, heteroarylene or arylene; A is optionally substituted with 1, 2, 3 or 4 independent $R^2$;
E is $C_{3-6}$ heterocyclyl, cycloalkyl, spiro heterobicyclyl, fused heterobicyclyl, bridged heterobicyclyl, $C_{6-12}$ aryl or $C_{1-9}$ heteroaryl; E is optionally substituted with 1, 2, 3 or 4 independent $R^{2c}$;
$L^1$ is —O—, —S(=O)$_t$—, —S—, —N($R^1$)—, —CH$_2$—, —CH(OH)—, —C(=O)O—, —N($R^1$)—C(=O)—, —C(=O)—(CH$_2$)$_n$—, —C(=O)—, —OC(=O)—, —C(=S)—, —C(=O)—N($R^1$)—, —C(=S)—N($R^1$)— or —(CH$_2$)$_n$—C(=O)—;
each $L^2$ is independently a bond, —O—, —S(=O)$_t$—, —S—, —N($R^1$)—, —C(=O)O—, —N($R^1$)—C(=O)—, —C(=O)—(CH$_2$)$_n$—, —CH$_2$—, —C(=O)—, —OC(=O)—, —C(=S)—, —C(=O)—N($R^1$)—, —C(=S)—N($R^1$)— or —(CH$_2$)$_n$—C(=O)—;
w is 0, 1, 2, 3 or 4;
each n is independently 0, 1, 2, 3 or 4;
each t is independently 0, 1 or 2;
each $R^{1a}$ and $R^1$ is independently H, $C_{1-4}$ alkyl, halo-$C_{1-4}$-alkyl, $C_{1-4}$alkylacyl or hydroxy;
each $R^{2c}$ and $R^2$ is independently H, $C_{1-4}$alkyl, $C_{1-4}$ haloalkyl, hydroxy, nitro, amino, cyano, halogen, carboxy, $C_{1-4}$ alkoxy, $C_{1-4}$ alkylamino, $C_{1-4}$ alkylthio, $C_{1-4}$ alkylacyl, $C_{3-12}$ cycloalkyl, $C_{3-9}$ heterocyclyl, $C_{6-12}$ aryl, $C_{1-9}$ heteroaryl, amino-$C_{1-4}$-alkyl, hydroxy-$C_{1-4}$-alkyl, sulfo, $R^2$b-L-, aminosulfonyl or aminoacyl;
each L is independently —O—, —S(=O)$_t$—, —S—, —N($R^{1a}$)—, —CH$_2$—, —C(=O)—, —OC(=O)—, —C(=S)—, —C(=O)—N(R$^{1a}$)—, —C(=S)—N(R$^{1a}$)— or —(CH$_2$)$_n$—C(=O)—; and each R$^{2b}$ is independently H, C$_{1-4}$ alkyl, C$_{1-4}$ haloalkyl, C$_{3-9}$ cycloalkyl, C$_{3-6}$ heterocyclyl, C$_{6-12}$ aryl, C$_{1-9}$ heteroaryl, amino-C$_{1-4}$-alkyl, amino or hydroxy-C$_{1-4}$-alkyl.

2. The compound of claim 1, wherein

A is 6- to 9-membered heterocyclylene, 4-membered heterocyclylene, C$_{5-12}$ spiro heterobicyclylene, C$_{5-12}$ fused heterobicyclylene, C$_{5-12}$ bridged heterobicyclylene, C$_{5-12}$ spiro bicyclylene, C$_{5-12}$ fused bicyclylene, C$_{5-12}$ bridged bicyclylene, C$_{3-12}$ cycloalkylene, C$_{1-9}$ heteroarylene or C$_{6-12}$ arylene; and each of 6- to 9-membered heterocyclylene, 4-membered heterocyclylene, C$_{5-12}$ spiro bicyclylene, C$_{5-12}$ fused bicyclylene, C$_{5-12}$ bridged bicyclylene, C$_{5-12}$ spiro heterobicyclylene, C$_{5-12}$ fused heterobicyclylene, C$_{5-12}$ bridged heterobicyclylene, C$_{3-12}$ cycloalkylene, C$_{1-9}$ heteroarylene and C$_{6-12}$ arylene is optionally and independently substituted with 1, 2, 3 or 4 independent R$^2$; or A is one of the following sub-structures:

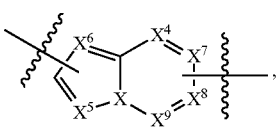

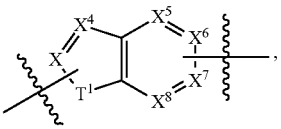

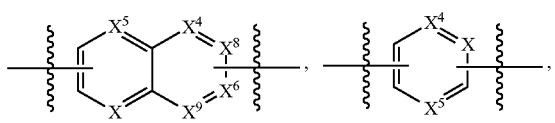

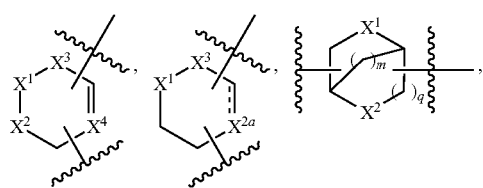

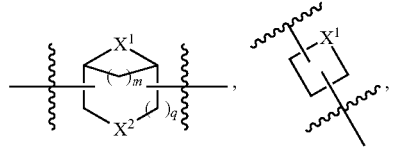

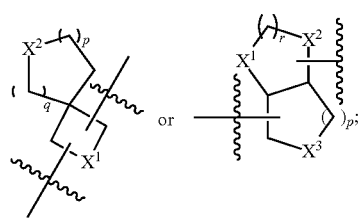

wherein when ----- X$^{2a}$ is a single bond,

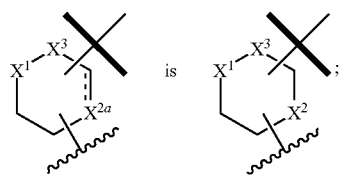

when ----- X$^{2a}$ is a double bond

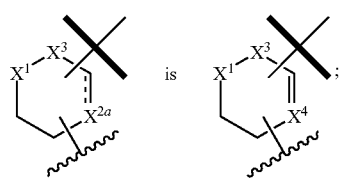

each X$^1$, X$^2$, T$^1$ and X$^3$ is independently —(CR$^3$R$^{3a}$)$_b$—, —O—, —N(R$^4$)— or —S—;

each X$^4$, X$^5$, X$^6$, X$^7$, X$^8$, X$^9$ and X is independently C(R$^3$) or N;

each b is independently 1, 2, 3 or 4;

each q, m, p and r is independently 0, 1, 2, 3 or 4;

each R$^3$ and R$^{3a}$ is independently H, C$_{1-4}$ alkyl, C$_{1-4}$ haloalkyl, hydroxy, nitro, cyano, halogen, amino, carboxy, C$_{1-4}$ alkoxy, C$_{1-4}$ alkylamino, C$_{1-4}$ alkylthio, C$_{1-4}$ alkylacyl, C$_{3-12}$ cycloalkyl, C$_{3-9}$ heterocyclyl, C$_{6-12}$ aryl, C$_{1-9}$ heteroaryl, amino-C$_{1-4}$-alkyl, hydroxy-C$_{1-4}$-alkyl, sulfo, aminosulfonyl or aminoacyl;

each R$^4$ is independently H, C$_{1-4}$ alkyl, C$_{1-4}$ haloalkyl, hydroxy, C$_{3-12}$ cycloalkyl, C$_{3-9}$ heterocyclyl, C$_{6-12}$ aryl, C$_{1-9}$ heteroaryl, amino-C$_{1-4}$-alkyl or hydroxy-C$_{1-4}$-alkyl; and each moiety represented by A is optionally and independently substituted with 1, 2, 3 or 4 independent R$^2$.

3. The compound of claim 1, wherein

A is

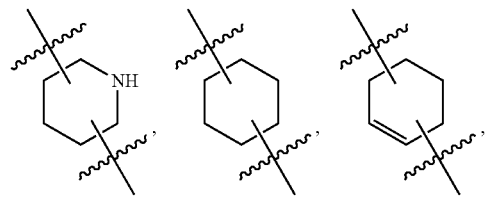

167
-continued

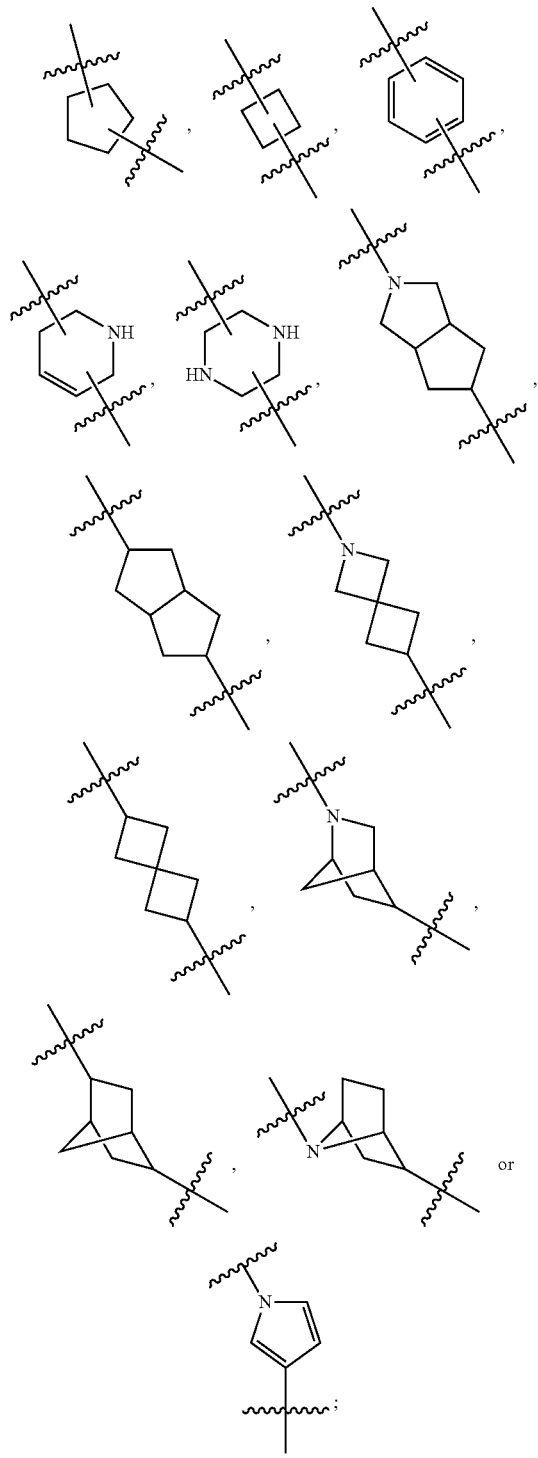

each moiety represented by A is optionally and independently substituted with 1, 2, 3 or 4 independent R².

4. The compound of claim 1, wherein

E is C₁₋₉ heterocyclyl, C₅₋₁₂spiro heterobicyclyl, C₅₋₁₂fused heterobicyclyl, C₅₋₁₂bridged heterobicyclyl, C₃₋₁₂cycloalkyl, C₆₋₁₂ aryl or C₁₋₁₂ heteroaryl; and each of C₁₋₉ heterocyclyl, C₅₋₁₂spiro heterobicyclyl, C₅₋₁₂fused heterobicyclyl, C₅₋₁₂bridged heterobicyclyl,

168

C₃₋₁₂cycloalkyl, C₆₋₁₂ aryl and C₁₋₁₂ heteroaryl is optionally and independently substituted with 1, 2, 3 or 4 independent $R^{2c}$; or E is one of the following monovalent groups:

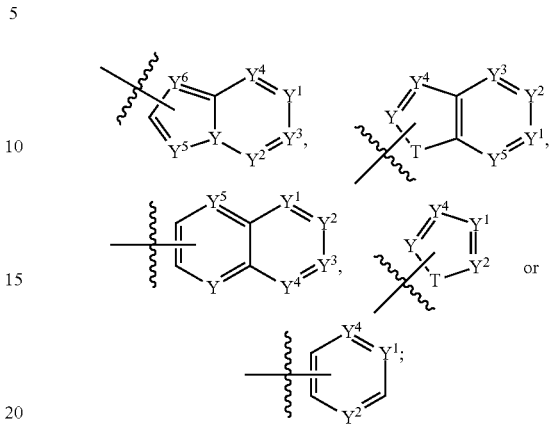

wherein each Y, Y¹, Y², Y³, Y⁴, Y⁵ and Y⁶ is independently N or CH;

each T is independently —O—, —S—, —NH— or —CH₂—; and each of the monovalent groups is optionally and independently substituted with 1, 2, 3 or 4 independent $R^{2c}$.

5. The compound of claim 1 having Formula (II) or a stereoisomer, a geometric isomer, a tautomer, or a pharmaceutically acceptable salt thereof,

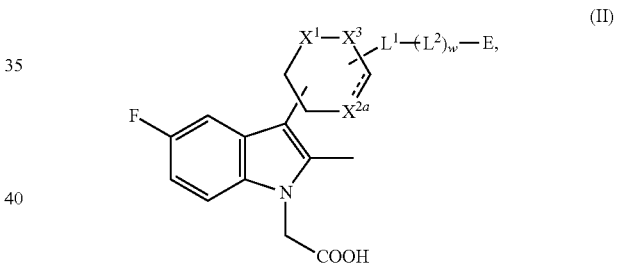

wherein when ----- $X^{2a}$ is a single bond,

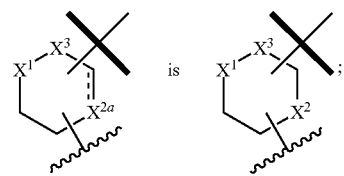

when ----- $X^{2a}$ is a double bond,

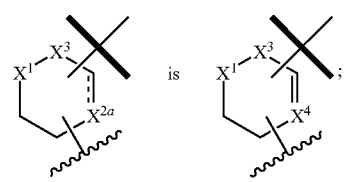

each X¹, X² and X³ is independently —(CR³R³ᵃ)ᵦ—, —O—, —N(R⁴)— or —S—;

each $X^4$ is independently $C(R^3)$ or N;
each b is independently 1, 2, 3 or 4;
each $R^3$ and $R^{3a}$ is independently H, $C_{1-4}$ alkyl, $C_{1-4}$ haloalkyl, hydroxy, nitro, cyano, halogen, amino, carboxy, $C_{1-4}$ alkoxy, $C_{1-4}$ alkylamino, $C_{1-4}$ alkylthio, $C_{1-4}$ alkylacyl, $C_{3-12}$ cycloalkyl, $C_{3-9}$ heterocyclyl, $C_{6-12}$ aryl, $C_{1-9}$ heteroaryl, amino-$C_{1-4}$-alkyl, hydroxy-$C_{1-4}$-alkyl, sulfo, aminosulfonyl or aminoacyl; and
each $R^4$ is independently H, $C_{1-4}$ alkyl, $C_{1-4}$ haloalkyl, hydroxy, $C_{3-12}$ cycloalkyl, $C_{3-9}$ heterocyclyl, $C_{6-12}$ aryl, $C_{1-9}$ heteroaryl, amino-$C_{1-4}$-alkyl or hydroxy-$C_{1-4}$-alkyl.

6. The compound of claim 1 having Formula (IIa) or a stereoisomer, a geometric isomer, a tautomer, or a pharmaceutically acceptable salt thereof,

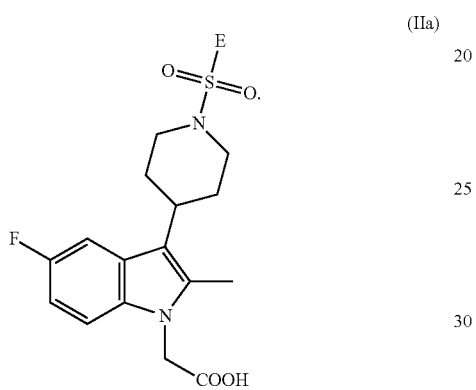

(IIa)

7. The compound of claim 1, wherein
E is one of the following $C_{6-12}$ aryl and $C_{1-9}$ heteroaryl groups:

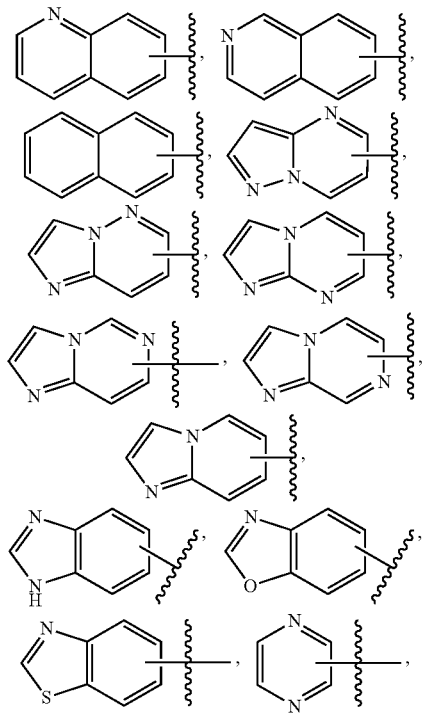

each moiety represented by E is optionally and independently substituted with 1, 2, 3 or 4 independent $R^{2c}$.

8. The compound of claim 1, wherein
each $R^{2c}$ and $R^2$ is independently H, methyl, ethyl, n-propyl, isopropyl, t-butyl, n-butyl, trifluoromethyl, hydroxy, nitro, amino, cyano, F, Cl, Br, carboxy, methoxy, ethoxy, isopropoxy, methylamino, ethylamino, dimethylamino, methylacyl, aminomethyl, hydroxymethyl, sulfo, $R^{2b}$-L-, aminosulfonyl or aminoacyl; and
each $R^{2b}$ is independently H, methyl, ethyl, n-propyl, isopropyl, n-butyl, trifluoromethyl, cyclopentyl, cyclohexyl, cyclobutyl, morpholinyl, piperidyl, pyrrolyl, hydroxymethyl or amino.

9. The compound of claim 1, wherein the pharmaceutically acceptable salt is an inorganic acid salt, organic acid salt, inorganic base salt, alkali metal salt or organic base salt.

10. The compound of claim 9, wherein the pharmaceutically acceptable salt is hydrochloride, hydrobromide, hydriodate, nitrate, sulfate, disulfate, phosphate, acetate, propionate, butyrate, lactate, mesylate, tosilate, maleate, benzoate, succinate, tartrate, citrate, oxalate, fumarate, taurinate, sodium salt, potassium salt or ammonium salt.

11. The compound of claim 1 having one of the following structures or a stereoisomer, a geometric isomer, a tautomer, or a pharmaceutically acceptable salt thereof:

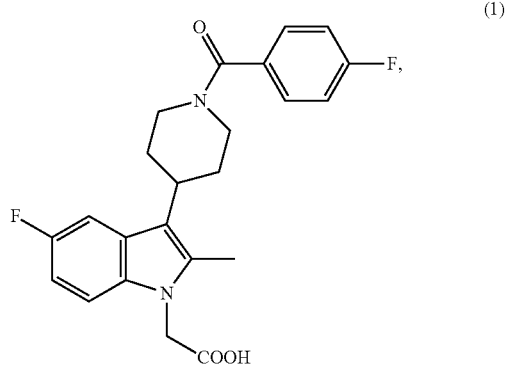

(1)

-continued
(2)
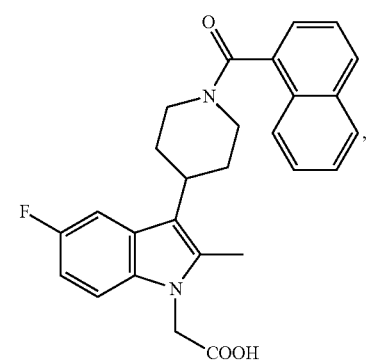
(3)
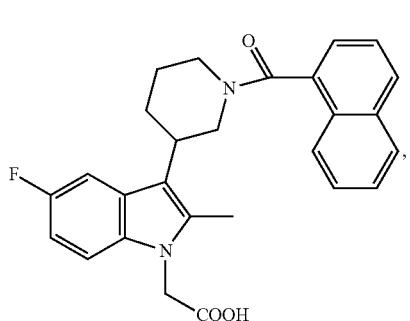
(4)
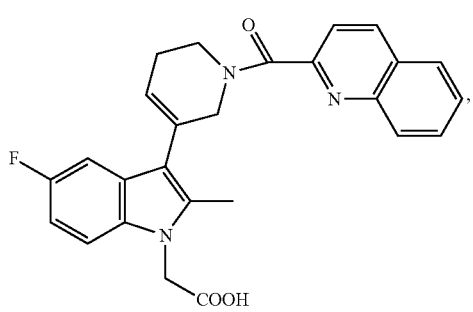
(5)
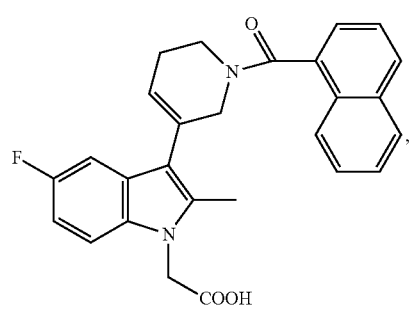
-continued
(6)
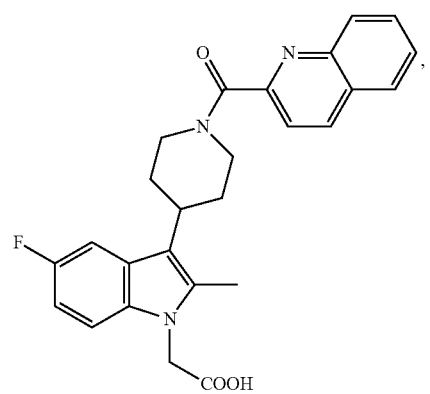
(7)
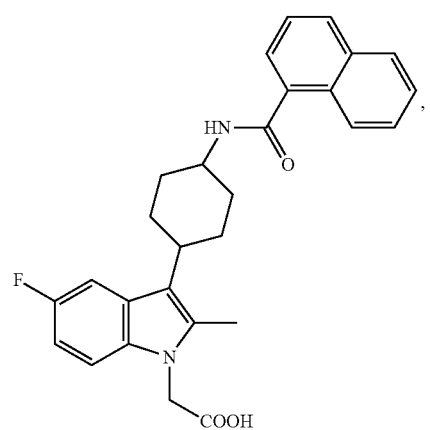
(8)
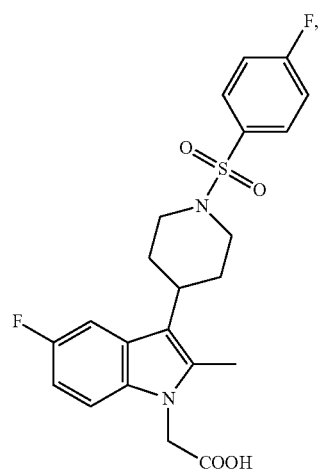

(9)
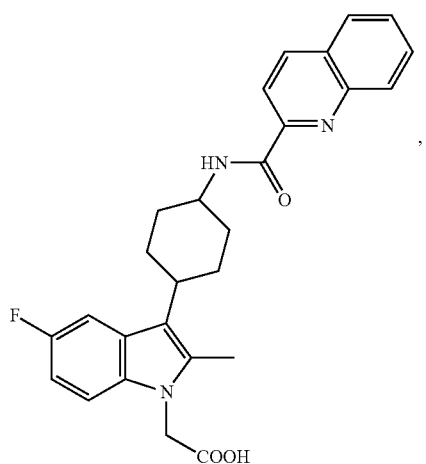
(10)
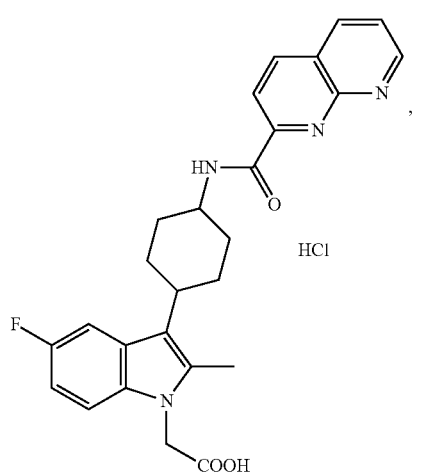
HCl
(11)
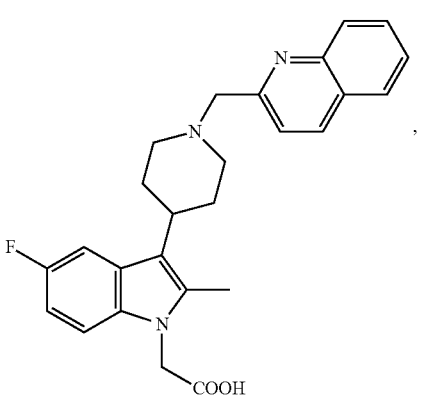
(12)
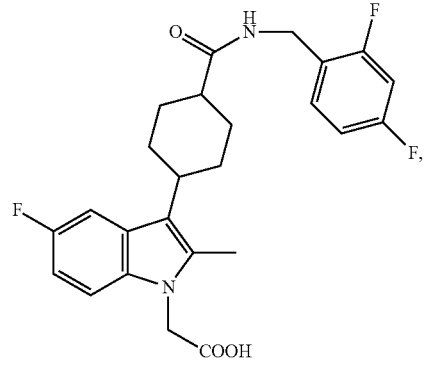
(13)
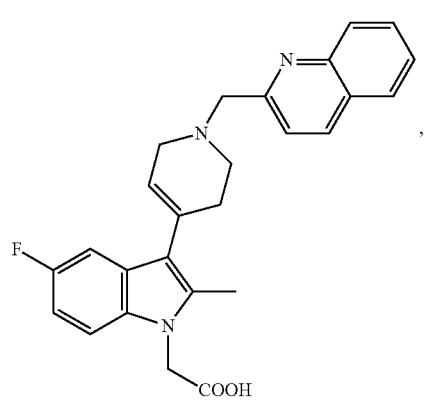
(14)
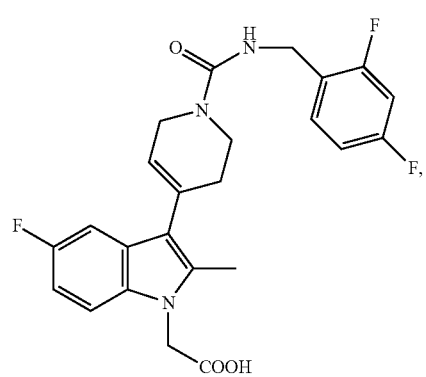
(15)
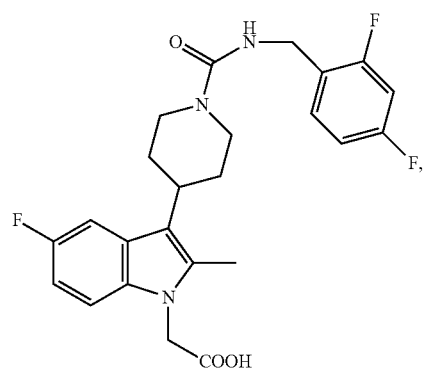

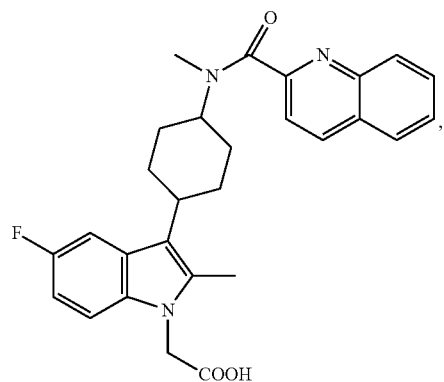
(16)
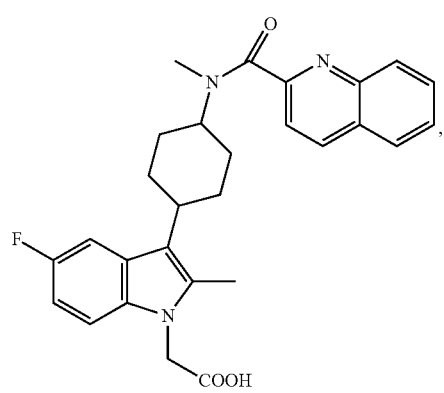
(17)
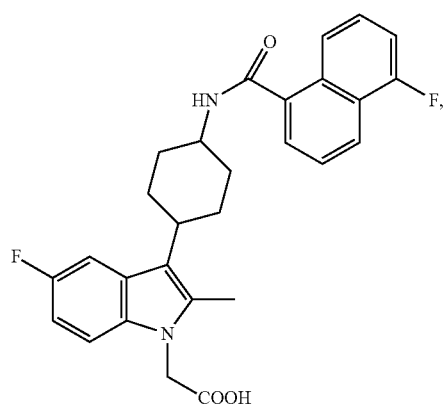
(18)
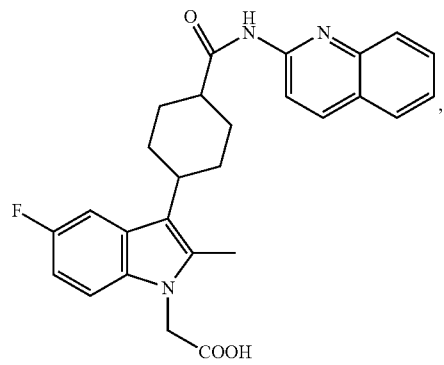
(19)
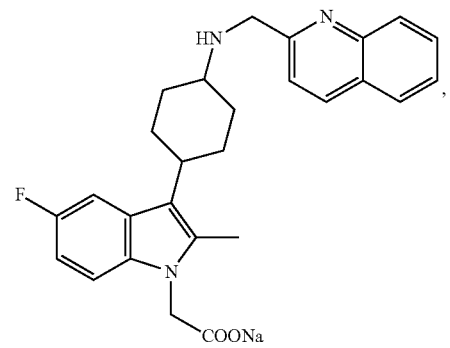
(20)
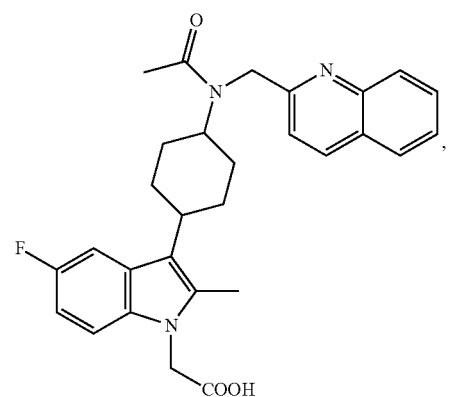
(21)
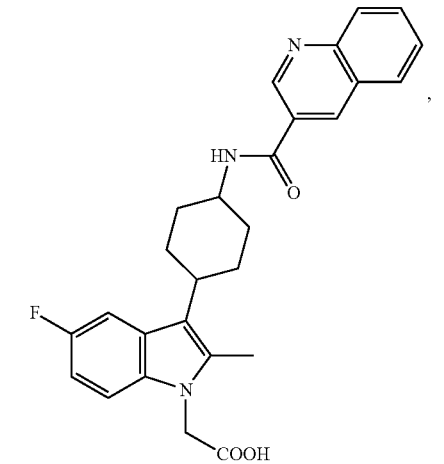
(22)
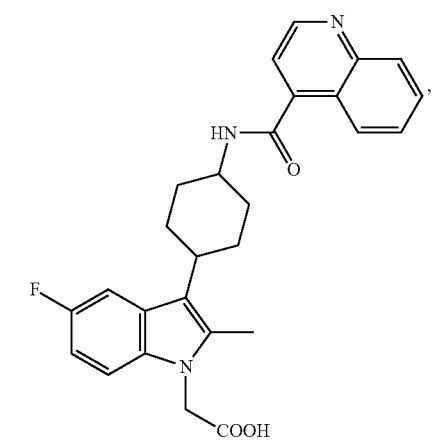
(23)

-continued
(24)
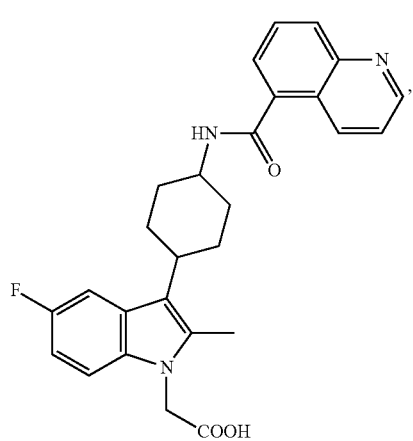
(25)
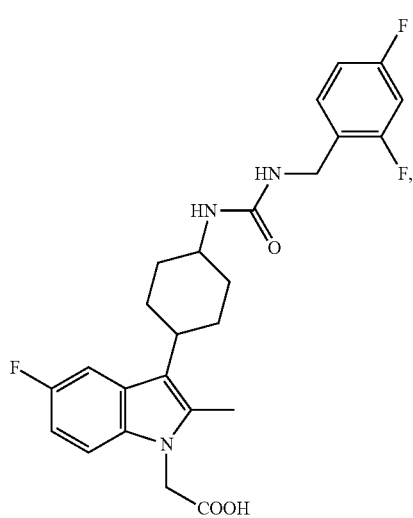
(26)
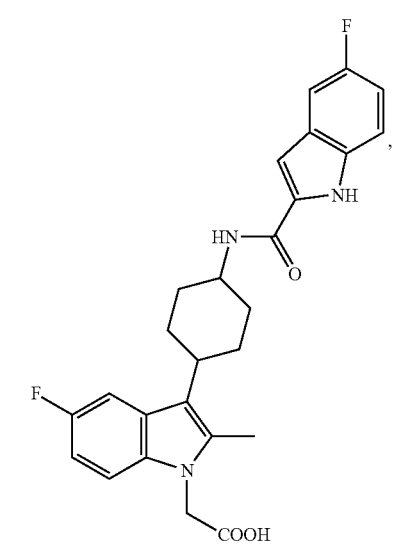
-continued
(27)
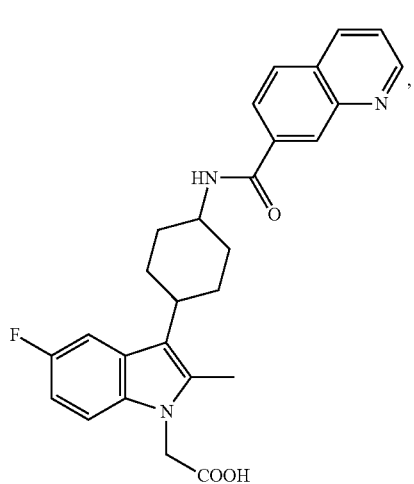
(28)
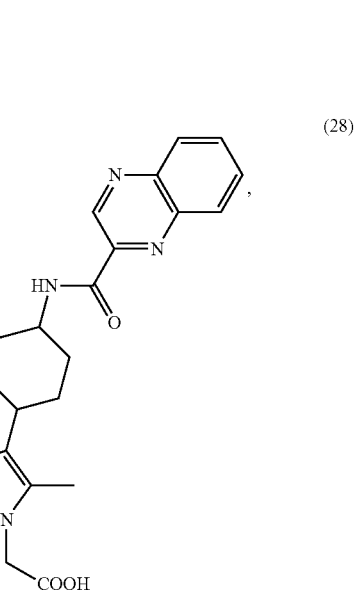
(29)
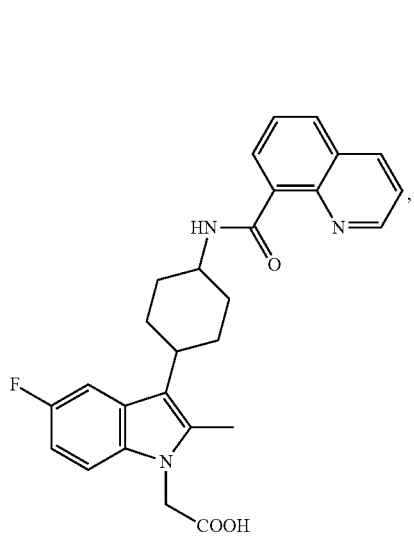

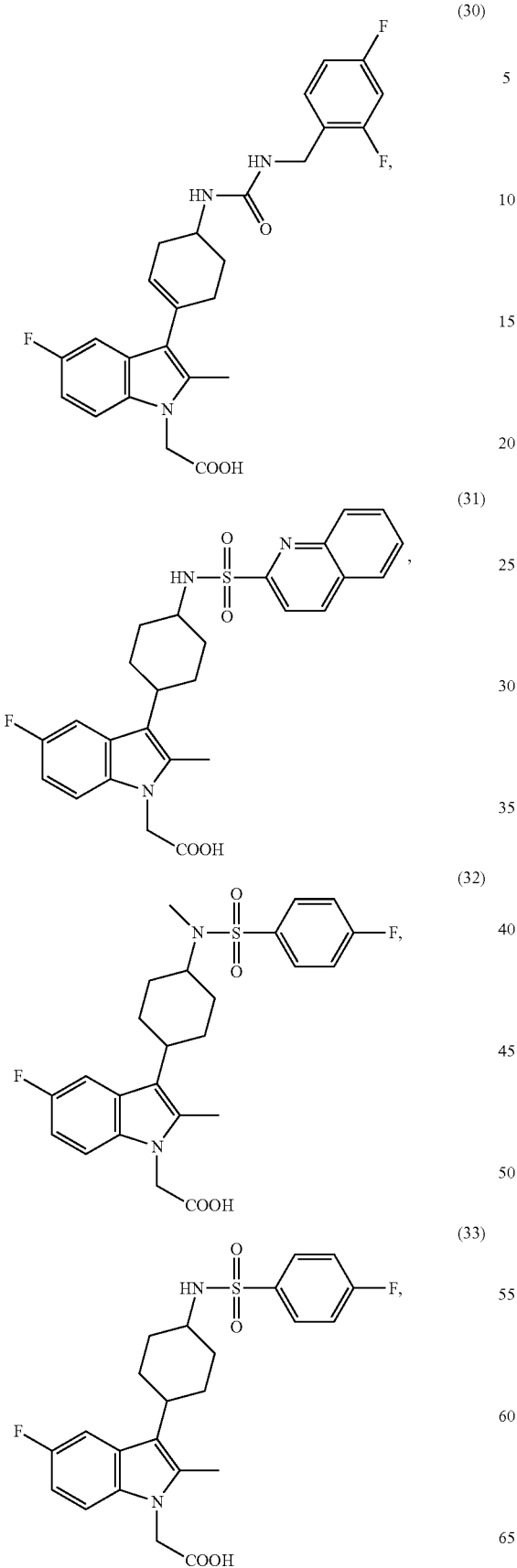
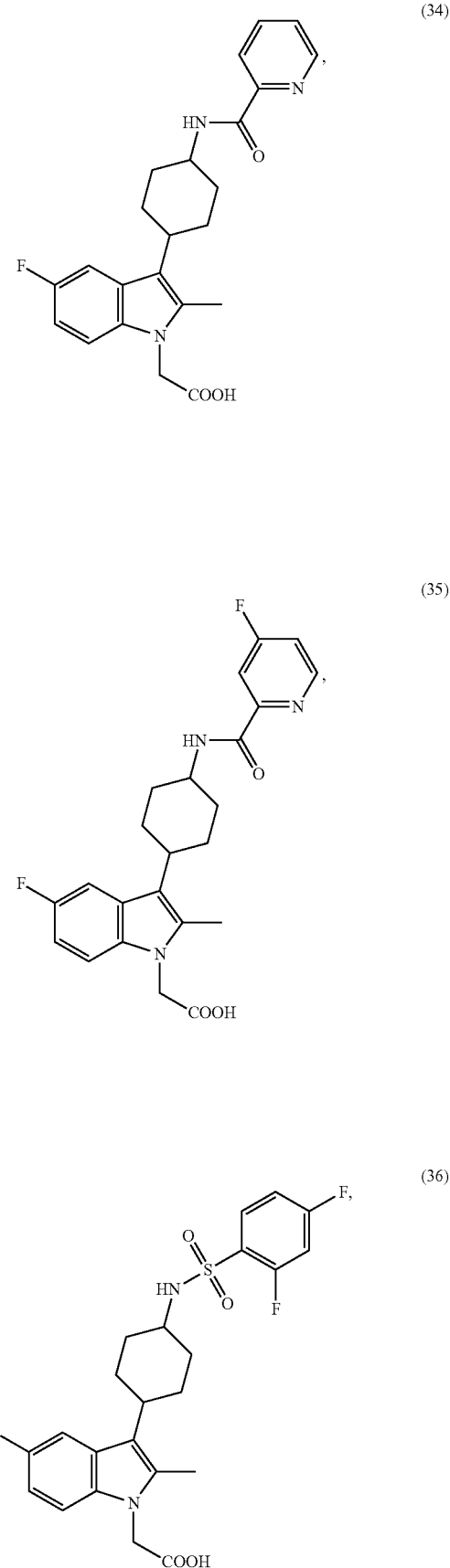

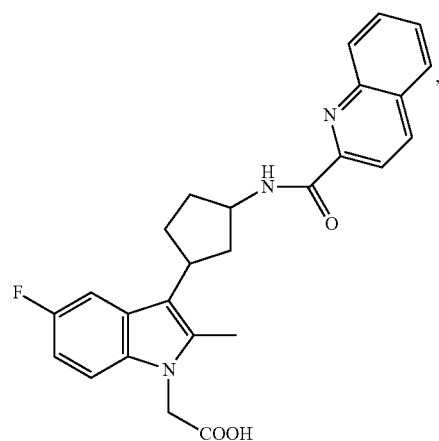
(37)
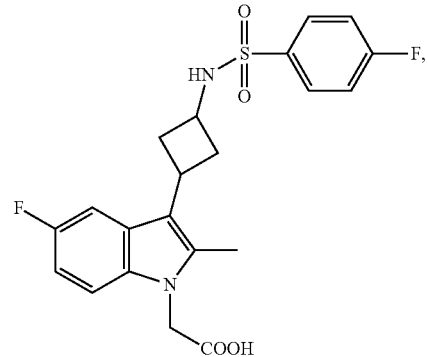
(40)
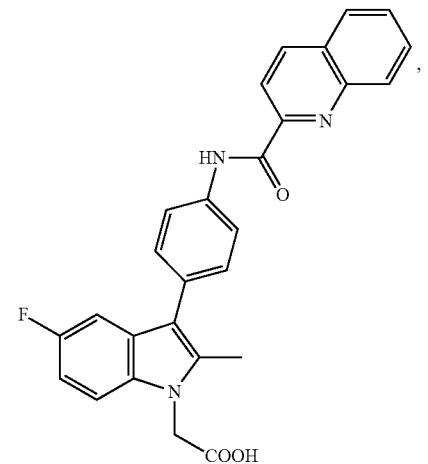
(41)
(38)
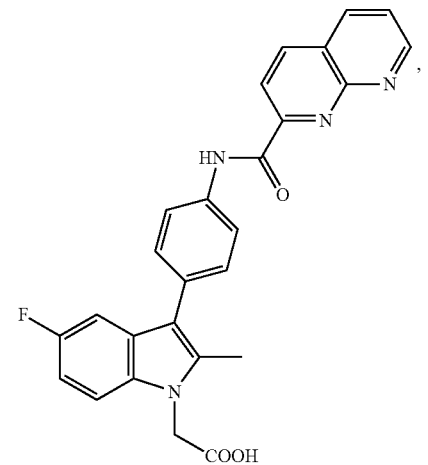
(42)
(39)
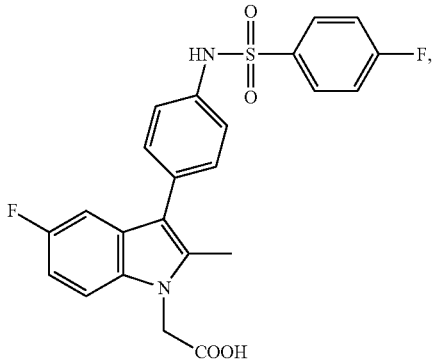
(43)

(44)
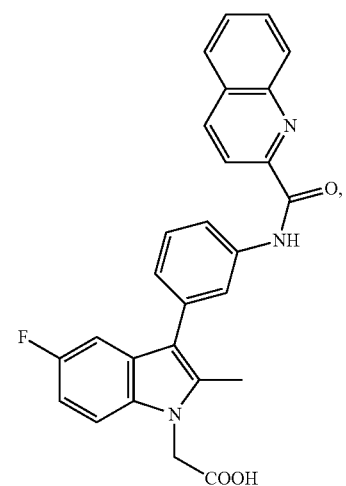
(45)
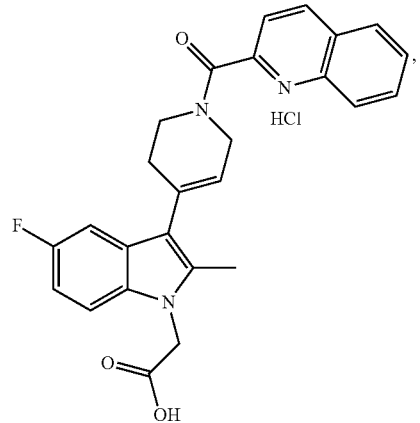
(46)
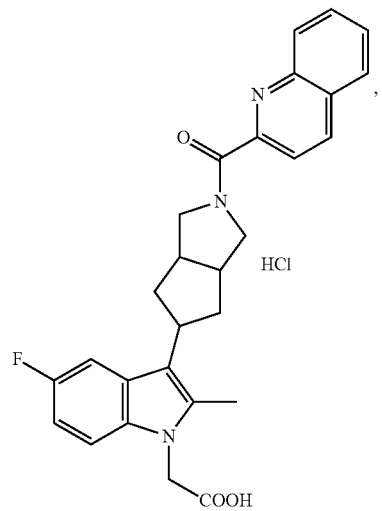
(47)
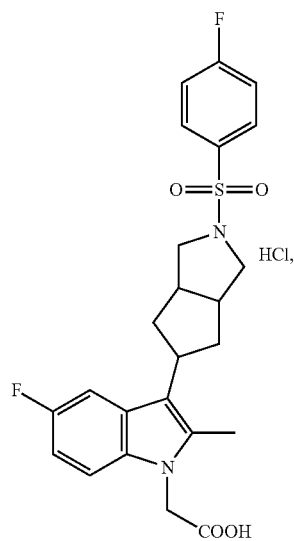
(48)
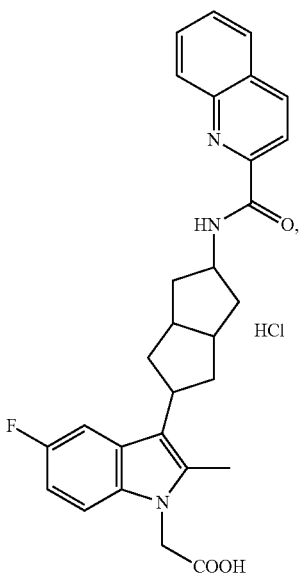
(49)
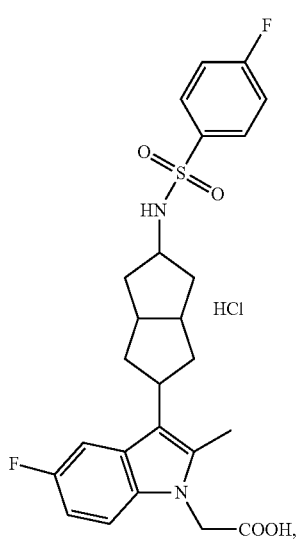

(50)
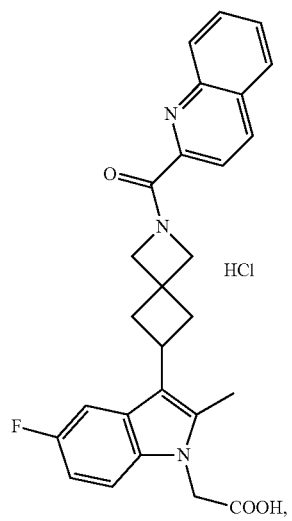
(51)
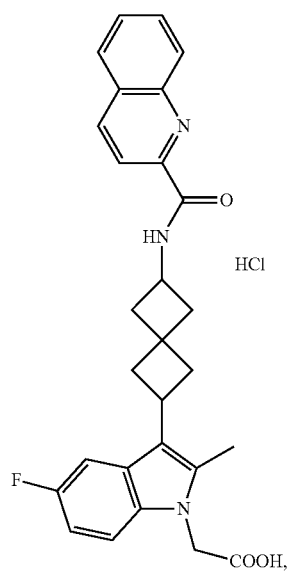
(52)
(53)
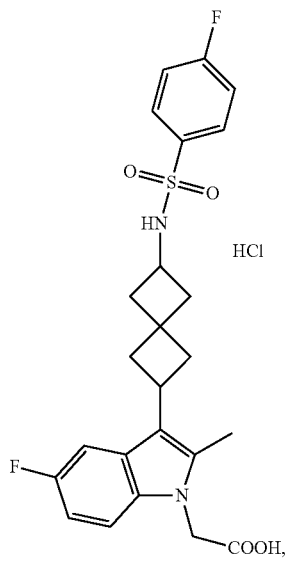
(54)
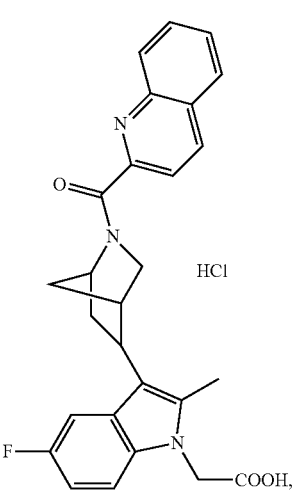
(55)
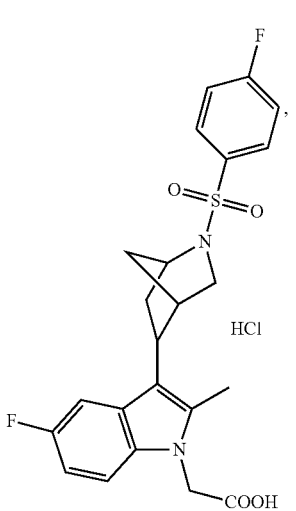

-continued
(56)
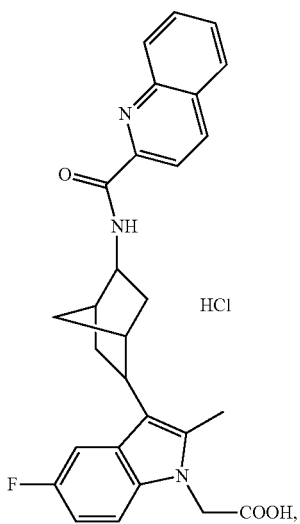
(57)
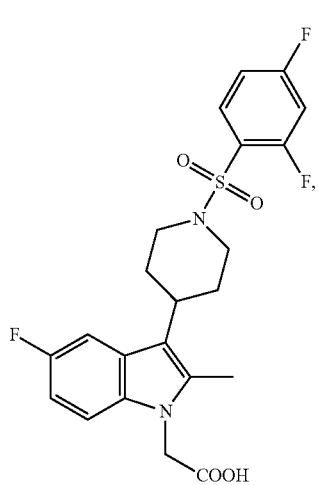
(58)
-continued
(59)
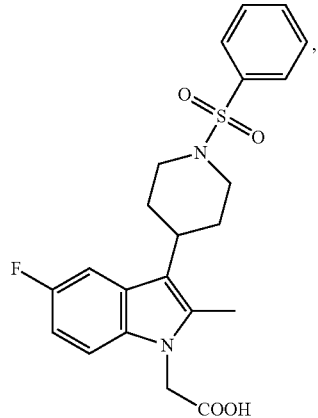
(60)
(61)

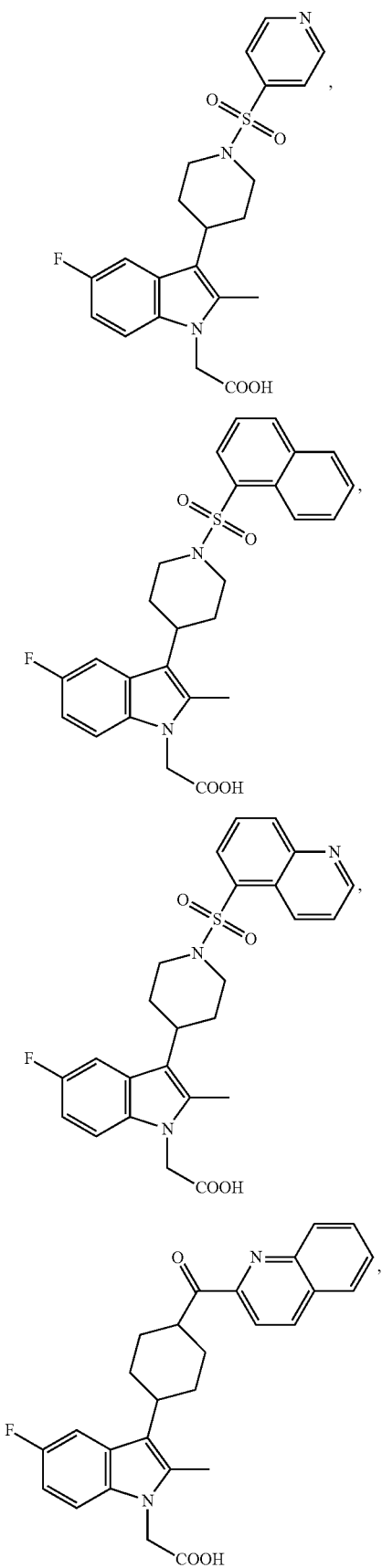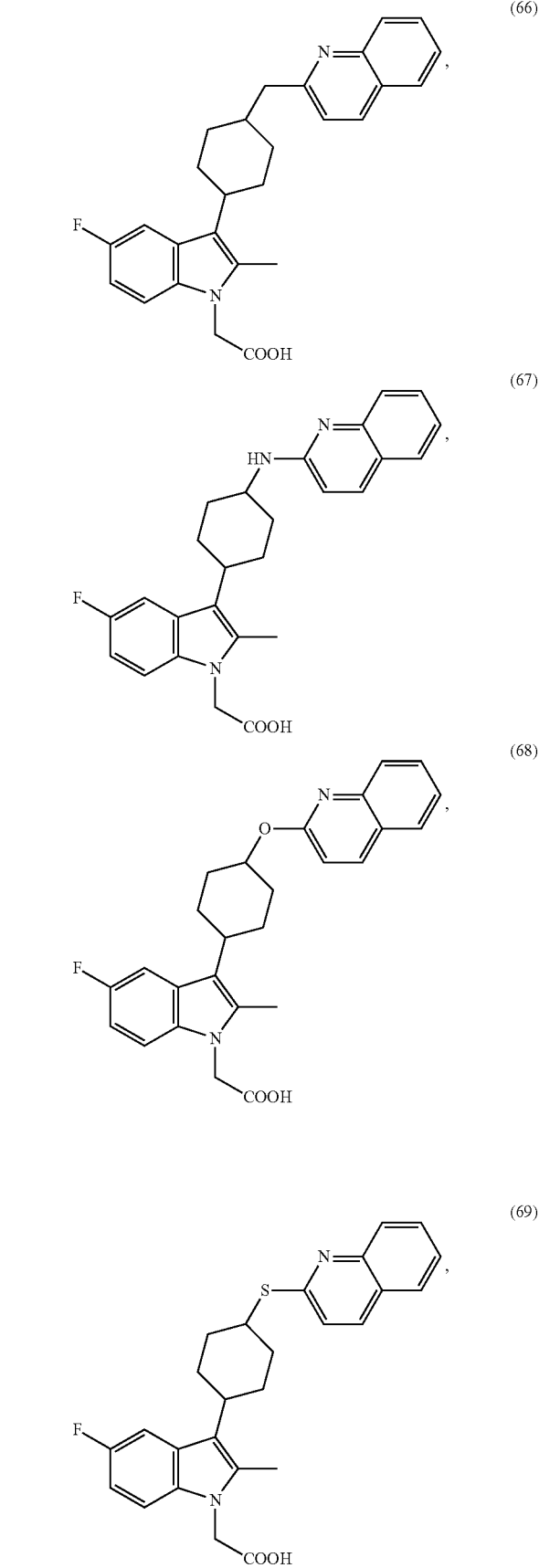

(70)
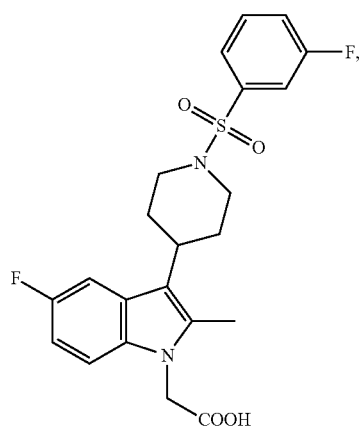
(71)
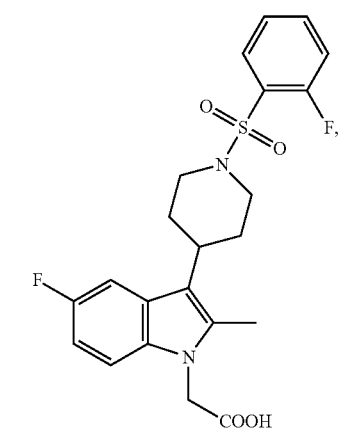
(72)
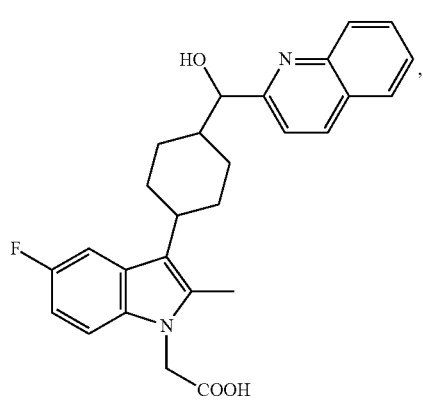
(73)
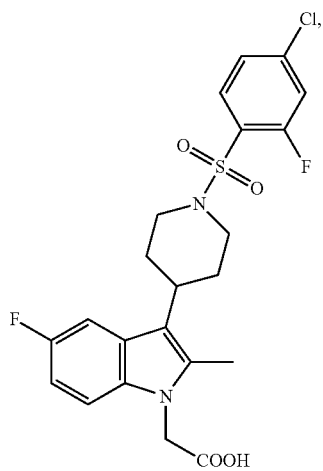
(74)
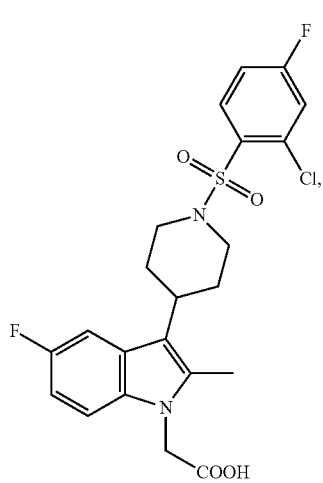
(75)
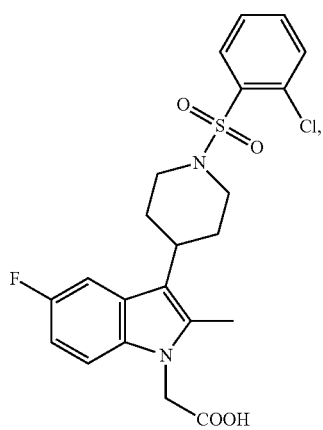

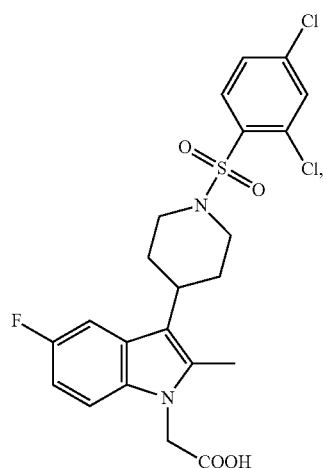
(76)
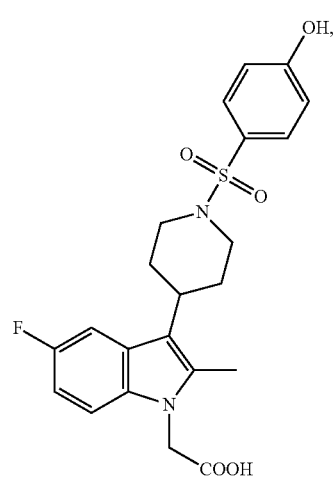
(77)
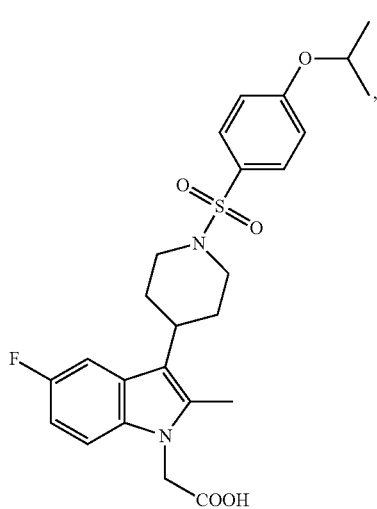
(78)
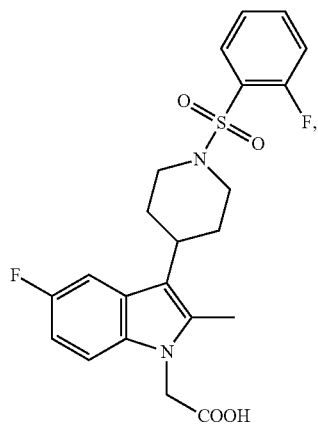
(79)
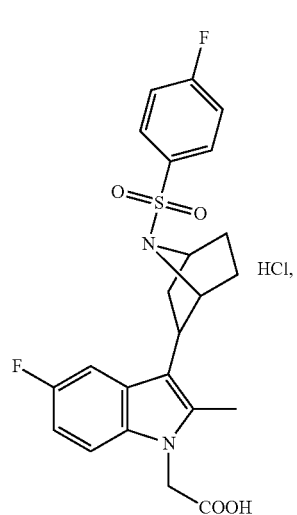
(80)
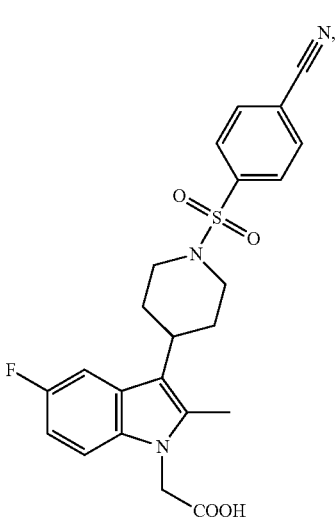
(81)

(82)
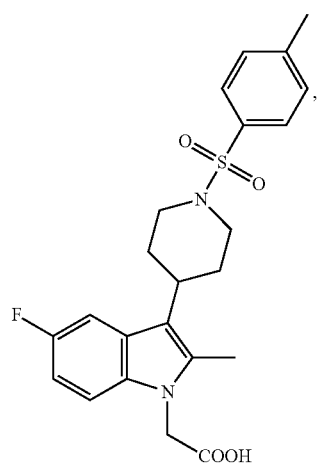
(83)
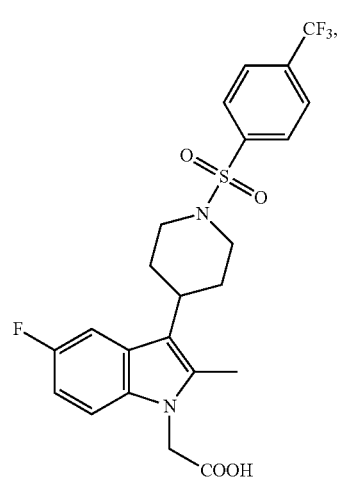
(84)
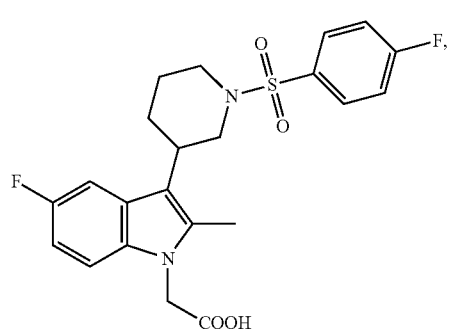
(85)
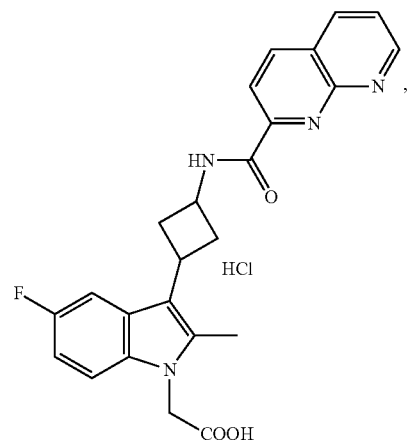
(86)
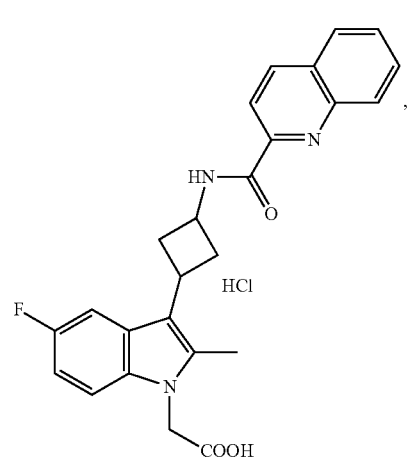
(87)
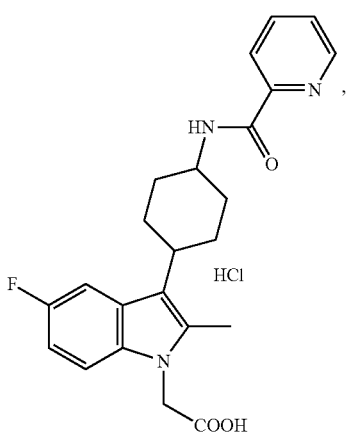

(88) 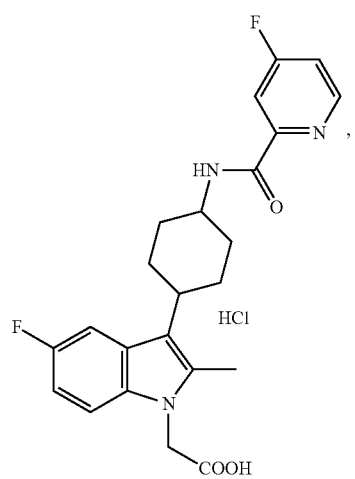
(89) 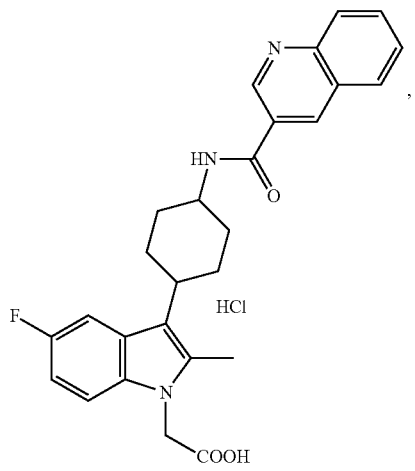
(90) 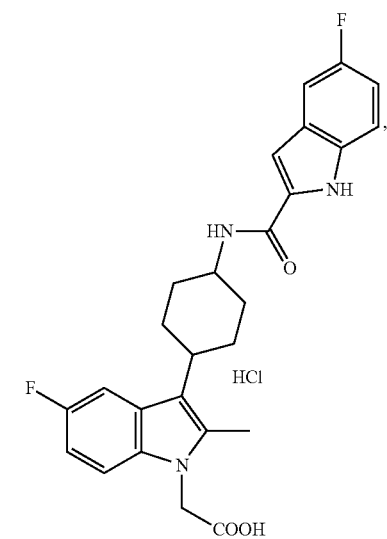
(91) 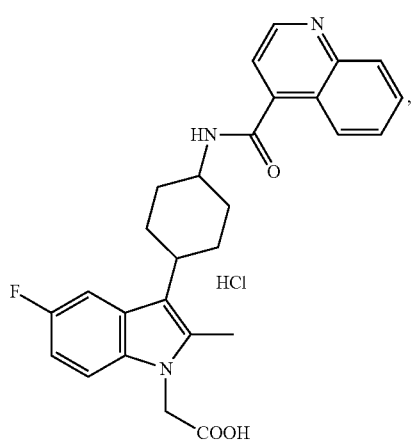
(92) 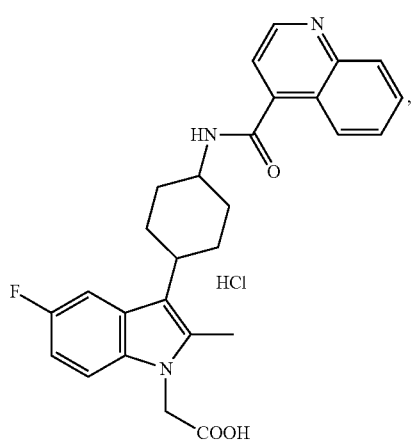
(93) 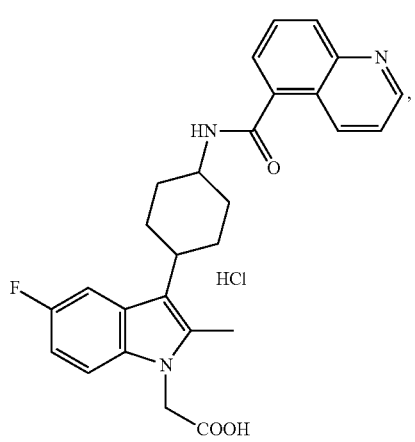

-continued
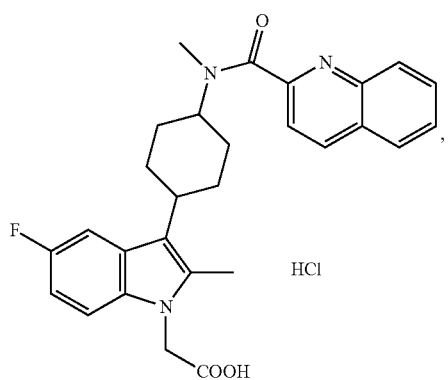
(94)
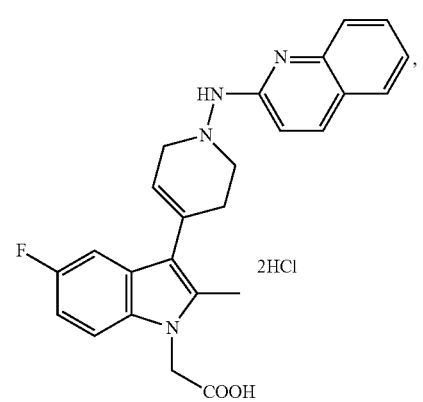
(95)
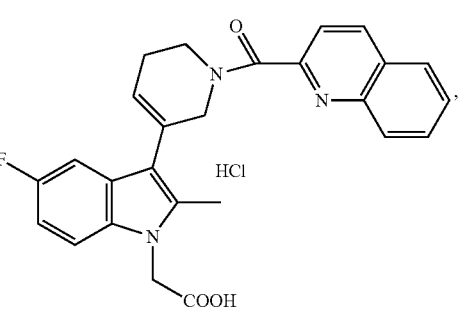
(96)
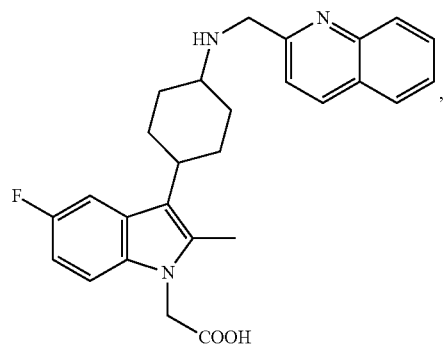
(97)
-continued
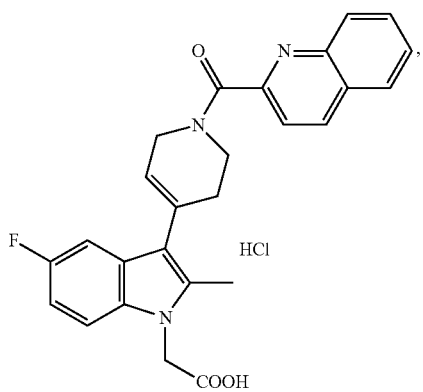
(98)
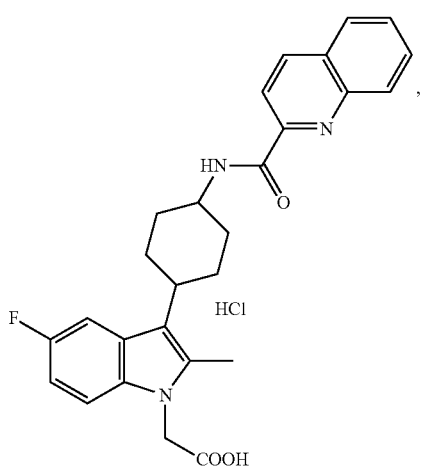
(99)
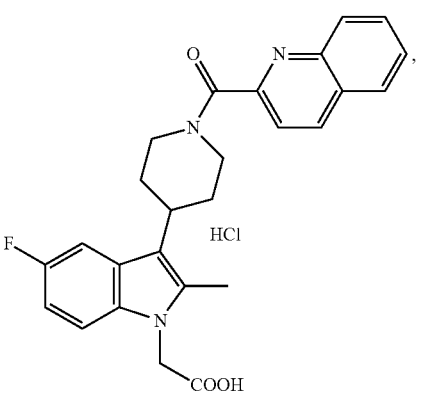
(100)

-continued

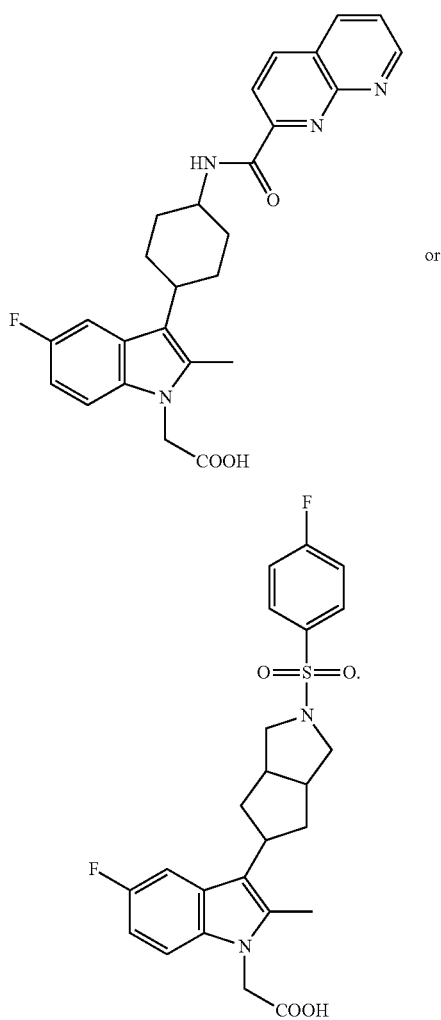

(101)

(102)

12. A crystalline form of 2-(5-fluoro-3-(1-((4-fluorophenyl)sulfonyl)piperidin-4-yl)-2-methyl-1H-indol-1-yl)acetic acid (Formula VI), wherein the crystalline form is crystalline form I, crystalline form II, crystalline form III, crystalline form IV, crystalline form V or crystalline form VI:

(VI)

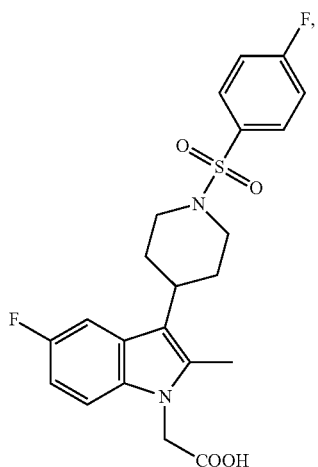

wherein:

crystalline form I has an X-ray powder diffraction (XRPD) pattern comprising peaks expressed in degrees 2θ at 3.80°, 13.20°, 15.46°, 17.24°, 18.90°, 19.27°, 19.57°, 23.84° and 28.39°, where the error margin is ±0.2°;

crystalline form II has an X-ray powder diffraction (XRPD) pattern comprising peaks expressed in degrees 2θ at 5.96°, 12.09°, 13.17°, 14.14°, 15.96°, 16.85°, 17.97°, 20.77°, 24.07°, 24.64° and 28.99°, where the error margin is ±0.2°;

crystalline form III has an X-ray powder diffraction (XRPD) pattern comprising peaks expressed in degrees 2θ at 15.67°, 16.20°, 18.28°, 20.02°, 20.89°, 23.28° and 24.62°, where the error margin is ±0.2°;

crystalline form IV has an X-ray powder diffraction (XRPD) pattern comprising peaks expressed in degrees 2θ at 16.09°, 18.19°, 20.57°, 20.98°, 24.11°, 24.82° and 25.93°, where the error margin is ±0.2°;

crystalline form V has an X-ray powder diffraction (XRPD) pattern comprising peaks expressed in degrees 2θ at 5.88°, 12.86°, 15.68°, 17.69°, 20.50°, 23.60° and 24.17°, where the error margin is ±0.2°; and crystalline form VI has an X-ray powder diffraction (XRPD) pattern comprising peaks expressed in degrees 2θ at 5.84°, 12.83°, 13.20°, 15.72°, 17.63°, 23.62° and 28.94°, where the error margin is ±0.2°.

13. A pharmaceutical composition comprising the compound of claim 1; and at least one of pharmaceutically acceptable carriers, excipients, diluents, adjuvants and vehicles.

14. The pharmaceutical composition of claim 13 further comprising one or more other active agents, wherein the other active agent is salmeterol, fluticasone, loratadine, montelukast, omalizumab, fusidic acid, clotrimazole, tacrolimus, pimecrolimus, DP antagonist, cilomilast, TNF-α converting enzyme (TACE) inhibitor, blocking monoclonal antibody or soluble receptor of IL-4 and IL-5 or zileuton.

15. A method of treating a disease mediated by $PGD_2$ at the CRTH2 receptor in a patient comprising administering the compound of claim 1 to the patient, wherein the disease mediated by $PGD_2$ at the CRTH2 receptor is asthma, COPD, allergic asthma, perennial allergic rhinitis, seasonal allergic rhinitis, atopic dermatitis, contact hypersensitivity, conjunctivitis, eosinophilic bronchitis, food allergies, eosinophilic gastroenteritis, inflammatory bowel disease, ulcerative colitis, Crohn's disease, and mastocytosis.

16. A method of treating a disease mediated by $PGD_2$ at the CRTH2 receptor in a patient comprising administering the pharmaceutical composition of claim 13 to the patient, wherein the disease mediated by $PGD_2$ at the CRTH2 receptor is asthma, COPD, allergic asthma, perennial allergic rhinitis, seasonal allergic rhinitis, atopic dermatitis, contact hypersensitivity, conjunctivitis, eosinophilic bronchitis, food allergies, eosinophilic gastroenteritis, inflammatory bowel disease, ulcerative colitis, Crohn's disease, and mastocytosis.

* * * * *